(12) United States Patent
Bandiera et al.

(10) Patent No.: US 10,745,407 B2
(45) Date of Patent: Aug. 18, 2020

(54) HETEROCYCLIC DERIVATIVES FOR THE TREATMENT OF CYSTIC FIBROSIS

(71) Applicants: Fondazione Istituto Italiano Di Tecnologia, Genoa (IT); Istituto Giannina Gaslini, Genoa (IT); Fondazione Per la Ricerca Sulla Fibrosi Cistica—Onlus, Verona (IT)

(72) Inventors: Tiziano Bandiera, Genoa (IT); Fabio Bertozzi, Genoa (IT); Paolo Di Fruscia, Genoa (IT); Federico Sorana, Verona (IT); Francesco Berti, Verona (IT); Alejandra Rodriguez Gimeno, Genoa (IT); Emanuela Caci, Verona (IT); Loretta Ferrera, Verona (IT); Nicoletta Pedemonte, Genoa (IT); Luis Juan Vicente Galietta, Genoa (IT)

(73) Assignee: Fondazione Istituto Italiano Di Tecnologia (IT)

( * ) Notice: Subject to any disclaimer, the term of this patent is extended or adjusted under 35 U.S.C. 154(b) by 0 days.

(21) Appl. No.: 16/493,532

(22) PCT Filed: Mar. 14, 2018

(86) PCT No.: PCT/IB2018/051709
§ 371 (c)(1),
(2) Date: Sep. 12, 2019

(87) PCT Pub. No.: WO2018/167690
PCT Pub. Date: Sep. 20, 2018

(65) Prior Publication Data
US 2020/0002348 A1 Jan. 2, 2020

(30) Foreign Application Priority Data
Mar. 14, 2017 (IT) .................... 102017000028184

(51) Int. Cl.
| | | |
|---|---|---|
| *C07D 491/056* | (2006.01) |
| *C07D 498/04* | (2006.01) |
| *C07D 471/04* | (2006.01) |
| *C07D 405/12* | (2006.01) |
| *C07D 405/14* | (2006.01) |
| *C07D 471/08* | (2006.01) |
| *C07D 413/12* | (2006.01) |
| *C07D 413/14* | (2006.01) |

(52) U.S. Cl.
CPC ....... *C07D 491/056* (2013.01); *C07D 405/12* (2013.01); *C07D 405/14* (2013.01); *C07D 413/12* (2013.01); *C07D 413/14* (2013.01); *C07D 471/04* (2013.01); *C07D 471/08* (2013.01); *C07D 498/04* (2013.01)

(58) Field of Classification Search
CPC C07D 491/056; C07D 405/12; C07D 405/14; C07D 413/12; C07D 413/14; C07D 471/04; C07D 471/08; C07D 498/04
USPC .......................................................... 514/293
See application file for complete search history.

(56) References Cited

FOREIGN PATENT DOCUMENTS

| WO | 2004080972 A1 | 9/2004 |
| WO | 2005075435 A1 | 8/2005 |

OTHER PUBLICATIONS

International Search Report and Written Opinion for PCT Patent Application No. PCT/IB2018/051709 dated May 15, 2018.
Ke Zheng et al., "Design and Synthesis of Highly Potent and Isoform Selective JNK3 Inhibitors: SAR Studies on Aminopyrazole Derivatives", Journal of Medicinal Chemistry, vol. 57, No. 23, Dec. 11, 2014.
G. Bertuzzi et al., "Straightforward Synthesis of a Novel Ring-Fused Pyrazole-Lactam and in Vitro Cytotoxic Activity on Cancer Cell Lines", European Journal of Medicinal Chemistry Editions Scientifique Elsevier, Paris, FR, vol. 117, Apr. 5, 2016.

*Primary Examiner* — Kristin A Vajda
(74) *Attorney, Agent, or Firm* — McAndrews, Held & Malloy, Ltd.

(57) ABSTRACT

The present invention relates to compounds of Formula (I) or pharmaceutically acceptable salts or solvates thereof: It further discloses a pharmaceutical composition comprising the compounds of Formula (I) and their uses, in particular to modulate CFTR protein or ABC protein activities.

10 Claims, 1 Drawing Sheet

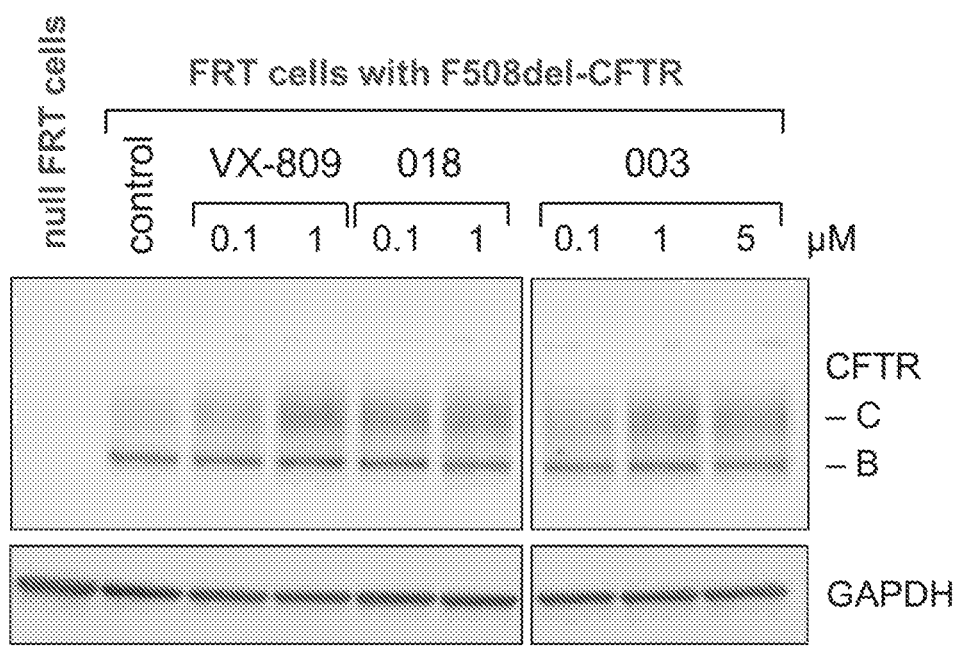

HETEROCYCLIC DERIVATIVES FOR THE TREATMENT OF CYSTIC FIBROSIS

PRIORITY CLAIM

The present application is filed pursuant to 35 U.S.C. 371 as a U.S. National Phase application of International Patent Application No. PCT/IB2018/051709, which was filed Mar. 14, 2018, claiming the benefit of priority from Italian Patent Application No. 102017000028184 filed on Mar. 14, 2017. The entire text of the aforementioned applications is incorporated herein by reference in its entirety.

TECHNICAL FIELD

The present invention relates to novel compounds to modulate CFTR protein or ABC protein activities, in particular for the treatment of cystic fibrosis.

BACKGROUND ART

Cystic fibrosis is an autosomal recessive genetic disorder caused by mutations of the gene encoding for the cystic fibrosis transmembrane conductance regulator (CFTR). The incidence of the disease among the Caucasian population is 1/2000-3000 newborns, whereas it is much lower among native Africans and Asians. Despite progress in the treatment of cystic fibrosis, there is no cure.

The cystic fibrosis transmembrane conductance regulator (CFTR) gene encodes an epithelial ion channel responsible for aiding in the regulation of salt and water absorption and secretion in various tissues.

Specifically, CFTR is a 1480 amino acid plasma membrane protein that belongs to the superfamily of ATP-binding cassette (ABC) transporters. CFTR structure consists of a cytosolic N-terminus followed by six transmembrane helices, a nucleotide-binding domain (NBD1), a regulatory (R) domain, six additional transmembrane helices, a second nucleotide-binding domain (NBD2), and a cytosolic C-terminus (Riordan, *Annu Rev Biochem* 77:701-726, 2008). The transmembrane helices form a pore permeable to chloride, bicarbonate, iodide, and other anions. Opening of the pore requires the phosphorylation of the R domain by the cAMP-dependent protein kinase A as well as binding of two ATP molecules in two pockets formed by the assembly of NBD1 and NBD2.

CFTR is a cAMP/ATP-modulated anion channel that is expressed in a variety of cells types, and particularly in epithelial cells of various organs including lungs, pancreas, liver, and intestine (Mall and Hartl, *Eur Respir J* 44:1042-1054, 2014). Physiological signals that increase intracellular cAMP levels elicit CFTR activation. In most tissues, opening of CFTR pore leads to chloride and bicarbonate secretion. A notable exception is represented by the sweat gland duct in which CFTR mediates chloride absorption and not secretion.

In epithelial cells, normal functioning of CFTR is critical for the maintenance of electrolyte transport throughout the body, including respiratory and digestive tissues.

The important role of CFTR is demonstrated by the severe pathological manifestations occurring in cystic fibrosis (CF), an inherited disease caused by mutations that lead to CFTR loss of function. In the lungs, lack of CFTR-dependent anion secretion impairs mucociliary clearance and innate antimicrobial mechanisms (Collawn and Matalon, *Am J Physiol* 307: L917-L923, 2014). Consequently, the airways become colonized by antibiotic-resistant bacteria that trigger a severe inflammatory response and a progressive loss of respiratory function.

The gene encoding CFTR has been identified and sequenced (See Gregory, R. J. et al. (1990) Nature 347:382-386; Rich, D. P. et al. (1990) Nature 347:358-362; Riordan, J. R. et al. (1989) Science 245:1066-1073). Defects in this gene cause mutations in CFTR protein resulting in cystic fibrosis, the most common fatal genetic disease in humans. Within the general United States population, up to 10 million people carry a single copy of the defective gene without apparent ill effects. In contrast, individuals with two copies of the cystic fibrosis associated gene suffer from the debilitating and fatal effects of cystic fibrosis, including chronic lung disease.

In addition to respiratory disease, cystic fibrosis patients typically suffer from gastrointestinal problems and pancreatic insufficiency. If left untreated, cystic fibrosis results in death. In addition, the majority of males with cystic fibrosis are infertile and fertility is decreased among females with cystic fibrosis. In contrast to the severe effects of two copies of the cystic fibrosis associated gene, individuals with a single copy of the cystic fibrosis associated gene may exhibit increased resistance to dehydration resulting from diarrhea. This heterozygote advantage could explain the relatively high frequency of the cystic fibrosis gene within the population.

Sequence analysis of the CFTR gene of cystic fibrosis patients has revealed a variety of disease causing mutations (Cutting, G. R. et al. (1990) Nature 346:366-369; Dean, M. et al. (1990) Cell 61:863:870; Kerem, B-S. et al. (1989) Science 245: 1073-1080; Kerem, B-S. et al. (1990) Proc. Natl. Acad. Sci. USA 87:8447-8451). To date, more than 2000 CF-causing mutations in the cystic fibrosis gene have been identified, involving 6 classes of molecular defects of the protein (Class I: premature stop of CFTR protein synthesis; Class II: defective maturation and intracellular localization of the CFTR protein; Class III: impaired opening of CFTR pore; Class IV: reduced ability of CFTR pore to translocate anions; Class V: reduced CFTR protein synthesis due to altered RNA splicing; Class VI: reduced stability of CFTR at the plasma membrane leading to accelerated internalization and degradation).

A large majority of mutations have low or very low frequency (Bobadilla et al., *Hum Mutat* 19:575-606, 2002). However, a single mutation, F508del, is present in 50-90% of CF patients. F508del, i.e. loss of phenylalanine at position 508 within NBD1, causes multiple defects to CFTR protein (Okiyoneda et al., *Nat Chem Biol* 9:444-454, 2013). First of all, F508del-CFTR folding and stability are severely impaired. Such problems, which arise from the intrinsic instability of NBD1 and the altered interaction between NBD1 and the cytosolic loop 4, strongly reduce the trafficking of F508del-CFTR to the plasma membrane (trafficking defect). Indeed, mutant CFTR remains trapped in the endoplasmic reticulum (ER) where it is rapidly degraded by the ubiquitin-proteasome system (Lukacs and Verkman, *Trends Mol Med* 18:81-91, 2012). A second defect caused by F508del is the reduction of the open channel probability, i.e. the fraction of time spent by the channel in the open state (gating defect). Furthermore, if moved to the plasma membrane by rescue maneuvers, F508del-CFTR shows also a decreased half-time. Because of such defects, F508del mutation has combined class II, class III, and class VI characteristics.

The trafficking and gating defects can also be caused, often separately, by other CF mutations. For example, G85E, L1077P, A455E, and N1303K, defined as class II mutations, impair CFTR trafficking (Van Goor et al., *J Cyst Fibros* 13:29-36, 2014). Instead, G551D, G1349D, G178R, and G970R, defined as class III mutations, do not affect trafficking but strongly reduce CFTR open time (Yu et al., *J Cyst Fibros* 11:237-245, 2012).

The most prevalent mutation, i.e. the F508del, is associated with a severe disease.

The reduced number of channels in the membrane and the defective gating lead to reduced anion transport across epithelia leading to defective ion and fluid transport.

As discussed above, it is believed that the deletion of residue 508 in CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. This cellular phenomenon of defective ER processing of ABC transporters by the ER machinery has been shown to be the underlying basis not only for cystic fibrosis disease, but for other diseases (Loo et al., *Journal of Bioenergetics and Biomembranes*, 2005, 37, 501-507).

At present, the treatment of lung disorders in cystic fibrosis requires the development of innovative drugs aimed at the concomitant aspects of the disease and, consequently, modulators of the defective CFTR protein, new antibacterials and new anti-inflammatory agents, which can be used in parallel to obtain a synergistic action. Trafficking and gating defects caused by mutations in the CFTR protein are amenable to pharmacological treatment (Veit et al., *Mol Biol Cell* 27:424-433, 2016). Mistrafficking can be targeted with small molecules called correctors. Gating can be improved with so-called potentiators. There have been several attempts to identify potentiators and correctors (Galietta, *Pediatr Drugs* 15:393-402, 2013). The most advanced molecule is VX-770, also known as ivacaftor, developed by Vertex Pharmaceuticals (Van Goor et al., *Proc Natl Acad Sci USA* 106:18825-18830, 2009). Given its high efficacy in clinical trials (Ramsey et al., *N Engl J Med* 365:1663-1672, 2011), VX-770 has been approved for the treatment of patients with G551D and other eight mutations belonging to class III, who represent about 5% of all the cystic fibrosis patients. VX-770 has no significant therapeutic efficacy in patients who are homozygous for the F508del-CFTR mutation, confirming the need for customized treatments for sub-groups of patients suffering from cystic fibrosis depending on the specific CFTR protein molecular defect. For patients with the F508del-CFTR mutation, new molecules functioning as "correctors" of the mutated CFTR protein are under study. The VX-809 molecule, also known as lumacaftor, has been extensively characterized in cell models in vitro. In clinical trials on cystic fibrosis patients with F508del mutation, VX-809 did not show a clear therapeutic benefit (Clancy et al., *Thorax* 67:12-18, 2012). However, the combination of VX-809 and VX-770, commercially named Orkambi, elicited a significant although modest improvement in respiratory function (Wainwright et al., *N Engl J Med* 373: 220-231, 2015) Briefly, the treatment of cystic fibrosis patients requires different modulators of the mutated CFTR protein, namely "correctors" and/or "potentiators", depending on the mutations of the CFTR gene, which divide the patients into genetically distinct sub-groups, and complementary medicaments with an antibacterial action and an anti-inflammatory action.

Accordingly, there is a need for novel compounds to be used for the treatment of CFTR mediated diseases which involve CFTR modulator compounds.

DISCLOSURE OF INVENTION

The aim of the present invention is to provide novel compounds acting as CFTR modulators.

The aforementioned objective has been met according to compounds of claim 1, to a pharmaceutical composition of claim 5, to the uses of claims 6, 7 and 8. Preferred embodiments are set out within the dependent claims.

BRIEF DESCRIPTION OF THE DRAWINGS

The present invention will be now described in detail also with reference to the annexed FIGURE wherein:

FIG. 1 illustrates the analysis of electrophoretic mobility of mutant CFTR.

BEST MODE FOR CARRYING OUT THE INVENTION

The following paragraphs provide definitions of the various chemical moieties of the compounds according to the invention and are intended to apply uniformly through-out the specification and claims unless an otherwise expressly set out definition provides a broader definition.

The term "alkyl", as used herein, refers to saturated aliphatic hydrocarbon groups. Such term includes straight (unbranched) chains or branched chains.

Non-limiting examples of alkyl groups according to the invention are, for example, methyl, ethyl, propyl, isopropyl, n-butyl, iso-butyl, tert-butyl, n-pentyl, iso-pentyl, n-hexyl and the like.

Alkyl groups according to the present invention may be unsubstituted or substituted by one or more substituents as defined below.

The term "alkoxy", as used herein, refers to an alkyl group as defined above that is linked to the remainder of the compound by an oxygen atom.

The term "cycloalkyl", as used herein, refers to a saturated or partially unsaturated carbocyclic group having a single ring. It includes cycloalkenyl groups.

Non-limiting examples of cycloalkyl groups according to the invention are, for example, cyclopropane, cyclobutane, cyclopentane, cyclohexane, cycloheptane, cyclopentene, cyclohexene, cyclohexadiene and the like.

Cycloalkyl groups according to the present invention may be unsubstituted or substituted by one or more substituents as defined below.

The term "heterocycloalkyl" group, ("non-aromatic heterocycle" group), refers to a cycloalkyl group (non aromatic group) wherein at least one of the carbon atoms has been replaced by a heteroatom selected from nitrogen, oxygen and sulfur. Heterocycloalkyl groups can be unsubstituted or substituted by one or more substituents as defined below.

Examples of heterocycloalkyls include, but are not limited to, lactams, lactones, cyclic imides, cyclic thioimides, cyclic carbamates, 1-(1,2,5,6-tetrahydropyridyl), tetrahydrothiopyran, 4H-pyran, tetrahydropyran, piperidine (2-piperidinyl, 3-piperidinyl), 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, morpholine (4-morpholinyl, 3-morpholinyl, 2-morpholinyl) trioxane, hexahydro-1,3,5-triazine, tetrahydrothiophene, tetrahydrofuran (tetrahydrofuran-2-yl, tetrahydrofuran-3-yl), pyrroline, pyrrolidine, pyrrolidone, pyrrolidindione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

The term "halogen", as used herein, refers to fluorine, chlorine, bromine and iodine.

The term "aryl", as used herein, refers to a hydrocarbon consisting of an unsubstituted or substituted mono-, bi- or tricarbocyclic ring system, wherein the rings are fused together and at least one of the carbocyclic ring is aromatic. The term "aryl" means for example a cyclic aromatic such as a 6-membered hydrocarbon ring, a two six-membered fused hydrocarbon rings. Non-limiting examples of aryl groups are, for example, phenyl, alpha- or beta-naphthyl, 9,10-dihydroanthracenyl, indanyl, fluorenyl and the like. Aryl groups according to the present invention may be unsubstituted or substituted by one or more substituents as defined below.

The term "aromatic ring", as used herein, refers to a moiety wherein the constituent carbon atoms make up an unsaturated ring system, all atoms in the ring system are $sp^2$ hybridized and the total number of n-electrons is equal to 4n+2, wherein n is an integer.

The term "heteroaryl", as used herein, refers to an aryl as defined above wherein one to four carbon atoms are independently replaced by heteroatoms chosen from the group consisting of nitrogen, oxygen and sulphur. Non-limiting examples of heteroaryl groups are, for example, pyrrolyl, furyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl. Heteroaryl groups according to the present invention may be unsubstituted or substituted by one or more substituents as defined below.

Unless otherwise indicated, the term "substituted", as used herein, means that one or more hydrogen atoms of the above mentioned groups are replaced with another non-hydrogen atom or functional group referred to as substituent, provided that normal valencies are maintained and that the substitution results in a stable compound. Non-limiting example of substituents are, for example, OH, $C_{1-6}$alkyl, aryl, $C_{1-6}$alkylaryl, $C_{3-6}$cycloalkyl, O—$C_{1-6}$alkyl, O—$C_{3-6}$cycloalkyl, O-aryl, O—$C_{1-6}$alkylaryl, heteroaryl, heterocycloalkyl, O-heteroaryl, O-heterocycloalkyl, O—$C_{1-6}$alkylheterocycloalkyl, trifluoromethyl, difluoromethyl, trifluoromethoxy, difluoromethoxy, acyl, aroyl, heteroaroyl, halogen, nitro, cyano, COOR$^z$, alkylthio, arylthio, alkylsulfinyl, arylsulfinyl, alkylsulfonyl, arylsulfonyl, —O—C(=O)—NR$^h$R$^k$, —C(=O)—NR$^h$R$^k$, and —NR$^p$R$^q$, wherein each of R$^z$, R$^h$, and R$^k$, independently represents hydrogen, $C_{1-6}$alkyl, $C_{3-6}$cycloalkyl, aryl, $C_{1-6}$alkylaryl, heteroaryl, heterocycloalkyl, and R$^p$ and R$^q$ independently represents hydrogen, $C_{1-6}$alkyl, $C_{3-6}$cycloalkyl, aryl, $C_{1-6}$alkylaryl, heteroaryl, heterocycloalkyl, COR$^z$, COOR$^z$, —C(=O)—NR$^h$R$^k$, —S(=O) 2-R$^z$, and —S(=O)$_2$—NR$^h$R$^k$, and when R$^h$ and R$^k$, or R$^p$ and R$^q$ are taken together with the nitrogen atom to which they are bound, the group —NR$^h$R$^k$ or the group NR$^p$R$^q$ represent a heterocycloalkyl residue, and wherein the terms alkyl, cycloalkyl, aryl, heteroaryl, heterocyclyl are as above defined.

Preferred substituents are OH, $C_{1-6}$alkyl, O—$C_{1-6}$alkyl, trifluoromethyl, difluoromethyl, halogen, $C_{3-6}$cycloalkyl, O—$C_{3-6}$cycloalkyl, trifluoromethoxy, difluoromethoxy, cyano, O-aryl, O-heteroaryl, O—$C_{3-6}$cycloalkyl, O-heterocycloalkyl, $C_{1-6}$alkylaryl, $C_{1-6}$alkylheteroaryl, C(=O)—NR$^h$R$^k$, —NR$^p$R$^q$, and COOR$^z$ wherein each of R$^z$, R$^h$, and R$^k$, independently represents H, methyl, ethyl, propyl, butyl, i-propyl, t-butyl, —CH$_2$-phenyl and R$^p$ and R$^q$ are independently selected from H, methyl, ethyl, butyl, i-propyl, phenyl, COR$^z$, COOR$^z$, —C(=O)—NR$^h$R$^k$, and —S(=O)$_2$—R$^z$. More preferred substituents are selected from OH, methyl, methoxy, chlorine, fluorine, trifluoromethyl, trifluoromethoxy, cyano, C(=O)—NR$^h$R$^k$, —NR$^p$R$^q$ and COOR$^z$ wherein each of R$^z$, R$^h$, and R$^k$, independently represents H, methyl, ethyl and t-butyl, —CH$_2$-phenyl and R$^p$ and R$^q$ are independently selected from H, methyl, ethyl, butyl, i-propyl, phenyl, and acyl.

The term "pharmaceutically acceptable salts" refers to salts of the below identified compounds of Formula (I) that retain the desired biological activity and are accepted by regulatory authorities.

As used herein, the term "salt" refers to any salt of a compound according to the present invention prepared from an inorganic or organic acid or base and internally formed salts. Typically, such salts have a physiologically acceptable anion or cation.

Furthermore, the compounds of Formula (I) may form an acid addition salt or a salt with a base, depending on the kind of the substituents, and these salts are included in the present invention, as long as they are pharmaceutically acceptable salts.

Examples of such salts include, but are not restricted to acid addition salts formed with inorganic acids (e. g. hydrochloric acid, hydrobromic acid, sulfuric acid, phosphoric acid, nitric acid, and the like), salts formed with organic acids such as acetic acid, trifluoroacetic acid, oxalic acid, tartaric acid, succinic acid, malic acid, fumaric acid, maleic acid, ascorbic acid, benzoic acid, alginic acid, polyglutamic acid and naphthalene sulfonic acid.

The compounds of formula (I) containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Physiologically or pharmaceutically acceptable salts are particularly suitable for medical applications because of their greater aqueous solubility relative to the parent compound.

Pharmaceutically acceptable salts may also be prepared from other salts including other pharmaceutically acceptable salts of the compounds of Formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The compounds of Formula (I) may readily be isolated in association with solvent molecules by crystallization or evaporation of an appropriate solvent to give the corresponding solvates.

The compounds of Formula (I) may be in crystalline form. In certain embodiments, the crystalline forms of the compounds of Formula (I) are polymorphs.

The subject invention also includes isotopically-labelled compounds, which are identical to those recited in Formula (I) and following, but differ for the fact that one or more atoms are replaced by an atom having an atomic mass or mass number different from the atomic mass or mass number usually found in nature. Examples of isotopes that can be incorporated into the compounds of the invention and pharmaceutically acceptable salts thereof include isotopes of hydrogen, carbon, nitrogen, oxygen, sulfur, fluorine, and chlorine, such as $^{2}H$, $^{3}H$, $^{11}C$, $^{13}C$, $^{14}C$, $^{15}N$, $^{17}O$, $^{18}O$, $^{35}S$, $^{18}F$, $^{36}Cl$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^{3}H$, $^{14}C$ are incorporated, are useful in drug and/or substrate tissue distribution assays. Tritiated, i.e. $^{3}H$, and carbon-14, i.e. $^{14}C$, isotopes are particularly preferred for their ease of preparation and detectability. $^{11}C$ and $^{18}F$ isotopes are particularly useful in PET (Positron Emission Tomography). Furthermore, substitution with heavier isotopes such as deuterium, i.e. $^{2}H$, can afford certain therapeutic advantages resulting from greater metabolic stability, for example increased in vivo half-life or reduced dosage requirements and, hence, may be preferred in some circumstances. Isotopically-labelled compounds of Formula (I) and following of this invention can generally be prepared by carrying out the procedures disclosed in the Schemes and/or in the Examples below, by replacing a non-isotopically-labelled reagent with a readily available isotopically-labelled reagent.

Certain groups/substituents included in the present invention may be present as isomers or in one or more tautomeric forms. Accordingly, in certain embodiments, the compounds of Formula (I) may exist in the form of other tautomers or geometrical isomers in some cases, depending on the kinds of the substituents. In the present specification, the compounds may be described in only one form of such isomers, but the present invention includes all such isomers, isolated forms of the isomers, or a mixture thereof. Furthermore, the compounds of Formula (I) may have asymmetric carbon atoms or axial asymmetries in some cases and, correspondingly, they may exist in the form of optical isomers such as an (R)-form, an (S)-form, and the like. The present invention includes within the scope all such isomers, including racemates, enantiomers and mixtures thereof.

In particular, within the scope of the present invention are included all stereoisomeric forms, including enantiomers, diastereoisomers, and mixtures thereof, including racemates and the general reference to the compounds of Formula (I) includes all the stereoisomeric forms, unless otherwise indicated.

In general, the compounds or salts of the invention should be interpreted as excluding those compounds (if any) which are so chemically unstable, either per se or in water, that they are clearly unsuitable for pharmaceutical use through all administration routes, whether oral, parenteral, or otherwise. Such compounds are known to the skilled chemist.

According to a first aspect of the invention, compounds of Formula (I):

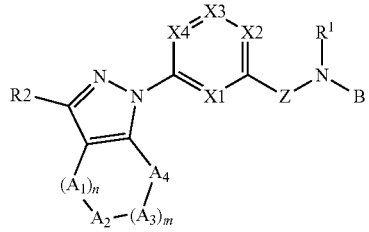

or pharmaceutically acceptable salts or solvates thereof are provided.

In the compounds of Formula (I):

$R_1$ is selected from the group consisting of $C_{1-6}$alkyl, $C_{3-6}$cycloalkyl, and hydroxy-$C_{1-6}$alkyl;

$Z$ is $C=O$ or $SO_2$;

$X_1$, $X_2$, $X_3$ and $X_4$ are independently selected from the group consisting of $CR^{vii}$ and N, with the proviso that the number of nitrogen atoms in the ring is comprised from 0 to 2;

$R_2$ is selected from the group consisting of hydrogen, $C_{1-6}$alkyl, halo$C_{1-6}$alkyl, $C_{3-6}$cycloalkyl, aryl, heteroaryl, $COR^{viii}$, $COOR^{viii}$, heterocycloalkyl, $CONHR^{viii}$, $CONR^{viii}R^{ix}$, OH, O—$C_{1-6}$alkyl, O—$C_{1-6}$alkylaryl, O—$C_{3-6}$cycloalkyl, O-heterocycloalkyl, O-heteroaryl, O-aryl, O-halo$C_{1-6}$alkyl, $C_{1-6}$alkyl-O—$C_{1-6}$alkyl, $C_{1-6}$alkyl-O—$C_{3-6}$cycloalkyl, $C_{1-6}$alkyl-O-heterocycloalkyl, $C_{1-6}$alkyl-O-aryl, $C_{1-6}$alkyl-O-heteroaryl, CN, $NO_2$, $NR^xR^{xi}$, $N(R^{ix})COR^x$, $N(R^{ix})COOR^{xi}$, $N(R^{ix})CONR^{xi}R^x$, $N(R^{ix})SO_2R^x$, $SO_2R^x$, $SO_2NR^{ix}R^x$, halogen, and hydroxy-$C_{1-6}$alkyl;

$A_1$, $A_2$, $A_3$, and $A_4$, are independently selected from the group consisting of $CR^{xii}R^{xiii}$, O, $NR^{xiv}$, CO and $SO_2$, wherein $R^{xii}$ and $R^{xiii}$ are independently selected from the group consisting of hydrogen, $C_{1-6}$alkyl, $C_{3-6}$cycloalkyl, heterocyloalkyl, halo$C_{1-6}$alkyl, $COR^{viii}$, $COOR^{viii}$, $CONHR^{viii}$, $CONR^{viii}R^{ix}$, OH, O—$C_{1-6}$alkyl, O-aryl, O—$C_{1-6}$alkylaryl, O-heteroaryl, O—$C_{3-6}$cycloalkyl, O-heterocycloalkyl, $C_{1-6}$alkylaryl, $C_{3-6}$cycloalkylaryl, $C_{3-6}$cycloalkylheteroaryl, $C_{3-6}$cycloheteroalkylaryl, $C_{3-6}$cycloheteroalkylheteroaryl, $C_{1-6}$alkylheteroaryl, S-aryl, S-heteroaryl, SO-aryl, SO-heteroaryl, $SO_2$-aryl, $SO_2$-heteroaryl, $C_{1-6}$alkyl-O—$C_{1-6}$alkyl, CN, halogen, $NR^xR^{xi}$, $N(R^{ix})COR^x$;

$R^{xiv}$ is selected from the group consisting of hydrogen, $C_{1-6}$alkyl, $C_{1-6}$alkylaryl, $C_{1-6}$alkyl-$C_{3-6}$cycloalkyl, $C_{1-6}$alkyl-heterocycloalkyl, $C_{3-6}$cycloalkyl, heterocycloalkyl, hydroxyl-$C_{1-6}$alkyl, $COR^{viii}$, $COOR^{viii}$, $CONHR^{viii}$, $CONR^{viii}R^{ix}$, $SO_2R^{viii}$, $C_{1-6}$alkyl-O—$C_{1-6}$alkyl, $C_{1-6}$alkyl-O-aryl, $C_{1-6}$alkyl-O-heteroaryl, $C_{1-6}$alkyl-O-heterocycloalkyl, $C_{1-6}$alkylCOOR^{viii}$;

or when each of $A_1$ and $A_3$, or $A_2$ and $A_4$, or $A_1$ and $A_4$ represents $CR^{xii}R^{xiii}$, the two groups $R^{xii}$ can be linked together to form a ring and thus the moiety

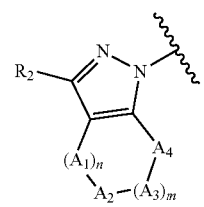

has a meaning selected from the group consisting of:
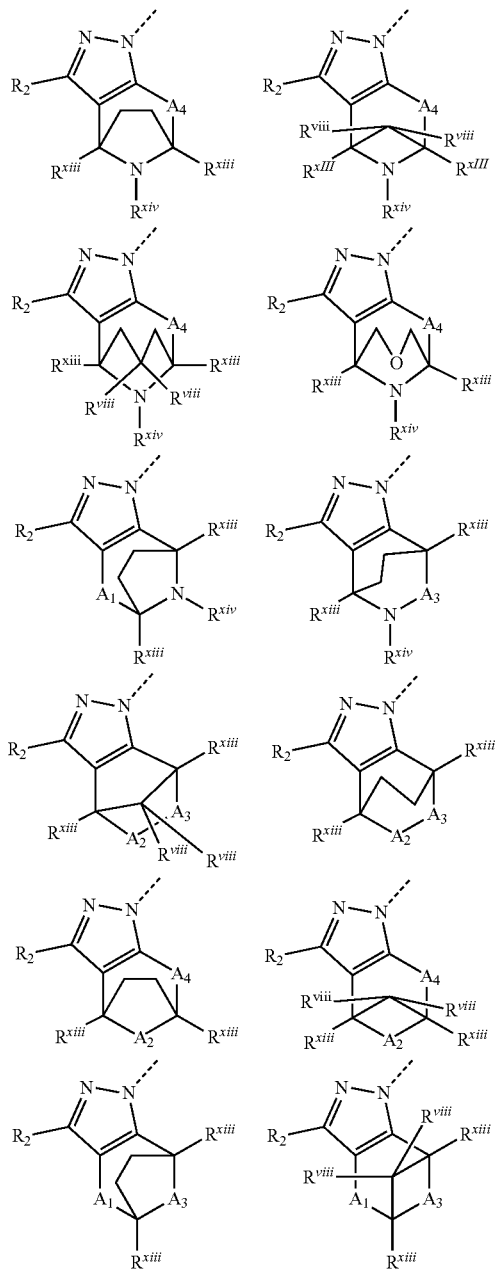
n and m are each independently selected from the group consisting of 0, 1, 2;
B represents an unsubstituted or a substituted aromatic or heteroaromatic ring selected from the group consisting of:
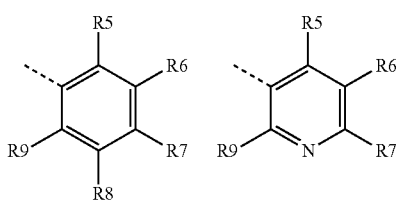
-continued
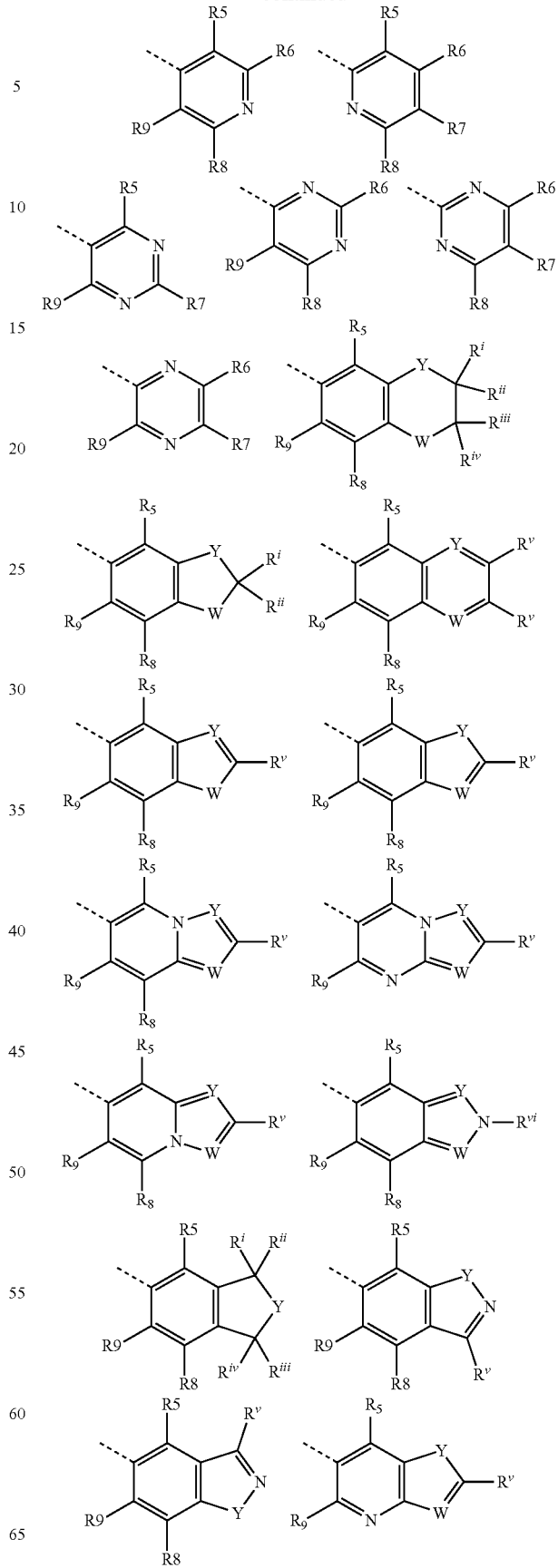

-continued

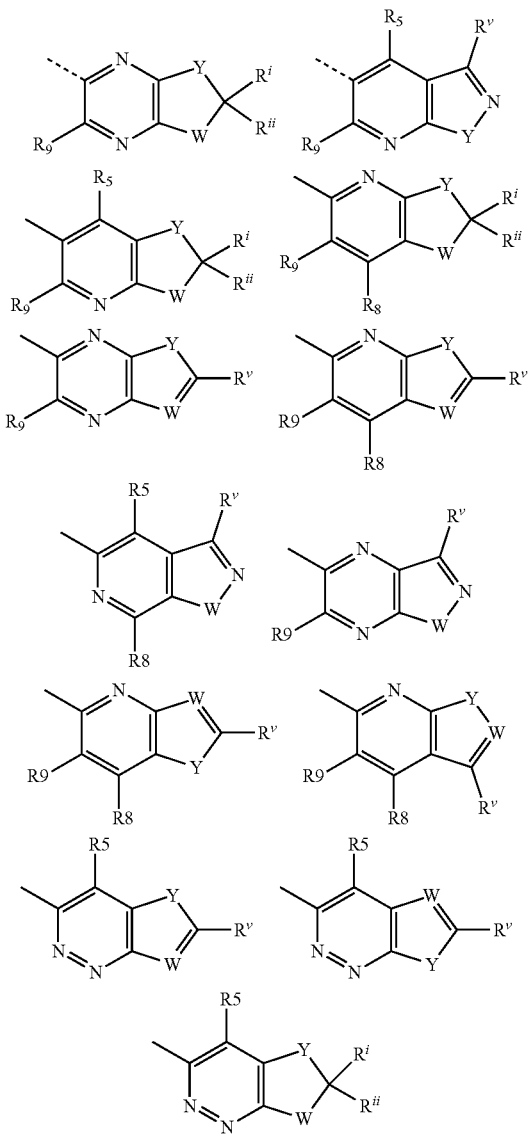

wherein $R_5$, $R_6$, $R_7$, $R_8$, and $R_9$ are independently selected from the group consisting of hydrogen, halogen, $C_{1-6}$alkyl, halo$C_{1-6}$alkyl, $C_{3-6}$cycloalkyl, O—$C_{1-6}$alkyl, O—$C_{3-6}$cycloalkyl, O-heterocycloalkyl, O-halo$C_{1-6}$alkyl, COR$^{viii}$, COOR$^{viii}$, CONHR$^{viii}$, CONR$^{viii}$R$^{ix}$, OH, CN, NR$^x$R$^{xi}$, N(R$^{ix}$)COR$^x$, N(R$^{ix}$)CONR$^x$R$^{xi}$ and hydroxy-$C_{1-6}$alkyl or when $R_6$ and $R_7$ are present on a 6-membered heteroaromatic ring, taken together with the carbon atoms to whom they are bound, they can form a saturated or unsaturated 5-membered or 6-membered carbocyclic ring or a 5-membered or 6-membered heterocycloalkyl containing from 1 to 3 heteroatoms selected from O, N, and S or a 5-membered or 6-membered heteroaryl ring containing from 1 to 3 heteroatoms selected from O, N, and S;

Y and W are independently selected from the group consisting of O, S, SO$_2$, CR$^{ii}$R$^v$, CR$^v$, N, and NR$^{vi}$;

R$^i$, R$^{ii}$, R$^{iii}$ and R$^{iv}$ are independently selected from the group consisting of hydrogen, $C_{1-6}$alkyl, halo$C_{1-6}$alkyl, halogen, OH, O—$C_{1-6}$alkyl and O-halo$C_{1-6}$alkyl or when R$^i$ and R$^{ii}$, or R$^{iii}$ and R$^{iv}$ are taken together with the carbon atoms to whom they are bound, they can represent C=O;

R$^v$ is selected from the group consisting of hydrogen, $C_{1-6}$alkyl, halo$C_{1-6}$alkyl, O—$C_{1-6}$alkyl, halogen, $C_{3-6}$cycloalkyl, OH and O-halo$C_{1-6}$alkyl;

R$^{vi}$ is selected from the group consisting of hydrogen and $C_{1-6}$alkyl;

R$^{vii}$ is selected from the group consisting of hydrogen, $C_{1-6}$alkyl, $C_{3-6}$cycloalkyl, halo$C_{1-6}$alkyl, O-halo$C_{1-6}$alkyl, COR$^{viii}$, COOR$^{viii}$, CONHR$^{viii}$, CONR$^{viii}$R$^{ix}$, OH, O—$C_{1-6}$alkyl, halogen, CN, NO$_2$, NR$^x$R$^{xi}$, N(R$^{ix}$)COR$^x$, N(R$^{ix}$) COOR$^{xi}$, N(R$^{ix}$)CONR$^x$R$^{xi}$, and N(R$^{ix}$)SO$_2$R$^x$;

R$^{viii}$ is selected from the group consisting of hydrogen, $C_{1-6}$alkyl, $C_{3-6}$cycloalkyl, aryl, heteroaryl, heterocycloalkyl, hydroxy-$C_{1-6}$alkyl and $C_{1-6}$alkyl-O—$C_{1-6}$alkyl;

R$^{ix}$ is selected from the group consisting of hydrogen, $C_{1-6}$alkyl, hydroxy-$C_{1-6}$alkyl, and $C_{1-6}$alkyl-O—$C_{1-6}$alkyl;

R$^x$ is selected from the group consisting of hydrogen, $C_{1-6}$alkyl, $C_{3-6}$cycloalkyl, heterocycloalkyl, aryl, heteroaryl, hydroxy-$C_{1-6}$alkyl, and $C_{1-6}$alkyl-O—$C_{1-6}$alkyl;

R$^{xi}$ is selected from the group consisting of hydrogen, $C_{1-6}$alkyl, hydroxy-$C_{1-6}$alkyl, $C_{1-6}$alkyl-O—$C_{1-6}$alkyl, aryl-$C_{1-6}$alkyl, heteroaryl-$C_{1-6}$alkyl, and heterocycloalkyl-$C_{1-6}$alkyl.

According to a first embodiment:

$R_1$ is selected from the group consisting of $C_{1-6}$alkyl and $C_{3-6}$cycloalkyl;

Z is C=O or SO$_2$;

$X_1$, $X_2$, $X_3$ and $X_4$ are independently selected from the group consisting of CR$^{vii}$ and N, with the proviso that the number of nitrogen atoms in the ring is comprised from 0 to 2;

$R_2$ is selected from the group consisting of hydrogen, $C_{1-6}$alkyl, halo$C_{1-6}$alkyl, $C_{3-6}$cycloalkyl, aryl, heteroaryl, COR$^{viii}$, COOR$^{viii}$, CONHR$^{viii}$, CONR$^{viii}$R$^{ix}$, O—$C_{1-6}$alkyl, O—$C_{1-6}$alkylaryl, O-heterocycloalkyl, O-aryl, O-halo$C_{1-6}$alkyl, $C_{1-6}$alkyl-O—$C_{1-6}$alkyl, $C_{1-6}$alkyl-O-aryl, CN, NR$^x$R$^{xi}$, halogen, and hydroxy-$C_{1-6}$alkyl;

$A_1$, $A_2$, $A_3$, and $A_4$, are independently selected from the group consisting of CR$^{xii}$R$^{xiii}$, O, NR$^{xiv}$, and CO, wherein R$^{xii}$ and R$^{xiii}$ are independently selected from the group consisting of hydrogen, $C_{1-6}$alkyl, halo$C_{1-6}$alkyl, COR$^{viii}$, COOR$^{viii}$, CONHR$^{viii}$, CONR$^{viii}$R$^{ix}$, OH, O—$C_{1-6}$alkyl, O-aryl, O—$C_{1-6}$alkylaryl, O-heteroaryl, O—$C_{3-6}$cycloalkyl, O-heterocycloalkyl, $C_{1-6}$alkylaryl, $C_{1-6}$alkylheteroaryl, NR$^x$R$^{xi}$, N(R$^{ix}$)COR$^x$, $C_{1-6}$alkyl-O—$C_{1-6}$alkyl, CN and halogen;

R$^{xiv}$ is selected from the group consisting of hydrogen, $C_{1-6}$alkyl, $C_{1-6}$alkylaryl, $C_{1-6}$alkyl-$C_{3-6}$cycloalkyl, $C_{1-6}$alkyl-heterocycloalkyl, $C_{3-6}$cycloalkyl, hydroxy-$C_{1-6}$alkyl, heterocycloalkyl, COR$^{viii}$, COOR$^{viii}$, CONHR$^{viii}$ and SO$_2$R$^{viii}$, $C_{1-6}$alkylCOOR$^{viii}$;

or when each of $A_1$ and $A_3$, or $A_2$ and $A_4$, or $A_1$ and $A_4$ represents CR$^{xii}$R$^{xiii}$, the two groups R$^{xii}$ can be linked together to form a ring and thus the moiety

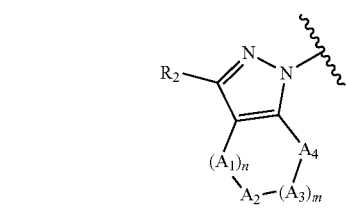
has a meaning selected from the group consisting of:
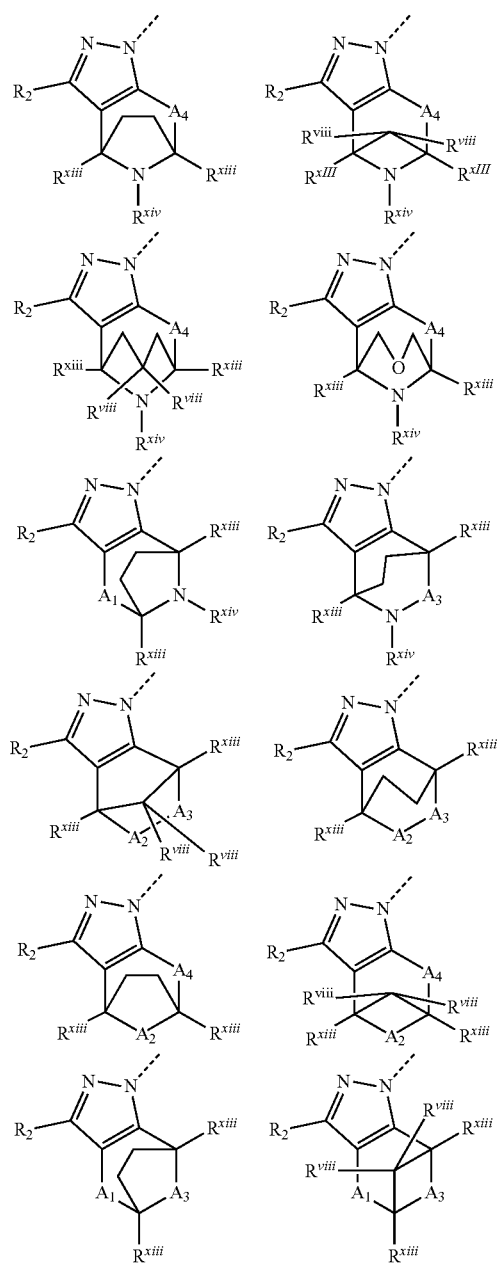
n and m are each independently selected from the group consisting of 0, 1, 2;
B represents an unsubstituted or a substituted aromatic or heteroaromatic ring selected from the group consisting of:
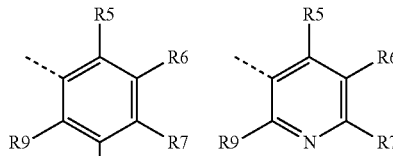
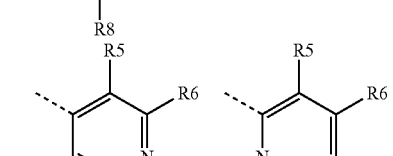
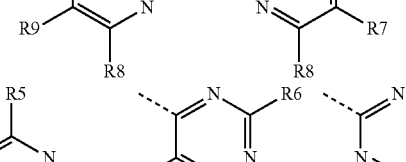
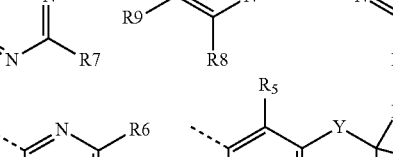
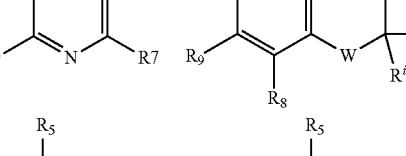
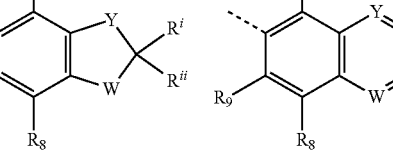
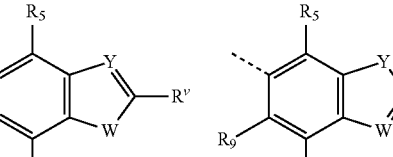
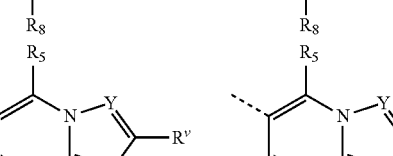
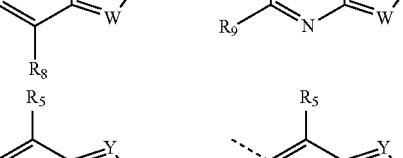
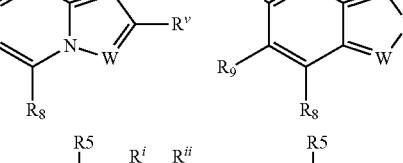
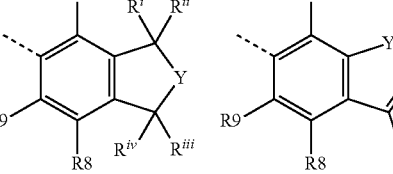

-continued

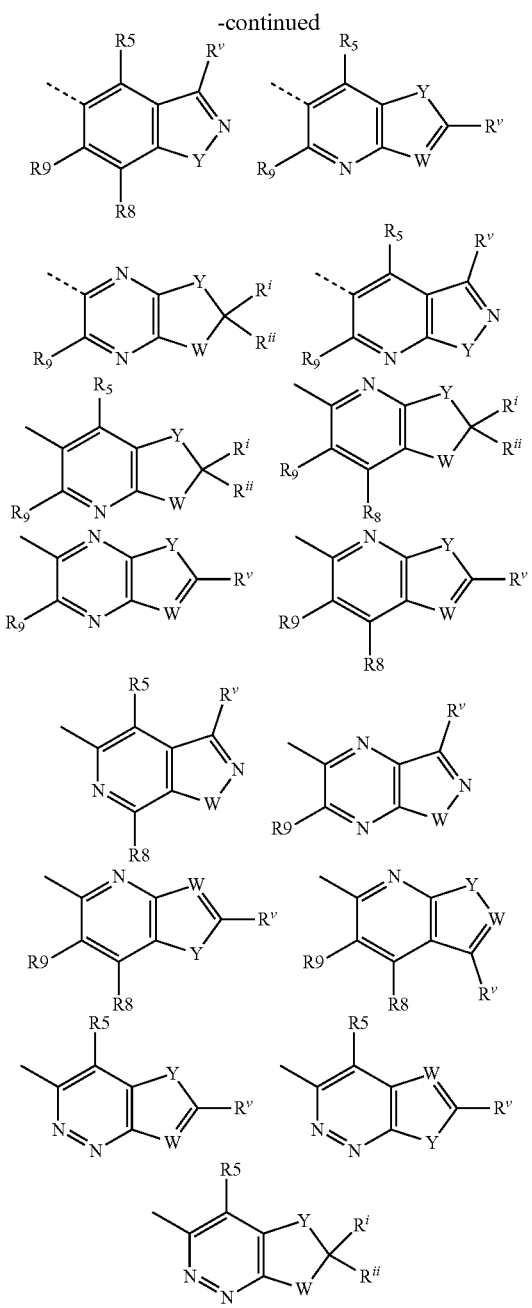

wherein $R_5$, $R_6$, $R_7$, $R_8$, and $R_9$ are independently selected from the group consisting of hydrogen, halogen, $C_{1-6}$alkyl, O—$C_{1-6}$alkyl, $COR^{viii}$, $COOR^{viii}$, OH, CN, $NR^xR^{xi}$ and hydroxy-$C_{1-6}$alkyl or when $R_6$ and $R_7$ are present on a 6-membered heteroaromatic ring, taken together with the carbon atoms to whom they are bound, they can form a saturated or unsaturated 5-membered or 6-membered carbocyclic ring or a 5-membered or 6-membered heterocycloalkyl containing from 1 to 3 heteroatoms selected from O, N, and S or a 5-membered or 6-membered heteroaryl ring containing from 1 to 3 heteroatoms selected from O, N, and S;

Y and W are independently selected from the group consisting of O, S, $CR^{iv}R^v$, $CR^v$, N, and $NR^{vi}$;

$R^i$, $R^{ii}$, $R^{iii}$ and $R^{iv}$ are independently selected from the group consisting of hydrogen, $C_{1-6}$alkyl, halogen, and O—$C_{1-6}$alkyl;

$R^v$ is selected from the group consisting of hydrogen, $C_{1-6}$alkyl, halo$C_{1-6}$alkyl, O—$C_{1-6}$alkyl, halogen and $C_{3-6}$cycloalkyl;

$R^{vi}$ is selected from the group consisting of hydrogen and $C_{1-6}$alkyl;

$R^{vii}$ is selected from the group consisting of hydrogen, $C_{1-6}$alkyl, halo$C_{1-6}$alkyl, $COOR^{viii}$, OH, O—$C_{1-6}$alkyl, O-aryl, halogen and $NR^xR^{xi}$;

$R^{viii}$ is selected from the group consisting of hydrogen, $C_{1-6}$alkyl, $C_{3-6}$cycloalkyl, aryl, heteroaryl, heterocycloalkyl, hydroxy$C_{1-6}$alkyl and $C_{1-6}$alkyl-O—$C_{1-6}$alkyl;

$R^{ix}$ is selected from the group consisting of hydrogen, $C_{1-6}$alkyl, and $C_{1-6}$alkyl-O—$C_{1-6}$alkyl;

$R^x$ is selected from the group consisting of hydrogen, $C_{1-6}$alkyl, $C_{3-6}$cycloalkyl, heterocycloalkyl, aryl, heteroaryl and hydroxy-$C_{1-6}$alkyl;

$R^{xi}$ is selected from the group consisting of hydrogen, $C_{1-6}$alkyl, $C_{1-6}$alkyl-O—$C_{1-6}$alkyl, aryl-$C_{1-6}$alkyl, heteroaryl-$C_{1-6}$alkyl, and heterocycloalkyl-$C_{1-6}$alkyl.

According to a second embodiment:

$R_1$ is selected from the group consisting of $C_{1-4}$alkyl;

Z is C=O $X_1$, $X_2$, $X_3$ and $X_4$ are $CR^{vii}$;

$R_2$ is selected from the group consisting of hydrogen, $C_{1-4}$alkyl, halo$C_{1-4}$alkyl, $COOR^{viii}$, $CONHR^{viii}$, CN, $NR^xR^{xi}$ and hydroxy-$C_{1-6}$alkyl;

$A_1$, $A_2$, $A_3$, and $A_4$, are independently selected from the group consisting of $CR^{xii}R^{xiii}$, O, and $NR^{xiv}$, wherein $R^{xii}$ and $R^{xiii}$ are independently selected from the group consisting of hydrogen, $C_{1-4}$alkyl, $COOR^{viii}$, $CONHR^{viii}$, O-aryl, O—$C_{1-6}$alkylaryl, O-heteroaryl, O—$C_{3-6}$cycloalkyl, O-heterocycloalkyl, $C_{1-6}$alkylaryl, $C_{1-6}$alkylheteroaryl, $NR^xR^{xi}$, $N(R^{ix})COR^x$, and CN;

$R^{xiv}$ is selected from the group consisting of hydrogen, $C_{1-4}$alkyl, $C_{3-6}$cycloalkyl, $COR^{viii}$, $COOR^{viii}$, $CONHR^{viii}$, $SO_2R^{viii}$, $C_{1-6}$alkyl$COOR^{viii}$;

or when each of $A_1$ and $A_3$, or $A_2$ and $A_4$, or $A_1$ and $A_4$ represents $CR^{xii}R^{xiii}$, the two groups $R^{xii}$ can be linked together to form a ring and thus the moiety

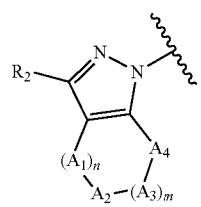

has a meaning selected from the group consisting of:

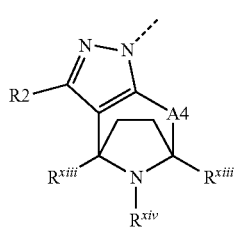 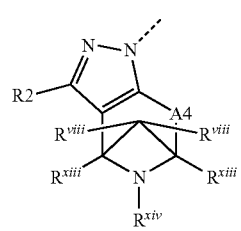

-continued
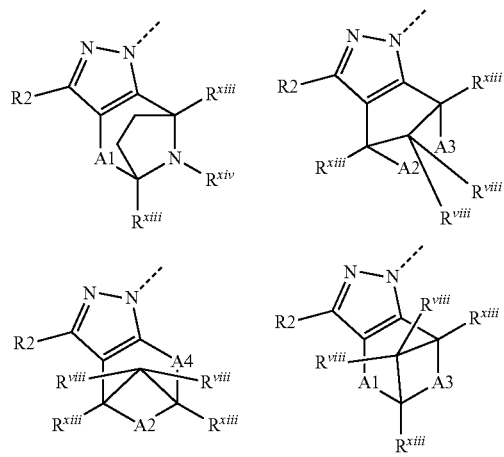
n and m are each independently selected from the group consisting of 0, 1, 2;
B represents an unsubstituted or a substituted aromatic or heteroaromatic ring selected from the group consisting of:
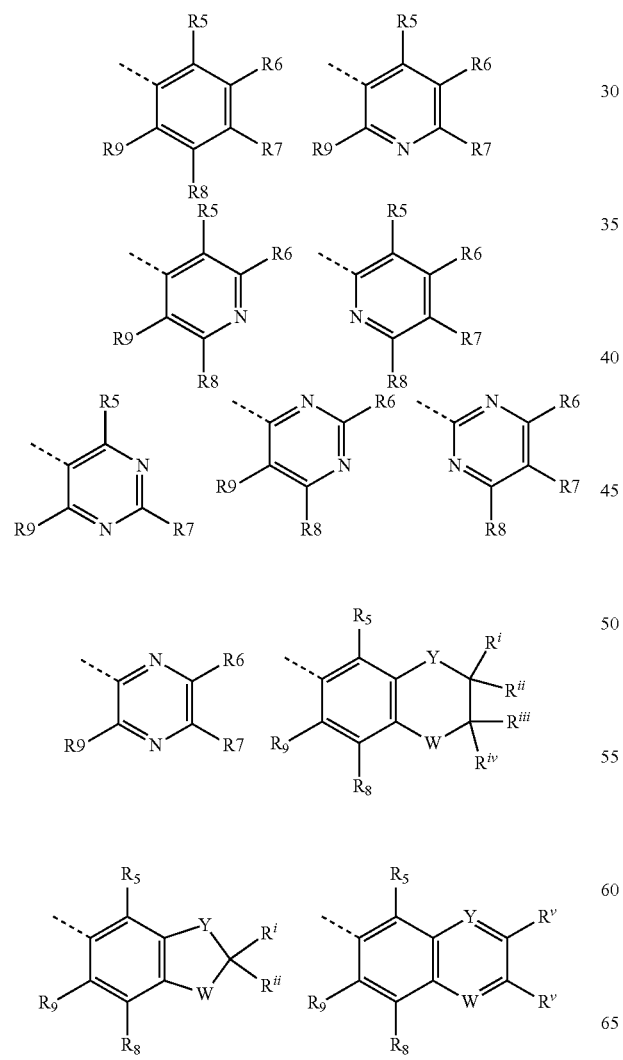
-continued
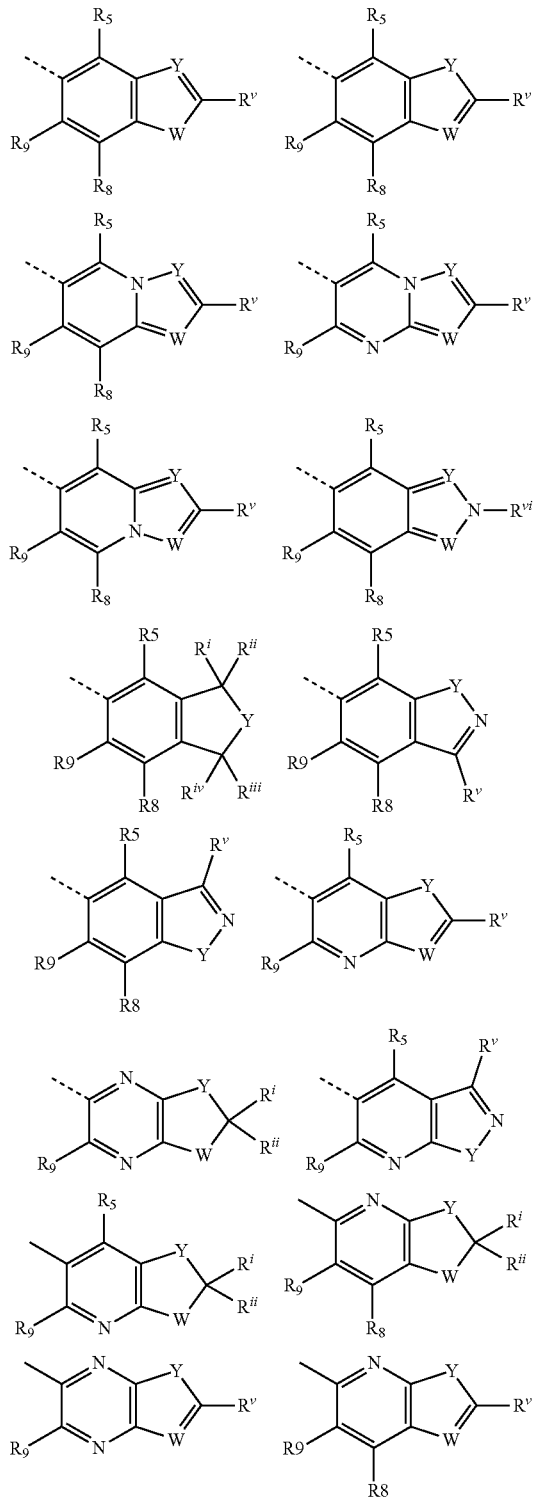
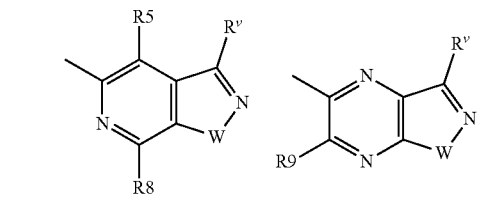

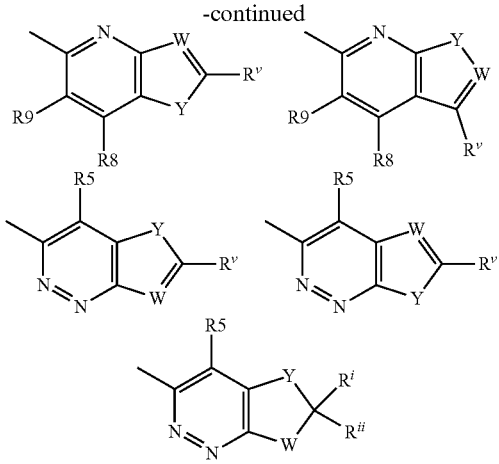

wherein $R_5$, $R_6$, $R_7$, $R_8$, and $R_9$ are independently selected from the group consisting of hydrogen, fluorine, chlorine, $C_{1-4}$alkyl O—$C_{1-4}$alkyl, $COR^{viii}$, $COOR^{viii}$, $CONHR^{viii}$, OH and $N(R^{ix})COR^x$ or when $R_6$ and $R_7$ are present on a 6-membered heteroaromatic ring, taken together with the carbon atoms to whom they are bound, they can form a saturated or unsaturated 5-membered or 6-membered carbocyclic ring or a 5-membered or 6-membered heterocycloalkyl containing from 1 to 3 heteroatoms selected from O, N, and S or a 5-membered or 6-membered heteroaryl ring containing from 1 to 3 heteroatoms selected from O, N, and S;

Y and W are independently selected from the group consisting of O, $CR^v$, N, and $NR^{vi}$;

$R^i$, $R^{ii}$, $R^{iii}$ and $R^{iv}$ are independently selected from the group consisting of hydrogen, fluorine, chlorine, and O—$C_{1-6}$alkyl;

$R^v$ is selected from the group consisting of hydrogen, $C_{1-4}$alkyl, and O—$C_{1-6}$alkyl;

$R^{vi}$ is selected from the group consisting of hydrogen and $C_{1-6}$alkyl;

$R^{vii}$ is hydrogen;

$R^{viii}$ is selected from the group consisting of hydrogen, $C_{1-4}$alkyl, $C_{3-6}$cycloalkyl, aryl, heterocycloalkyl, hydroxy-$C_{1-6}$alkyl and $C_{1-6}$alkyl-O—$C_{1-6}$alkyl;

$R^{ix}$ is hydrogen;

$R^x$ is selected from the group consisting of hydrogen and $C_{1-4}$alkyl;

$R^{xi}$ is selected from the group consisting of hydrogen, $C_{1-4}$alkyl, hydroxy-$C_{1-6}$alkyl, and $C_{1-4}$alkyl-O—$C_{1-4}$alkyl.

According to a third embodiment of the invention, the compounds of Formula (I) can be selected from the group consisting of:

| # | Substance Name |
|---|---|
| 1 | tert-butyl 1-[3-[1,3-benzodioxol-5-yl(methyl)carbamoyl]phenyl]-3-(trifluoromethyl)-6,7-dihydro-4H-pyrazolo[4,3-c]pyridine-5-carboxylate |
| 2 | N-(1,3-benzodioxol-5-yl)-N-methyl-3-[3-(trifluoromethyl)-4,5,6,7-tetrahydropyrazolo[4,3-c]pyridin-1-yl]benzamide hydrochloride |
| 3 | N-(1,3-benzodioxol-5-yl)-N-methyl-3-[5-methyl-3-(trifluoromethyl)-6,7-dihydro-4H-pyrazolo[4,3-c]pyridin-1-yl]benzamide |
| 4 | 3-[5-acetyl-3-(trifluoromethyl)-6,7-dihydro-4H-pyrazolo[4,3-c]pyridin-1-yl]-N-(1,3-benzodioxol-5-yl)-N-methyl-benzamide |
| 5 | N-(1,3-benzodioxol-5-yl)-N-methyl-3-[3-(trifluoromethyl)-4,5,6,7-tetrahydroindazol-1-yl]benzamide |
| 6 | N-(1,3-benzodioxol-5-yl)-N-methyl-3-[5-methylsulfonyl-3-(trifluoromethyl)-6,7-dihydro-4H-pyrazolo[4,3-c]pyridin-1-yl]benzamide |
| 7 | 3-[5-(benzenesulfonyl)-3-(trifluoromethyl)-6,7-dihydro-4H-pyrazolo[4,3-c]pyridin-1-yl]-N-(1,3-benzodioxol-5-yl)-N-methyl-benzamide |
| 8 | N-(1,3-benzodioxol-5-yl)-3-[5-benzoyl-3-(trifluoromethyl)-6,7-dihydro-4H-pyrazolo[4,3-c]pyridin-1-yl]-N-methyl-benzamide |
| 9 | methyl 1-[3-[1,3-benzodioxol-5-yl(methyl)carbamoyl]phenyl]-3-(trifluoromethyl)-6,7-dihydro-4H-pyrazolo[4,3-c]pyridine-5-carboxylate |
| 10 | 1-[3-[1,3-benzodioxol-5-yl(methyl)carbamoyl]phenyl]-N-phenyl-3-(trifluoromethyl)-6,7-dihydro-4H-pyrazolo[4,3-c]pyridine-5-carboxamide |
| 11 | N-(1,3-benzodioxol-5-yl)-3-[5-(2,2-dimethylpropanoyl)-3-(trifluoromethyl)-6,7-dihydro-4H-pyrazolo[4,3-c]pyridin-1-yl]-N-methyl-benzamide |
| 12 | N-(1,3-benzodioxol-5-yl)-3-[5-benzyl-3-(trifluoromethyl)-6,7-dihydro-4H-pyrazolo[4,3-c]pyridin-1-yl]-N-methyl-benzamide |
| 13 | N-(1,3-benzodioxol-5-yl)-3-[5-[[(4R)-2,2-dimethyl-1,3-dioxolan-4-yl]methyl]-3-(trifluoromethyl)-6,7-dihydro-4H-pyrazolo[4,3-c]pyridin-1-yl]-N-methyl-benzamide |
| 14 | N-(1,3-benzodioxol-5-yl)-3-[5-[[(4S)-2,2-dimethyl-1,3-dioxolan-4-yl]methyl]-3-(trifluoromethyl)-6,7-dihydro-4H-pyrazolo[4,3-c]pyridin-1-yl]-N-methyl-benzamide |
| 15 | N-(1,3-benzodioxol-5-yl)-3-[5-[(2R)-2,3-dihydroxypropyl]-3-(trifluoromethyl)-6,7-dihydro-4H-pyrazolo[4,3-c]pyridin-1-yl]-N-methyl-benzamide |
| 16 | N-(1,3-benzodioxol-5-yl)-3-[5-[(2S)-2,3-dihydroxypropyl]-3-(trifluoromethyl)-6,7-dihydro-4H-pyrazolo[4,3-c]pyridin-1-yl]-N-methyl-benzamide |
| 17 | N-(1,3-benzodioxol-5-yl)-N-methyl-3-[5-methyl-3-(trifluoromethyl)-6,7-dihydro-4H-pyrazolo[4,3-f][1,4]oxazepin-1-yl]benzamide |
| 18 | tert-butyl 1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate |
| 19 | N-(1,3-benzodioxol-5-yl)-3-[5-(cyclopropylmethyl)-3-(trifluoromethyl)-6,7-dihydro-4H-pyrazolo[4,3-c]pyridin-1-yl]-N-methyl-benzamide |
| 20 | methyl 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]methyl]benzoate |
| 21 | N-(1,3-benzodioxol-5-yl)-3-[5-isopropyl-3-(trifluoromethyl)-6,7-dihydro-4H-pyrazolo[4,3-c]pyridin-1-yl]-N-methyl-benzamide |
| 22 | N-(benzo[d][1,3]dioxol-5-yl)-N-methyl-3-(3-(trifluoromethyl)-5,6,7,8-tetrahydro-4,7-epiminocyclohepta[c]pyrazol-1(4H)-yl)benzamide hydrochloride |
| 23 | N-(benzo[d][1,3]dioxol-5-yl)-N-methyl-3-(9-methyl-3-(trifluoromethyl)-5,6,7,8-tetrahydro-4,7-epiminocyclohepta[c]pyrazol-1(4H)-yl)benzamide |
| 24 | N-(1,3-benzodioxol-5-yl)-N-methyl-3-[5-[rac-(1S)-1-methylpropyl]-3-(trifluoromethyl)-6,7-dihydro-4H-pyrazolo[4,3-c]pyridin-1-yl]benzamide |
| 25 | 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]methyl]benzoic acid |
| 26 | 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]methyl]benzoic acid |
| 27 | tert-butyl 1-[3-[1,3-benzodioxol-5-yl(methyl)carbamoyl]phenyl]-3-(trifluoromethyl)-5,7-dihydro-4H-pyrazolo[3,4-c]pyridine-6-carboxylate |
| 28 | tert-butyl 1-[3-[1,3-benzodioxol-5-yl(methyl)carbamoyl]phenyl]-3-(trifluoromethyl)-6,7-dihydro-5H-pyrazolo[4,3-b]pyridine-4-carboxylate |

| # | Substance Name |
|---|---|
| 29 | N-(1,3-benzodioxol-5-yl)-N-methyl-3-[6-methyl-3-(trifluoromethyl)-5,7-dihydro-4H-pyrazolo[3,4-c]pyridin-1-yl]benzamide |
| 30 | N-methyl-N-(2-methyl-1,3-benzoxazol-6-yl)-3-[3-(trifluoromethyl)-4,5,6,7-tetrahydropyrazolo[4,3-c]pyridin-1-yl]benzamide hydrochloride |
| 31 | N-(1,3-benzodioxol-5-yl)-N-methyl-3-[5-(2-methylpropanoyl)-3-(trifluoromethyl)-6,7-dihydro-4H-pyrazolo[4,3-c]pyridin-1-yl]benzamide |
| 32 | N-(1,3-benzodioxol-5-yl)-3-[5-cyclobutyl-3-(trifluoromethyl)-6,7-dihydro-4H-pyrazolo[4,3-c]pyridin-1-yl]-N-methyl-benzamide |
| 33 | N-(1,3-benzodioxol-5-yl)-N-methyl-3-[5-(3,3,3-trifluoro-2,2-dimethyl-propanoyl)-3-(trifluoromethyl)-6,7-dihydro-4H-pyrazolo[4,3-c]pyridin-1-yl]benzamide |
| 34 | N-(1,3-benzodioxol-5-yl)-3-[5-(1-hydroxycyclopropanecarbonyl)-3-(trifluoromethyl)-6,7-dihydro-4H-pyrazolo[4,3-c]pyridin-1-yl]-N-methyl-benzamide |
| 35 | N-(1,3-benzodioxol-5-yl)-N-methyl-3-[5-(2-methyl-2-phenyl-propanoyl)-3-(trifluoromethyl)-6,7-dihydro-4H-pyrazolo[4,3-c]pyridin-1-yl]benzamide |
| 36 | tert-butyl 1-[3-[(5-fluoro-2-methyl-1,3-benzoxazol-6-yl)-methyl-carbamoyl]phenyl]-3-(trifluoromethyl)-6,7-dihydro-4H-pyrazolo[4,3-c]pyridine-5-carboxylate |
| 38 | N-(1,3-benzodioxol-5-yl)-N-methyl-3-[3-(trifluoromethyl)-4,5,6,7-tetrahydropyrazolo[3,4-c]pyridin-1-yl]benzamide hydrochloride |
| 39 | tert-butyl 1-[3-[methyl-(2-methyl-1,3-benzoxazol-6-yl)carbamoyl]phenyl]-3-(trifluoromethyl)-6,7-dihydro-4H-pyrazolo[4,3-c]pyridine-5-carboxylate |
| 40 | N-methyl-N-(2-methyl-1,3-benzoxazol-6-yl)-3-[5-methyl-3-(trifluoromethyl)-6,7-dihydro-4H-pyrazolo[4,3-c]pyridin-1-yl]benzamide |
| 41 | N-(4-acetamido-3-hydroxy-phenyl)-N-methyl-3-[5-methyl-3-(trifluoromethyl)-6,7-dihydro-4H-pyrazolo[4,3-c]pyridin-1-yl]benzamide |
| 42 | methyl 4-[1-[3-[1,3-benzodioxol-5-yl(methyl)carbamoyl]phenyl]-3-(trifluoromethyl)-6,7-dihydro-4H-pyrazolo[4,3-c]pyridine-5-carbonyl]benzoate |
| 43 | methyl 3-[1-[3-[1,3-benzodioxol-5-yl(methyl)carbamoyl]phenyl]-3-(trifluoromethyl)-6,7-dihydro-4H-pyrazolo[4,3-c]pyridin-5-yl]-3-oxo-propanoate |
| 44 | 4-[1-[3-[1,3-benzodioxol-5-yl(methyl)carbamoyl]phenyl]-3-(trifluoromethyl)-6,7-dihydro-4H-pyrazolo[4,3-c]pyridine-5-carbonyl]benzoic acid |
| 45 | 3-[1-[3-[1,3-benzodioxol-5-yl(methyl)carbamoyl]phenyl]-3-(trifluoromethyl)-6,7-dihydro-4H-pyrazolo[4,3-c]pyridin-5-yl]-3-oxo-propanoic acid |
| 46 | N-(5-fluoro-2-methyl-1,3-benzoxazol-6-yl)-N-methyl-3-[5-methyl-3-(trifluoromethyl)-6,7-dihydro-4H-pyrazolo[4,3-c]pyridin-1-yl]benzamide |
| 48 | (4S,7R)- or (4R,7S)-N-(benzo[d][1,3]dioxol-5-yl)-N-methyl-3-(3-(trifluoromethyl)-5,6,7,8-tetrahydro-4,7-epiminocyclohepta[c]pyrazol-1(4H)-yl)benzamide |
| 49 | (4R,7S)- or (4S,7R)-N-(benzo[d][1,3]dioxol-5-yl)-N-methyl-3-(3-(trifluoromethyl)-5,6,7,8-tetrahydro-4,7-epiminocyclohepta[c]pyrazol-1(4H)-yl)benzamide |
| 50 | (4S,7R)- or (4R,7S)-N-(benzo[d][1,3]dioxol-5-yl)-N-methyl-3-(9-methyl-3-(trifluoromethyl)-5,6,7,8-tetrahydro-4,7-epiminocyclohepta[c]pyrazol-1(4H)-yl)benzamide |
| 51 | (4R,7S)- or (4S,7R)-N-(benzo[d][1,3]dioxol-5-yl)-N-methyl-3-(9-methyl-3-(trifluoromethyl)-5,6,7,8-tetrahydro-4,7-epiminocyclohepta[c]pyrazol-1(4H)-yl)benzamide |
| 52 | (4S,7R)- or (4R,7S)-tert-butyl-1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate |
| 53 | (4R,7S)- or (4S,7R)-tert-butyl-1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate |
| 54 | N-(1,3-benzodioxol-5-yl)-N-methyl-3-[3-(trifluoromethyl)-6,7-dihydro-4H-pyrano[4,3-c]pyrazol-1-yl]benzamide |
| 55 | methyl 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoate |
| 56 | 1-[3-[1,3-benzodioxol-5-yl(methyl)carbamoyl]phenyl]-N-methyl-3-(trifluoromethyl)-6,7-dihydro-4H-pyrazolo[4,3-c]pyridine-5-carboxamide |
| 57 | 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoic acid |
| 58 | N-(1,3-benzodioxol-5-yl)-3-[5-(2-hydroxy-2-methyl-propanoyl)-3-(trifluoromethyl)-6,7-dihydro-4H-pyrazolo[4,3-c]pyridin-1-yl]-N-methyl-benzamide |
| 59 | methyl 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoate |
| 60 | methyl 2-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoate |
| 61 | 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoic acid |
| 62 | 2-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoic acid |
| 63 | N-(1,3-benzodioxol-5-yl)-3-[5-(4-cyanophenyl)sulfonyl-3-(trifluoromethyl)-6,7-dihydro-4H-pyrazolo[4,3-c]pyridin-1-yl]-N-methyl-benzamide |
| 64 | N-(1,3-benzodioxol-5-yl)-3-[5-(1,2-dimethylimidazol-4-yl)sulfonyl-3-(trifluoromethyl)-6,7-dihydro-4H-pyrazolo[4,3-c]pyridin-1-yl]-N-methyl-benzamide |
| 65 | tert-butyl 1-[3-[1,3-benzodioxol-5-yl(methyl)sulfamoyl]phenyl]-3-(trifluoromethyl)-6,7-dihydro-4H-pyrazolo[4,3-c]pyridine-5-carboxylate |
| 66 | N-(1,3-benzodioxol-5-yl)-N-methyl-3-[3-(trifluoromethyl)-4,5,6,7-tetrahydropyrazolo[4,3-c]pyridin-1-yl]benzenesulfonamide; hydrochloride |
| 67 | N-(1,3-benzodioxol-5-yl)-3-[5-(3,5-dimethylisoxazol-4-yl)sulfonyl-3-(trifluoromethyl)-6,7-dihydro-4H-pyrazolo[4,3-c]pyridin-1-yl]-N-methyl-benzamide |
| 68 | N-(1,3-benzodioxol-5-yl)-3-[5-(2-methoxyethylsulfonyl)-3-(trifluoromethyl)-6,7-dihydro-4H-pyrazolo[4,3-c]pyridin-1-yl]-N-methyl-benzamide |
| 69 | N-(1,3-benzodioxol-5-yl)-3-[5-[(3,5-dimethyl-1H-pyrazol-4-yl)sulfonyl]-3-(trifluoromethyl)-6,7-dihydro-4H-pyrazolo[4,3-c]pyridin-1-yl]-N-methyl-benzamide |
| 70 | methyl 4-((1-(3-(benzo[d][1,3]dioxol-5-yl)(methyl)carbamoyl)phenyl)-3-(trifluoromethyl)-1,4,5,6,7,8-hexahydro-4,7-epiminocyclohepta[c]pyrazol-9-yl)sulfonyl)benzoate |
| 71 | N-(1,3-benzodioxol-5-yl)-N-methyl-3-[5-methyl-3-(trifluoromethyl)-6,7-dihydro-4H-pyrazolo[4,3-c]pyridin-1-yl]benzenesulfonamide |
| 72 | N-(1,3-benzodioxol-5-yl)-3-[6-(2,2-dimethylpropanoyl)-3-(trifluoromethyl)-5,7-dihydro-4H-pyrazolo[3,4-c]pyridin-1-yl]-N-methyl-benzamide |
| 73 | N-(1,3-benzodioxol-5-yl)-3-[5-(2,4-dimethylpyrazol-3-yl)-3-(trifluoromethyl)-6,7-dihydro-4H-pyrazolo[4,3-c]pyridin-1-yl]-N-methyl-benzamide |
| 74 | N-(1,3-benzodioxol-5-yl)-N-methyl-3-[3-(trifluoromethyl)-5-(1,3,5-trimethylpyrazol-4-yl)-6,7-dihydro-4H-pyrazolo[4,3-c]pyridin-1-yl]benzamide |
| 75 | methyl 4-[[1-[3-[1,3-benzodioxol-5-yl(methyl)carbamoyl]phenyl]-3-(trifluoromethyl)-5,7-dihydro-4H-pyrazolo[3,4-c]pyridin-6-yl]sulfonyl]benzoate |
| 76 | N-(1,3-benzodioxol-5-yl)-N-methyl-3-[5-tetrahydropyran-4-ylsulfonyl-3-(trifluoromethyl)-6,7-dihydro-4H-pyrazolo[4,3-c]pyridin-1-yl]benzamide |
| 77 | 4-[[1-[3-[1,3-benzodioxol-5-yl(methyl)carbamoyl]phenyl]-3-(trifluoromethyl)-5,7-dihydro-4H-pyrazolo[3,4-c]pyridin-6-yl]sulfonyl]benzoic acid |
| 82 | tert-butyl 3-[4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]-3,5-dimethyl-pyrazol-1-yl]propanoate |
| 85 | 3-[5-(2,2-dimethylpropanoyl)-3-(trifluoromethyl)-6,7-dihydro-4H-pyrazolo[4,3-c]pyridin-1-yl]-N-(6-methoxy-3-pyridyl)-N-methyl-benzamide |

| # | Substance Name |
|---|---|
| 86 | 3-[4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]-3,5-dimethyl-pyrazol-1-yl]propanoic acid |
| 87 | (4R,7S)- or (4S,7R)-N-(benzo[d][1,3]dioxol-5-yl)-N-methyl-3-[(9-pivaloyl-3-(trifluoromethyl)-5,6,7,8-tetrahydro-4,7-epiminocyclohepta[c]pyrazol-1(4H)-yl)]benzamide |
| 88 | (4S,7R)- or (4R,7S)-N-(benzo[d][1,3]dioxol-5-yl)-N-methyl-3-[(9-pivaloyl-3-(trifluoromethyl)-5,6,7,8-tetrahydro-4,7-epiminocyclohepta[c]pyrazol-1(4H)-yl)]benzamide |
| 89 | 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]-5-methyl-1H-pyrazole-3-carboxylic acid |
| 90 | 3-[5-(2,2-dimethylpropanoyl)-3-(trifluoromethyl)-6,7-dihydro-4H-pyrazolo[4,3-c]pyridin-1-yl]-N-(2-methoxy-4-pyridyl)-N-methyl-benzamide |
| 91 | 3-[5-(2,2-dimethylpropanoyl)-3-(trifluoromethyl)-6,7-dihydro-4H-pyrazolo[4,3-c]pyridin-1-yl]-N-methyl-N-(2-methylimidazo[1,2-a]pyridin-6-yl)benzamide |
| 92 | N-(2,2-difluoro-1,3-benzodioxol-5-yl)-N-methyl-3-[3-(trifluoromethyl)-4,5,6,7-tetrahydropyrazolo[4,3-c]pyridin-1-yl]benzamide |
| 93 | 3-[5-cyclobutyl-3-(trifluoromethyl)-6,7-dihydro-4H-pyrazolo[4,3-c]pyridin-1-yl]-N-(2,2-difluoro-1,3-benzodioxol-5-yl)-N-methyl-benzamide |
| 94 | N-(2,2-difluoro-1,3-benzodioxol-5-yl)-3-[5-(2,2-dimethylpropanoyl)-3-(trifluoromethyl)-6,7-dihydro-4H-pyrazolo[4,3-c]pyridin-1-yl]-N-methyl-benzamide |
| 95 | tert-butyl 1-(3-((2,2-difluorobenzo[d][1,3]dioxol-5-yl)(methyl)carbamoyl)phenyl)-3-(trifluoromethyl)-1,4,5,6,7,8-hexahydro-4,7-epiminocyclohepta[c]pyrazole-9-carboxylate |
| 96 | N-(2,2-difluoro-1,3-benzodioxol-5-yl)-3-[5-(3,5-dimethylisoxazol-4-yl)sulfonyl-3-(trifluoromethyl)-6,7-dihydro-4H-pyrazolo[4,3-c]pyridin-1-yl]-N-methyl-benzamide |
| 97 | methyl 4-((1-(3-((2,2-difluorobenzo[d][1,3]dioxol-5-yl)(methyl)carbamoyl)phenyl)-3-(trifluoromethyl)-1,4,5,6,7,8-hexahydro-4,7-epiminocyclohepta[c]pyrazol-9-yl)sulfonyl)benzoate yl)sulfonyl]benzoate |
| 98 | N-(2,2-difluorobenzo[d][1,3]dioxol-5-yl)-N-methyl-3-(9-pivaloyl-3-(trifluoromethyl)-5,6,7,8-tetrahydro-4,7-epiminocyclohepta[c]pyrazol-1(4H)-yl)benzamide benzamide |
| 99 | N-methyl-N-(2-methylbenzo[d]oxazol-6-yl)-3-(9-pivaloyl-3-(trifluoromethyl)-5,6,7,8-tetrahydro-4,7-epiminocyclohepta[c]pyrazol-1(4H)-yl)benzamide |
| 100 | 3-(9-((3,5-dimethylisoxazol-4-yl)sulfonyl)-3-(trifluoromethyl)-5,6,7,8-tetrahydro-4,7-epiminocyclohepta[c]pyrazol-1(4H)-yl)-N-methyl-N-(2-methylbenzo[d]oxazol-6-yl)benzamide |
| 101 | 3-(9-((3,5-dimethylisoxazol-4-yl)sulfonyl)-3-(trifluoromethyl)-5,6,7,8-tetrahydro-4,7-epiminocyclohepta[c]pyrazol-1(4H)-yl)-N-methyl-N-(2-methylpyrazolo[1,5-a]pyridin-5-yl)benzamide |
| 102 | N-(2,2-difluoro-1,3-benzodioxol-5-yl)-3-(3-isopropyl-4,5,6,7-tetrahydroindazol-1-yl)-N-methyl-benzamide |
| 103 | N-(2,2-difluoro-1,3-benzodioxol-5-yl)-N-methyl-3-(3-methyl-4,5,6,7-tetrahydroindazol-1-yl)benzamide |
| 104 | ethyl 1-[3-[(2,2-difluoro-1,3-benzodioxol-5-yl)-methylcarbamoyl]phenyl]-5-methyl-6,7-dihydro-4H-pyrazolo[4,3-c]pyridine-3-carboxylate |
| 105 | 3-(3-isopropyl-4,5,6,7-tetrahydroindazol-1-yl)-N-methyl-N-(2-methylpyrazolo[1,5-a]pyridin-5-yl)benzamide |
| 106 | N-(2,2-difluoro-1,3-benzodioxol-5-yl)-N-methyl-3-[7-(4-methylphenoxy)-3-(trifluoromethyl)-6,7-dihydro-4H-pyrano[4,3-c]pyrazol-1-yl]benzamide |
| 107 | N-methyl-N-(2-methyl-1,3-benzoxazol-6-yl)-3-[7-(4-methylphenoxy)-3-(trifluoromethyl)-6,7-dihydro-4H-pyrano[4,3-c]pyrazol-1-yl]benzamide |
| 108 | 4-[[1-[3-[(2,2-difluoro-1,3-benzodioxol-5-yl)-methylcarbamoyl]phenyl]-5-methyl-3-(trifluoromethyl)-6,7-dihydro-4H-pyrazolo[4,3-c]pyridin-7-yl]oxy]benzoic acid |
| 109 | 4-[[1-[3-[(2,2-difluoro-1,3-benzodioxol-5-yl)-methylcarbamoyl]phenyl]-3-(trifluoromethyl)-4,5,6,7-tetrahydroindazol-7-yl]oxy]benzoic acid |
| 110 | N-(1,3-benzodioxol-5-yl)-N-methyl-3-[4-methyl-3-(trifluoromethyl)-6,7-dihydro-5H-pyrazolo[4,3-b]pyridin-1-yl]benzamide |
| 111 | N-(2,2-difluoro-1,3-benzodioxol-5-yl)-3-[4-(2,2-dimethylpropanoyl)-3-(trifluoromethyl)-6,7-dihydro-5H-pyrazolo[4,3-b]pyridin-1-yl]-N-methyl-benzamide |
| 112 | N-(1,3-benzodioxol-5-yl)-N-methyl-3-[5-methyl-6-oxo-3-(trifluoromethyl)-4,7-dihydropyrazolo[4,3-c]pyridin-1-yl]benzamide |
| 113 | N-methyl-N-(2-methyl-1,3-benzoxazol-6-yl)-3-[5-methyl-6-oxo-3-(trifluoromethyl)-4,7-dihydropyrazolo[4,3-c]pyridin-1-yl]benzamide |
| 114 | 3-[5-(2,2-dimethylpropanoyl)-3-(trifluoromethyl)-6,7-dihydro-4H-pyrazolo[4,3-c]pyridin-1-yl]-N-methyl-N-(3-methyl-1H-pyrazolo[3,4-b]pyridin-5-yl)benzamide |
| 115 | 3-[5-(2,2-dimethylpropanoyl)-3-(trifluoromethyl)-6,7-dihydro-4H-pyrazolo[4,3-c]pyridin-1-yl]-N-(2-methoxypyrimidin-5-yl)-N-methyl-benzamide |
| 116 | N-(1,3-benzodioxol-5-yl)-N-methyl-3-[5-methyl-3-(trifluoromethyl)-4,6-dihydropyrrolo[3,4-c]pyrazol-1-yl]benzamide |
| 117 | N-(2,2-difluoro-1,3-benzodioxol-5-yl)-3-[5-(2,2-dimethylpropanoyl)-3-(trifluoromethyl)-4,6-dihydropyrrolo[3,4-c]pyrazol-1-yl]-N-methyl-benzamide |
| 118 | N-(1,3-benzodioxol-5-yl)-N-methyl-3-[6-methyl-3-(trifluoromethyl)-4,5,7,8-tetrahydropyrazolo[3,4-d]azepin-1-yl]benzamide |
| 119 | N-(2,2-difluoro-1,3-benzodioxol-5-yl)-3-[6-(2,2-dimethylpropanoyl)-3-(trifluoromethyl)-4,5,7,8-tetrahydropyrazolo[3,4-d]azepin-1-yl]-N-methyl-benzamide |
| 120 | N-(2,2-difluoro-1,3-benzodioxol-5-yl)-3-[5,7-dimethyl-3-(trifluoromethyl)-6,7-dihydro-4H-pyrazolo[4,3-c]pyridin-1-yl]-N-methyl-benzamide |
| 121 | 1-[3-[[(2,2-difluoro-1,3-benzodioxol-5-yl)-methylcarbamoyl]phenyl]-5-methyl-3-(trifluoromethyl)-6,7-dihydro-4H-pyrazolo[4,3-c]pyridine-7-carboxylic acid |
| 122 | 3-[7-cyano-5-methyl-3-(trifluoromethyl)-6,7-dihydro-4H-pyrazolo[4,3-c]pyridin-1-yl]-N-(2,2-difluoro-1,3-benzodioxol-5-yl)-N-methyl-benzamide |
| 123 | N-(2,2-difluoro-1,3-benzodioxol-5-yl)-N-methyl-3-[5,7,7-trimethyl-3-(trifluoromethyl)-4,6-dihydropyrazolo[4,3-c]pyridin-1-yl]benzamide |
| 124 | 1-[3-[[(2,2-difluoro-1,3-benzodioxol-5-yl)-methylcarbamoyl]phenyl]-5-methyl-3-(trifluoromethyl)-6,7-dihydro-4H-pyrazolo[4,3-c]pyridine-6-carboxylic acid |
| 125 | N-(2,2-difluoro-1,3-benzodioxol-5-yl)-3-[5,6-dimethyl-3-(trifluoromethyl)-6,7-dihydro-4H-pyrazolo[4,3-c]pyridin-1-yl]-N-methyl-benzamide |
| 126 | N-(2,2-difluoro-1,3-benzodioxol-5-yl)-3-[5-(2,2-dimethylpropanoyl)-3-(trifluoromethyl)-6,7-dihydro-4H-pyrazolo[4,3-c]pyridin-1-yl]-N-(trideuteromethyl)benzamide |
| 127 | 3-[5-(2,2-dimethylpropanoyl)-3-(trifluoromethyl)-6,7-dihydro-4H-pyrazolo[4,3-c]pyridin-1-yl]-N-(2-methyl-1,3-benzoxazol-6-yl)-N-(trideuteromethyl)benzamide |
| 128 | (4S,7R)- or (4R,7S)-N-(benzo[d][1,3]dioxol-5-yl)-3-(9-((3,5-dimethylisoxazol-4-yl)sulfonyl)-3-(trifluoromethyl)-5,6,7,8-tetrahydro-4,7-epiminocyclohepta[c]pyrazol-1(4H)-yl)-N-methylbenzamide |
| 129 | (4R,7S)- or (4S,7R)-N-(benzo[d][1,3]dioxol-5-yl)-3-(9-((3,5-dimethylisoxazol-4-yl)sulfonyl)-3-(trifluoromethyl)-5,6,7,8-tetrahydro-4,7-epiminocyclohepta[c]pyrazol-1(4H)-yl)-N-methylbenzamide |
| 130 | (4R,7S)- or (4S,7R)-N-(benzo[d][1,3]dioxol-5-yl)-3-(9-((3,5-dimethyl-1H-pyrazol-4-yl)sulfonyl)-3-(trifluoromethyl)-5,6,7,8-tetrahydro-4,7-epiminocyclohepta[c]pyrazol-1(4H)-yl)-N-methylbenzamide |
| 131 | (4R,7S)- or (4S,7R)-N-(benzo[d][1,3]dioxol-5-yl)-3-((4R,7S)-9-cyclobutyl-3-(trifluoromethyl)-5,6,7,8-tetrahydro-4,7-epiminocyclohepta[c]pyrazol-1(4H)-yl)-N-methylbenzamide |
| 132 | N-(1,3-benzodioxol-5-yl)-N-methyl-3-(3-methyl-4,5,6,7-tetrahydroindazol-1-yl)benzamide |
| 133 | N-(1,3-benzodioxol-5-yl)-3-(3-isopropyl-4,5,6,7-tetrahydroindazol-1-yl)-N-methyl-benzamide |

| # | Substance Name |
|---|---|
| 134 | ethyl 4-[1-[3-[1,3-benzodioxol-5-yl(methyl)carbamoyl]phenyl]-3-(trifluoromethyl)-6,7-dihydro-4H-pyrazolo[4,3-c]pyridin-5-yl]butanoate |
| 135 | 4-[1-[3-[1,3-benzodioxol-5-yl(methyl)carbamoyl]phenyl]-3-(trifluoromethyl)-6,7-dihydro-4H-pyrazolo[4,3-c]pyridin-5-yl]butanoic acid |
| 136 | tert-butyl 1-[3-[(2,2-difluoro-1,3-benzodioxol-5-yl)-methyl-carbamoyl]phenyl]-3-(trifluoromethyl)-6,7-dihydro-4H-pyrazolo[4,3-c]pyridine-5-carboxylate |
| 137 | 3-[5-(3,5-dimethylisoxazol-4-yl)sulfonyl-3-(trifluoromethyl)-6,7-dihydro-4H-pyrazolo[4,3-c]pyridin-1-yl]-N-methyl-N-(2-methyl-1,3-benzoxazol-6-yl)benzamide |
| 138 | 3-[5-(3,5-dimethylisoxazol-4-yl)sulfonyl-3-(trifluoromethyl)-6,7-dihydro-4H-pyrazolo[4,3-c]pyridin-1-yl]-N-(5-fluoro-2-methyl-1,3-benzoxazol-6-yl)-N-methyl-benzamide |
| 139 | benzyl 3-[1-[3-[1,3-benzodioxol-5-yl(methyl)carbamoyl]phenyl]-3-(trifluoromethyl)-6,7-dihydro-4H-pyrazolo[4,3-c]pyridin-5-yl]cyclobutanecarboxylate |
| 140 | 3-[1-[3-[1,3-benzodioxol-5-yl(methyl)carbamoyl]phenyl]-3-(trifluoromethyl)-6,7-dihydro-4H-pyrazolo[4,3-c]pyridin-5-yl]cyclobutanecarboxylic acid |
| 141 | 3-[5-(2,2-dimethylpropanoyl)-3-(trifluoromethyl)-6,7-dihydro-4H-pyrazolo[4,3-c]pyridin-1-yl]-N-methyl-N-quinoxalin-6-yl-benzamide |
| 142 | 3-[5-(2,2-dimethylpropanoyl)-3-(trifluoromethyl)-6,7-dihydro-4H-pyrazolo[4,3-c]pyridin-1-yl]-N-(2-methoxypyrimidin-5-yl)-N-methyl-benzamide |
| 143 | tert-butyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 144 | N-(2,2-difluoro-1,3-benzodioxol-5-yl)-N-methyl-3-[7-oxo-3-(trifluoromethyl)-5,6-dihydro-4H-indazol-1-yl]benzamide |
| 145 | N-(2,2-difluoro-1,3-benzodioxol-5-yl)-N-methyl-3-[7-oxo-3-(trifluoromethyl)-5,6-dihydro-4H-indazol-1-yl]benzamide |
| 146 | methyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-fluoro-benzoate |
| 147 | 2-fluoro-4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 148 | (R) or (S)-tert-butyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 149 | (S) or (R)-tert-butyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 150 | (R) or (S)-4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 151 | (S) or (R)-4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 152 | tert-butyl 4-[[1-[3-[(5-fluoro-2-methyl-1,3-benzoxazol-6-yl)-methyl-carbamoyl]phenyl]-3-(trifluoromethyl)-4,5,6,7-tetrahydroindazol-7-yl]oxy]benzoate |
| 153 | 4-[[1-[3-[(5-fluoro-2-methyl-1,3-benzoxazol-6-yl)-methyl-carbamoyl]phenyl]-3-(trifluoromethyl)-4,5,6,7-tetrahydroindazol-7-yl]oxy]benzoic acid |
| 154 | tert-butyl 4-[[1-[3-[(2,2-difluoro-1,3-benzodioxol-5-yl)-(trideuteriomethyl)carbamoyl]phenyl]-3-(trifluoromethyl)-4,5,6,7-tetrahydroindazol-7-yl]oxy]benzoate |
| 155 | 4-[[1-[3-[(2,2-difluoro-1,3-benzodioxol-5-yl)-(trideuteriomethyl)carbamoyl]phenyl]-3-(trifluoromethyl)-4,5,6,7-tetrahydroindazol-7-yl]oxy]benzoic acid |
| 156 | tert-butyl 4-[[1-[3-[methyl-(2-methyl-1,3-benzoxazol-6-yl)carbamoyl]phenyl]-3-(trifluoromethyl)-4,5,6,7-tetrahydroindazol-7-yl]oxy]benzoate |
| 157 | 4-[[1-[3-[methyl-(2-methyl-1,3-benzoxazol-6-yl)carbamoyl]phenyl]-3-(trifluoromethyl)-4,5,6,7-tetrahydroindazol-7-yl]oxy]benzoic acid |
| 158 | tert-butyl 4-[[1-[3-[methyl-(2-methyloxazolo[4,5-b]pyridin-6-yl)carbamoyl]phenyl]-3-(trifluoromethyl)-4,5,6,7-tetrahydroindazol-7-yl]oxy]benzoate |
| 159 | 4-[[1-[3-[methyl-(2-methyloxazolo[4,5-b]pyridin-6-yl)carbamoyl]phenyl]-3-(trifluoromethyl)-4,5,6,7-tetrahydroindazol-7-yl]oxy]benzoic acid |
| 160 | methyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-methoxy-benzoate |
| 161 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-methoxy-benzoic acid |
| 162 | 3-[7-(4-carbamoylphenoxy)-3-(trifluoromethyl)-4,5,6,7-tetrahydroindazol-1-yl]-N-(2,2-difluoro-1,3-benzodioxol-5-yl)-N-methyl-benzamide |
| 163 | methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylate |
| 164 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylic acid |
| 165 | tert-butyl 4-[[1-[3-[(5-methoxy-3-pyridyl)-methyl-carbamoyl]phenyl]-3-(trifluoromethyl)-4,5,6,7-tetrahydroindazol-7-yl]oxy]benzoate |
| 166 | 4-[[1-[3-[(5-methoxy-3-pyridyl)-methyl-carbamoyl]phenyl]-3-(trifluoromethyl)-4,5,6,7-tetrahydroindazol-7-yl]oxy]benzoic acid |
| 167 | tert-butyl 4-[[1-[3-[(2-methoxypyrimidin-5-yl)-methyl-carbamoyl]phenyl]-3-(trifluoromethyl)-4,5,6,7-tetrahydroindazol-7-yl]oxy]benzoate |
| 168 | 4-[[1-[3-[(2-methoxypyrimidin-5-yl)-methyl-carbamoyl]phenyl]-3-(trifluoromethyl)-4,5,6,7-tetrahydroindazol-7-yl]oxy]benzoic acid |
| 169 | ethyl 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 170 | 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 171 | tert-butyl 4-[[1-[3-[methyl-(2-methyl-[1,2,4]triazolo[1,5-a]pyridin-6-yl)carbamoyl]phenyl]-3-(trifluoromethyl)-4,5,6,7-tetrahydroindazol-7-yl]oxy]benzoate |
| 172 | 4-[[1-[3-[methyl-(2-methyl-[1,2,4]triazolo[1,5-a]pyridin-6-yl)carbamoyl]phenyl]-3-(trifluoromethyl)-4,5,6,7-tetrahydroindazol-7-yl]oxy]benzoic acid |
| 173 | tert-butyl 4-[[1-[3-[methyl-(2-methylpyrazolo[1,5-a]pyrimidin-6-yl)carbamoyl]phenyl]-3-(trifluoromethyl)-4,5,6,7-tetrahydroindazol-7-yl]oxy]benzoate |
| 174 | 4-[[1-[3-[methyl-(2-methylpyrazolo[1,5-a]pyrimidin-6-yl)carbamoyl]phenyl]-3-(trifluoromethyl)-4,5,6,7-tetrahydroindazol-7-yl]oxy]benzoic acid |
| 175 | methyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-methyl-benzoate |
| 176 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-methyl-benzoic acid |
| 177 | methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate |
| 178 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid |
| 179 | methyl 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate |
| 180 | 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid |
| 181 | methyl 2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylate |
| 182 | 2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylic acid |
| 183 | (S)- or (R)-methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylate |

| # | Substance Name |
|---|---|
| 184 | (R)- or (S)-methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylate |
| 185 | (R) or (S)-5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylic acid |
| 186 | (S) or (R)-5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylic acid |
| 187 | (S) or (R)-ethyl 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 188 | (S) or (R)-3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 189 | (R) or (S)-ethyl 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 190 | (R) or (S)-3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 191 | (S) or (R)-methyl 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate |
| 192 | (S) or (R)-6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid |
| 193 | (R) or (S)-methyl 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate |
| 194 | (R) or (S)-6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid |
| 195 | (S) or (R)-methyl 2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylate |
| 196 | (S) or (R)-2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylic acid |
| 197 | (R) or (S)-methyl 2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylate |
| 198 | (R) or (S)-2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylic acid |
| 199 | 3-[7-benzyloxy-3-(trifluoromethyl)-6,7-dihydro-4H-pyrano[4,3-c]pyrazol-1-yl]-N-(2,2-difluoro-1,3-benzodioxol-5-yl)-N-methyl-benzamide |
| 200 | N-(2,2-difluoro-1,3-benzodioxol-5-yl)-3-[7-hydroxy-3-(trifluoromethyl)-6,7-dihydro-4H-pyrano[4,3-c]pyrazol-1-yl]-N-methyl-benzamide |
| 201 | tert-butyl 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoate |
| 202 | 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoic acid |
| 203 | (R)- or (S)-tert-butyl 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoate |
| 204 | (S)- or (R)-tert-butyl 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoate |
| 205 | (R)- or (S)-4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoic acid |
| 206 | (S)- or (R)-4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoic acid |
| 207 | tert-butyl 4-[[1-[3-[(2,2-difluoro-1,3-benzodioxol-5-yl)-methyl-carbamoyl]phenyl]-3-(difluoromethyl)-4,5,6,7-tetrahydroindazol-7-yl]oxy]benzoate |
| 208 | 4-[[1-[3-[(2,2-difluoro-1,3-benzodioxol-5-yl)-methyl-carbamoyl]phenyl]-3-(difluoromethyl)-4,5,6,7-tetrahydroindazol-7-yl]oxy]benzoic acid |
| 209 | Methyl 5-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylate |
| 210 | 5-[[1-[3-[(2,2-Difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylic acid |
| 211 | Methyl 6-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylate |
| 212 | Methyl 1-[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]-6-oxo-pyridine-3-carboxylate |
| 213 | 6-[[1-[3-[(2,2-Difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylic acid |
| 214 | 1-[1-[3-[(2,2-Difluoro-1,3-benzodioxol-5-yl)-methyl-carbamoyl]phenyl]-3-(trifluoromethyl)-6,7-dihydro-4H-pyrano[4,3-c]pyrazol-7-yl]-6-oxo-pyridine-3-carboxylic acid |
| 215 | (S) or (R)-tert-Butyl 4-[[1-[3-[methyl-(2-methylpyrazolo[1,5-a] pyrimidin-6-yl)carbamoyl]phenyl]-3-(trifluoromethyl)-4,5,6,7-tetrahydroindazol-7-yl]oxy]benzoate |
| 216 | (R) or (S)-tert-Butyl 4-[[1-[3-[methyl-(2-methylpyrazolo[1,5-a] pyrimidin-6-yl)carbamoyl]phenyl]-3-(trifluoromethyl)-4,5,6,7-tetrahydroindazol-7-yl]oxy]benzoate |
| 217 | (S) or (R)-4-[[1-[3-[Methyl-(2-methylpyrazolo[1,5-a]pyrimidin-6-yl)carbamoyl]phenyl]-3-(trifluoromethyl)-4,5,6,7-tetrahydroindazol-7-yl]oxy]benzoic acid |
| 218 | (R) or (S)-4-[[1-[3-[Methyl-(2-methylpyrazolo[1,5-a]pyrimidin-6-yl)carbamoyl]phenyl]-3-(trifluoromethyl)-4,5,6,7-tetrahydroindazol-7-yl]oxy]benzoic acid |
| 219 | 4-[[1-[3-[[2-(difluoromethoxy)pyrimidin-5-yl]-methyl-carbamoyl]phenyl]-3-(trifluoromethyl)-4,5,6,7-tetrahydroindazol-7-yl]oxy]benzoic acid |
| 220 | 4-[[1-[3-[methyl-[2-(trifluoromethoxy)pyrimidin-5-yl]carbamoyl]phenyl]-3-(trifluoromethyl)-4,5,6,7-tetrahydroindazol-7-yl]oxy]benzoic acid |
| 221 | 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridazine-3-carboxylic acid |
| 222 | 4-[[1-[3-[(2,2-difluoro-3H-furo[3,2-b]pyridin-6-yl)-methyl-carbamoyl]phenyl]-3-(trifluoromethyl)-4,5,6,7-tetrahydroindazol-7-yl]oxy]benzoic acid |
| 223 | 4-[[1-[3-[methyl-[5-(trifluoromethoxy)-3-pyridyl]carbamoyl]phenyl]-3-(trifluoromethyl)-4,5,6,7-tetrahydroindazol-7-yl]oxy]benzoic acid |
| 224 | 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]cyclobutanecarboxylic acid |
| 225 | 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]bicyclo[1.1.1]pentane-1-carboxylic acid |
| 226 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]cyclohexanecarboxylic acid |
| 227 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]cyclohexanecarboxylic acid |
| 228 | 5-[[1-[3-[methyl-(2-methyl-1,3-benzoxazol-6-yl)carbamoyl]phenyl]-3-(trifluoromethyl)-6,7-dihydro-4H-pyrano[4,3-c]pyrazol-7-yl]oxy]pyridine-2-carboxylic acid |
| 229 | 5-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-2-carboxylic acid |
| 230 | 4-[[1-[3-[[2-(difluoromethoxy)pyrimidin-5-yl]-methyl-carbamoyl]phenyl]-3-(trifluoromethyl)-6,7-dihydro-4H-pyrano[4,3-c]pyrazol-7-yl]oxy]benzoic acid |

-continued

| # | Substance Name |
|---|---|
| 231 | 2-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-4-carboxylic acid |
| 232 | 6-[[1-[3-[methyl-(2-methyloxazolo[4,5-b]pyridin-6-yl)carbamoyl]phenyl]-3-(trifluoromethyl)-6,7-dihydro-4H-pyrano[4,3-c]pyrazol-7-yl]oxy]pyridine-3-carboxylic acid |
| 233 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]amino]benzoic acid |
| 234 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]amino]pyridine-2-carboxylic acid |
| 235 | 4-[methyl-[1-[3-[methyl-(2-methyl-1,3-benzoxazol-6-yl)carbamoyl]phenyl]-3-(trifluoromethyl)-4,5,6,7-tetrahydroindazol-7-yl]amino]benzoic acid |
| 236 | 4-[methyl-[1-[3-[methyl-(2-methyl-1,3-benzoxazol-6-yl)carbamoyl]phenyl]-3-(trifluoromethyl)-4,5,6,7-tetrahydroindazol-7-yl]amino]benzoic acid |
| 237 | 4-[[1-[6-[methyl(pyrazolo[1,5-a]pyrimidin-5-yl)carbamoyl]-2-pyridyl]-3-(trifluoromethyl)-4,5,6,7-tetrahydroindazol-7-yl]oxy]benzoic acid |
| 238 | 4-[[1-[3-[methyl-(2-methyloxazolo[4,5-b]pyridin-6-yl)carbamoyl]phenyl]-3-(trifluoromethyl)-5,6-dihydro-4H-cyclopenta[c]pyrazol-6-yl]oxy]benzoic acid |
| 239 | 4-[[1-[3-[methyl-(2-methylpyrazolo[1,5-a]pyrimidin-6-yl)carbamoyl]phenyl]-3-(trifluoromethyl)-5,6-dihydro-4H-cyclopenta[c]pyrazol-6-yl]oxy]benzoic acid |
| 240 | 4-[[1-[3-[(2,2-difluoro-1,3-benzodioxol-5-yl)-methyl-carbamoyl]phenyl]-3-(trifluoromethyl)-5,6-dihydro-4H-cyclopenta[c]pyrazol-6-yl]oxy]benzoic acid |
| 241 | 4-[[1-[3-[(2,2-difluoro-1,3-benzodioxol-5-yl)-methyl-carbamoyl]phenyl]-3-(trifluoromethoxy)-4,5,6,7-tetrahydroindazol-7-yl]oxy]benzoic acid |
| 242 | 4-[[1-[3-[(2,2-difluoro-1,3-benzodioxol-5-yl)-methyl-carbamoyl]phenyl]-3-(difluoromethoxy)-4,5,6,7-tetrahydroindazol-7-yl]oxy]benzoic acid |
| 243 | 4-[1-[1-[3-[(2,2-difluoro-1,3-benzodioxol-5-yl)-methyl-carbamoyl]phenyl]-3-(trifluoromethyl)-4,5,6,7-tetrahydroindazol-7-yl]-1-methyl-ethyl]benzoic acid |
| 244 | 4-[1-[1-[3-[(2,2-difluoro-1,3-benzodioxol-5-yl)-methyl-carbamoyl]phenyl]-3-(difluoromethyl)-4,5,6,7-tetrahydroindazol-7-yl]cyclopropyl]benzoic acid |
| 245 | 4-[[1-[3-[(2,2-difluoro-1,3-benzodioxol-5-yl)-methyl-carbamoyl]phenyl]-3-(difluoromethyl)-4,5,6,7-tetrahydroindazol-7-yl]sulfonyl]benzoic acid |
| 246 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]methyl]pyridine-2-carboxylic acid |
| 247 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]methyl]pyridine-2-carboxylic acid |
| 248 | 4-[[1-[3-[(2,2-difluoro-1,3-benzodioxol-5-yl)-methyl-carbamoyl]phenyl]-3-(trifluoromethyl)-5,7-dihydro-4H-pyrano[3,4-c]pyrazol-7-yl]methyl]benzoic acid |
| 249 | 4-[[1-[3-[(2,2-difluoro-1,3-benzodioxol-5-yl)-methyl-carbamoyl]phenyl]-3-(trifluoromethyl)-6,7-dihydro-5H-pyrano[3,2-c]pyrazol-7-yl]oxy]benzoic acid |
| 250 | 4-[[1-[3-[methyl-(2-methylimidazo[1,2-b]pyridazin-6-yl)carbamoyl]phenyl]-3-(trifluoromethyl)-4,5,6,7-tetrahydroindazol-7-yl]oxy]benzoic acid |
| 251 | 4-[[1-[3-[(6-methoxypyrazin-2-yl)-methyl-carbamoyl]phenyl]-3-(trifluoromethyl)-4,5,6,7-tetrahydroindazol-7-yl]oxy]benzoic acid |
| 252 | 4-[[1-[3-[(2-methoxypyrimidin-4-yl)-methyl-carbamoyl]phenyl]-3-(trifluoromethyl)-4,5,6,7-tetrahydroindazol-7-yl]oxy]benzoic acid |

According to a further embodiment of the invention $R^{viii}$ can be selected from the group consisting of hydrogen, optionally substituted $C_{1-6}$alkyl, optionally substituted $C_{3-6}$cycloalkyl, optionally substituted aryl, heteroaryl, optionally substituted heterocycloalkyl, hydroxy-$C_{1-6}$alkyl and $C_{1-6}$alkyl-O—$C_{1-6}$alkyl, wherein the substitution is selected from the group consisting of $C_{1-6}$alkyl, halo-$C_{1-6}$alkyl, COOH, COO—$C_{1-6}$alkyl, CN, OH, aryl, $C_{1-6}$alkyl-COOH, $C_{1-6}$alkyl-COO—$C_{1-6}$alkyl.

According to a further embodiment of the invention $R^{xiv}$ can be selected from the group consisting of hydrogen, $C_{1-6}$alkyl, optionally substituted $C_{1-6}$alkylaryl, $C_{1-6}$alkyl-$C_{3-6}$cycloalkyl, optionally substituted $C_{1-6}$alkyl-heterocycloalkyl, $C_{3-6}$cycloalkyl, optionally substituted heterocycloalkyl, hydroxyl-$C_{1-6}$alkyl, $COR^{viii}$, $COOR^{viii}$, $CONHR^{viii}$, $CONR^{viii}R^{ix}$, $SO_2R^{viii}$, $C_{1-6}$alkyl-O—$C_{1-6}$alkyl, $C_{1-6}$alkyl-O-aryl, $C_{1-6}$alkyl-O-heteroaryl, $C_{1-6}$alkyl-O-heterocycloalkyl wherein the substitution is selected from the group consisting of $C_{1-6}$alkyl and COOH.

The compounds exemplified in this invention may be prepared from readily available starting materials using the following general methods and procedures for example exemplified in Michael B. Smith—March's Advanced Organic Chemistry: reactions, mechanisms, and structure—7th Edition, John Wiley & Sons Inc., 2013.

It is well known to one of ordinary skill in the art that transformation of a chemical function into another may require that one or more reactive centers in the compound containing this function be protected in order to avoid undesired side reactions. Protection of such reactive centers, and subsequent de-protection at the end of the synthetic transformations, can be accomplished following standard procedures described, for instance, in Peter G. M. Wuts—Green's Protective Groups in Organic Synthesis, Fifth Edition, John Wiley & Sons Inc., 2014.

It will be appreciated that where typical or preferred experimental conditions (i.e. reaction temperatures, time, moles of reagents, solvents, etc.) are given, other experimental conditions can also be used unless otherwise stated. Optimum reaction conditions may vary with the particular reactants or solvents used, but such conditions can be determined by the person skilled in the art, using routine optimization procedures.

The synthesis of a compound of Formula (I), according to the synthetic processes described below, can be conducted in a stepwise manner, whereby each intermediate is isolated and purified by standard purification techniques such as, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

The compounds of Formula (I), prepared with the methods described herein below, may be treated or purified by conventional techniques or means for example by filtration, distillation, chromatography, recrystallization and combination thereof.

The salts of compounds of Formula (I) may be prepared by reacting a basic compound with the desired acid in solution, or by reacting an acidic compound with the desired base in solution.

A second aspect of the present invention is related to a pharmaceutical composition comprising a compound of Formula (I) as disclosed above and a pharmaceutically acceptable carrier, stabilizer, diluent or excipient thereof.

A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral administration (including subcutaneous and intravenous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing a compound of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, subcutaneous, intravenous, intramuscular, intranasal and pulmonary routes. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampoules or syringes of the liquid compositions or pills, tablets, capsules or the like in the case of solid compositions.

Liquid forms suitable for oral administration may include a suitable aqueous or non-aqueous vehicle with buffers, suspending and dispensing agents, colorants, flavours and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel or corn starch; a lubricant such as magnesium stearate; a glidant such as colloidal silicon dioxide; a sweetening agent such as sucrose or saccharin; or a flavouring agent such as peppermint, methyl salicylate, or orange flavouring.

Injectable compositions are typically based upon injectable sterile saline or phosphate-buffered saline or other injectable carriers known in the art.

The pharmaceutical compositions may be in the form of tablets, pills, capsules, solutions, suspensions, emulsion, powders, suppository and as sustained release formulations.

If desired, tablets may be coated by standard aqueous or non-aqueous techniques. In certain embodiments, such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that therapeutically active dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring agent such as cherry or orange flavor. To prevent breakdown during transit through the upper portion of the gastrointestinal tract, the composition be an enteric coated formulation.

Compositions for pulmonary administration include, but are not limited to, dry powder compositions consisting of the powder of a compound of Formula (I) or a salt thereof, and the powder of a suitable carrier and/or lubricant. The compositions for pulmonary administration can be inhaled from any suitable dry powder inhaler device known to a person skilled in the art.

Administration of the compositions is performed under a protocol and at a dosage sufficient to reduce the inflammation and pain in the subject. In some embodiments, in the pharmaceutical compositions of the present invention the active principle or active principles are generally formulated in dosage units. The dosage unit may contain from 0.1 to 1000 mg of a compound of Formula (I) per dosage unit for daily administration.

In some embodiments, the amounts effective for a specific formulation will depend on the severity of the disease, disorder or condition, previous therapy, the individual's health status and response to the drug. In some embodiments, the dose is in the range from 0.001% by weight to about 60% by weight of the formulation.

When used in combination with one or more other active ingredients, the compound of the present invention and the other active ingredient may be used in lower doses than when each is used singly.

Concerning formulations with respect to any variety of routes of administration, methods and formulations for the administration of drugs are disclosed in Remington's Pharmaceutical Sciences, 17th Edition, Gennaro et al. Eds., Mack Publishing Co., 1985, and Remington's Pharmaceutical Sciences, Gennaro A R ed. 20th Edition, 2000, Williams & Wilkins PA, USA, and Remington: The Science and Practice of Pharmacy, 21st Edition, Lippincott Williams & Wilkins Eds., 2005; and in Loyd V. Allen and Howard C. Ansel, Ansel's Pharmaceutical Dosage Forms and Drug Delivery Systems, 10th Edition, Lippincott Williams & Wilkins Eds., 2014.

The above described components for orally administered or injectable compositions are merely representative.

The compounds of this invention can also be administered in sustained release forms or from sustained release drug delivery systems.

A third aspect of the present invention is related to compounds of Formula (I) as disclosed above or the pharmaceutical composition thereof, for the use as a medicament.

In particular, compounds of Formula (I) as disclosed above included those wherein $R^1$ is hydrogen or the pharmaceutical composition thereof can be used to modulate CFTR protein or ABC protein activities.

Compounds of Formula (I) as disclosed above included those wherein R1 is hydrogen may also be effective for the treatment of patients with other protein misfolding diseases.

In this respect, other, structurally different CFTR correctors were found to rescue proteins (AVPR2, HCNH2, and ABCC8) with mutations causing trafficking defects (Sampson et al., *Orphanet J Rare Dis* 8:11, 2013). The compounds of formula (I) included those wherein R1 is hydrogen may be indicated in particular for ABC proteins that share with CFTR a similar structure, particularly at the level of nucleotide-binding domains (Rudashevskaya et al., *Drug Discov Today Technol* 12:e87-94, 2014). A list of ABC proteins with trafficking defects and associated diseases that could benefit from CFTR correctors includes: ABCA1 (Tangier disease), ABCA3 (fatal surfactant deficiency), ABCA4 (Stargardt disease), ABCB4 (progressive familial intrahepatic cholestasis type 3), ABCB11 (progressive familial intrahepatic cholestasis type 2), ABCC2 (Dubin-Johnson syndrome), ABCC8 (hyperinsulinemic hypoglycemia of infancy) and ABCG2 (gout).

According to an aspect of the present invention, compounds of Formula (I) as disclosed above included those wherein $R^1$ is hydrogen or the pharmaceutical composition thereof can be used in the treatment of a disease selected from the group consisting of cystic fibrosis, Tangier disease, fatal surfactant deficiency, Stargardt disease, progressive familial intrahepatic cholestasis type 3, progressive familial intrahepatic cholestasis type 2, Dubin-Johnson syndrome, hyperinsulinemic hypoglycemia of infancy and gout, preferably cystic fibrosis.

In the following, the present invention shall be illustrated by means of some examples, which are not construed to be viewed as limiting the scope of the invention.

The following abbreviations are hereinafter used in the accompanying examples: acetyl (Ac), Acetic acid (AcOH), aryl (Ar), Apparent triplet (app-t), Apparent doublet of triplet (app-dt), Apparent doublet (app-d), Apparent singlet (app-s), aqueous (aq), atmospheres (atm), benzyl (Bn), broad signal (bs), normal-butyl (nBu), normal-butyl lithium (nBuLi), tert-butyl (tBu), carbon nuclear magnetic resonance spectroscopy ($^{13}$C NMR), correlated spectroscopy (COSY), Cyclohexane (CyH), Deuterium (D), doublet (d), 1,8-diazabicyclo[5.4.0]undec-7-ene (DBU), dichloroethane (DCE), dichloromethane (DCM), doublet of doublet (dd), doublet of doublet of triplets (ddt), ethyldiisopropylamine (DIPEA), doublet of quartet (dq), N,N-dimethylformamide (DMF), dimethyl sulfoxide (DMSO), hexadeuterodimethyl sulfoxide (DMSO-d$_6$), doublet of triplet (dt), N-(3-dimethylaminopropyl)-N'-ethylcarbodiimide (EDC), half maximal effective concentration (EC50), equivalents (equiv. or eq.), enantiomeric excess (ee), electrospray ionization (ESI), ethyl (Et), diethyl ether (Et$_2$O), ethyl acetate (EtOAc or AcOEt), hour (h), proton nuclear magnetic resonance spectroscopy ($^1$H NMR), 1-[bis(dimethylamino)methylene]-1H-1,2,3-triazolo[4,5-b] pyridinium 3-oxid hexafluorophosphate (HATU), 1-hydroxybenzotriazole hydrate (HOBt), high performance liquid chromatography (HPLC), hertz (Hz), infrared spectroscopy (IR), half maximal inhibitory concentration (IC50), half maximal effective concentration (EC50), isopropyl alcohol (IPA), coupling constant (J), Potassium carbonate (K$_2$CO$_3$), liter (L), Lithium Hydroxide (LiOH), lithium diisopropylamide (LDA), molarity (M), multiplet (m), methyl (Me), acetonitrile (MeCN), methanol (MeOH), Methyl Iodide (MeI), milligram (mg), megahertz (MHz), minutes (min), milliliter (mL), millimole (mmol), melting point (mp), Mass Spectrometry (MS), molecular weight (mw), number of atoms or counterions (n), Sodium Hydride (NaH), Sodium bicarbonate (NaHCO$_3$), Sodium carbonate (Na$_2$CO$_3$), Sodium sulphate (Na$_2$SO$_4$), Sodium thiosulphate (Na$_2$S$_2$O$_3$), Sodium tert-butoxide (NaO$^t$Bu), Ammonium Chloride (NH$_4$Cl), not determined (nd), nanomolar (nM), Nuclear Magnetic Resonace (NMR), nuclear Overhauser enhancement (NOE), nuclear Overhauser enhancement spectroscopy (NOESY), nucleophile (Nu), protecting group (Pg), Phosphorous oxychoride (POCl$_3$), iso-propyl (i-Pr), Potassium tert-butoxide ($^t$BuOK), quartet (q), substituent (R), racemic (rac), room temperature (rt), singlet (s), strong cation exchange cartridge (SCX), temperature (T), triplet or time (t), retention time (t$_R$), triethylamine (TEA), trifluoroacetic acid (TFA), tetrahydrofuran (THF), thin-layer chromatography (TLC), sodium triacetoxyborohydride (Na(OAc)$_3$BH), Ultra Performance Liquid Chromatography-Mass Spectrometry (UPLC-MS), ultraviolet (UV), anionic ligand, halide, substituent, or number (X), optical rotation ([α]), chemical shift (δ), microliter (µL), Micromolar (µM), Watt (W).

Chemicals, Materials and Methods

Solvents and reagents were obtained from commercial suppliers and were used without further purification.

Automated column chromatography purifications were performed on Teledyne ISCO apparatus (CombiFlash® Rf) with pre-packed silica gel columns of different sizes (Redisep). Hydrogenation reactions were performed on H-Cube® continuous hydrogenation equipment (SS-reaction line version), employing disposable catalyst cartridges (CatCart®) preloaded with the required heterogeneous catalyst. NMR experiments were run on a Bruker Avance III 400 system (400.13 MHz for 1H, and 100.62 MHz for $^{13}$C), equipped with a BBI probe and Z-gradients and Bruker FT NMR Avance III 600 MHz spectrometer equipped with a 5 mm CryoProbe™ QCI $^1$H/$^{19}$F-$^{13}$C/15N-D quadruple resonance, a shielded z-gradient coil and the automatic sample changer SampleJet™ NMR system (600 MHz for $^1$H, 151 MHz for $^{13}$C and 565 MHz for $^{19}$F). Chemical shifts for $^1$H and $^{13}$C spectra were recorded in parts per million using the residual non-deuterated solvent as the internal standard (for CDCl$_3$: 7.26 ppm, 1H and 77.16 ppm, $^{13}$C; for DMSO-d$_6$: 2.50 ppm, 1H; 39.52 ppm, $^{13}$C, for D$_2$O: TSP as internal standard 0.00 ppm).

The analyses by UPLC/MS were run on a Waters ACQUITY UPLC/MS system consisting of a SQD (Single Quadrupole Detector) Mass Spectrometer equipped with an Electrospray Ionization interface and a Photodiode Array Detector. The PDA range was 210-400 nm. The analyses were performed on either an ACQUITY UPLC HSS T3 C$_{18}$ column (50×2.1 mmID, particle size 1.8 µm) with a VanGuard HSS T3 C$_{18}$ pre-column (5×2.1 mmID, particle size 1.8 µm) (Log D<1) or an ACQUITY UPLC BEH C$_{18}$ column (50×2.1 mmID, particle size 1.7 µm) with a VanGuard BEH C$_{18}$ pre-column (5×2.1 mmID, particle size 1.7 µm) (Log D>1).

The mobile phase was 10 mM NH$_4$OAc in H$_2$O at pH 5 adjusted with AcOH (A) and 10 mM NH$_4$OAc in MeCN—H$_2$O (95:5) at pH 5 (B).

Electrospray ionization in positive and negative mode was applied in the mass scan range 100-650 Da or 150-750 Da.

Analyses were performed either with "Polar method", "Generic method" and "Apolar Method" herein reported:

Polar method:
Column: Waters ACQUITY UPLC HSS T3 $C_{18}$, 1.8 μm, 50×2.1 mmID
Pre-column: VanGuard HSS T3 $C_{18}$, 1.8 μm, 5×2.1 mmID
Linear gradient: 0-0.2 min: 0% B, 0.2-2.7 min: 0-50% B, 2.7-2.8 min: 50-100% B, 2.8-3.0 min: 100% B
Flow rate: 0.5 mL/min Generic method:
Column: Waters ACQUITY UPLC BEH $C_{18}$, 1.7 μm, 50×2.1 mmID
Pre-column: VanGuard BEH $C_{18}$, 1.7 μm, 5×2.1 mmID
Linear gradient: 0-0.2 min: 5% B, 0.2-2.7 min: 5-95% B, 2.7-2.8 min: 95-100% B, 2.8-3.0 min: 100% B
Flow rate: 0.5 mL/min Apolar method:
Column: Waters ACQUITY UPLC BEH $C_{18}$, 1.7 μm, 50×2.1 mmID
Pre-column: VanGuard BEH $C_{18}$, 1.7 μm, 5×2.1 mmID
Gradient: 0-0.2 min: 50% B, 0.2-2.7 min: 50-100% B, 2.7-3.0 min: 100% B
Flow rate: 0.5 mL/min The chiral separations by HPLC were run on a Waters Alliance HPLC instrument consisting of an e2695 Separation Module and a 2998 Photodiode Array Detector.

The PDA range was 210-400 nm. The analyses were performed in isocratic mode on a Daicel ChiralCel OD-H column (250×4.6 mmID, particle size 5 μm) at 25° C.

With the aim of better illustrating the present invention, the syntheses of example compounds illustrated in the table 1 are provided.

PREPARATIONS AND EXAMPLES

General Protocol 1

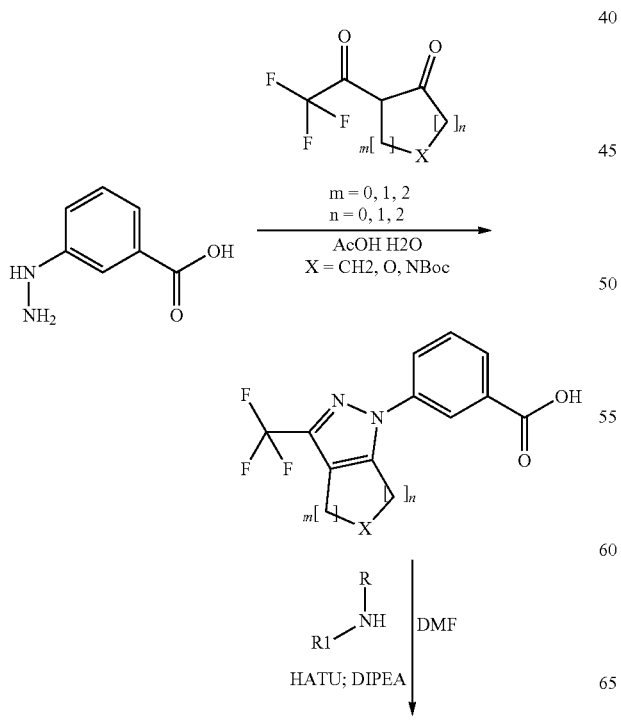

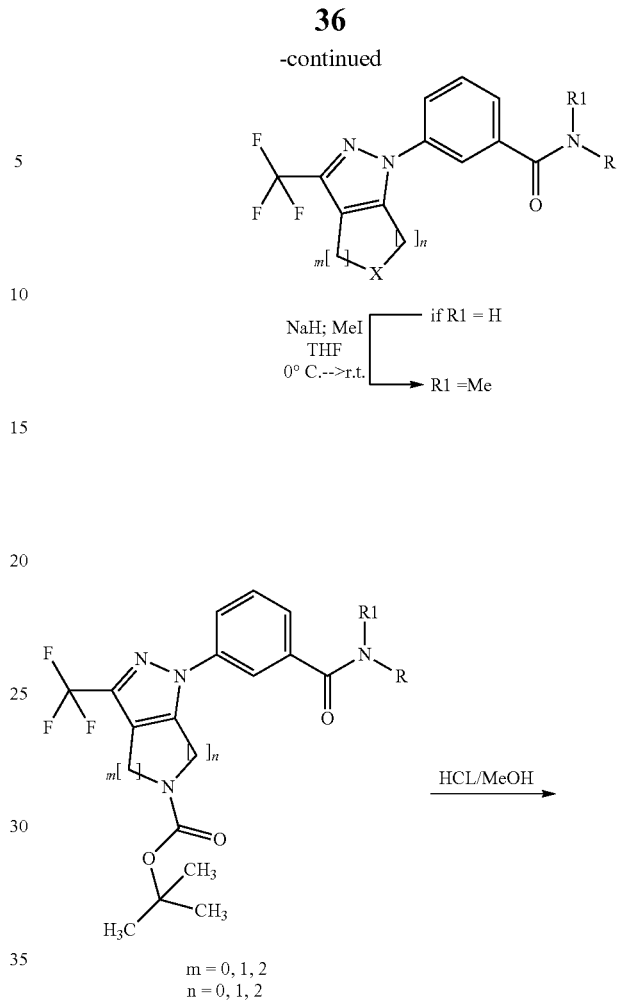

Example of General Protocol 1

General Procedure 1a

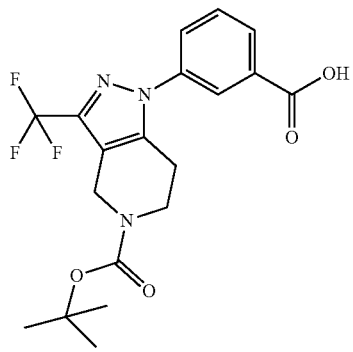 [SMILES: CC(C)(C)OC(=O)N1CCc2c(c(C(F)(F)F)nn2-c2cccc(C(=O)O)c2)C1]

[Int-1.1] 3-[5-Tert-butoxycarbonyl-3-(trifluoromethyl)-6,7-dihydro-4H-pyrazolo[4,3-c]pyridin-1-yl]benzoic acid To a solution of 3-hydrazinobenzoic acid (250.0 mg, 1.64 mmol) in AcOH (5 mL), tert-butyl 4-oxo-3-(2,2,2-trifluoroacetyl)piperidine-1-carboxylate (424.3 µL, 1.68 mmol) was added. Mixture was stirred for 18 h at room temperature. Water (20 mL) was added, with the formation of a precipitate. The title compound was obtained, after filtration of the precipitate, as a brown solid in 56% yield (553 mg): $^1$H NMR (400 MHz, DMSO-$d_6$) δ 13.35 (bs, 1H), 8.11 (app-t, J=1.9 Hz, 1H), 8.03 (app-dt, J=7.8, 1.3 Hz, 1H), 7.90 (app-d, J=8.0 Hz, 1H), 7.69 (app-t, J=7.9 Hz, 1H), 4.52 (s, 2H), 3.64 (t, J=5.7 Hz, 2H), 2.90 (t, J=5.7 Hz, 2H), 1.45 (s, 9H). UPLC-MS: $t_R$=1.92 min (Generic method); MS (ESI) m/z calcd for $C_{19}H_{21}F_3N_3O_4$ (M+H)$^+$: 412.1, found: 412.2.

General Procedure 1b

Tert-butyl 1-[3-[1,3-benzodioxol-5-yl(methyl)carbamoyl]phenyl]-3-(trifluoromethyl)-6,7-dihydro-4H-pyrazolo[4,3-c]pyridine-5-carboxylate To a solution of [Int-1.1] (553 mg, 1.34 mmol) in DMF (4 mL), N-methyl-1,3-benzodioxol-5-amine hydrochloride (277.4 mg, 1.48 mmol), HATU (562.2 mg, 1.48 mmol) and DIPEA (515.3 µL, 2.96 mmol) were added. Mixture was stirred at room temperature for 6 h and diluted with Et$_2$O (40 mL). Organic layer was washed with sat. aq. NH$_4$Cl (3×10 mL), water (20 mL) and brine (20 mL). Organic layer was dried with Na$_2$SO$_4$, filtered and solvent evaporated. The title compound was obtained, after purification by silica gel flash-column chromatography with Cyclohexane/EtOAc (70/30) as the eluent, as a yellow solid in 74% yield (540 mg): $^1$H NMR (400 MHz, DMSO-$d_6$) δ 7.56-7.49 (m, 2H), 7.46 (app-d, J=7.6 Hz, 1H), 7.42 (app-t, J=7.3 Hz, 1H), 6.99 (d, J=2.1 Hz, 1H), 6.76 (d, J=8.2 Hz, 1H), 6.64 (dd, J=8.2, 2.1 Hz, 1H), 6.00 (s, 2H), 4.48 (s, 2H), 3.59 (t, J=5.6 Hz, 2H), 3.33 (s, 3H), 2.63-2.51 (m, 2H), 1.45 (s, 9H). UPLC-MS: $t_R$=2.65 min (Generic method); MS (ESI) m/z calcd for $C_{27}H_{28}F_3N_4O_5$ (M+H)$^+$: 545.2, found: 545.3.

General Procedure 1c

N-(1,3-Benzodioxol-5-yl)-N-methyl-3-[3-(trifluoromethyl)-4,5,6,7-tetrahydropyrazolo[4,3-c]pyridin-1-yl]benzamide hydrochloride Compound [001] (269.0 mg, 0.49 mmol) was dissolved in a HCl solution in MeOH (3M, 5 mL). Mixture was stirred for 5 h at room temperature and solvent was evaporated. The title compound was obtained, after trituration with Et$_2$O, as a pale yellow solid in 94% yield (223 mg): $^1$H NMR (400 MHz, DMSO-$d_6$) δ 9.67 (s, 2H), 7.57-7.50 (m, 2H), 7.47 (app-t, J=8.0 Hz, 1H), 7.40 (app-d, J=7.5 Hz, 1H), 6.98 (d, J=2.1 Hz, 1H), 6.79 (d, J=8.2 Hz, 1H), 6.68 (dd, J=8.2, 2.1 Hz, 1H), 5.99 (s, 2H), 4.29 (s, 2H), 3.38 (t, J=6.0 Hz, 2H), 3.33 (s, 3H), 2.92 (t, J=6.0 Hz, 2H). UPLC-MS: $t_R$=1.75 min (Generic method); MS (ESI) m/z calcd for $C_{22}H_{20}F_3N_4O_3$ (M+H)$^+$: 445.1, found: 445.2.

General Procedure 1d

N-(1,3-Benzodioxol-5-yl)-N-methyl-3-[5-methyl-3-(trifluoromethyl)-6,7-dihydro-4H-pyrazolo[4,3-c]pyridin-1-yl]benzamide To a solution of compound [002] (80 mg, 0.17 mmol) in DCE (5 mL), formaldehyde (30% solution in water, 50 µL, 0.25 mmol), and sodium triacetoxyborohydride (70.5 mg, 0.33 mmol) were added. Mixture was stirred for 18 h and quenched with sat. aq. NH$_4$Cl (5 mL). Aqueous layer was washed with EtOAc (3×15 mL). Collected organic layers were washed with water (20 mL) and Brine (20 mL) dried with Na$_2$SO$_4$, filtered and solvent evaporated. The title compound was obtained, after purification with silica gel flash-column chromatography with DCM/MeOH (95/5) as the eluent, as a white solid in 55% yield (43 mg): $^1$H NMR (400 MHz, DMSO-$d_6$) δ 7.57-7.52 (m, 1H), 7.50 (s, 1H), 7.45 (app-t, J=7.7 Hz, 1H), 7.40 (app-d, J=7.7 Hz, 1H), 6.98 (d, J=2.1 Hz, 1H), 6.78 (d, J=8.2 Hz, 1H), 6.66 (dd, J=8.2, 2.1 Hz, 1H), 5.99 (s, 2H), 3.46 (s, 2H), 3.33 (s, 3H), 2.66-2.55 (m, 4H), 2.41 (s, 3H). UPLC-MS: $t_R$=2.05 min (Generic method); MS (ESI) m/z calcd for $C_{23}H_{22}F_3N_4O_3$ (M+H)$^+$: 459.2, found: 459.2.

General Procedure 1e

N-(1,3-Benzodioxol-5-yl)-N-methyl-3-[5-methylsulfonyl-3-(trifluoromethyl)-6,7-dihydro-4H-pyrazolo[4,3-c]pyridin-1-yl]benzamide To a solution of compound [002] (50 mg, 0.10 mmol) in DCM (3 mL), DIPEA (39.8 µL, 0.23 mmol) was added and mixture cooled to 0° C. (ice-bath). Methanesulfonyl chloride (8.9 µL, 0.11 mmol) was added and mixture stirred at room temperature for 2 h. Sat. aq. NH$_4$Cl (5 mL) was added and aqueous layer was extracted with EtOAc (3×15 mL). Collected organic layers were washed with water (20 mL) and Brine (20 mL) dried with Na$_2$SO$_4$, filtered and solvent evaporated. The title compound was obtained, after purification silica gel flash-column chromatography with Cyclohexane/EtOAc (70/30) as the eluent, as a white solid in 78% yield (41 mg): $^1$H NMR (400 MHz, DMSO-$d_6$) δ 7.58-7.50 (m, 1H), 7.47 (app-d, J=7.6 Hz, 1H), 7.43 (app-t, J=7.4 Hz, 1H), 7.00 (d, J=2.1 Hz, 1H), 6.76 (d, J=8.2 Hz, 1H), 6.64 (dd, J=8.2, 2.1 Hz, 1H), 6.00 (s, 2H), 4.38 (s, 2H), 3.48 (t, J=5.7 Hz, 2H), 3.33 (s, 3H), 3.03 (s, 3H), 2.72 (t, J=5.7 Hz, 2H). UPLC-MS: $t_R$=2.18 min (Generic method); MS (ESI) m/z calcd for $C_{23}H_{22}F_3N_4O_5S$ (M+H)$^+$: 523.1, found: 523.2.

General Procedure 1f

N-(1,3-Benzodioxol-5-yl)-3-[5-benzoyl-3-(trifluoromethyl)-6,7-dihydro-4H-pyrazolo[4,3-c]pyridin-1-yl]-N-methyl-benzamide To a solution of compound [002] (40 mg, 0.08 mmol) in DMF (2 mL), benzoic acid (10.1 mg, 0.09 mmol), HATU (34.4 mg, 0.09 mmol) and DIPEA (31.9 µL, 0.18 mmol) were added. Mixture was stirred at room temperature for 6 h and diluted with Et$_2$O (40 mL). Organic layer was washed with sat. aq. NH$_4$Cl (3×10 mL), water (20 mL) and brine (20 mL). Organic layer was dried with Na$_2$SO$_4$, filtered and solvent evaporated. The title compound was obtained, after purification by silica gel flash-column chromatography with Cyclohexane/EtOAc (70/30) as the eluent, as a yellow solid in 70% yield (31 mg): $^1$H NMR (400 MHz, DMSO-d$_6$) δ 7.59-7.49 (m, 7H), 7.49-7.43 (m, 1H), 7.40 (d, J=7.7 Hz, 1H), 6.95 (bs, 1H), 6.85-6.55 (m, 2H), 6.20-5.71 (m, 2H), 4.93-4.35 (m, 2H), 3.96-3.45 (m, 2H), 3.33 (s, 3H), 2.83-2.57 (m, 2H). UPLC-MS: $t_R$=2.33 min (Generic method); MS (ESI) m/z calcd for $C_{29}H_{24}F_3N_4O_4$ (M+H)$^+$: 549.2, found: 549.3.

General Procedure 1g

1-[3-[1,3-Benzodioxol-5-yl(methyl)carbamoyl]phenyl]-N-methyl-3-(trifluoromethyl)-6,7-dihydro-4H-pyrazolo[4,3-c]pyridine-5-carboxamide To a solution of 1,1'-carbonyldiimidazole (53 mg, 0.296 mmol) in DMF/CH$_3$CN (1:3, 1 ml) at rt, methylamine hydrochloride (20 mg, 0.326 mmol) was added. The mixture was allowed to stir for 2 h at rt. Then, the reaction was evaporated to yield N-methylimidazole-1-carboxamide quantitatively.

To a solution of [002] (131.7 mg, 0.296 mmol) in DCM (1.2 ml) at 0° C., triethylamine (1.66 mL, 1.18 mmol) was added followed by N-methylimidazole-1-carboxamide. The reaction was allowed to stir for 12 h at rt. Then, the reaction was extracted with water, the organic phase was dried over Na$_2$SO$_4$ and concentrated under vacuum. The title compound was obtained after purification by silica gel flash-column chromatography with 60% AcOEt in cyclohexane as eluent, as a white solid in 67% yield (99.5 mg). $^1$H NMR (400 MHz, DMSO-d$_6$) δ 7.57-7.32 (m, 4H), 6.98 (d, J=2.1 Hz, 1H), 6.78 (d, J=8.2 Hz, 1H), 6.74-6.60 (m, 2H), 6.02 (s, 2H), 4.47 (s, 2H), 3.59 (t, J=5.6 Hz, 2H), 3.33 (s, 3H), 2.62 (d, J=4.2 Hz, 3H), 2.60-2.54 (m, 2H); UPLC-MS: $t_R$=1.93 min (generic method); MS (ESI) m/z calcd for $C_{24}H_{23}F_3N_5O_4$ (M+H)$^+$: 502.5, found: 502.6.

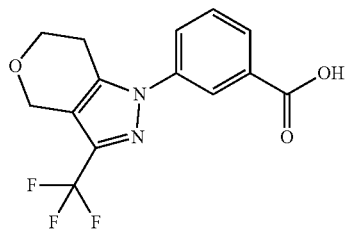 [SMILES: O=C(O)c1cccc(-n2nc(C(F)(F)F)c3c2CCOC3)c1]

[Int-1.2] 3-[3-(Trifluoromethyl)-6,7-dihydro-4H-pyrano[4,3-c]pyrazol-1-yl]benzoic acid Following general procedure 1a, starting from 3-(2,2,2-trifluoroacetyl)tetrahydropyran-4-one, the title compound was obtained as a pale yellow solid in 23% yield. $^1$H NMR signal of carboxylic acid was not observed: $^1$H NMR (400 MHz, DMSO-d$_6$) δ 8.13 (t, J=1.9 Hz, 1H), 8.03 (d, J=8.1 Hz, 1H), 7.91 (dd, J=8.1, 2.3 Hz, 1H), 7.70 (t, J=7.9 Hz, 1H), 4.74 (s, 2H), 3.88 (t, J=5.4 Hz, 2H), 2.95 (t, J=5.5 Hz, 2H); UPLC-MS: $t_R$=1.5 min (generic method); MS (ESI) m/z calcd for $C_{14}H_{12}F_3N_2O_3$ (M+H)$^+$: 313.2, found: 313.4.

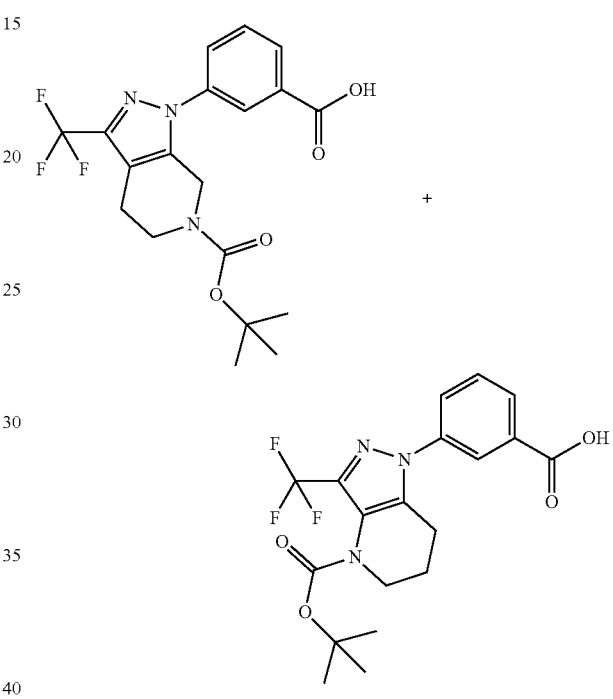

[Int-1.3] Mixture of 3-[6-tert-butoxycarbonyl-3-(trifluoromethyl)-5,7-dihydro-4H-pyrazolo[3,4-c]pyridin-1-yl]benzoic acid and 3-[4-tert-butoxycarbonyl-3-(trifluoromethyl)-6,7-dihydro-5H-pyrazolo[4,3-b]pyridin-1-yl]benzoic acid To a solution of tert-butyl 3-oxopiperidine-1-carboxylate (0.5 g, 2.5 mmol) in THF (5 mL), under nitrogen and cooled to −78° C., LDA solution (2M in THF, 1.37 mL, 2.63 mmol) was added dropwise over a period of 20 min. Mixture was stirred for 10 min and ethyl 2,2,2-trifluoroacetate (0.32 mL, 2.63 mmol) was added dropwise. Mixture was stirred at −78° C. for 4 h and quenched with sat. aq. NH$_4$Cl (5 mL). Aqueous layer was extracted with EtOAc (3×30 ml). Collected organic layers were washed with water (20 mL), brine (20 mL), dried over Na$_2$SO$_4$, filtered and solvent evaporated. The crude compound was dissolved in AcOH (10 mL), and 3-hydrazinobenzoic acid (334 mg, 2.2 mmol) was added. Mixture was stirred for 5 h at room temperature and water was added. The collected precipitate was filtered and washed with water. Crude compound was obtained as a 90:10 mixture of regioisomers. (3-[6-tert-butoxycarbonyl-3-(trifluoromethyl)-5,7-dihydro-4H-pyrazolo[3,4-c]pyridin-1-yl]benzoic acid) [Major compound]: $^1$H NMR (400 MHz, DMSO-d$_6$) δ 13.34 (s, 1H), 8.09 (app-t, J=1.9 Hz, 1H), 8.05

(d, J=7.8 Hz, 1H), 7.86 (ddd, J=8.0, 2.3, 1.1 Hz, 1H), 7.73 (t, J=7.9 Hz, 1H), 4.69 (s, 2H), 3.65 (t, J=5.8 Hz, 2H), 2.69 (t, J=5.8 Hz, 2H), 1.39 (s, 9H).

General Procedure 1h

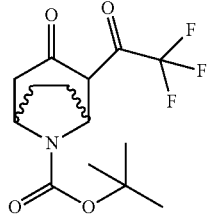 [SMILES: CC(C)(C)OC(=O)N1C2CCC1C(C(=O)C(F)(F)F)C(=O)C2]

[Int-1.4] tert-Butyl 3-oxo-4-(2,2,2-trifluoroacetyl)-8-azabicyclo[3.2.1]octane-8-carboxylate A solution of tert-butyl 3-oxo-8-azabicyclo[3.2.1]octane-8-carboxylate (300 mg, 1.33 mmol) in dry tetrahydrofuran (2.7 mL) under $N_2$ was cooled to −70° C. with stirring. The solution was then treated with a 2M solution of LDA (0.67 mL, 1.33 mmol) in THF dropwise over 30 min. The mixture was then stirred for 30 min at −70° C., treated dropwise with ethyl trifluoroacetate (0.16 mL, 1.33 mmol) and then allowed to stir for 2 h. The reaction was quenched with water (20 ml) and 2M HCl solution until pH=6 and the resulting aqueous layer was extracted with AcOEt (20 mL). The organic phase was dried over $Na_2SO_4$ and concentrated under vacuum to afford a brown oil. The title compound was obtained, after purification by silica gel flash-column chromatography with cyclohexane/EtOAc (90:10) as the eluent, as a brown oil in 73% yield (312.25 mg). $^1$H NMR (400 MHz, DMSO-$d_6$) δ 13.71 (bs, 1H), 4.81 (bs, 1H), 4.29 (t, J=6.3 Hz, 1H), 3.06-2.84 (m, 1H), 2.44 (d, J=19.1 Hz, 1H), 2.24-1.94 (m, 2H), 1.83 (t, J=9.4 Hz, 1H), 1.78-1.64 (m, 1H), 1.37 (s, 9H); UPLC-MS: $t_R$=2.11 min (generic method); MS (ESI) m/z calcd for $C_{14}H_{17}F_3NO_4$ (M)$^-$: 320.3, found: 320.2.

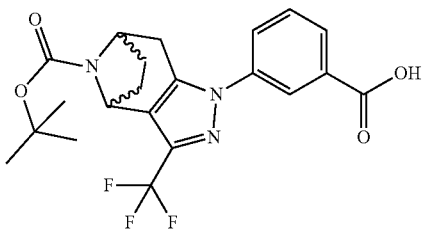 [SMILES: CC(C)(C)OC(=O)N1C2CCC1c1c(C(F)(F)F)nn(-c3cccc(C(=O)O)c3)c1C2]

[Int-1.5] 3-(9-(tert-Butoxycarbonyl)-3-(trifluoromethyl)-5,6,7,8-tetrahydro-4,7-epiminocyclohepta[c]pyrazol-1(4H)-yl)benzoic acid Following general procedure 1a, the title compound was obtained from [Int-1.4] as a pale brown solid: $^1$H NMR (400 MHz, DMSO-$d_6$) δ 13.36 (bs, 1H), 8.10 (bs, 1H), 8.06-7.99 (m, 1H), 7.96-7.86 (m, 1H), 7.69 (t, J=7.9 Hz, 1H), 5.00 (bs, 1H), 4.50 (dd, J=7.3, 4.5 Hz, 1H), 3.49-3.36 (m, 1H), 2.76 (d, J=16.5 Hz, 1H), 2.30-2.04 (m, 2H), 1.90-1.79 (m, 1H), 1.79-1.65 (m, 1H), 1.41 (bs, 9H); UPLC-MS: $t_R$=1.95 min (generic method); MS (ESI) m/z calcd for $C_{21}H_{23}F_3N_3O_4$ (M+H)$^+$: 438.4, found: 438.5.

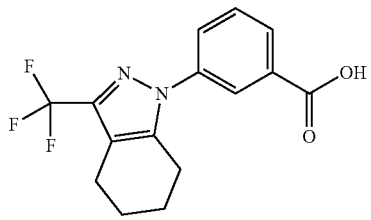 [SMILES: O=C(O)c1cccc(-n2nc(C(F)(F)F)c3c2CCCC3)c1]

[Int-1.6] 3-[3-(Trifluoromethyl)-4,5,6,7-tetrahydroindazol-1-yl]benzoic acid

Following general procedure 1a, the title compound was obtained from 3-hydrazinobenzoic acid, after purification by trituration with $H_2O$ as the solvent, as a beige solid in 92% yield: $^1$H NMR (400 MHz, DMSO-$d_6$) δ 13.33 (br s, 1H), 8.07 (app-t, J=1.9 Hz, 1H), 8.01 (app-dt, J=7.7, 1.3 Hz, 1H), 7.87 (ddd, J=8.1, 2.3, 1.1 Hz, 1H), 7.69 (app-t, J=7.9 Hz, 1H), 2.77 (br s, 2H), 2.61 (br s, 2H), 1.77 (br s, 4H); UPLC-MS: $t_R$=1.87 min (generic method); MS (ESI) m/z calcd for $C_{15}H_{14}F_3N_2O_2$ (M+H)$^+$: 311.1, found: 311.1.

3-[5-Acetyl-3-(trifluoromethyl)-6,7-dihydro-4H-pyrazolo[4,3-c]pyridin-1-yl]-N-(1,3-benzodioxol-5-yl)-N-methyl-benzamide Following general procedure 1f, the title compound was obtained from compound [002], after purification by silica gel flash-column chromatography with DCM/EtOAc (70/30) as the eluent, as a white solid in 60% yield: $^1$H NMR showed the presence of two conformers. Major conformer: $^1$H NMR (400 MHz, DMSO-$d_6$) δ 7.57-7.37 (m, 4H), 7.00 (d, J=2.2 Hz, 1H), 6.79 (d, J=8.3 Hz, 1H), 6.66 (dd, J=8.3, 2.2 Hz, 1H), 6.01 (s, 2H), 4.60 (s, 2H), 3.68 (t, J=5.7 Hz, 2H), 3.33 (s, 3H), 2.74-2.68 (m, 2H), 2.16 (s, 3H). UPLC-MS: $t_R$=2.04 min (Generic method); MS (ESI) m/z calcd for $C_{24}H_{22}F_3N_4O_4$ (M+H)$^+$: 487.2, found: 487.2.

N-(1,3-Benzodioxol-5-yl)-N-methyl-3-[3-(trifluoromethyl)-4,5,6,7-tetrahydroindazol-1-yl]benzamide Following general procedure 1b, the title compound was obtained from [Int-1.6], after purification by silica gel flash-column chromatography with DCM/EtOAc (9:1) as the eluent, as a white solid in 70% yield: $^1$H NMR (400 MHz, DMSO-$d_6$) δ 7.63-7.28 (m, 4H), 6.97 (d, J=2.2 Hz, 1H), 6.78 (d, J=8.2 Hz, 1H), 6.65 (dd, J=8.2, 2.2 Hz, 1H), 5.98 (s, 2H), 3.32 (s, 3H), 2.58 (bs, 2H), 2.42 (bs, 2H), 1.72 (bs, 4H); UPLC-MS: $t_R$=1.55 min (apolar method); MS (ESI) m/z calcd for $C_{23}H_{21}F_3N_3O_3$ (M+H)$^+$: 444.2, found: 444.2.

3-[5-(Benzenesulfonyl)-3-(trifluoromethyl)-6,7-dihydro-4H-pyrazolo[4,3-c]pyridin-1-yl]-N-(1,3-benzodioxol-5-yl)-N-methyl-benzamide Following general procedure 1e, the title compound was obtained from compound [002], after purification by silica gel flash-column chromatography with cyclohexane/EtOAc (60/40) as the eluent, as a white solid in 90% yield: $^1$H NMR (400 MHz, DMSO-$d_6$) δ 7.89-7.80 (m, 2H), 7.71 (ddd, J=8.2, 6.1, 1.3 Hz, 1H), 7.67-7.58 (m, 2H), 7.50-7.32 (m, 4H), 7.04-6.97 (m, 1H), 6.78 (d, J=8.2 Hz, 1H), 6.63 (d, J=8.2 Hz, 1H), 6.02 (d, J=1.1 Hz, 2H), 4.28 (s, 2H), 3.43 (t, J=5.8 Hz, 2H), 3.33 (d, J=1.1 Hz, 3H), 2.60 (t, J=5.8 Hz, 2H). UPLC-MS: $t_R$=2.48 min (Generic method); MS (ESI) m/z calcd for $C_{28}H_{24}F_3N_4O_5S$ (M+H)$^+$: 585.1, found: 585.2.

Methyl 1-[3-[1,3-benzodioxol-5-yl(methyl)carbamoyl]phenyl]-3-(trifluoromethyl)-6,7-dihydro-4H-pyrazolo[4,3-c]pyridine-5-carboxylate Following general procedure 1e, the title compound was obtained from compound [002], after purification by silica gel flash-column chromatography with cyclohexane/EtOAc (70/30) as the eluent, as a white solid in 83% yield: $^1$H NMR (400 MHz, DMSO-$d_6$) δ 7.56-7.48 (m, 2H), 7.47 (app-d, J=7.7 Hz, 1H), 7.42 (app-t, J=6.9 Hz, 1H), 6.99 (d, J=2.1 Hz, 1H), 6.76 (d, J=8.2 Hz, 1H), 6.64 (dd, J=8.2, 2.1 Hz, 1H), 6.00 (s, 2H), 4.53 (s, 2H), 3.68 (s, 3H), 3.64 (t, J=5.7 Hz, 2H), 3.32 (s, 3H), 2.59 (bs, 2H). UPLC-MS: $t_R$=2.27 min (Generic method); MS (ESI) m/z calcd for $C_{24}H_{22}F_3N_4O_5$ (M+H)$^+$: 503.2, found: 503.2.

1-[3-[1,3-Benzodioxol-5-yl(methyl)carbamoyl]phenyl]-N-phenyl-3-(trifluoromethyl)-6,7-dihydro-4H-pyrazolo[4,3-c]pyridine-5-carboxamide Following general procedure 1g, the title compound was obtained from compound [002], after purification by silica gel flash-column chromatography with cyclohexane/EtOAc (50/50) as the eluent, as a white solid in 84% yield: $^1$H NMR (400 MHz, DMSO-$d_6$) δ 8.75 (s, 1H), 7.58-7.52 (m, 2H), 7.50-7.41 (m, 3H), 7.38 (d, J=7.7 Hz, 1H), 7.30-7.22 (m, 2H), 6.98 (d, J=2.1 Hz, 1H), 6.96 (app-dt, J=7.3, 1.2 Hz, 1H), 6.77 (d, J=8.2 Hz, 1H), 6.65 (dd, J=8.2, 2.1 Hz, 1H), 6.01 (s, 2H), 4.64 (s, 2H), 3.74 (t, J=5.5 Hz, 2H), 3.32 (s, 3H), 2.70 (bs, 2H). UPLC-MS: $t_R$=2.32 min (Generic method); MS (ESI) m/z calcd for $C_{29}H_{25}F_3N_5O_4$ (M+H)$^+$: 564.2, found: 564.3.

N-(1,3-Benzodioxol-5-yl)-3-[5-(2,2-dimethylpropanoyl)-3-(trifluoromethyl)-6,7-dihydro-4H-pyrazolo[4,3-c]pyridin-1-yl]-N-methyl-benzamide Following general procedure 1f, the title compound was obtained from compound [002], after purification by silica gel flash-column chromatography with cyclohexane/EtOAc (70/30) as the eluent, as a white solid in 73% yield: $^1$H NMR (400 MHz, DMSO-$d_6$) δ 7.64-7.50 (m, 2H), 7.44 (app-t, J=8.1 Hz, 1H), 7.38 (app-d, J=7.6 Hz, 1H), 6.98 (d, J=2.1 Hz, 1H), 6.76 (d, J=8.2 Hz, 1H), 6.65 (dd, J=8.2, 2.1 Hz, 1H), 5.99 (s, 2H), 4.63 (s, 2H), 3.81 (t, J=5.6 Hz, 2H), 3.33 (s, 3H), 2.68 (bs, 2H), 1.26 (s, 9H). UPLC-MS: $t_R$=2.28 min (Generic method); MS (ESI) m/z calcd for $C_{27}H_{28}F_3N_4O_4$ (M+H)$^+$: 529.2, found: 529.3.

N-(1,3-Benzodioxol-5-yl)-3-[5-benzyl-3-(trifluoromethyl)-6,7-dihydro-4H-pyrazolo[4,3-c]pyridin-1-yl]-N-methyl-benzamide Following general procedure 1d, the title compound was obtained from compound [002], after purification by silica gel flash-column chromatography with DCM/MeOH (95/5) as the eluent, as a white solid in 38% yield: $^1$H NMR (400 MHz, DMSO-$d_6$) δ 7.53 (app-dt, J=7.8, 1.7 Hz, 1H), 7.50 (s, 1H), 7.44 (app-t, J=7.7 Hz, 1H), 7.42-7.33 (m, 5H), 7.29 (ddt, J=8.6, 5.7, 3.0 Hz, 1H), 6.98 (d, J=2.1 Hz, 1H), 6.73 (d, J=8.2 Hz, 1H), 6.62 (dd, J=8.2, 2.1 Hz, 1H), 5.87 (s, 2H), 3.73 (s, 2H), 3.54 (s, 2H), 3.32 (s, 3H), 2.70 (t, J=5.6 Hz, 2H), 2.56 (bs, 2H). UPLC-MS: $t_R$=2.65 min (Generic method); MS (ESI) m/z calcd for $C_{29}H_{26}F_3N_4O_3$ (M+H)$^+$: 535.2, found: 535.3.

N-(1,3-Benzodioxol-5-yl)-3-[5-[[(4R)-2,2-dimethyl-1,3-dioxolan-4-yl]methyl]-3-(trifluoromethyl)-6,7-dihydro-4H-pyrazolo[4,3-c]pyridin-1-yl]-N-methyl-benzamide Following general procedure 1d, the title compound was obtained from compound [002], after purification by silica gel flash-column chromatography with DCM/MeOH (95/5) as the eluent, as a white solid in 95% yield: $^1$H NMR (400 MHz, DMSO-$d_6$) δ 7.59-7.52 (m, 1H), 7.50 (s, 1H), 7.45 (app-t, J=7.7 Hz, 1H), 7.40 (app-d, J=7.6 Hz, 1H), 6.99 (d, J=2.1 Hz, 1H), 6.77 (d, J=8.2 Hz, 1H), 6.65 (dd, J=8.2, 2.1 Hz, 1H), 5.99 (s, 2H), 4.30 (p, J=6.4 Hz, 1H), 4.05 (dd, J=8.0, 6.3 Hz, 1H), 3.72-3.56 (m, 3H), 3.33 (s, 3H), 2.92-2.82 (m, 1H), 2.78-2.65 (m, 3H), 2.64-2.54 (m, 2H), 1.35 (s, 3H), 1.30 (s, 3H). UPLC-MS: $t_R$=2.37 min (Generic method); MS (ESI) m/z calcd for $C_{28}H_{30}F_3N_4O_5$ (M+H)$^+$: 559.2, found: 535.3. ee: 34.3%.

N-(1,3-Benzodioxol-5-yl)-3-[5-[[(4S)-2,2-dimethyl-1,3-dioxolan-4-yl]methyl]-3-(trifluoromethyl)-6,7-dihydro-4H-pyrazolo[4,3-c]pyridin-1-yl]-N-methyl-benzamide Following general procedure 1d, the title compound was obtained from compound [002], after purification by silica gel flash-column chromatography with DCM/MeOH (95/5) as the eluent, as a white solid in 91% yield: $^1$H NMR (400 MHz, DMSO-$d_6$) δ 7.59-7.52 (m, 1H), 7.50 (s, 1H), 7.45 (app-t, J=7.7 Hz, 1H), 7.40 (app-d, J=7.6 Hz, 1H), 6.99 (d, J=2.1 Hz, 1H), 6.77 (d, J=8.2 Hz, 1H), 6.65 (dd, J=8.2, 2.1 Hz, 1H), 5.99 (s, 2H), 4.30 (p, J=6.4 Hz, 1H), 4.05 (dd, J=8.0, 6.3 Hz, 1H), 3.72-3.56 (m, 3H), 3.33 (s, 3H), 2.92-2.82 (m, 1H), 2.78-2.65 (m, 3H), 2.64-2.54 (m, 2H), 1.35 (s, 3H), 1.30 (s, 3H). UPLC-MS: $t_R$=2.37 min (Generic method); MS (ESI) m/z calcd for $C_{28}H_{30}F_3N_4O_5$ (M+H)$^+$: 559.2, found: 535.3. ee: 64.0%.

N-(1,3-Benzodioxol-5-yl)-3-[5-[(2R)-2,3-dihydroxy propyl]-3-(trifluoromethyl)-6,7-dihydro-4H-pyrazolo[4,3-c]pyridin-1-yl]-N-methyl-benzamide To a solution of compound [013] (65 mg, 0.12 mmol) in DCM (5 mL) at 0° C., TFA (100 μL) was added slowly. Mixture was stirred at room temperature for 4 h and quenched with sat. aq. NaHCO$_3$ until pH=8/9. The aqueous layer was extracted with EtOAc (2×20 mL) and the collected organic layer was washed with brine (20 mL). The title compound was obtained, after purification by silica gel flash-column chromatography with DCM/MeOH (95/5) as the eluent, as a white solid in 34% yield (21 mg): $^1$H NMR (400 MHz, DMSO-$d_6$) δ 7.53 (app-d, J=7.7 Hz, 1H), 7.49 (s, 1H), 7.45 (app-t, J=7.8 Hz, 1H), 7.39 (app-d, J=7.6 Hz, 1H), 6.98 (d, J=2.1 Hz, 1H), 6.77 (d, J=8.2 Hz, 1H), 6.64 (dd, J=8.2, 2.1 Hz, 2H), 5.99 (s, 2H), 4.52-4.46 (m, 2H), 3.68 (h, J=5.4 Hz, 1H), 3.61 (s, 2H), 3.36 (t, J=5.4 Hz, 2H), 3.33 (s, 3H), 2.77 (h, J=6.2 Hz, 2H), 2.65 (dd, J=13.0, 4.4 Hz, 1H), 2.56 (bs, 2H), 2.47 (d, J=7.9 Hz, 1H). UPLC-MS: $t_R$=1.78 min (Generic method); MS (ESI) m/z calcd for $C_{25}H_{26}F_3N_4O_5$ (M+H)$^+$: 519.2, found: 519.3.

N-(1,3-Benzodioxol-5-yl)-3-[5-[(2S)-2,3-dihydroxypropyl]-3-(trifluoromethyl)-6,7-dihydro-4H-pyrazolo[4,3-c]pyridin-1-yl]-N-methyl-benzamide To a solution of compound [014] (65 mg, 0.12 mmol) in DCM (5 mL) at 0° C., TFA (100 μL) was added slowly. Mixture was stirred at room temperature for 4 h and quenched with sat. aq. NaHCO$_3$ until pH=8/9. The aqueous layer was extracted with EtOAc (2×20 mL) and the collected organic layer was washed with brine (20 mL). The title compound was obtained, after purification by silica gel flash-column chromatography with DCM/MeOH (95/5) as the eluent, as a white solid in 48% yield (28 mg): $^1$H NMR (400 MHz, DMSO-d$_6$) δ 7.53 (app-d, J=7.7 Hz, 1H), 7.49 (s, 1H), 7.45 (app-t, J=7.8 Hz, 1H), 7.39 (app-d, J=7.6 Hz, 1H), 6.98 (d, J=2.1 Hz, 1H), 6.77 (d, J=8.2 Hz, 1H), 6.64 (dd, J=8.2, 2.1 Hz, 2H), 5.99 (s, 2H), 4.52-4.46 (m, 2H), 3.68 (h, J=5.4 Hz, 1H), 3.61 (s, 2H), 3.36 (t, J=5.4 Hz, 2H), 3.33 (s, 3H), 2.77 (h, J=6.2 Hz, 2H), 2.65 (dd, J=13.0, 4.4 Hz, 1H), 2.56 (bs, 2H), 2.47 (d, J=7.9 Hz, 1H). UPLC-MS: t$_R$=1.78 min (Generic method); MS (ESI) m/z calcd for C$_{25}$H$_{26}$F$_3$N$_4$O$_5$ (M+H)$^+$: 519.2, found: 519.3.

tert-Butyl 1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate Following general procedure 1b, the title compound was obtained from [Int-1.5], after purification by silica gel flash-column chromatography with 25% AcOEt in cyclohexane as eluent, as a pale yellow solid in 68% yield: $^1$H NMR (400 MHz, DMSO-d$_6$) δ 7.63-7.48 (m, 2H), 7.49-7.34 (m, 2H), 6.98 (d, J=2.1 Hz, 1H), 6.77 (d, J=8.2 Hz, 1H), 6.65 (dd, J=8.2, 2.1 Hz, 1H), 6.00 (d, J=1.7 Hz, 2H), 4.96 (s, 1H), 4.45 (dd, J=8.0, 4.5 Hz, 1H), 3.34 (s, 3H), 3.19-2.99 (m, 1H), 2.41 (d, J=16.4 Hz, 1H), 2.30-2.18 (m, 1H), 2.18-2.03 (m, 1H), 1.83 (s, 1H), 1.73-1.57 (m, 1H), 1.35 (bs, 9H); UPLC-MS: t$_R$=2.39 min (generic method); MS (ESI) m/z calcd for C$_{29}$H$_{30}$F$_3$N$_4$O$_5$ (M+H)$^+$: 571.6, found: 571.3.

N-(1,3-Benzodioxol-5-yl)-3-[5-(cyclopropylmethyl)-3-(trifluoromethyl)-6,7-dihydro-4H-pyrazolo[4,3-c]pyridin-1-yl]-N-methyl-benzamide Following general procedure 1d, the title compound was obtained from compound [002], after purification by silica gel flash-column chromatography with 70% EtOAc in cyclohexane as the eluent, as a white solid in 58% yield: $^1$H NMR (400 MHz, DMSO-d$_6$) δ 7.60-7.35 (m, 4H), 6.98 (d, J=2.2 Hz, 1H), 6.77 (d, J=8.2 Hz, 1H), 6.64 (dd, J=8.3, 2.2 Hz, 1H), 5.98 (s, 2H), 3.60 (s, 2H), 3.33 (s, 3H), 2.76 (t, J=5.6 Hz, 2H), 2.64-2.53 (m, 2H), 2.45 (d, J=6.6 Hz, 2H), 1.00-0.87 (m, 1H), 0.58-0.45 (m, 2H), 0.23-0.07 (m, 2H); UPLC-MS: t$_R$=2.13 min (generic method); MS (ESI) m/z calcd for C$_{26}$H$_{26}$F$_3$N$_4$O$_3$ (M+H)$^+$: 499.5, found: 499.3.

Methyl 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]methyl]benzoate Following general procedure 1d, the title compound was obtained from compound [002], after purification by silica gel flash-column chromatography with 40% EtOAc in cyclohexane as the eluent, as a white solid in 89% yield: $^1$H NMR (400 MHz, DMSO-d$_6$) δ 7.99 (t, J=1.8 Hz, 1H), 7.90 (dt, J=7.8, 1.5 Hz, 1H), 7.70-7.63 (m, 2H), 7.58-7.49 (m, 3H), 7.48-7.35 (m, 2H), 6.97 (d, J=2.2 Hz, 1H), 6.73 (d, J=8.1 Hz, 1H), 6.63 (d, J=8.3 Hz, 1H), 5.89 (s, 2H), 3.87 (s, 3H), 3.81 (s, 2H), 3.57 (s, 2H), 3.32 (s, 3H), 2.71 (t, J=5.6 Hz, 2H), 2.62-2.54 (m, 2H); UPLC-MS: t$_R$=2.34 min (generic method); MS (ESI) m/z calcd for C$_{31}$H$_{28}$F$_3$N$_4$O$_5$ (M+H)$^+$: 593.2, found: 593.3.

N-(1,3-Benzodioxol-5-yl)-3-[5-isopropyl-3-(trifluoromethyl)-6,7-dihydro-4H-pyrazolo[4,3-c]pyridin-1-yl]-N-methyl-benzamide Following general procedure 1d, the title compound was obtained from compound [002], after purification by silica gel flash-column chromatography with 70% EtOAc in cyclohexane as the eluent, as a white solid in 66% yield: $^1$H NMR (400 MHz, DMSO-d$_6$) δ 7.46 (ddd, J=32.8, 19.2, 7.6 Hz, 4H), 6.99 (d, J=2.1 Hz, 1H), 6.78 (d, J=8.2 Hz, 1H), 6.66 (dd, J=8.3, 1.9 Hz, 1H), 5.99 (s, 2H), 3.58 (s, 2H), 3.33 (s, 3H), 3.00 (dq, J=13.1, 6.2 Hz, 1H), 2.70 (q, J=4.6, 3.7 Hz, 2H), 2.60-2.54 (m, 2H), 1.07 (d, J=6.6 Hz, 6H); UPLC-MS: t$_R$=1.99 min (generic method); MS (ESI) m/z calcd for C$_{25}$H$_{26}$F$_3$N$_4$O$_3$ (M+H)$^+$: 487.5, found: 487.3.

N-(Benzo[d][1,3]dioxol-5-yl)-N-methyl-3-(3-(trifluoromethyl)-5,6,7,8-tetrahydro-4,7-epiminocyclohepta[c]pyrazol-1(4H)-yl)benzamide hydrochloride Following general procedure 1c, the title compound was obtained from compound [018], after precipitation with diethylether as a pale purple solid in 83% yield: $^1$H NMR (400 MHz, DMSO-d$_6$) δ 9.96 (bs, 1H), 9.47 (bs, 1H), 7.64-7.52 (m, 2H), 7.47 (t, J=7.8 Hz, 1H), 7.39 (d, J=7.7 Hz, 1H), 6.98 (d, J=2.1 Hz, 1H), 6.80 (d, J=8.2 Hz, 1H), 6.68 (dd, J=8.0, 2.1 Hz, 1H), 6.01 (s, 2H), 5.01 (d, J=4.5 Hz, 1H), 4.38 (bs, 1H), 3.34 (s, 3H), 3.30-3.21 (m, 1H), 2.89 (d, J=16.8 Hz, 1H), 2.36-2.19 (m, 3H), 2.14-2.02 (m, 1H), 1.98-1.86 (m, 1H); UPLC-MS: t$_R$=1.64 min (generic method); MS (ESI) m/z calcd for C$_{24}$H$_{22}$F$_3$N$_4$O$_3$(M)$^+$: 471.6, found: 471.3.

N-(Benzo[d][1,3]dioxol-5-yl)-N-methyl-3-(9-methyl-3-(trifluoromethyl)-5,6,7,8-tetrahydro-4,7-epiminocyclohepta[c]pyrazol-1(4H)-yl)benzamide Following general procedure 1d, the title compound was obtained from compound [022], after purification by silica gel flash-column chromatography in CH$_2$Cl$_2$/MeOH (8:2) as eluent, as a white solid in 80% yield: $^1$H NMR (400 MHz, DMSO-d$_6$) δ 7.57 (d, J=8.0 Hz, 1H), 7.52 (s, 1H), 7.45 (t, J=7.8 Hz, 1H), 7.39 (d, J=7.7 Hz, 1H), 6.99 (d, J=2.2 Hz, 1H), 6.77 (d, J=8.2 Hz, 1H), 6.65 (d, J=7.3 Hz, 1H), 5.99 (s, 2H), 3.97 (d, J=4.4 Hz, 1H), 3.45 (t, J=5.3 Hz, 2H), 3.34 (s, 3H), 2.97 (dd, J=16.3, 4.4 Hz, 1H), 2.22 (s, 3H), 2.17-1.98 (m, 3H), 1.68 (t, J=9.2 Hz, 1H), 1.44 (t, J=7.9 Hz, 1H); UPLC-MS: t$_R$=1.77 min (generic method); MS (ESI) m/z calcd for C$_{25}$H$_{24}$F$_3$N$_4$O$_3$ (M+H)$^+$: 485.4, found: 485.2.

N-(1,3-Benzodioxol-5-yl)-N-methyl-3-[5-sec-butyl-3-(trifluoromethyl)-6,7-dihydro-4H-pyrazolo[4,3-c]pyridin-1-yl]benzamide Following general procedure 1d, the title compound was obtained from compound [002], after purification by silica gel flash-column chromatography in CH$_2$Cl$_2$:MeOH (8:2) as the eluent, as an orange solid in 80% yield: $^1$H NMR (400 MHz, DMSO-d$_6$) δ 7.63-7.33 (m, 4H), 6.99 (d, J=2.1 Hz, 1H), 6.78 (d, J=8.2 Hz, 1H), 6.66 (dd, J=8.2, 2.0 Hz, 1H), 5.99 (s, 2H), 3.58 (q, J=14.2 Hz, 2H), 3.33 (s, 3H), 2.74 (dq, J=13.5, 6.4 Hz, 2H), 2.65-2.53 (m, 5H), 1.58 (dp, J=14.3, 7.3 Hz, 1H), 1.38 (dq, J=14.0, 7.2 Hz, 1H), 1.01 (d, J=6.5 Hz, 3H), 0.90 (t, J=7.4 Hz, 3H); UPLC-MS: $t_R$=2.30 min (generic method); MS (ESI) m/z calcd for $C_{26}H_{28}F_3N_4O_3$ (M+H)$^+$: 501.5, found: 501.3.

General Procedure 1i

3-[[1-[3-[1,3-Benzodioxol-5-yl(methyl)carbamoyl]phenyl]-3-(trifluoromethyl)-6,7-dihydro-4H-pyrazolo[4,3-c]pyridin-5-yl]methyl]benzoic acid To a solution of [020] (42 mg, 0.087 mmol) in MeOH/H$_2$O (70:30; 0.7 mL), lithium hydroxide (5 mg, 0.175 mmol) was added and the reaction was stirred for 12 h at rt. Then, the reaction was acidified with 1M HCl until pH=2-3 and extracted with CH$_2$Cl$_2$ (20 mL). The organic phase was dried over Na$_2$SO$_4$ and concentrated under vacuum. The title compound was obtained after purification by silica gel flash-column chromatography in CH$_2$Cl$_2$/MeOH (8:2) as the eluent, as a white solid in 60% yield (30.5 mg): $^1$H NMR (400 MHz, DMSO-d$_6$) δ 12.93 (bs, 1H), 7.97 (app-t, J=1.7 Hz, 1H), 7.87 (dt, J=7.7, 1.5 Hz, 1H), 7.62 (dt, J=7.6, 1.5 Hz, 1H), 7.57-7.37 (m, 5H), 6.97 (d, J=2.1 Hz, 1H), 6.73 (d, J=8.2 Hz, 1H), 6.63 (dd, J=8.4, 2.1 Hz, 1H), 5.88 (s, 2H), 3.80 (s, 2H), 3.56 (s, 2H), 3.32 (s, 3H), 2.71 (t, J=5.6 Hz, 2H), 2.59-2.54 (m, 2H); UPLC-MS: $t_R$=1.78 min (generic method); MS (ESI) m/z calcd for $C_{30}H_{26}F_3N_4O_5$ (M+H)$^+$: 579.5, found: 579.3.

4-[[1-[3-[1,3-Benzodioxol-5-yl(methyl)carbamoyl]phenyl]-3-(trifluoromethyl)-6,7-dihydro-4H-pyrazolo[4,3-c]pyridin-5-yl]methyl]benzoic acid Following general procedure 1i, the title compound was obtained from compound [002], after purification by silica gel flash-column chromatography with 70% EtOAc in cyclohexane as the eluent, as a white solid in 66% yield: $^1$H NMR (400 MHz, DMSO-d$_6$) δ 12.7 (bs, 1H), δ 8.02-7.85 (m, 2H), 7.65-7.33 (m, 6H), 6.98 (d, J=2.1 Hz, 1H), 6.73 (d, J=8.2 Hz, 1H), 6.63 (d, J=8.1 Hz, 1H), 5.90 (s, 2H), 3.82 (s, 2H), 3.57 (s, 2H), 3.32 (s, 3H), 2.71 (t, J=5.5 Hz, 2H), 2.63-2.54 (m, 2H); UPLC-MS: $t_R$=1.78 min (generic method); MS (ESI) m/z calcd for $C_{30}H_{26}F_3N_4O_5$ (M+H)$^+$: 579.5, found: 579.3.

tert-Butyl 1-[3-[1,3-benzodioxol-5-yl(methyl)carbamoyl]phenyl]-3-(trifluoromethyl)-5,7-dihydro-4H-pyrazolo[3,4-c]pyridine-6-carboxylate Following general procedure 1b, the title compound was obtained from [Int-1.3], after purification by silica gel flash-column chromatography with cyclohexane/EtOAc (70/30) as the eluent, as a white yellow solid in 54% yield: $^1$H NMR (400 MHz, DMSO-d$_6$) δ 7.54 (bs, 1H), 7.50 (app-d, J=8.3 Hz, 1H), 7.45 (app-t, J=7.7 Hz, 1H), 7.36 (app-d, J=7.4 Hz, 1H), 6.97 (d, J=2.1 Hz, 1H), 6.75 (d, J=8.2 Hz, 1H), 6.66 (t, J=8.2, 2.1 Hz, 1H), 5.97 (s, 2H), 4.49 (s, 2H), 3.62 (t, J=5.8 Hz, 2H), 3.33 (s, 3H), 2.67 (t, J=5.8 Hz, 3H), 1.39 (s, 9H). UPLC-MS: $t_R$=2.20 min (Generic method); MS (ESI) m/z calcd for $C_{27}H_{28}F_3N_4O_5$ (M+H)$^+$: 545.2, found: 545.3.

tert-Butyl 1-[3-[1,3-benzodioxol-5-yl(methyl)carbamoyl]phenyl]-3-(trifluoromethyl)-6,7-dihydro-5H-pyrazolo[4,3-b]pyridine-4-carboxylate Following general procedure 1b, the title compound was obtained from [Int-1.3], after purification by silica gel flash-column chromatography with cyclohexane/EtOAc (70/30) as the eluent, as a white yellow solid in 8% yield: $^1$H NMR (400 MHz, DMSO-d$_6$) δ 7.59-7.50 (m, 2H), 7.46 (app-t, J=8.1 Hz, 1H), 7.41 (app-d, J=7.6 Hz, 1H), 6.97 (d, J=2.1 Hz, 1H), 6.78 (d, J=8.2 Hz, 1H), 6.65 (dd, J=8.3, 2.1 Hz, 1H), 6.00 (s, 2H), 3.70-3.52 (m, 2H), 3.33 (s, 3H), 2.63 (t, J=6.3 Hz, 3H), 1.84 (p, J=6.2 Hz, 3H). UPLC-MS: $t_R$=2.35 min (Generic method); MS (ESI) m/z calcd for $C_{27}H_{28}F_3N_4O_5$ (M+H)$^+$: 545.2, found: 545.3.

N-(1,3-Benzodioxol-5-yl)-N-methyl-3-[6-methyl-3-(trifluoromethyl)-5,7-dihydro-4H-pyrazolo[3,4-c]pyridin-1-yl]benzamide Following general procedure 1d, the title compound was obtained from compound [038], as a white yellow solid in 80% yield: $^1$H NMR (400 MHz, DMSO-d$_6$) δ 7.51-7.46 (m, 2H), 7.43 (app-t, J=7.8 Hz, 1H), 7.36 (app-d, J=7.5 Hz, 1H), 6.96 (d, J=2.1 Hz, 1H), 6.77 (d, J=8.2 Hz, 1H), 6.67 (dd, J=8.2, 2.1 Hz, 1H), 5.98 (s, 2H), 3.44 (s, 2H), 3.33 (s, 3H), 2.71-2.60 (m, 4H), 2.37 (s, 3H). UPLC-MS: $t_R$=1.89 min (Generic method); MS (ESI) m/z calcd for $C_{23}H_{22}F_3N_4O_3$ (M+H)$^+$: 459.2, found: 459.3.

tert-Butyl 1-[3-[methyl-(2-methyl-1,3-benzoxazol-6-yl)carbamoyl]phenyl]-3-(trifluoromethyl)-6,7-dihydro-4H-pyrazolo[4,3-c]pyridine-5-carboxylate Following general procedure 1b, the title compound was obtained from [Int-1.1], after purification by silica gel flash-column chromatography with cyclohexane/EtOAc (50/50) as the eluent, as a white solid in 90% yield: $^1$H NMR (400 MHz, DMSO-d$_6$) δ 7.77-7.66 (m, 1H), 7.55-7.47 (m, 3H), 7.46-7.38 (m, 2H), 7.25-7.12 (m, 1H), 4.45 (s, 2H), 3.48 (t, J=5.6 Hz, 2H), 3.44 (s, 3H), 2.59 (s, 3H), 2.45-2.27 (m, 2H), 1.46 (s, 9H). UPLC-MS: $t_R$=2.19 min (Generic method); MS (ESI) m/z calcd for $C_{28}H_{29}F_3N_5O_4$ (M+H)$^+$: 556.2, found: 556.3.

N-Methyl-N-(2-methyl-1,3-benzoxazol-6-yl)-3-[3-(trifluoromethyl)-4,5,6,7-tetrahydropyrazolo[4,3-c]pyridin-1-yl]benzamide hydrochloride Following general procedure 1c, the title compound was obtained from compound [039], as a pale yellow solid in 92% yield: $^1$H NMR (400 MHz, DMSO-d$_6$) δ 9.82 (bs, 2H), 7.69 (d, J=2.0 Hz, 1H), 7.57-7.51 (m, 2H), 7.48 (app-dt, J=7.4, 2.1 Hz, 1H), 7.42 (q, J=7.7 Hz, 2H), 7.23 (dd, J=8.4, 2.0 Hz, 1H), 4.25 (s, 2H), 3.44 (s, 3H), 3.29 (t, J=5.9 Hz, 2H), 2.79 (d, J=5.9 Hz, 2H), 2.57 (s, 3H). UPLC-MS: $t_R$=1.59 min (Generic method); MS (ESI) m/z calcd for $C_{23}H_{21}F_3N_5O_2$ (M+H)$^+$: 456.2, found: 456.6.

N-(1,3-Benzodioxol-5-yl)-N-methyl-3-[5-(2-methylpropanoyl)-3-(trifluoromethyl)-6,7-dihydro-4H-pyrazolo[4,3-c]pyridin-1-yl]benzamide Following general procedure 1f, the title compound was obtained from compound [002], after purification by silica gel flash-column chromatography with 30% AcOEt in cyclohexane as the eluent, as a white solid in 62% yield. $^1$H NMR spectrum showed a 70:30 mixture of rotamers. Major rotamer: $^1$H NMR (400 MHz, DMSO-d$_6$) δ 7.66-7.35 (m, 4H), 6.99 (s, 1H), 6.79 (d, J=8.4 Hz, 1H), 6.66 (d, J=9.0 Hz, 1H), 6.01 (s, 2H), 4.63 (s, 2H), 3.75 (t, J=5.6 Hz, 2H), 3.33 (s, 3H), 3.00 (hept, J=6.7 Hz, 1H), 2.80-2.65 (m, 1H), 2.61-2.53 (m, 2H), 1.14-0.94 (m, 6H); UPLC-MS: $t_R$=1.97 min (generic method); MS (ESI) m/z calcd for C$_{26}$H$_{26}$F$_3$N$_4$O$_4$ (M+H)$^+$: 515.5, found: 515.3.

N-(1,3-Benzodioxol-5-yl)-3-[5-cyclobutyl-3-(trifluoro methyl)-6,7-dihydro-4H-pyrazolo[4,3-c]pyridin-1-yl]-N-methyl-benzamide Following general procedure 1d, the title compound was obtained from compound [002], after purification by silica gel flash-column chromatography in CH$_2$Cl$_2$/MeOH (8:2) as the eluent, as a white solid in 51% yield: $^1$H NMR (400 MHz, DMSO-d$_6$) δ 7.57-7.37 (m, 4H), 6.99 (d, J=2.1 Hz, 1H), 6.77 (d, J=8.2 Hz, 1H), 6.69-6.60 (m, 1H), 5.98 (s, 2H), 3.38 (s, 2H), 3.32 (s, 2H), 3.00 (p, J=7.9 Hz, 1H), 2.54 (s, 3H), 2.17-1.98 (m, 2H), 1.94-1.75 (m, 2H), 1.75-1.61 (m, 2H); UPLC-MS: t$_R$=2.15 min (generic method); MS (ESI) m/z calcd for C$_{26}$H$_{26}$F$_3$N$_4$O$_3$ (M+H)$^+$: 499.5, found: 499.3.

N-(1,3-Benzodioxol-5-yl)-N-methyl-3-[5-(3,3,3-trifluoro-2,2-dimethyl-propanoyl)-3-(trifluoromethyl)-6,7-dihydro-4H-pyrazolo[4,3-c]pyridin-1-yl] benzamide Following general procedure 1f, the title compound was obtained from compound [002], after purification by silica gel flash-column chromatography with 50% AcOEt in cyclohexane as the eluent, as a white solid in 59% yield: $^1$H NMR (400 MHz, DMSO-d$_6$) δ 7.65-7.50 (m, 2H), 7.45 (t, J=7.8 Hz, 1H), 7.37 (d, J=7.8 Hz, 1H), 6.98 (d, J=2.1 Hz, 1H), 6.77 (d, J=8.2 Hz, 1H), 6.65 (d, J=8.4 Hz, 1H), 5.99 (s, 2H), 4.66 (s, 2H), 3.84 (t, J=5.6 Hz, 2H), 3.33 (s, 3H), 2.74 (s, 2H), 1.55 (s, 6H); UPLC-MS: t$_R$=2.45 min (generic method); MS (ESI) m/z calcd for C$_{27}$H$_{25}$F$_6$N$_4$O$_4$ (M+H)$^+$: 583.5, found: 583.6.

N-(1,3-Benzodioxol-5-yl)-3-[5-(1-hydroxycyclopropane carbonyl)-3-(trifluoromethyl)-6,7-dihydro-4H-pyrazolo[4,3-c]pyridin-1-yl]-N-methyl-benzamide Following general procedure 1f, the title compound was obtained from compound [002], after purification by silica gel flash-column chromatography with 50% AcOEt in cyclohexane as the eluent, as a white solid in 59% yield. $^1$H NMR spectrum showed a 70:30 mixture of rotamers. Major rotamer: $^1$H NMR (400 MHz, DMSO-d$_6$) δ 7.64-7.36 (m, 4H), 6.98 (d, J=2.1 Hz, 1H), 6.77 (d, J=8.2 Hz, 1H), 6.66 (d, J=8.3 Hz, 1H), 6.45 (s, 1H), 6.01 (s, 2H), 5.09-4.44 (m, 2H), 4.28-3.55 (m, 2H), 3.34 (s, 3H), 2.76-2.61 (m, 2H), 1.10-0.91 (m, 2H), 0.91-0.70 (m, 2H); UPLC-MS: t$_R$=2.00 min (generic method); MS (ESI) m/z calcd for C$_{26}$H$_{24}$F$_3$N$_4$O$_5$ (M+H)$^+$: 529.5, found 529.6.

N-(1,3-Benzodioxol-5-yl)-N-methyl-3-[5-(2-methyl-2-phenyl-propanoyl)-3-(trifluoromethyl)-6,7-dihydro-4H-pyrazolo[4,3-c]pyridin-1-yl]benzamide Following general procedure 1f, the title compound was obtained from compound [002], after purification by silica gel flash-column chromatography with 50% AcOEt in cyclohexane as the eluent, as a white solid in 36% yield. $^1$H NMR spectrum showed a mixture of rotamers. Major rotamer: $^1$H NMR (400 MHz, DMSO-d$_6$) δ 7.74-7.08 (m, 9H), 6.98 (bs, 1H), 6.87-6.68 (m, 1H), 6.66-6.44 (m, 1H), 5.98 (bs, 2H), 4.91-3.97 (m, 2H), 3.88-3.03 (m, 2H), 3.31 (s, 3H), 2.80-2.04 (m, 2H), 1.50 (bs, 6H); UPLC-MS: t$_R$=2.53 min (generic method); MS (ESI) m/z calcd for C$_{32}$H$_{30}$F$_3$N$_4$O$_4$ (M+H)$^+$: 591.6, found: 591.6.

tert-Butyl 1-[3-[(5-fluoro-2-methyl-1,3-benzoxazol-6-yl) carbamoyl]phenyl]-3-(trifluoromethyl)-6,7-dihydro-4H-pyrazolo[4,3-c]pyridine-5-carboxylate Following the general 1b, the title compound was prepared from [Int-1.1] and 5-fluoro-2-methyl-1,3-benzoxazol-6-amine, after purification by silica gel flash-column chromatography with cyclohexane/AcOEt (0 to 50%) as white solid in 58% yield: 1H NMR (400 MHz, DMSO-d$_6$) δ 10.38 (s, 1H), 8.20 (bs, 1H), 8.15-8.06 (m, 1H), 7.97 (d, J=6.3 Hz, 1H), 7.89 (ddd, J=8.1, 2.2, 1.0 Hz, 1H), 7.74 (app-t, J=7.9 Hz, 1H), 7.67 (d, J=10.0 Hz, 1H), 4.54 (s, 2H), 3.65 (app-t, J=5.6 Hz, 2H), 2.93 (app-t, J=5.6 Hz, 2H), 2.63 (s, 3H), 1.45 (s, 9H). UPLC-MS: t$_R$=2.59 min (Generic method); MS (ESI) m/z calcd for C$_{27}$H$_{26}$F$_4$N$_5$O$_4$ (M+H)$^+$: 560.2, found: 560.6.

General Procedure 1j tert-Butyl 1-[3-[(5-fluoro-2-methyl-1,3-benzoxazol-6-yl)-methylcarbamoyl] phenyl]-3-(trifluoromethyl)-6,7-dihydro-4H-pyrazolo[4,3-c]pyridine-5-carboxylate To a solution of [037] (224 mg, 0.40 mmol) in THF (3 mL) NaH (60% dispersion in mineral oil, 48 mg, 1.20 mmol) was added at 0° C. under nitrogen atmosphere and the suspension stirred at the same temperature for 30 min. MeI (170 mg, 1.20 mmol) was added and the mixture stirred at room temperature for 5 h. The suspension was partitioned between EtOAc (50 mL) and H$_2$O (50 mL). The organic phase was separated, washed with brine (50 mL), dried over anhydrous Na$_2$SO$_4$, filtered and the solvent evaporated under reduced pressure. The resultant residue was purified by silica gel flash-column chromatography, eluting with cyclohexane/AcOEt (0 to 50%), to afford the title compound as white solid in 68% yield: 1H NMR (400 MHz, DMSO-d$_6$) δ 8.01 (d, J=6.5 Hz, 1H), 7.60-7.35 (m, 5H), 4.55-4.38 (m, 2H), 3.67-3.42 (m, 2H), 3.38 (s, 3H), 2.64 (s, 3H), 2.53-2.48 (m, 2H). UPLC-MS: t$_R$=2.56 min (Generic method); MS (ESI) m/z calcd for C$_{28}$H$_{28}$F$_4$N$_5$O$_4$ (M+H)$^+$: 574.2, found: 574.5.

N-(1,3-Benzodioxol-5-yl)-N-methyl-3-[3-(trifluoro methyl)-4,5,6,7-tetrahydropyrazolo[3,4-c]pyridin-1-yl]benzamide hydrochloride Following general procedure 1c, the title compound was obtained from compound [027], as a white yellowish solid in 91% yield: $^1$H NMR (400 MHz, DMSO-d$_6$) δ 9.97 (s, 2H), 7.60 (t, J=2.1 Hz, 1H), 7.52 (app-d, J=8.2 Hz, 1H), 7.46 (app-t, J=7.8 Hz, 1H), 7.35 (app-d, J=7.6 Hz, 1H), 6.97 (d, J=2.0 Hz, 1H), 6.84 (d, J=8.2 Hz, 1H), 6.71 (dd, J=8.2, 2.0 Hz, 1H), 6.00 (s, 2H), 4.42 (s, 2H), 3.38 (t, J=6.0 Hz, 2H), 3.34 (s, 3H), 2.96 (t, J=6.0 Hz, 2H). UPLC-MS: t$_R$=1.79 min (Generic method); MS (ESI) m/z calcd for C$_{22}$H$_{20}$F$_3$N$_4$O$_3$ (M+H)$^+$: 445.1, found: 445.5.

N-Methyl-N-(2-methyl-1,3-benzoxazol-6-yl)-3-[5-methyl-3-(trifluoromethyl)-6,7-dihydro-4H-pyrazolo[4,3-c]pyridin-1-yl]benzamide Following general procedure 1d, the title compound was obtained from compound [030], as a white solid in 24% yield: ¹H NMR (400 MHz, DMSO-d₆) δ 7.69 (d, J=2.0 Hz, 1H), 7.52 (d, J=8.4 Hz, 1H), 7.51-7.45 (m, 2H), 7.43-7.38 (m, 2H), 7.19 (dd, J=8.4, 2.0 Hz, 1H), 3.43 (s, 3H), 3.41 (s, 2H), 2.56 (s, 3H), 2.49-2.47 (m, 2H), 2.40-2.33 (m, 5H). UPLC-MS: $t_R$=1.83 min (Generic method); MS (ESI) m/z calcd for $C_{24}H_{23}F_3N_5O_2$ (M+H)⁺: 470.2, found: 470.5.

N-(4-Acetamido-3-hydroxy-phenyl)-N-methyl-3-[5-methyl-3-(trifluoromethyl)-6,7-dihydro-4H-pyrazolo[4,3-c]pyridin-1-yl]benzamide Following general procedure 1d, the title compound was obtained as by-product from compound [030], as a pale yellow solid in 31% yield: ¹H NMR (400 MHz, DMSO-d₆) δ 10.01 (bs, 1H), 9.23 (s, 1H), 7.62 (app-d, J=8.5 Hz, 1H), 7.55 (app-dt, J=8.0, 1.8 Hz, 1H), 7.51-7.37 (m, 3H), 6.70 (d, J=2.4 Hz, 1H), 6.60 (dd, J=8.5, 2.4 Hz, 1H), 3.44 (s, 2H), 3.35 (s, 3H), 2.59 (t, J=5.5 Hz, 2H), 2.48-2.43 (m, 2H), 2.40 (s, 3H), 2.06 (s, 3H). UPLC-MS: $t_R$=1.57 min (Generic method); MS (ESI) m/z calcd for $C_{24}H_{25}F_3N_5O_3$ (M+H)⁺: 488.2, found: 488.6.

Methyl 4-[1-[3-[1,3-benzodioxol-5-yl(methyl)carbamoyl]phenyl]-3-(trifluoromethyl)-6,7-dihydro-4H-pyrazolo[4,3-c]pyridine-5-carbonyl]benzoate Following general procedure 1f, the title compound was obtained from compound [002], after purification by silica gel flash-column chromatography with 60% AcOEt in cyclohexane as the eluent, as a white solid in 80% yield: ¹H NMR spectrum showed a mixture of rotamers. Major rotamer: ¹H NMR (400 MHz, DMSO-d₆) δ 8.08 (d, J=7.9 Hz, 2H), 7.75-7.60 (m, 2H), 7.60-7.51 (m, 2H), 7.51-7.37 (m, 2H), 7.06-6.89 (m, 1H), 6.81-6.59 (m, 1H), 6.09-5.81 (m, 2H), 4.89-4.34 (m, 2H), 4.05-3.91 (m, 1H), 3.90 (s, 3H), 3.63-3.46 (m, 1H), 3.34 (s, 3H), 2.80-2.59 (m, 2H); UPLC-MS: $t_R$=2.25 min (generic method); MS (ESI) m/z calcd for $C_{31}H_{26}F_3N_4O_6$ (M+H)⁺: 607.6, found: 607.5.

Methyl 3-[4-[1-[3-[1,3-benzodioxol-5-yl(methyl) carbamoyl]phenyl]-3-(trifluoromethyl)-6,7-dihydro-4H-pyrazolo[4,3-c]pyridine-5-carbonyl]phenyl]-3-oxo-propanoate Following general procedure 1f, the title compound was obtained from compound [002], after purification by silica gel flash-column chromatography with 60% AcOEt in cyclohexane as the eluent, as a white solid in 72% yield. ¹H NMR spectrum showed a mixture of rotamers in 60:40 ratio. Major rotamer: ¹H NMR (400 MHz, DMSO-d₆) δ 7.57-7.35 (m, 4H), 6.99 (d, J=2.1 Hz, 1H), 6.78 (t, J=8.7 Hz, 1H), 6.71-6.60 (m, 1H), 6.00 (s, 2H), 4.63 (s, 2H), 3.87-3.58 (m, 7H), 3.33 (s, 3H), 2.83-2.69 (m, 1H), 2.62-2.54 (m, 1H); UPLC-MS: $t_R$=2.03 min (generic method); MS (ESI) m/z calcd for $C_{26}H_{24}F_3N_4O_6$ (M+H)⁺: 545.5, found: 545.5.

4-[1-[3-[1,3-Benzodioxol-5-yl(methyl)carbamoyl]phenyl]-3-(trifluoromethyl)-6,7-dihydro-4H-pyrazolo[4,3-c]pyridine-5-carbonyl]benzoic acid Following general procedure 1i, the title compound was obtained from compound [042], after purification by silica gel flash-column chromatography with 50% AcOEt in cyclohexane as the eluent, as a white solid in 40% yield. ¹H NMR spectrum showed a mixture of rotamers. Major rotamer: ¹H NMR (400 MHz, DMSO-d₆) δ 8.06 (d, J=7.8 Hz, 2H), 7.68-7.52 (m, 4H), 7.51-7.35 (m, 2H), 6.96 (bs, 1H), 6.84-6.52 (m, 1H), 6.26-5.71 (m, 2H), 4.96-4.37 (m, 2H), 3.85-2.99 (m, 5H), 2.81-2.60 (m, 2H); UPLC-MS: $t_R$=1.7 min (generic method); MS (ESI) m/z calcd for $C_{30}H_{24}F_3N_4O_6$ (M+H)⁺: 593.5, found: 593.5.

3-[4-[1-[3-[1,3-Benzodioxol-5-yl(methyl)carbamoyl]phenyl]-3-(trifluoromethyl)-6,7-dihydro-4H-pyrazolo[4,3-c]pyridine-5-carbonyl]phenyl]-3-oxo-propanoic acid Following general procedure 1i, the title compound was obtained from compound [043], after purification by silica gel flash-column chromatographyin $CH_2Cl_2$/MeOH (8:2) as eluent, as a white solid in 46% yield. ¹H NMR spectrum showed a mixture of rotamers. Major rotamer: ¹H NMR (400 MHz, DMSO-d₆) δ 7.65-7.33 (m, 4H), 6.98 (d, J=2.1 Hz, 1H), 6.78 (dd, J=14.1, 8.1 Hz, 1H), 6.80 (d, J=8.2 Hz, 1H), 6.02 (d, J=2.0 Hz, 2H), 4.58 (s, 2H), 3.87-3.16 (m, 7H), 2.76-2.59 (m, 2H); UPLC-MS: $t_R$=1.53 min (generic method); MS (ESI) m/z calcd for $C_{25}H_{22}F_3N_4O_6$ (M+H)⁺: 531.1, found: 531.6.

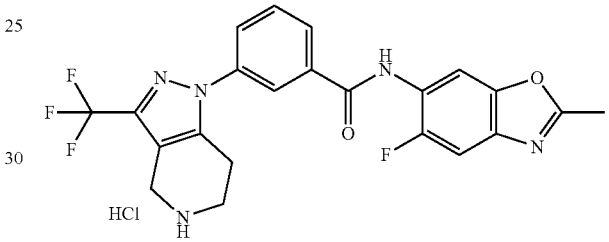

[Int-1.7] N-(5-Fluoro-2-methyl-1,3-benzoxazol-6-yl)-3-[3-(trifluoromethyl)-4,5,6,7-tetrahydropyrazolo[4,3-c]pyridin-1-yl]benzamide hydrochloride Following the general procedure 1c, the title compound was prepared from [037], as a white solid in 62% yield. UPLC-MS: $t_R$=1.66 min (Generic method); MS (ESI) m/z calcd for $C_{22}H_{18}F_4N_5O_2$ (M+H)⁺: 460.1, found: 460.6.

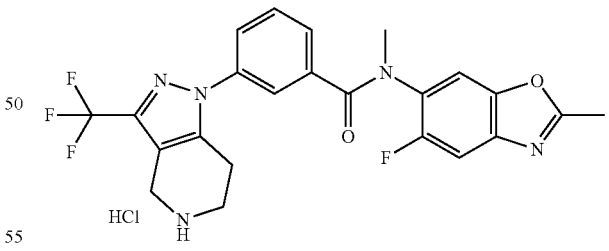

[Int-1.8] N-(5-Fluoro-2-methyl-1,3-benzoxazol-6-yl)-N-methyl-3-[3-(trifluoromethyl)-4,5,6,7-tetrahydropyrazolo[4,3-c]pyridin-1-yl]benzamide hydrochloride Following the general procedure 1c, the title compound was prepared from [036], as a white solid in 52% yield. UPLC-MS: $t_R$=1.67 min (Generic method); MS (ESI) m/z calcd for $C_{23}H_{20}F_4N_5O_2$ (M+H)⁺: 474.1, found: 474.6.

N-(5-Fluoro-2-methyl-1,3-benzoxazol-6-yl)-N-methyl-3-[5-methyl-3-(trifluoromethyl)-6,7-dihydro-4H-pyrazolo[4,3-c]pyridin-1-yl]benzamide Following the general procedure 1d, the title compound was prepared from [Int-1.8]. Subsequent flash chromatography, eluting with DCM/MeOH (0 to 5%), afforded the title compound as white solid in 68% yield: $^1$H NMR (400 MHz, DMSO-$d_6$) δ 8.00 (d, J=6.6 Hz, 1H), 7.61-7.34 (m, 5H), 3.43 (s, 2H), 3.38 (s, 3H), 2.59 (s, 3H), 2.57-2.50 (m, 4H), 2.40 (s, 3H). UPLC-MS: $t_R$=1.94 min (Generic method); MS (ESI) m/z calcd for $C_{24}H_{21}F_4N_5O_2$ (M+H)$^+$: 488.2, found: 488.6.

N-(5-Fluoro-2-methyl-1,3-benzoxazol-6-yl)-3-[5-methyl-3-(trifluoromethyl)-6,7-dihydro-4H-pyrazolo[4,3-c]pyridin-1-yl]benzamide Following the general procedure 1d, the title compound was prepared from [Int-1.7]. Subsequent flash chromatography, eluting with DCM/MeOH (0 to 5%), afforded the title compound as white solid in 78% yield: 1H NMR (400 MHz, DMSO-$d_6$) δ 10.42 (s, 1H), 8.22 (t, J=1.9 Hz, 1H), 8.10 (d, J=7.8 Hz, 1H), 7.98 (d, J=6.4 Hz, 1H), 7.89 (dd, J=8.1, 2.1 Hz, 1H), 7.74 (app-t, J=7.9 Hz, 1H), 7.67 (d, J=10.0 Hz, 1H), 3.50 (s, 2H), 2.94 (app-t, J=5.7 Hz, 2H), 2.69 (app-t, J=5.6 Hz, 2H), 2.64 (s, 3H), 2.43 (bs, 3H). UPLC-MS: $t_R$=1.98 min (Generic method); MS (ESI) m/z calcd for $C_{23}H_{20}F_4N_5O_2$ (M+H)$^+$: 474.1, found: 474.5.

(4R,7S)- or (4S,7R)—N-(Benzo[d][1,3]dioxol-5-yl)-N-methyl-3-(3-(trifluoromethyl)-5,6,7,8-tetrahydro-4,7-epimino cyclohepta [c]pyrazol-1(4H)-yl)benzamide The title compound as pure enantiomer was obtained from the racemate [022], after purification by chiral column chromatography using a column ChiralPak AD, 250×10 mm, 10 μm, 215 nm, Heptane-IPA (75:25) (isocratic) as a mobile phase with a flow rate of 5 mL/min. The pure enantiomer was obtained as a white solid: $^1$H NMR (400 MHz, DMSO-$d_6$) δ 9.96 (bs, 1H), 9.47 (bs, 1H), 7.64-7.52 (m, 2H), 7.47 (t, J=7.8 Hz, 1H), 7.39 (d, J=7.7 Hz, 1H), 6.98 (d, J=2.1 Hz, 1H), 6.80 (d, J=8.2 Hz, 1H), 6.68 (dd, J=8.0, 2.1 Hz, 1H), 6.01 (s, 2H), 5.01 (d, J=4.5 Hz, 1H), 4.38 (bs, 1H), 3.34 (s, 3H), 3.30-3.21 (m, 1H), 2.89 (d, J=16.8 Hz, 1H), 2.36-2.19 (m, 3H), 2.14-2.02 (m, 1H), 1.98-1.86 (m, 1H); $t_R$=15.303 min, >99.5% ee.

(4S,7R)- or (4R,7S)—N-(Benzo[d][1,3]dioxol-5-yl)-N-methyl-3-(3-(trifluoromethyl)-5,6,7,8-tetrahydro-4,7-epiminocyclohepta [c]pyrazol-1(4H)-yl)benzamide The title compound as pure enantiomer was obtained from the racemate [022] after purification by chiral column chromatography using a column ChiralPak AD, 250×10 mm, 10 μm, 215 nm, Heptane-IPA (75:25) (isocratic) as a mobile phase with a flow rate of 5 mL/min. The pure enantiomer was obtained as a white solid: $^1$H NMR (400 MHz, DMSO-$d_6$) δ 9.96 (bs, 1H), 9.47 (bs, 1H), 7.64-7.52 (m, 2H), 7.47 (t, J=7.8 Hz, 1H), 7.39 (d, J=7.7 Hz, 1H), 6.98 (d, J=2.1 Hz, 1H), 6.80 (d, J=8.2 Hz, 1H), 6.68 (dd, J=8.0, 2.1 Hz, 1H), 6.01 (s, 2H), 5.01 (d, J=4.5 Hz, 1H), 4.38 (bs, 1H), 3.34 (s, 3H), 3.30-3.21 (m, 1H), 2.89 (d, J=16.8 Hz, 1H), 2.36-2.19 (m, 3H), 2.14-2.02 (m, 1H), 1.98-1.86 (m, 1H); $t_R$=8.358 min, >99.5% ee.

(4R,7S)- or (4S,7R)—N-(Benzo[d][1,3]dioxol-5-yl)-N-methyl-3-(9-methyl-3-(trifluoromethyl)-5,6,7,8-tetrahydro-4,7-epiminocyclohepta[c]pyrazol-1(4H)-yl)benzamide The title compound was obtained as pure enantiomer from the racemate [023], after purification by chiral column chromatography using a column ChiralPak AD, 250×10 mm, 10 μm, 215 nm, Heptane-IPA (50:50) (isocratic) as a mobile phase with a flow rate of 5 mL/min. The pure enantiomer was obtained as a white solid: $^1$H NMR (400 MHz, DMSO-$d_6$) δ 7.57 (d, J=8.1 Hz, 1H), 7.52 (s, 1H), 7.44 (t, J=7.8 Hz, 1H), 7.39 (d, J=7.7 Hz, 1H), 7.00 (d, J=2.1 Hz, 1H), 6.78 (d, J=8.2 Hz, 1H), 6.65 (d, J=8.4 Hz, 1H), 5.99 (s, 2H), 3.98 (s, 1H), 3.46 (s, 1H), 3.33 (s, 3H), 3.10-2.83 (m, 3H), 2.23 (s, 3H), 2.17-1.98 (m, 3H), 1.68 (t, J=9.1 Hz, 1H), 1.52-1.38 (m, 1H); $t_R$=10.777 min, >99.5% ee.

(4S,7R)- or (4R,7S)—N-(Benzo[d][1,3]dioxol-5-yl)-N-methyl-3-(9-methyl-3-(trifluoromethyl)-5,6,7,8-tetrahydro-4,7-epiminocyclohepta[c]pyrazol-1(4H)-yl)benzamide The title compound was obtained as pure enantiomer from the racemate [023], after purification by chiral column chromatography using a column ChiralPak AD, 250×10 mm, 10 μm, 215 nm, Heptane-IPA (50:50) (isocratic) as a mobile phase with a flow rate of 5 mL/min. The pure enantiomer was obtained as a white solid: $^1$H NMR (400 MHz, DMSO-$d_6$) δ 7.57 (d, J=8.1 Hz, 1H), 7.52 (s, 1H), 7.44 (t, J=7.8 Hz, 1H), 7.39 (d, J=7.7 Hz, 1H), 7.00 (d, J=2.1 Hz, 1H), 6.78 (d, J=8.2 Hz, 1H), 6.65 (d, J=8.4 Hz, 1H), 5.99 (s, 2H), 3.98 (s, 1H), 3.46 (s, 1H), 3.33 (s, 3H), 3.10-2.83 (m, 3H), 2.23 (s, 3H), 2.17-1.98 (m, 3H), 1.68 (t, J=9.1 Hz, 1H), 1.52-1.38 (m, 1H); $t_R$=5.289 min, >99.5% ee.

(4R,7S)- or (4S,7R)-tert-Butyl-1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate The title compound was obtained as pure enantiomer from the racemate [018], after purification by chiral column chromatography using a column ChiralPak AD, 250×10 mm, 10 μm, 215 nm, Heptane-IPA (98:2) (isocratic) as a mobile phase with a flow rate of 5 mL/min. The pure enantiomer was obtained as a pale yellow solid: $^1$H NMR (400 MHz, DMSO-$d_6$) δ 7.63-7.48 (m, 2H), 7.49-7.34 (m, 2H), 6.98 (d, J=2.1 Hz, 1H), 6.77 (d, J=8.2 Hz, 1H), 6.65 (dd, J=8.2, 2.1 Hz, 1H), 6.00 (d, J=1.7 Hz, 2H), 4.96 (s, 1H), 4.45 (dd, J=8.0, 4.5 Hz, 1H), 3.34 (s, 3H), 3.19-2.99 (m, 1H), 2.41 (d, J=16.4 Hz, 1H), 2.30-2.18 (m, 1H), 2.18-2.03 (m, 1H), 1.83 (s, 1H), 1.73-1.57 (m, 1H), 1.35 (s, 9H); $t_R$=88.915 min, >99.5% ee.

(4S,7R)- or (4R,7S)-tert-Butyl-1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate The title compound was obtained as pure enantiomer from the racemate [018], after purification by chiral column chromatography using a column ChiralPak AD, 250×10 mm, 10 μm, 215 nm, Heptane-IPA (98:2) (isocratic) as a mobile phase with a flow rate of 5 mL/min: The pure enantiomer was obtained as a pale yellow solid. $^1$H NMR (400 MHz, DMSO-$d_6$) δ 7.63-7.48 (m, 2H), 7.49-7.34 (m, 2H), 6.98 (d, J=2.1 Hz, 1H), 6.77 (d, J=8.2 Hz, 1H), 6.65 (dd, J=8.2, 2.1 Hz, 1H), 6.00 (d, J=1.7 Hz, 2H), 4.96 (s, 1H), 4.45 (dd, J=8.0, 4.5 Hz, 1H), 3.34 (s, 3H), 3.19-2.99 (m, 1H), 2.41 (d, J=16.4 Hz, 1H), 2.30-2.18 (m, 1H), 2.18-2.03 (m, 1H), 1.83 (s, 1H), 1.73-1.57 (m, 1H), 1.35 (s, 9H); $t_R$=70.495 min, >99.5% ee.

N-(1,3-Benzodioxol-5-yl)-N-methyl-3-[3-(trifluoro methyl)-6,7-dihydro-4H-pyrano[4,3-c]pyrazol-1-yl]benzamide Following general procedure 1b, the title compound was obtained from [Int-1.2], after purification by silica gel flash-column chromatography with 45% AcOEt in Cyclohexane as eluent, as a white solid in 27% yield. $^1$H NMR (400 MHz, DMSO-$d_6$) δ 7.65-7.33 (m, 4H), 6.99 (d, J=2.1 Hz, 1H), 6.78 (d, J=8.2 Hz, 1H), 6.66 (dd, J=8.2, 2.1 Hz, 1H), 5.99 (s, 2H), 4.71 (s, 2H), 3.84 (t, J=5.4 Hz, 2H), 3.34 (s, 3H), 2.74-2.59 (m, 2H); UPLC-MS: $t_R$=2.20 min (generic method); MS (ESI) m/z calcd for $C_{22}H_{19}F_3N_3O_4$ (M+H)$^+$: 446.1, found: 446.5.

Methyl 4-[[1-[3-[1,3-benzodioxol-5-yl(methyl) carbamoyl]phenyl]-3-(trifluoromethyl)-6,7-dihydro-4H-pyrazolo[4,3-c]pyridin-5-yl]sulfonyl]benzoate Following general procedure 1e, the title compound was obtained from compound [002], after purification by silica gel flash-column chromatography with 60% AcOEt in cyclohexane as eluent, as a white solid in 63% yield. $^1$H NMR (400 MHz, DMSO-$d_6$) δ 8.28-8.09 (m, 2H), 8.07-7.91 (m, 2H), 7.52-7.31 (m, 4H), 6.99 (d, J=2.1 Hz, 1H), 6.78 (d, J=8.2 Hz, 1H), 6.63 (d, J=8.2 Hz, 1H), 6.01 (s, 2H), 4.33 (s, 2H), 3.91 (s, 3H), 3.48 (t, J=5.8 Hz, 2H), 3.33 (s, 3H), 2.66-2.59 (m, 2H); UPLC-MS: $t_R$=2.42 min (generic method); MS (ESI) m/z calcd for $C_{30}H_{26}F_3N_4O_7S$ (M+H)$^+$: 643.6, found: 643.5.

4-[[1-[3-[1,3-Benzodioxol-5-yl(methyl)carbamoyl]phenyl]-3-(trifluoromethyl)-6,7-dihydro-4H-pyrazolo[4,3-c]pyridin-5-yl]sulfonyl]benzoic acid Following general procedure 1i, the title compound was obtained from compound [055], after purification by silica gel flash-column chromatography in CH$_2$Cl$_2$/MeOH (8:2) as eluent, as a white solid in 44% yield: $^1$H NMR (400 MHz, DMSO-$d_6$) δ 8.10 (d, J=8.4 Hz, 2H), 7.89 (d, J=8.3 Hz, 2H), 7.53-7.32 (m, 4H), 7.00 (d, J=2.1 Hz, 1H), 6.78 (d, J=8.2 Hz, 1H), 6.63 (d, J=7.6 Hz, 1H), 6.01 (s, 2H), 4.29 (bs, 2H), 3.44 (t, J=5.7 Hz, 11H), 3.33 (s, 3H), 2.63 (bs, 2H); UPLC-MS: $t_R$=1.53 min (generic method); MS (ESI) m/z calcd for $C_{29}H_{24}F_3N_4O_7S$ (M+H)$^+$: 629.6, found: 629.6.

N-(1,3-Benzodioxol-5-yl)-3-[5-(2-hydroxy-2-methyl-propanoyl)-3-(trifluoromethyl)-6,7-dihydro-4H-pyrazolo[4,3-c]pyridin-1-yl]-N-methyl-benzamide Following general procedure 1f, the title compound was obtained from compound [002], after purification by silica gel flash-column chromatography with 60% AcOEt in cyclohexane as eluent, as a white solid in 24% yield. $^1$H NMR spectrum showed a mixture of rotamers. Major rotamer: $^1$H NMR (400 MHz, DMSO-$d_6$) δ 7.59-7.35 (m, 4H), 6.98 (d, J=2.1 Hz, 1H), 6.77 (d, J=8.2 Hz, 1H), 6.65 (d, J=8.3 Hz, 1H), 6.01 (s, 2H), 5.55 (s, 1H), 5.24-4.49 (m, 2H), 4.26-3.63 (m, 2H), 3.34 (s, 3H), 2.73-2.59 (m, 2H), 1.37 (s, 6H); UPLC-MS: $t_R$=2.00 min (generic method); MS (ESI) m/z calcd for $C_{26}H_{26}F_3N_4O_5$ (M+H)$^+$: 531.5, found: 531.5.

Methyl 3-[[1-[3-[1,3-benzodioxol-5-yl(methyl) carbamoyl]phenyl]-3-(trifluoromethyl)-6,7-dihydro-4H-pyrazolo[4,3-c]pyridin-5-yl]sulfonyl]benzoate Following general procedure 1e, the title compound was obtained from compound [002], after purification by silica gel flash-column chromatography with 50% AcOEt in cyclohexane as eluent, as a white solid in 33% yield. $^1$H NMR (400 MHz, DMSO-$d_6$) δ 8.28-8.19 (m, 2H), 8.14 (dt, J=8.0, 1.4 Hz, 1H), 7.78 (t, J=7.8 Hz, 1H), 7.53-7.28 (m, 4H), 6.99 (d, J=2.1 Hz, 1H), 6.78 (d, J=8.2 Hz, 1H), 6.63 (d, J=7.5 Hz, 1H), 6.01 (s, 2H), 4.36 (s, 2H), 3.90 (s, 3H), 3.51 (t, J=5.8 Hz, 2H), 3.33 (s, 3H), 2.65-2.54 (m, 2H); UPLC-MS: $t_R$=2.46 min (generic method); MS (ESI) m/z calcd for $C_{30}H_{26}F_3N_4O_7S$ (M+H)$^+$: 643.1, found: 643.5.

Methyl 2-[[1-[3-[1,3-benzodioxol-5-yl(methyl) carbamoyl]phenyl]-3-(trifluoromethyl)-6,7-dihydro-4H-pyrazolo[4,3-c]pyridin-5-yl]sulfonyl]benzoate Following general procedure 1e, the title compound was obtained from compound [002], after purification by silica gel flash-column chromatography with 50% AcOEt in cyclohexane as eluent, as a white solid in 73% yield: $^1$H NMR (400 MHz, DMSO-$d_6$) δ 7.97 (dd, J=7.6, 1.6 Hz, 1H), 7.86-7.70 (m, 2H), 7.66 (dd, J=7.3, 1.8 Hz, 1H), 7.55-7.31 (m, 4H), 6.99 (d, J=2.1 Hz, 1H), 6.77 (d, J=8.2 Hz, 1H), 6.65 (d, J=8.3 Hz, 1H), 6.01 (s, 2H), 4.39 (s, 2H), 3.86 (s, 3H), 3.55 (t, J=5.7 Hz, 2H), 3.33 (s, 3H), 2.76-2.60 (m, 2H); UPLC-MS: $t_R$=2.42 min (generic method); MS (ESI) m/z calcd for $C_{30}H_{26}F_3N_4O_7S$ (M+H)$^+$: 643.6, found: 643.5.

3-[[1-[3-[1,3-Benzodioxol-5-yl(methyl)carbamoyl]phenyl]-3-(trifluoromethyl)-6,7-dihydro-4H-pyrazolo[4,3-c]pyridin-5-yl]sulfonyl]benzoic acid Following general procedure 1i, the title compound was obtained from compound [059], after purification by silica gel flash-column chromatography in CH$_2$Cl$_2$/MeOH (8:2) as eluent, as a white solid in 54% yield: $^1$H NMR (400 MHz, DMSO-$d_6$) δ 13.59 (s, 1H), 8.25 (t, J=1.8 Hz, 1H), 8.21 (dt, J=7.7, 1.4 Hz, 1H), 8.07 (dt, J=8.0, 1.4 Hz, 1H), 7.74 (t, J=7.8 Hz, 1H), 7.64-7.30 (m, 4H), 6.99 (d, J=2.1 Hz, 1H), 6.78 (d, J=8.2 Hz, 1H), 6.62 (d, J=7.7 Hz, 1H), 6.01 (s, 2H), 4.32 (s, 2H), 3.48 (t, J=5.7 Hz, 2H), 3.33 (s, 3H), 2.65-2.54 (m, 2H); UPLC-MS: $t_R$=1.81 min (generic method); MS (ESI) m/z calcd for $C_{29}H_{24}F_3N_4O_7S$ (M+H)$^+$: 629.6, found: 629.6.

2-[[1-[3-[1,3-Benzodioxol-5-yl(methyl)carbamoyl]phenyl]-3-(trifluoromethyl)-6,7-dihydro-4H-pyrazolo[4,3-c]pyridin-5-yl]sulfonyl]benzoic acid Following general procedure 1i, the title compound was obtained from compound [060], after purification by silica gel flash-column chromatography in CH$_2$Cl$_2$/MeOH (8:2) as eluent, as a white solid in 45% yield: $^1$H NMR (400 MHz, DMSO-$d_6$) δ 7.85 (d, J=8.0 Hz, 1H), 7.65 (t, J=7.4 Hz, 1H), 7.54 (t, J=7.7 Hz, 1H), 7.51-7.30 (m, 5H), 6.99 (d, J=2.1 Hz, 1H), 6.76 (d, J=8.2 Hz, 1H), 6.63 (d, J=7.3 Hz, 1H), 6.01 (s, 2H), 4.44 (s, 2H), 3.55 (t, J=5.7 Hz, 2H), 3.33 (s, 3H), 2.71-2.57 (m, 2H); UPLC-MS: $t_R$=1.70 min (generic method); MS (ESI) m/z calcd for $C_{29}H_{24}F_3N_4O_7S$ (M+H)$^+$: 629.6, found: 629.5.

N-(1,3-Benzodioxol-5-yl)-3-[5-(4-cyanophenyl)sulfonyl-3-(trifluoromethyl)-6,7-dihydro-4H-pyrazolo[4,3-c]pyridin-1-yl]-N-methyl-benzamide Following general procedure 1e, the title compound was obtained from compound [002], after purification by silica gel flash-column chromatography with 50% AcOEt in cyclohexane as eluent, as a white solid in 88% yield: $^1$H NMR (400 MHz, DMSO-$d_6$) δ 8.12 (d, J=8.5 Hz, 2H), 8.05 (d, J=8.5 Hz, 2H), 7.70-7.23 (m, 4H), 7.00 (d, J=2.1 Hz, 1H), 6.78 (d, J=8.2 Hz, 1H), 6.64 (d, J=7.8 Hz, 1H), 6.01 (s, 2H), 4.33 (s, 2H), 3.47 (t, J=5.7 Hz, 2H), 3.33 (s, 3H), 2.77-2.58 (m, 2H); UPLC-MS: $t_R$=2.40 min (generic method); MS (ESI) m/z calcd for $C_{29}H_{23}F_3N_5O_5S$ (M+H)$^+$: 610.6, found: 610.5.

N-(1,3-Benzodioxol-5-yl)-3-[5-(1,2-dimethylimidazol-4-yl)sulfonyl-3-(trifluoromethyl)-6,7-dihydro-4H-pyrazolo[4,3-c]pyridin-1-yl]-N-methyl-benzamide Following general procedure 1e, the title compound was obtained from compound [002], after purification by silica gel flash-column chromatography in $CH_2Cl_2$/MeOH (8:2) as eluent, as a white solid in 44% yield: $^1$H NMR (400 MHz, DMSO-$d_6$) δ 7.81 (s, 1H), 7.62-7.21 (m, 4H), 7.01 (d, J=2.1 Hz, 1H), 6.77 (d, J=8.2 Hz, 1H), 6.64 (d, J=8.0 Hz, 1H), 6.02 (s, 2H), 4.28 (s, 2H), 3.58 (s, 3H), 3.43 (t, J=5.8 Hz, 2H), 3.34 (s, 3H), 2.84-2.58 (m, 2H), 2.23 (s, 3H); UPLC-MS: $t_R$=2.09 min (generic method); MS (ESI) m/z calcd for $C_{27}H_{26}F_3N_6O_5S$ (M+H)$^+$: 603.6, found: 603.5.

N-(1,3-Benzodioxol-5-yl)-3-[5-(3,5-dimethylisoxazol-4-yl)sulfonyl-3-(trifluoromethyl)-6,7-dihydro-4H-pyrazolo [4,3-c]pyridin-1-yl]-N-methyl-benzamide Following general procedure 1e, the title compound was obtained from compound [002], after purification by silica gel flash-column chromatography with 30% AcOEt in cyclohexane as eluent, as a white solid in 81% yield: $^1$H NMR (400 MHz, DMSO-$d_6$) δ 7.70-7.49 (m, 2H), 7.49-7.31 (m, 1H), 7.00 (d, J=2.1 Hz, 1H), 6.78 (d, J=8.2 Hz, 1H), 6.66 (d, J=8.2 Hz, 1H), 6.00 (s, 2H), 4.38 (s, 2H), 3.51 (t, J=5.7 Hz, 2H), 3.33 (s, 3H), 2.86-2.68 (m, 2H), 2.67 (s, 3H), 2.36 (s, 3H); UPLC-MS: $t_R$=2.42 min (generic method); MS (ESI) m/z calcd for $C_{27}H_{25}F_3N_5O_6S$ (M+H)$^+$: 604.66, found: 604.4.

N-(1,3-Benzodioxol-5-yl)-3-[5-(2-methoxyethyl sulfonyl)-3-(trifluoromethyl)-6,7-dihydro-4H-pyrazolo[4,3-c]pyridin-1-yl]-N-methyl-benzamide Following general procedure 1e, the title compound was obtained from compound [002], after purification by silica gel flash-column chromatography with 60% AcOEt in cyclohexane as eluent, as a white solid in 74% yield: $^1$H NMR (400 MHz, DMSO-$d_6$) δ 7.71-7.50 (m, 2H), 7.50-7.33 (m, 2H), 7.02 (d, J=2.1 Hz, 1H), 6.77 (d, J=8.2 Hz, 1H), 6.65 (d, J=7.7 Hz, 1H), 6.01 (s, 2H), 4.40 (s, 2H), 3.69 (t, J=5.8 Hz, 2H), 3.50 (t, J=5.9 Hz, 2H), 3.33 (s, 3H), 3.24 (s, 3H), 2.79-2.59 (m, 2H); UPLC-MS: $t_R$=2.21 min (generic method); MS (ESI) m/z calcd for $C_{25}H_{26}F_3N_4O_6S$ (M+H)$^+$: 567.5, found: 567.5.

N-(1,3-Benzodioxol-5-yl)-3-[5-[(3,5-dimethyl-4H-pyrazol-4-yl) sulfonyl]-3-(trifluoromethyl)-6,7-dihydro-4H-pyrazolo[4,3-c]pyridin-1-yl]-N-methyl-benzamide Following general procedure 1e, the title compound was obtained from compound [002], after purification by silica gel flash-column chromatography with 80% AcOEt in cyclohexane as eluent, as a white solid in 56% yield: $^1$H NMR (400 MHz, DMSO-$d_6$) δ 13.14 (s, 1H), 7.64-7.33 (m, 4H), 7.00 (d, J=2.1 Hz, 1H), 6.77 (d, J=8.2 Hz, 1H), 6.65 (d, J=8.3 Hz, 1H), 6.00 (s, 2H), 4.21 (s, 2H), 3.38 (t, J=5.6 Hz, 2H), 3.33 (s, 3H), 2.71-2.58 (m, 2H), 2.40 (s, 3H), 2.29 (s, 3H); UPLC-MS: $t_R$=2.12 min (generic method); MS (ESI) m/z calcd for $C_{27}H_{26}F_3N_6O_5S$ (M+H)$^+$: 603.6, found: 603.5.

Methyl 4-((1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazol-9-yl)sulfonyl)benzoate Following general procedure 1e, the title compound was obtained from compound [022], after purification by silica gel flash-column chromatography with 50% AcOEt in cyclohexane as eluent, as a white solid in 55% yield: $^1$H NMR (400 MHz, DMSO-$d_6$) δ 7.92-7.84 (m, 2H), 7.79 (d, J=8.4 Hz, 2H), 7.46-7.29 (m, 2H), 7.29-7.11 (m, 2H), 7.00 (d, J=2.1 Hz, 1H), 6.84 (d, J=8.3 Hz, 1H), 6.61 (d, J=7.4 Hz, 1H), 6.06 (dd, J=4.3, 0.9 Hz, 2H), 5.05 (d, J=5.7 Hz, 1H), 4.56 (d, J=7.7 Hz, 1H), 3.88 (s, 3H), 3.34 (s, 3H), 2.63-2.54 (m, 2H), 2.27-2.10 (m, 2H), 2.07-1.95 (m, 1H), 1.92-1.79 (m, 1H), 1.79-1.66 (m, 1H); UPLC-MS: $t_R$=2.47 min (generic method); MS (ESI) m/z calcd for $C_{32}H_{28}F_3N_4O_7S$ (M+H)$^+$: 669.2, found: 669.5.

N-(1,3-Benzodioxol-5-yl)-3-[6-(2,2-dimethylpropanoyl)-3-(trifluoromethyl)-5,7-dihydro-4H-pyrazolo[3,4-c]pyridin-1-yl]-N-methyl-benzamide Following general procedure 1f, the title compound was obtained from compound [038], after purification by silica gel flash-column chromatography with 10% AcOEt in cyclohexane as eluent, as a white solid in 49% yield: $^1$H NMR (400 MHz, DMSO-$d_6$) δ 7.60-7.42 (m, 3H), 7.36 (d, J=7.3 Hz, 1H), 6.96 (d, J=2.1 Hz, 1H), 6.76 (d, J=8.2 Hz, 1H), 6.67 (d, J=8.2 Hz, 1H), 5.98 (s, 2H), 4.61 (s, 2H), 3.89 (t, J=5.8 Hz, 2H), 3.32 (s, 3H), 2.73 (t, J=4.9 Hz, 2H), 1.20 (s, 9H); UPLC-MS: $t_R$=2.45 min (generic method); MS (ESI) m/z calcd for $C_{27}H_{28}F_3N_4O_4$ (M+H)$^+$: 529.2, found: 529.5.

N-(1,3-Benzodioxol-5-yl)-3-[5-(2,4-dimethylpyrazol-3-yl) sulfonyl-3-(trifluoromethyl)-6,7-dihydro-4H-pyrazolo [4,3-c]pyridin-1-yl]-N-methyl-benzamide Following general procedure 1e, the title compound was obtained from compound [002], after purification by silica gel flash-column chromatography with 40% AcOEt in cyclohexane as eluent, as a white solid in 55% yield: $^1$H NMR (400 MHz, DMSO-$d_6$) δ 7.58-7.32 (m, 5H), 6.98 (d, J=2.1 Hz, 1H), 6.76 (d, J=8.2 Hz, 1H), 6.65 (d, J=8.2 Hz, 1H), 5.98 (s, 2H), 4.41 (s, 2H), 3.99 (s, 3H), 3.55 (t, J=5.7 Hz, 2H), 3.32 (s, 3H), 2.77-2.57 (m, 2H), 2.21 (s, 3H); UPLC-MS: $t_R$=2.34 min (generic method); MS (ESI) m/z calcd for $C_{27}H_{26}F_3N_6O_5S$ (M+H)$^+$: 603.2, found: 603.4.

N-(1,3-Benzodioxol-5-yl)-N-methyl-3-[3-(trifluoromethyl)-5-(1,3,5-trimethylpyrazol-4-yl)sulfonyl-6,7-dihydro-4H-pyrazolo[4,3-c]pyridin-1-yl]benzamide Following general procedure 1e, the title compound was obtained from compound [002], after purification by silica gel flash-column chromatography with 70% AcOEt in cyclohexane as eluent, as a white solid in 62% yield: $^1$H NMR (400 MHz, DMSO-$d_6$) δ 7.60-7.32 (m, 4H), 7.00 (d, J=2.1 Hz, 1H), 6.76 (d, J=8.3 Hz, 1H), 6.64 (d, J=8.2 Hz, 1H), 5.99 (s, 2H), 4.19 (s, 2H), 3.71 (s, 3H), 3.40-3.33 (m, 2H), 2.73-2.58 (m, 2H), 2.43 (s, 3H), 2.27 (s, 3H); UPLC-MS: $t_R$=2.2 min (generic method); MS (ESI) m/z calcd for $C_{28}H_{28}F_3N_6O_5S$ (M+H)$^+$: 617.2, found: 617.4.

Methyl 4-[[1-[3-[1,3-benzodioxol-5-yl(methyl) carbamoyl]phenyl]-3-(trifluoromethyl)-5,7-dihydro-4H-pyrazolo[3,4-c]pyridin-6-yl]sulfonyl]benzoate Following general procedure 1e, the title compound was obtained from compound [038], after purification by silica gel flash-column chromatography in $CH_2Cl_2$/MeOH (8:2) as eluent, as a white solid in 61% yield: $^1$H NMR (400 MHz, DMSO-$d_6$) δ 8.09-8.03 (m, 2H), 7.87-7.74 (m, 2H), 7.59-7.33 (m, 4H), 7.00 (d, J=2.1 Hz, 1H), 6.76 (d, J=8.2 Hz, 1H), 6.69 (d, J=8.5 Hz, 1H), 5.97 (s, 2H), 4.47 (s, 2H), 3.90 (s, 3H), 3.57 (t, J=6.0 Hz, 2H), 3.34 (s, 3H), 2.57 (t, J=6.0 Hz, 2H); UPLC-MS: $t_R$=2.41 min (generic method); MS (ESI) m/z calcd for $C_{30}H_{26}F_3N_4O_7S$ (M+H)$^+$: 643.1, found: 643.4.

N-(1,3-Benzodioxol-5-yl)-N-methyl-3-[5-tetrahydro pyran-4-ylsulfonyl-3-(trifluoromethyl)-6,7-dihydro-4H-pyrazolo[4,3-c]pyridin-1-yl]benzamide Following general procedure 1e, the title compound was obtained from compound [002], after purification by silica gel flash-column chromatography with in $CH_2Cl_2$/MeOH (8:2) as eluent, as a white solid in 24% yield: $^1$H NMR (400 MHz, DMSO-$d_6$) δ 7.59-7.31 (m, 4H), 7.00 (d, J=2.1 Hz, 1H), 6.76 (d, J=8.2 Hz, 1H), 6.64 (d, J=8.3 Hz, 1H), 6.00 (s, 2H), 4.46 (s, 2H), 4.09-3.82 (m, 2H), 3.73-3.48 (m, 3H), 3.42-3.30 (m, 5H), 2.79-2.58 (m, 2H), 1.99-1.80 (m, 2H), 1.66 (qd, J=12.2, 4.6 Hz, 2H); UPLC-MS: $t_R$=2.18 min (generic method); MS (ESI) m/z calcd for $C_{27}H_{28}F_3N_4O_6S$ (M+H)$^+$: 593.2, found: 593.4.

4-[[1-[3-[1,3-Benzodioxol-5-yl(methyl)carbamoyl]phenyl]-3-(trifluoromethyl)-5,7-dihydro-4H-pyrazolo[3,4-c]pyridin-6-yl]sulfonyl]benzoic acid Following general procedure 1i, the title compound was obtained from compound [075], after purification by silica gel flash-column chromatography in $CH_2Cl_2$:MeOH (8:2) as eluent, as a white solid in 62% yield: $^1$H NMR (400 MHz, DMSO-$d_6$) δ 13.47 (s, 1H), 8.07-7.99 (m, 2H), 7.77 (d, J=8.4 Hz, 2H), 7.61-7.32 (m, 4H), 6.99 (d, J=2.0 Hz, 1H), 6.82-6.64 (m, 2H), 5.97 (s, 2H), 4.46 (s, 2H), 3.56 (t, J=6.0 Hz, 2H), 3.34 (s, 3H), 2.63-2.54 (m, 2H); UPLC-MS: $t_R$=1.79 min (generic method); MS (ESI) m/z calcd for $C_{29}H_{24}F_3N_4O_7S$ (M+H)$^+$: 629.12, found: 629.4.

General Procedure 1k tert-Butyl 3-[4-[[1-[3-[1,3-benzodioxol-5-yl(methyl) carbamoyl]phenyl]-3-(trifluoromethyl)-6,7-dihydro-4H-pyrazolo[4,3-c]pyridin-5-yl]sulfonyl]-3,5-dimethyl-pyrazol-1-yl]propanoate To a solution of [069] (75 mg, 0.12 mmol) in DMF (1 mL) at room temperature, cesium carbonate (81 mg, 0.25 mmol) was added and the suspension stirred at the same temperature for 30 min. Tert-butyl 3-bromopropanoate (42 μL, 0.25 mmol) was added and the mixture stirred at room temperature for 14 h. The suspension was partitioned between EtOAc (20 mL) and $H_2O$ (20 mL). The organic phase was separated, washed with brine (50 mL), dried over anhydrous $Na_2SO_4$, filtered and the solvent evaporated under reduced pressure. The resultant residue was purified by silica gel flash-column chromatography, eluting with cyclohexane/AcOEt (0 to 20%) to afford the title compound as white solid in 70% yield: $^1$H NMR (400 MHz, DMSO-$d_6$) δ 7.55-7.35 (m, 4H), 7.00 (d, J=2.1 Hz, 1H), 6.76 (d, J=8.2 Hz, 1H), 6.64 (d, J=8.2 Hz, 1H), 5.99 (s, 2H), 4.20 (t, J=6.5 Hz, 2H), 4.15 (s, 2H), 3.41-3.33 (m, 2H), 3.32 (s, 3H), 2.74 (t, J=6.5 Hz, 2H), 2.71-2.60 (m, 2H), 2.48 (s, 3H), 2.28 (s, 3H), 1.31 (s, 9H); UPLC-MS: $t_R$=2.64 min (generic method); MS (ESI) m/z calcd for $C_{34}H_{38}F_3N_6O_7S$ (M+H)$^+$: 731.2, found: 731.5.

General Procedure 1l

3-[4-[[1-[3-[1,3-Benzodioxol-5-yl(methyl)carbamoyl]phenyl]-3-(trifluoromethyl)-6,7-dihydro-4H-pyrazolo[4,3-c]pyridin-5-yl]sulfonyl]-3,5-dimethyl-pyrazol-1-yl]propanoic acid Compound [082] (52 mg, 0.072 mmol) was dissolved in a solution 10% TFA in $CH_2Cl_2$ (1.7 mL) at room temperature and the mixture was stirred for 3 h at the same temperature. The solvent was evaporated under reduced pressure and the resultant residue was purified by silica gel flash-column chromatography in $CH_2Cl_2$/MeOH (8:2) as eluent, to afford the title compound as a white solid in 68% yield: $^1$H NMR (400 MHz, DMSO-$d_6$) δ 12.36 (s, 1H), 7.59-7.34 (m, 4H), 7.00 (d, J=2.2 Hz, 1H), 6.77 (d, J=8.2 Hz, 1H), 6.65 (d, J=8.2 Hz, 1H), 6.00 (s, 2H), 4.34-4.06 (m, 4H), 3.34 (d, J=8.3 Hz, 5H), 2.78 (t, J=6.7 Hz, 2H), 2.71-2.61 (m, 2H), 2.49 (s, 3H), 2.29 (s, 3H); UPLC-MS: $t_R$=1.88 min (generic method); MS (ESI) m/z calcd for $C_{30}H_{30}F_3N_6O_7S$ (M+H)$^+$: 675.2, found: 675.5.

(4R,7S)- or (4S,7R)—N-(Benzo[d][1,3]dioxol-5-yl)-N-methyl-3-[(9-pivaloyl-3-(trifluoromethyl)-5,6,7,8-tetrahydro-4,7-epiminocyclohepta[c]pyrazol-1(4H)-yl)]benzamide Following general procedure 1f, the title compound was obtained as pure enantiomer from compound [048], after purification by silica gel flash-column chromatography with 60% AcOEt in cyclohexane as eluent, as a white solid in 60% yield: $^1$H NMR (400 MHz, DMSO-$d_6$) δ 7.62-7.49 (m, 2H), 7.47-7.31 (m, 2H), 6.98 (d, J=2.1 Hz, 1H), 6.76 (d, J=8.2 Hz, 1H), 6.64 (app-d, J=8.2 Hz, 1H), 6.00 (dd, J=5.2, 1.0 Hz, 2H), 5.55-5.35 (m, 1H), 4.97-4.77 (m, 1H), 3.32 (s, 3H), 3.14 (dd, J=16.3, 4.5 Hz, 1H), 2.43 (d, J=16.4 Hz, 1H), 2.24-2.04 (m, 2H), 1.97-1.80 (m, 1H), 1.74-1.53 (m, 1H), 1.16 (s, 9H); UPLC-MS: $t_R$=2.55 min (generic method); MS (ESI) m/z calcd for $C_{29}H_{30}F_3N_4O_4$ (M+H)$^+$: 555.2, found: 555.5. Analytical chiral column chromatography was performed using Heptane-EtOH (90:10) (isocratic) as a mobile phase with a flow rate of 1 mL/min: $t_R$=18.662 min, >99.5% ee.

(4R,7S)- or (4S,7R)—N-(Benzo[d][1,3]dioxol-5-yl)-N-methyl-3-[(9-pivaloyl-3-(trifluoromethyl)-5,6,7,8-tetrahydro-4,7-epiminocyclohepta[c]pyrazol-1(4H)-yl)]benzamide Following general procedure 1f, the title compound was obtained as pure enantiomer from compound [049], after purification by silica gel flash-column chromatography with 60% AcOEt in cyclohexane as eluent, as a white solid in 50% yield: $^1$H NMR (400 MHz, DMSO-$d_6$) δ 7.62-7.49 (m, 2H), 7.47-7.31 (m, 2H), 6.98 (d, J=2.1 Hz, 1H), 6.76 (d, J=8.2 Hz, 1H), 6.64 (app-d, J=8.2 Hz, 1H), 6.00 (dd, J=5.2, 1.0 Hz, 2H), 5.55-5.35 (m, 1H), 4.97-4.77 (m, 1H), 3.32 (s, 3H), 3.14 (dd, J=16.3, 4.5 Hz, 1H), 2.43 (d, J=16.4 Hz, 1H), 2.24-2.04 (m, 2H), 1.97-1.80 (m, 1H), 1.74-1.53 (m, 1H), 1.16 (s, 9H); UPLC-MS: $t_R$=2.55 min (generic method); MS (ESI) m/z calcd for $C_{29}H_{30}F_3N_4O_4$ (M+H)$^+$: 555.2, found: 555.5. Analytical chiral column chromatography was performed using Heptane-EtOH (90:10) (isocratic) as a mobile phase with a flow rate of 1 mL/min: $t_R$=16.075 min, >99.5% ee.

4-[[1-[3-[1,3-Benzodioxol-5-yl(methyl)carbamoyl] phenyl]-3-(trifluoromethyl)-6,7-dihydro-4H-pyrazolo[4,3-c]pyridin-5-yl]sulfonyl]-5-methyl-1H-pyrazole-3-carboxylic acid Following general procedure 1e, the title compound was obtained from compound [002], after purification by silica gel flash-column chromatography in CH$_2$Cl$_2$/MeOH (8:2) as eluent, as a white solid in 23% yield: $^1$H NMR (400 MHz, DMSO-d$_6$) δ 13.82 (bs, 1H), 12.93 (bs, 1H), 7.61-7.35 (m, 4H), 7.00 (d, J=2.1 Hz, 1H), 6.76 (d, J=8.2 Hz, 1H), 6.64 (d, J=8.2 Hz, 1H), 6.01 (s, 2H), 4.42 (s, 2H), 3.50 (t, J=5.9 Hz, 2H), 3.33 (s, 3H), 2.65-2.54 (m, 2H), 2.45 (s, 3H); UPLC-MS: $t_R$=1.65 min (generic method); MS (ESI) m/z calcd for $C_{27}H_{24}F_3N_6O_7S$ (M+H)$^+$: 633.6, found: 633.3.

(4S,7R)- or (4R,7S)—N-(Benzo[d][1,3]dioxol-5-yl)-3-(9-((3,5-dimethylisoxazol-4-yl)sulfonyl)-3-(trifluoromethyl)-5,6,7,8-tetrahydro-4,7-epiminocyclohepta[c]pyrazol-1(4H)-yl)-N-methylbenzamide Following general procedure 1e, the title compound was obtained as pure enantiomer from pure enantiomer [048], after purification by silica gel flash-column chromatography with 60% AcOEt in cyclohexane as eluent, as a white solid in 65% yield: $^1$H NMR (400 MHz, DMSO-d$_6$) δ 7.58-7.29 (m, 4H), 6.97 (d, J=2.1 Hz, 1H), 6.77 (d, J=8.2 Hz, 1H), 6.72-6.53 (m, 1H), 5.99 (app-d, J=1.5 Hz, 2H), 5.02 (d, J=5.5 Hz, 1H), 4.52 (dd, J=7.5, 4.7 Hz, 1H), 3.33 (s, 3H), 3.11-2.89 (m, 1H), 2.66-2.54 (m, 4H), 2.27 (s, 3H), 2.25-2.16 (m, 1H), 2.16-2.02 (m, 1H), 1.96-1.85 (m, 1H), 1.83-1.68 (m, 1H); UPLC-MS: tR=2.53 min (generic method); MS (ESI) m/z calcd for $C_{29}H_{27}F_3N_5O_6S$ (M+H)$^+$: 630.2, found: 630.3.

(4R,7S)- or (4S,7R)—N-(Benzo[d][1,3]dioxol-5-yl)-3-(9-((3,5-dimethylisoxazol-4-yl)sulfonyl)-3-(trifluoromethyl)-5,6,7,8-tetrahydro-4,7-epiminocyclohepta[c]pyrazol-1 (4H)-yl)-N-methylbenzamide Following general procedure 1e, the title compound was obtained as pure enantiomer from pure enantiomer [049], after purification by silica gel flash-column chromatography with 60% AcOEt in cyclohexane as eluent, as a white solid in 38% yield: $^1$H NMR (400 MHz, DMSO-d$_6$) δ 7.58-7.29 (m, 4H), 6.97 (d, J=2.1 Hz, 1H), 6.77 (d, J=8.2 Hz, 1H), 6.72-6.53 (m, 1H), 5.99 (app-d, J=1.5 Hz, 2H), 5.02 (d, J=5.5 Hz, 1H), 4.52 (dd, J=7.5, 4.7 Hz, 1H), 3.33 (s, 3H), 3.11-2.89 (m, 1H), 2.66-2.54 (m, 4H), 2.27 (s, 3H), 2.25-2.16 (m, 1H), 2.16-2.02 (m, 1H), 1.96-1.85 (m, 1H), 1.83-1.68 (m, 1H); UPLC-MS: $t_R$=2.53 min (generic method); MS (ESI) m/z calcd for $C_{29}H_{27}F_3N_5O_6S$ (M+H)$^+$: 630.2, found: 630.3.

(4R,7S)- or (4S,7R)—N-(Benzo[d][1,3]dioxol-5-yl)-3-(9-((3,5-dimethyl-1H-pyrazol-4-yl)sulfonyl)-3-(trifluoromethyl)-5,6,7,8-tetrahydro-4,7-epiminocyclohepta[c]pyrazol-1(4H)-yl)-N-methylbenzamide Following general procedure 1e, the title compound was obtained as pure enantiomer from pure enantiomer [049], after purification by silica gel flash-column chromatography with 30% AcOEt in cyclohexane as eluent, as a white solid in 62% yield: 1H NMR (400 MHz, DMSO-d$_6$) δ 13.03 (s, 1H), 7.59-7.32 (m, 4H), 6.98 (d, J=2.0 Hz, 1H), 6.76 (d, J=8.2 Hz, 1H), 6.64 (d, J=7.8 Hz, 1H), 5.99 (s, 2H), 4.90 (d, J=5.4 Hz, 1H), 4.42 (dd, J=7.1, 4.8 Hz, 1H), 3.32 (s, 3H), 2.97-2.81 (m, 1H), 2.47-2.38 (m, 1H), 2.30 (s, 3H), 2.21 (s, 3H), 2.17-2.07 (m, 1H), 2.05-1.94 (m, 1H), 1.89-1.78 (m, 1H), 1.74-1.59 (m, 1H); UPLC-MS: tR=2.20 min (generic method); MS (ESI) m/z calcd for $C_{29}H_{28}F_3N_6O_5S$ (M+H)$^+$: 629.2, found: 629.4.

(4R,7S)- or (4S,7R)—N-(Benzo[d][1,3]dioxol-5-yl)-3-(9-cyclobutyl-3-(trifluoromethyl)-5,6,7,8-tetrahydro-4,7-epiminocyclohepta[c]pyrazol-1(4H)-yl)-N-methylbenzamide Following general procedure 1d, the title compound was obtained as pure enantiomer from pure enantiomer [049], after purification by silica gel flash-column chromatography with 10% AcOEt in cyclohexane as eluent, as a white solid in 62% yield. $^1$H NMR (400 MHz, DMSO-d$_6$) δ 7.64-7.50 (m, 2H), 7.48-7.32 (m, 2H), 7.00 (d, J=2.1 Hz, 1H), 6.77 (d, J=8.2 Hz, 1H), 6.64 (d, J=8.4 Hz, 1H), 5.99 (s, 2H), 4.01 (d, J=4.3 Hz, 1H), 3.63-3.48 (m, 1H), 3.34 (s, 3H), 3.05-2.92 (m, 1H), 2.91-2.77 (m, 1H), 2.15-1.98 (m, 4H), 1.95-1.55 (m, 6H), 1.52-1.36 (m, 1H); UPLC-MS: tR=2.39 min (generic method); MS (ESI) m/z calcd for $C_{28}H_{28}F_3N_4O_3$ (M+H)$^+$: 525.2, found: 525.5.

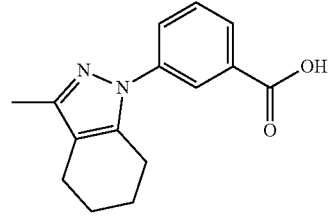 [SMILES: Cc1nn(-c2cccc(C(=O)O)c2)c2c1CCCC2]

[Int-1.9] 3-(3-Methyl-4,5,6,7-tetrahydroindazol-1-yl) benzoic acid

Following general procedure 1a, the title compound was obtained from 2-acetylcyclohexanone as a beige solid. The title compound was used in the next step without any purification. UPLC-MS: $t_R$=1.61 min (generic method); MS (ESI) m/z calcd for $C_{15}H_{17}N_2O_2$ (M+H)$^+$: 257.1, found: 257.5.

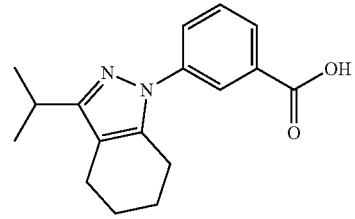 [SMILES: CC(C)c1nn(-c2cccc(C(=O)O)c2)c2c1CCCC2]

[Int-1.10] 3-(3-Isopropyl-4,5,6,7-tetrahydroindazol-1-yl)benzoic acid

Following general procedure 1a, the title compound was obtained from 2-(2-methylpropanoyl)cyclohexanone as a beige solid. The title compound was used in the next step without any purification. UPLC-MS: $t_R$=1.78 min (generic method); MS (ESI) m/z calcd for $C_{17}H_{21}N_2O_2$ (M+H)$^+$: 285.2, found: 285.5.

N-(1,3-Benzodioxol-5-yl)-N-methyl-3-(3-methyl-4,5,6,7-tetrahydroindazol-1-yl)benzamide Following general procedure 1b, the title compound was obtained from compound [Int.1-9], after purification by silica gel flash-column chromatography in 30% AcOEt in cyclohexane as eluent, as a white solid in 29% yield: $^1$H NMR (400 MHz, DMSO-d$_6$) δ 7.44-7.31 (m, 2H), 7.26 (app-d, J=7.1 Hz, 1H), 6.96 (d, J=2.1 Hz, 1H), 6.77 (d, J=8.2 Hz, 1H), 6.64 (dd, J=8.2, 2.1 Hz, 1H), 5.99 (s, 2H), 3.32 (s, 3H), 2.55 (t, J=6.0 Hz, 2H), 2.41 (t, J=5.9 Hz, 2H), 2.01 (s, 3H), 1.81-1.61 (m, 4H); UPLC-MS: tR=2.26 min (generic method); MS (ESI) m/z calcd for $C_{23}H_{24}N_3O_3$ (M+H)$^+$: 390.1, found: 390.5.

N-(1,3-Benzodioxol-5-yl)-3-(3-isopropyl-4,5,6,7-tetrahydroindazol-1-yl)-N-methyl-benzamide Following general procedure 1b, the title compound was obtained from compound [Int.1-10], after purification by silica gel flash-column chromatography in 20% AcOEt in cyclohexane as eluent, as a white solid in 29% yield: $^1$H NMR (400 MHz, DMSO-d$_6$) δ 7.46-7.34 (m, 2H), 7.27 (dt, J=7.0, 2.2 Hz, 1H), 7.14 (bs, 1H), 6.92 (d, J=2.1 Hz, 1H), 6.77 (d, J=8.2 Hz, 1H), 6.63 (dd, J=8.2, 2.1 Hz, 1H), 5.98 (s, 2H), 3.33 (s, 3H), 2.64-2.52 (m, 4H), 2.50 (s, 3H), 1.79-1.57 (m, 4H), 1.08 (d, J=7.0 Hz, 6H); UPLC-MS: tR=2.44 min (generic method); MS (ESI) m/z calcd for $C_{25}H_{28}N_3O_3$ (M+H)$^+$: 418.2, found: 418.5.

N-(2,2-Difluoro-1,3-benzodioxol-5-yl)-N-methyl-3-(3-methyl-4,5,6,7-tetrahydroindazol-1-yl)benzamide Following general procedure 1b, the title compound was obtained from compound [Int.1-9], after purification by silica gel flash-column chromatography in 10% AcOEt in cyclohexane as eluent, as a white solid in 5% yield: $^1$H NMR (400 MHz, DMSO-d$_6$) δ 7.54 (d, J=2.1 Hz, 1H), 7.47-7.23 (m, 5H), 7.04 (dd, J=8.6, 2.1 Hz, 1H), 3.37 (s, 3H), 2.60-2.52 (m, 2H), 2.40 (t, J=5.9 Hz, 2H), 1.96 (s, 3H), 1.82-1.60 (m, 4H); UPLC-MS: tR=2.57 min (generic method); MS (ESI) m/z calcd for $C_{23}H_{22}F_2N_3O_3$ (M+H)$^+$: 426.2, found: 426.5.

N-(2,2-Difluoro-1,3-benzodioxol-5-yl)-3-(3-isopropyl-4,5,6,7-tetrahydroindazol-1-yl)-N-methyl-benzamide Following general procedure 1b, the title compound was obtained from compound [Int.1-10], after purification by silica gel flash-column chromatography in 10% AcOEt in cyclohexane as eluent, as a white solid in 11% yield. $^1$H NMR (400 MHz, DMSO-d$_6$) δ 7.49 (d, J=2.1 Hz, 1H), 7.47-7.39 (m, 2H), 7.32 (d, J=8.6 Hz, 1H), 7.30-7.24 (m, 1H), 7.13 (s, 1H), 7.06 (dd, J=8.6, 2.2 Hz, 1H), 3.37 (s, 3H), 2.64-2.53 (m, 2H), 2.54-2.50 (m, 2H), 1.84-1.57 (m, 4H), 1.04 (d, J=7.0 Hz, 6H); UPLC-MS: tR=2.75 min (generic method); MS (ESI) m/z calcd for $C_{25}H_{26}F_2N_3O_3$ (M+H)$^+$: 454.2, found: 454.5.

Ethyl 4-[1-[3-[1,3-benzodioxol-5-yl(methyl) carbamoyl]phenyl]-3-(trifluoromethyl)-6,7-dihydro-4H-pyrazolo[4,3-c]pyridin-5-yl]butanoate Following general procedure 1k, the title compound was obtained from compound [002], after purification by silica gel flash-column chromatography in 20% AcOEt in cyclohexane as eluent, as a white solid in 88% yield. $^1$H NMR (400 MHz, Chloroform-d) δ 7.55-7.44 (m, 2H), 7.42-7.31 (m, 2H), 6.67 (d, J=8.2 Hz, 1H), 6.62 (d, J=2.1 Hz, 1H), 6.53 (dd, J=8.3, 2.2 Hz, 1H), 5.97 (s, 2H), 4.15 (q, J=7.2 Hz, 2H), 3.67 (bs, 2H), 3.46 (s, 3H), 2.93-2.54 (m, 6H), 2.43 (t, J=7.2 Hz, 2H), 1.97 (t, J=7.3 Hz, 2H), 1.28 (t, J=7.2 Hz, 3H); UPLC-MS: tR=2.44 min (generic method); MS (ESI) m/z calcd for $C_{28}H_{30}F_3N_4O_5$ (M+H)$^+$: 559.2, found: 559.4.

4-[1-[3-[1,3-Benzodioxol-5-yl(methyl)carbamoyl]phenyl]-3-(trifluoromethyl)-6,7-dihydro-4H-pyrazolo[4,3-c]pyridin-5-yl]butanoic acid Following general procedure 1i, the title compound was obtained from compound [134], after purification by silica gel flash-column chromatography in 10% DCM/MeOH (9:1) in DCM as eluent, as a white solid in 60% yield. $^1$H NMR (400 MHz, DMSO-d$_6$) δ 12.01 (s, 1H), 7.62-7.33 (m, 4H), 6.99 (d, J=2.1 Hz, 1H), 6.78 (d, J=8.2 Hz, 1H), 6.66 (d, J=8.3 Hz, 1H), 5.99 (s, 2H), 3.52 (s, 2H), 3.33 (s, 3H), 2.79-2.63 (m, 2H), 2.61-2.53 (m, 4H), 2.29 (t, J=7.2 Hz, 2H), 1.84-1.70 (m, 2H); UPLC-MS: tR=1.72 min (generic method); MS (ESI) m/z calcd for $C_{26}H_{26}F_3N_4O_5$ (M+H)$^+$: 531.2, found: 531.4.

tert-Butyl 1-[3-[(2,2-difluoro-1,3-benzodioxol-5-yl)-methyl-carbamoyl]phenyl]-3-(trifluoromethyl)-6,7-dihydro-4H-pyrazolo[4,3-c]pyridine-5-carboxylate Following general procedure 1b, the title compound was obtained from compound [Int-1.1] as a white solid. Crude product was used in the next step without purification; UPLC-MS: tR=2.09 min (apolar method); MS (ESI) m/z calcd for $C_{27}H_{26}F_5N_4O_5$ (M+H)$^+$: 581.2, found: 581.4.

N-(2,2-Difluoro-1,3-benzodioxol-5-yl)-N-methyl-3-[3-(trifluoromethyl)-4,5,6,7-tetrahydropyrazolo[4,3-c]pyridin-5-ium-1-yl]benzamide;2,2,2-trifluoroacetate Following general procedure 5i, the title compound was obtained from compound [136] as a white solid. Crude product was used in the next step without purification; UPLC-MS: tR=2.02 min (generic method); MS (ESI) m/z calcd for $C_{22}H_{18}F_5N_4O_3$ (M+H)$^+$: 481.2, found: 481.4.

N-(2,2-Difluoro-1,3-benzodioxol-5-yl)-3-[5-(3,5-dimethylisoxazol-4-yl)sulfonyl-3-(trifluoromethyl)-6,7-dihydro-4H-pyrazolo[4,3-c]pyridin-1-yl]-N-methyl-benzamide Following general procedure 1e, the title compound was obtained from compound [092], after purification by silica gel flash-column chromatography with 40% AcOEt in cyclohexane as eluent, as a white solid in 24% yield: 1H NMR (400 MHz, Chloroform-d) δ 7.53-7.33 (m, 4H), 6.98 (d, J=8.5 Hz, 1H), 6.91 (d, J=2.1 Hz, 1H), 6.83 (dd, J=8.5, 2.1 Hz, 1H), 4.41 (s, 2H), 3.53 (t, J=5.7 Hz, 2H), 3.50 (s, 3H), 2.78 (t, J=5.7 Hz, 2H), 2.71 (s, 3H), 2.44 (s, 3H); UPLC-MS: tR=2.67 min (generic method); MS (ESI) m/z calcd for $C_{27}H_{23}F_5N_5O_6S$ (M+H)$^+$: 640.1, found: 640.3.

3-[5-(3,5-Dimethylisoxazol-4-yl)sulfonyl-3-(trifluoromethyl)-6,7-dihydro-4H-pyrazolo[4,3-c]pyridin-1-yl]-N-methyl-N-(2-methyl-1,3-benzoxazol-6-yl)benzamide Following general procedure 1e, the title compound was obtained from compound [030], after purification by silica gel flash-column chromatography with 70% AcOEt in cyclohexane as eluent, as a white solid in 8% yield: $^1$H NMR (400 MHz, Chloroform-d) δ 7.54 (d, J=8.4 Hz, 1H), 7.46-7.38 (m, 3H), 7.38-7.30 (m, 1H), 7.26 (d, J=2.0 Hz, 1H), 7.07 (dd, J=8.4, 2.0 Hz, 1H), 4.36 (s, 2H), 3.57 (s, 3H), 3.41 (t, J=5.6 Hz, 2H), 2.72 (s, 3H), 2.65 (s, 3H), 2.55 (d, J=4.7 Hz, 3H); UPLC-MS: tR=2.38 min (generic method); MS (ESI) m/z calcd for $C_{28}H_{26}F_3N_6O_5S$ (M+H)$^+$: 615.2, found: 615.4.

3-[5-(3,5-Dimethylisoxazol-4-yl)sulfonyl-3-(trifluoromethyl)-6,7-dihydro-4H-pyrazolo[4,3-c]pyridin-1-yl]-N-(5-fluoro-2-methyl-1,3-benzoxazol-6-yl)-N-methyl-benzamide Following general procedure 1e, the title compound was obtained from compound [Int-1.8], after purification by silica gel flash-column chromatography with 55% AcOEt in cyclohexane as eluent, as a white solid in 49% yield: $^1$H NMR (400 MHz, Chloroform-d) δ 7.56-7.30 (m, 6H), 4.39 (s, 2H), 3.68-3.31 (m, 4H), 2.83-2.73 (m, 2H), 2.72 (s, 3H), 2.64 (s, 3H), 2.44 (s, 3H); UPLC-MS: tR=2.44 min (generic method); MS (ESI) m/z calcd for $C_{28}H_{25}F_4N_6O_5S$ (M+H)$^+$: 633.1, found: 633.4.

Benzyl 3-[1-[3-[1,3-benzodioxol-5-yl(methyl) carbamoyl]phenyl]-3-(trifluoromethyl)-6,7-dihydro-4H-pyrazolo[4,3-c]pyridin-5-yl]cyclobutane carboxylate Following general procedure 1d, the title compound was obtained from compound [002], after purification by silica gel flash-column chromatography with 20% AcOEt in cyclohexane as eluent, as a white solid in 53% yield; UPLC-MS: tR=1.81 min (apolar method); MS (ESI) m/z calcd for $C_{34}H_{32}F_3N_4O_5$ (M+H)$^+$: 633.2, found: 633.5.

General Procedure 1m

3-[1-[3-[1,3-Benzodioxol-5-yl(methyl)carbamoyl]phenyl]-3-(trifluoromethyl)-6,7-dihydro-4H-pyrazolo[4,3-c]pyridin-5-yl]cyclobutanecarboxylic acid Compound [139] (0.035 g, 0.055 mmol) was suspended in a 1:1 mixture EtOH/H$_2$O (1.4 mL) and a NaOH 2M solution (0.2 mL) was added. Mixture was stirred for 12 h at room temperature, upon completion of the reaction. After evaporation of the solvent, the crude mixture was dissolved in water and acidified until pH 7 with HCl 2M. The aqueous solution was then extracted with DCM. The collected organic layers were dried over Na$_2$SO$_4$, filtered and evaporated. The crude product was purified by silica gel flash-column chromatography with 10% of CH$_2$Cl$_2$:MeOH (8:2) in DCM To give the title compound as a white solid in 80% yield: $^1$H NMR (400 MHz, DMSO-d$_6$) δ 12.14 (s, 1H), 7.86-7.24 (m, 4H), 7.01 (d, J=2.1 Hz, 1H), 6.78 (d, J=8.2 Hz, 1H), 6.64 (d, J=7.4 Hz, 1H), 5.99 (s, 2H), 3.41 (s, 2H), 3.35 (s, 3H), 2.96 (p, J=8.0 Hz, 1H), 2.76 (p, J=9.0 Hz, 1H), 2.66-2.53 (m, 4H), 2.44-2.24 (m, 2H), 2.10-1.91 (m, 2H); UPLC-MS: tR=1.76 min (generic method); MS (ESI) m/z calcd for $C_{27}H_{26}F_3N_4O_5$ (M+H)$^+$: 543.2, found: 543.5.

General Protocol 2

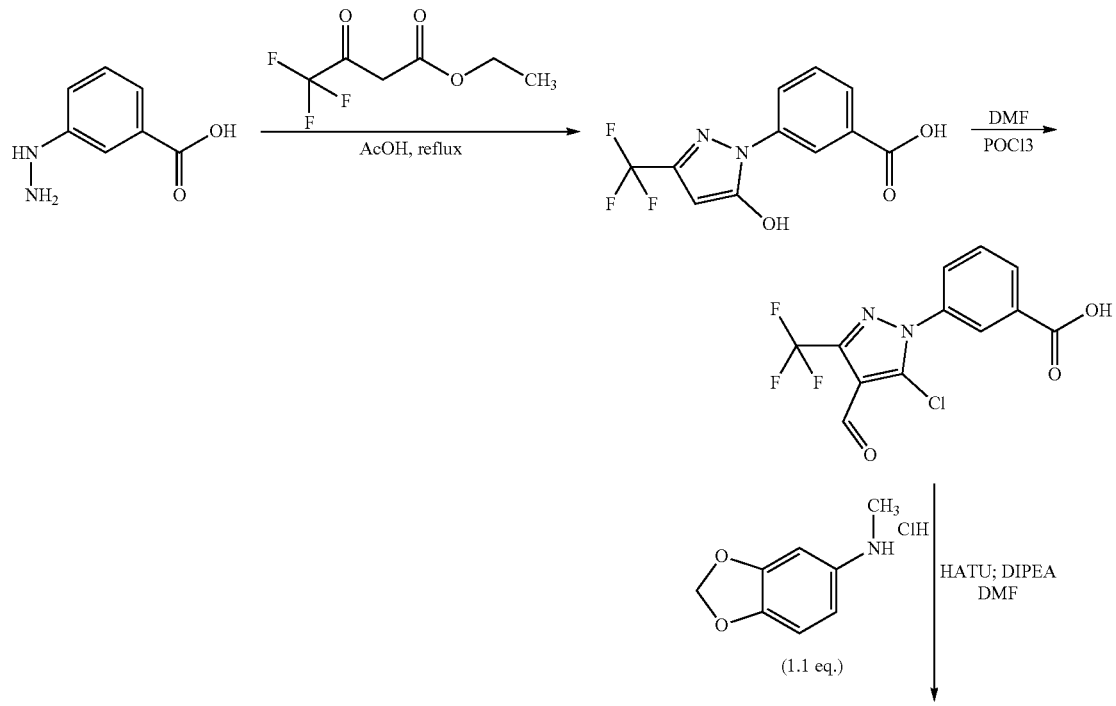

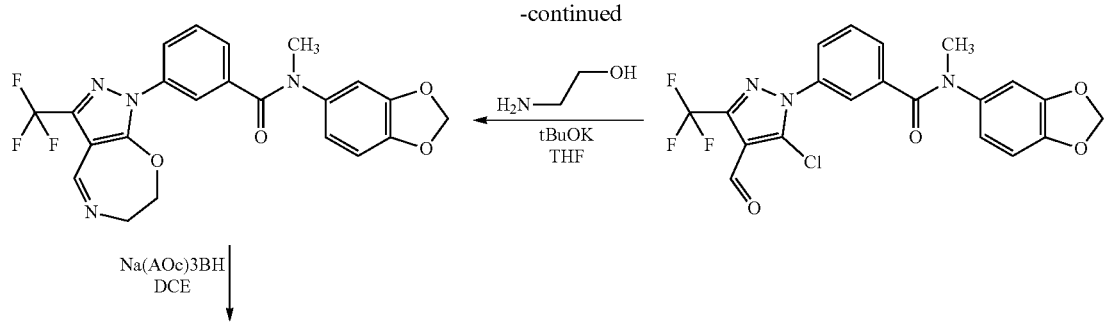

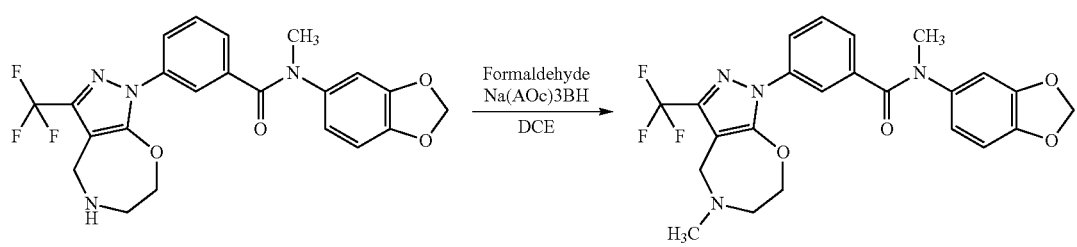

Example of General Protocol 2

Protocol 2a

Protocol 2b

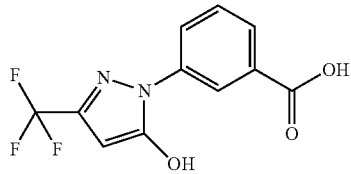 [SMILES: O=C(O)c1cccc(-n2nc(C(F)(F)F)cc2O)c1]

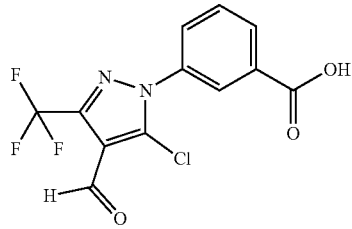 [SMILES: O=Cc1c(C(F)(F)F)nn(-c2cccc(C(=O)O)c2)c1Cl]

[Int-2.1] 3-[5-Hydroxy-3-(trifluoromethyl)pyrazol-1-yl]benzoic acid

To a solution of 3-hydrazinobenzoic acid (5.0 g, 32.9 mmol) in AcOH (30 mL), ethyl 4,4,4-trifluoro-3-oxo-butanoate (4.9 mL, 33.5 mmol) was added. Mixture was refluxed for 5 h and cooled to room temperature. Water (100 mL) was added, with the formation of a precipitate. The precipitate was filtered, washed with water, and dissolved in EtOAc. Organic layer was dried over $Na_2SO_4$, filtered and the solvent evaporated. The title compound (7.1 g) was obtained as a pale yellow solid in 79% yield: $^1$H NMR (400 MHz, DMSO-$d_6$) δ 13.25 (s, 1H), 12.71 (s, 1H), 8.30 (t, J=1.9 Hz, 1H), 8.01 (ddd, J=8.1, 2.3, 1.1 Hz, 1H), 7.94 (app-dt, J=7.8, 1.3 Hz, 1H), 7.65 (app-t, J=7.9 Hz, 1H), 5.98 (s, 1H). UPLC-MS: tR=1.30 min (Generic method); MS (ESI) m/z calcd for $C_{11}H_8F_3N_2O_3$ (M+H)$^+$: 273.0, found: 273.1.

[Int-2.2] 3-[5-Chloro-4-formyl-3-(trifluoromethyl) pyrazol-1-yl]benzoic acid

To a solution of [Int-2.1] (100 mg, 0.37 mmol) in $POCl_3$ (500 µl), DMF (114.0 µL, 1.47 mmol) was added. Mixture was refluxed for 5 h and cooled to 0° C. Mixture was cooled at 0° C., quenched with water (5 mL), and aqueous layer was extracted with EtOAc (3×10 mL). The collected organic layers were washed with brine (10 mL), dried over $Na_2SO_4$, filtered and the solvent evaporated. The title compound (100 mg) was obtained as a pale yellow solid in 85% yield: $^1$H NMR (400 MHz, DMSO-$d_6$) δ 9.96 (d, J=0.8 Hz, 1H), 8.20 (t, J=1.9 Hz, 1H), 8.17 (app-dt, J=7.8, 1.3 Hz, 1H), 7.98 (ddd, J=8.0, 2.3, 1.2 Hz, 1H), 7.95 (s, 1H), 7.79 (t, J=7.9 Hz, 1H). UPLC-MS: tR=1.44 min (Generic method); MS (ESI) m/z calcd for $C_{11}H_8F_3N_2O_3$ (M−H)$^-$: 317.1, found: 317.3.

Protocol 2c

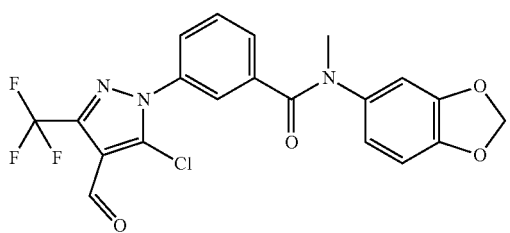 [SMILES: CN(C(=O)c1cccc(-n2nc(C(F)(F)F)c(C=O)c2Cl)c1)c1ccc2c(c1)OCO2]

[Int-2.3] N-(1,3-benzodioxol-5-yl)-3-[5-chloro-4-formyl-3-(trifluoromethyl)pyrazol-1-yl]-N-methyl-benzamide To a solution of [Int-2.2] (60.0 mg, 0.19 mmol) in DMF (2 mL), N-methyl-1,3-benzodioxol-5-amine hydrochloride (33.6 mg, 0.95 mmol), HATU (71.6 mg, 0.19 mmol) and DIPEA (65.6 μL, 0.38 mmol) were added. Mixture was stirred at room temperature for 6 h and then diluted with Et$_2$O (40 mL). The organic layer was washed with sat. aq. NH$_4$Cl (3×10 ml), water (20 mL) and brine (20 mL). The collected organic layers were dried with Na$_2$SO$_4$, filtered and evaporated. The title compound was obtained, after purification by silica gel flash-column chromatography with cyclohexane/EtOAc (50/50) as the eluent, as a yellow solid in 65% yield (56 mg): $^1$H NMR (400 MHz, DMSO-d$_6$) δ 9.93 (s, 1H), 7.70-7.45 (m, 4H), 6.96 (d, J=2.1 Hz, 1H), 6.79 (d, J=8.2 Hz, 1H), 6.66 (dd, J=8.2, 2.1 Hz, 1H), 6.00 (s, 2H), 3.34 (s, 3H). UPLC-MS: t$_R$=2.01 min (Generic method); MS (ESI) m/z calcd for C$_{20}$H$_{14}$ClF$_3$N$_3$O$_4$ (M+H)$^+$: 452.0, found: 452.1.

Protocol 2d

N-(1,3-Benzodioxol-5-yl)-N-methyl-3-[5-methyl-3-(trifluoromethyl)-6,7-dihydro-4H-pyrazolo[4,3-f][1,4]oxazepin-1-yl]benzamide To a solution of 2-aminoethanol (7.3 μL, 0.12 mmol) in dry THF (2 mL) under nitrogen, $^t$BuOK (18.6 mg, 0.17 mmol) was added at 0° C. was After stirring for 30 min a solution of [Int-2.3] (50 mg, 0.11 mmol) in THF (2 mL) was added. Solution was stirred at room temperature for 2 h and then quenched with 2M HCl, until pH=1-2. The aqueous layer was washed with Et$_2$O and basified with sat. aq. NaHCO$_3$ until pH 8-9. After extraction with EtOAc (3×10 mL), the collected organic layers were washed with brine (5 mL), dried over Na$_2$SO$_4$, filtered and the solvent evaporated. The intermediate compound was dissolved in DCE (3 mL) and Na(OAc)$_3$BH (70 mg, 0.33 mmol) was added. Mixture was stirred for 1 h, formaldehyde (aq. solution 30% v/v, 100 μL) was added and stirred for other 30 min. Solvent was evaporated and the corresponding solid dissolved in MeOH and worked-up with an SCX cartridge. The title compound was obtained, after purification by silica gel flash-column chromatography with DCM/MeOH (95/5) as the eluent, as a yellow solid in 29% yield over three steps (15 mg): $^1$H NMR (400 MHz, DMSO-d$_6$) δ 7.61 (t, J=1.8 Hz, 1H), 7.57 (app-dt, J=8.1, 1.5 Hz, 1H), 7.38 (app-t, J=7.9 Hz, 1H), 7.28 (app-d, J=7.7 Hz, 1H), 6.96 (d, J=2.1 Hz, 1H), 6.76 (d, J=8.2 Hz, 1H), 6.63 (dd, J=8.2, 2.1 Hz, 1H), 5.98 (s, 2H), 4.41-4.17 (m, 2H), 3.57 (s, 2H), 3.32 (s, 3H), 3.04-2.95 (m, 2H), 2.37 (s, 3H). UPLC-MS: tR=1.95 min (Generic method); MS (ESI) m/z calcd for C$_{23}$H$_{22}$F$_3$N$_4$O$_4$ (M+H)$^+$: 475.2, found: 475.3.

General Protocol 3

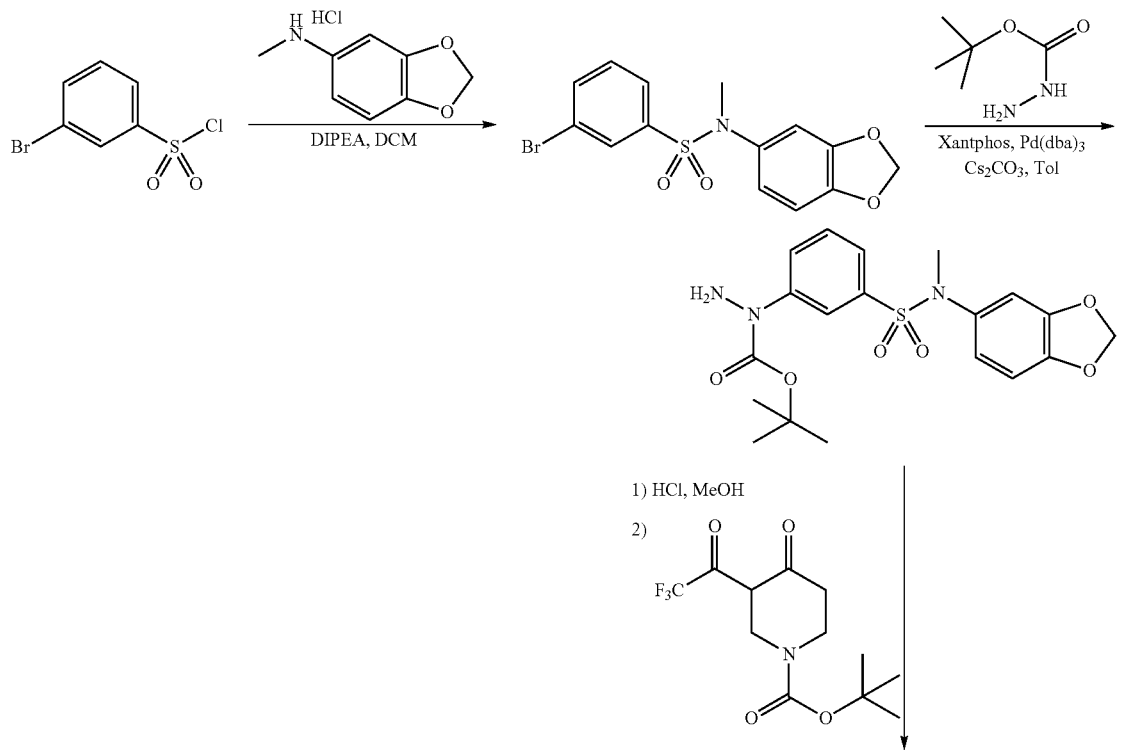

-continued

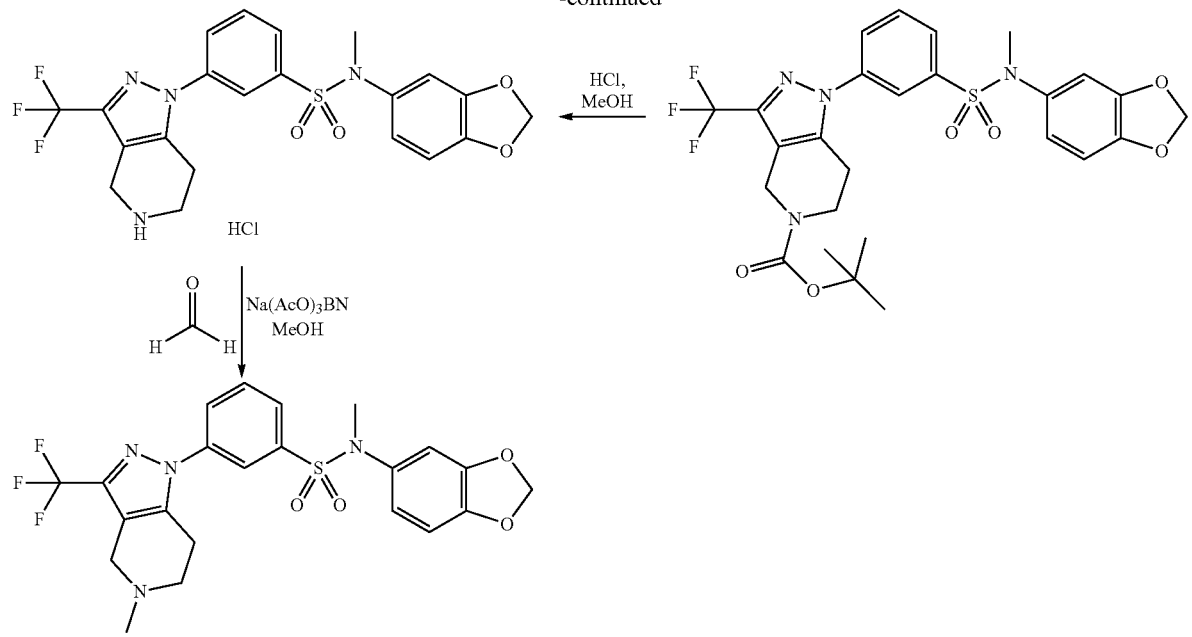

Example of General Protocol 3

Protocol 3a

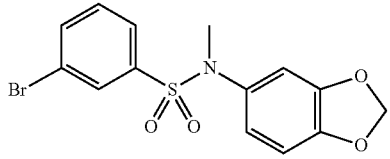 [SMILES: CN(c1ccc2c(c1)OCO2)S(=O)(=O)c1cccc(Br)c1]

[Int-3.1] N-(1,3-Benzodioxol-5-yl)-3-bromo-N-methyl-benzene sulfonamide

To a solution of 3-bromobenzenesulfonyl chloride (1.0 g, 3.91 mmol) in DCM (26 mL), TEA (1.8 g, 8.60 mmol) was added under nitrogen atmosphere at 0° C. N-Methyl-1,3-benzodioxol-5-amine hydrochloride was added and the mixture was stirred at the same temperature for 3 h. The reaction was quenched by adding sat. aq. NH$_4$Cl (10 mL), water (10 mL), sat. aq. NaHCO$_3$ (10 mL) and brine. The title compound was obtained, after purification by silica gel flash chromatography (DCM/EtOAc=85:15) as a colourless oil in 78% yield (1.1 g). $^1$H NMR (400 MHz, DMSO-d$_6$) δ 7.93 (dt, J=7.3, 1.9 Hz, 1H), 7.63-7.61 (m, 1H), 7.60-7.49 (m, 2H), 6.86 (d, J=8.3 Hz, 1H), 6.71 (d, J=2.2 Hz, 1H), 6.53 (dd, J=8.3, 2.2 Hz, 1H), 6.05 (s, 2H), 3.11 (s, 3H). UPLC-MS: t$_R$=2.27 min (Generic method); MS (ESI) m/z calcd for C$_{14}$H$_{13}$BrNO$_4$S (M+H)$^+$: 370.0, found: 370.3.

Protocol 3b

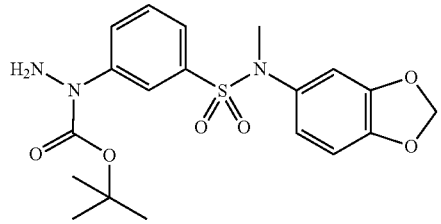 [SMILES: CN(c1ccc2c(c1)OCO2)S(=O)(=O)c1cccc(N(N)C(=O)OC(C)(C)C)c1]

[Int-3.2] tert-Butyl N-amino-N-[3-[1,3-benzodioxol-5-yl(methyl)sulfamoyl]phenyl]carbamate A flame-dried Schlenk tube was loaded with [Int-3.1] (1070 mg, 2.89 mmol), tert-butyl carbazate (1140 mg, 8.67 mmol), 4,5-bis(diphenylphosphino)-9,9-dimethylxanthene (250 mg, 0.43 mmol), tris(dibenzylideneacetone)dipalladium(0) (132 mg, 0.14 mmol), cesium carbonate (1410 mg, 4.33 mmol) and toluene (36.0 mL). The mixture was degassed with nitrogen and allowed to stir for 18 h at 100° C. The reaction was filtered over a short pad of Celite and concentrated. The title compound was used in the next step without any purification. UPLC-MS: t$_R$=2.18 min (Generic method); MS (ESI) m/z calcd for C$_{19}$H$_{24}$N$_3$O$_6$S (M+H)$^+$: 422.2, found: 422.5.

Protocol 3c tert-Butyl 1-[3-[1,3-benzodioxol-5-yl(methyl) sulfamoyl]phenyl]-3-(trifluoromethyl)-6,7-dihydro-4H-pyrazolo[4,3-c]pyridine-5-carboxylate To a solution of [Int-3.2] (421 mg, 1.00 mmol) in methanol (3.30 mL), a solution of HCl 3.0 M in methanol (1.67 mL, 5.00 mmol) was added dropwise at 0° C. The mixture was allowed to stir 5 h at room temperature and it was concentrated. The residue was taken up with AcOH (2 mL), added to a solution of tert-butyl 4-oxo-3-(2,2,2-trifluoroacetyl)piperidine-1-carboxylate (279 mg, 1.00 mmol) in AcOH (2.0 mL) and stirred for 5 h at room temperature. H$_2$O (15 mL) was added and the formed precipitate collected by filtration. Subsequent silica gel flash chromatography (DCM/AcOEt=9:1) afforded the title compound as a white solid 61% yield (354 mg): $^1$H NMR (400 MHz, DMSO-d$_6$) δ 7.98 (dd, J=7.4, 2.0 Hz, 1H), 7.79 (app-t, J=8.0 Hz, 1H), 7.71 (bs, 1H), 7.64 (dt, J=8.0, 1.3 Hz, 1H), 6.86 (d, J=8.3 Hz, 1H), 6.72 (d, J=2.1 Hz, 1H), 6.59 (dd, J=8.3, 2.1 Hz, 1H), 6.04 (s, 2H), 4.51 (s, 2H), 3.63 (app-t, J=5.6 Hz, 2H), 3.14 (s, 3H), 2.78 (app-t, J=5.6 Hz, 2H), 1.44 (s, 9H). UPLC-MS: t$_R$=2.79 min (Generic method); MS (ESI) m/z calcd for C$_{26}$H$_{28}$F$_3$N$_4$O$_6$S (M+H)$^+$: 581.2, found: 581.5.

N-(1,3-Benzodioxol-5-yl)-N-methyl-3-[3-(trifluoromethyl)-4,5,6,7-tetrahydropyrazolo[4,3-c]pyridin-1-yl]benzenesulfonamide hydrochloride Following general procedure 1c, the title compound was obtained from compound [065], after trituration with Et$_2$O, as a pale yellow solid in 90% yield (93 mg): $^1$H NMR (400 MHz, DMSO-d$_6$) δ 9.83 (bs, 2H), 7.98 (dd, J=8.1, 1.2 Hz, 1H), 7.84 (app-t, J=8.0 Hz, 1H), 7.69 (dt, J=7.9, 1.2 Hz, 1H), 7.65 (t, J=2.0 Hz, 1H), 6.87 (d, J=8.3 Hz, 1H), 6.73 (d, J=2.2 Hz, 1H), 6.59 (dd, J=8.3, 2.2 Hz, 1H), 6.05 (s, 2H), 4.30 (s, 2H), 3.40 (app-t, J=5.9 Hz, 2H), 3.14 (s, 3H), 3.07 (app-t, J=6.0 Hz, 2H). UPLC-MS: t$_R$=1.89 min (Generic method); MS (ESI) m/z calcd for C$_{21}$H$_{20}$F$_3$N$_4$O$_4$S (M+H)$^+$: 481.1, found: 481.5.

N-(1,3-Benzodioxol-5-yl)-N-methyl-3-[5-methyl-3-(trifluoromethyl)-6,7-dihydro-4H-pyrazolo[4,3-c]pyridin-1-yl]benzenesulfonamide Following general procedure 1d, the title compound was obtained from compound [066], after flash chromatography, eluting with DCM/MeOH (0 to 5%) as white solid in 84% yield: $^1$H NMR (400 MHz, DMSO-d$_6$) δ 8.01-7.95 (m, 1H), 7.78 (app-t, J=8.0 Hz, 1H), 7.70 (t, J=1.9 Hz, 1H), 7.63-7.56 (m, 1H), 6.85 (d, J=8.3 Hz, 1H), 6.71 (d, J=2.2 Hz, 1H), 6.58 (dd, J=8.3, 2.2 Hz, 1H), 6.03 (s, 2H), 3.47 (s, 2H), 3.13 (s, 3H), 2.80 (app-t, J=5.7 Hz, 2H), 2.66 (app-t, J=5.6 Hz, 2H), 2.41 (s, 3H). UPLC-MS: t$_R$=2.31 min (Generic method); MS (ESI) m/z calcd for C$_{22}$H$_{22}$F$_3$NO$_{44}$S (M+H)$^+$: 495.5, found: 495.5.

General Protocol 4

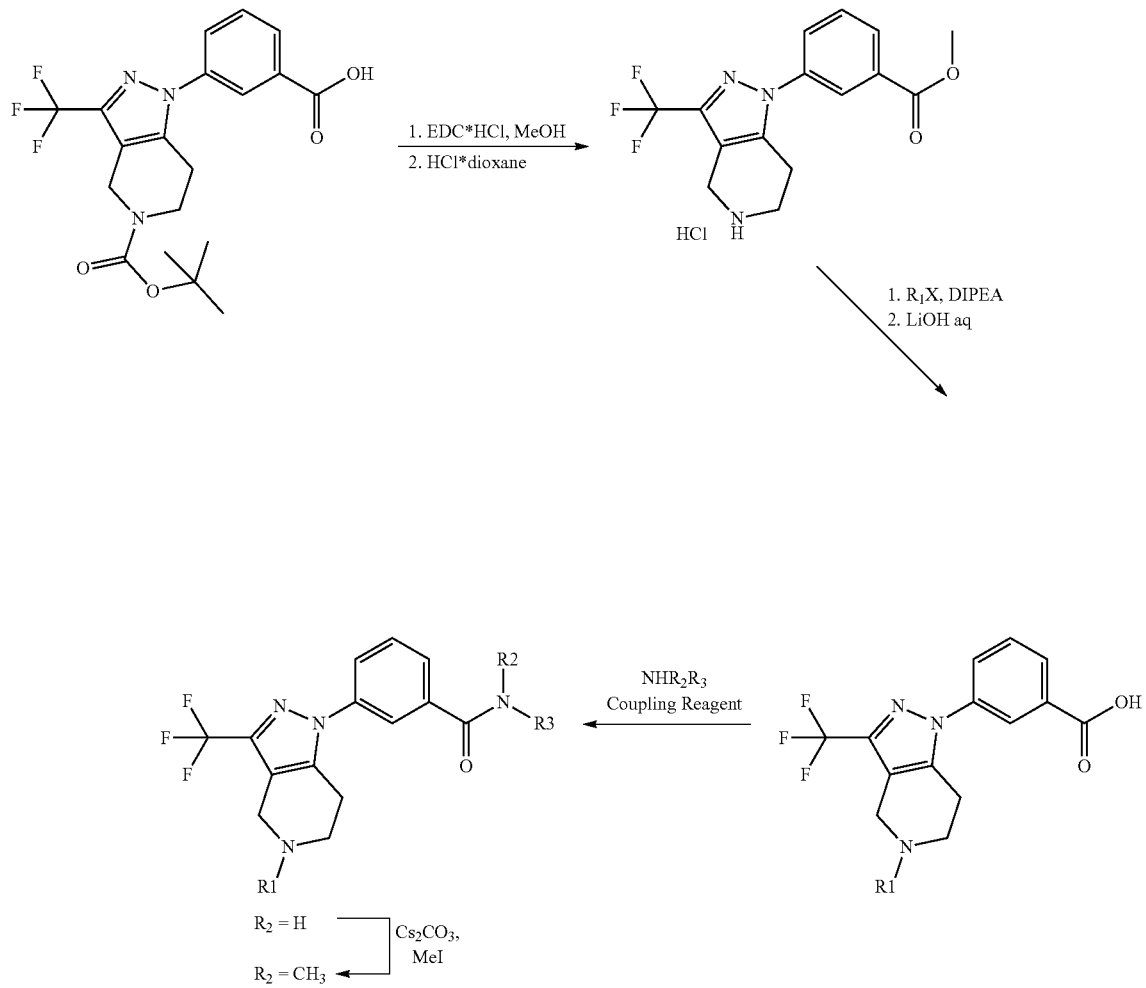

Example of General Protocol 4

General Procedure 4a

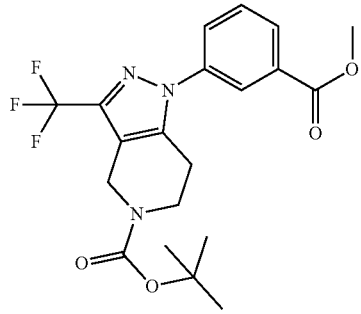 [SMILES: COC(=O)c1cccc(-n2nc(C(F)(F)F)c3c2CCN(C(=O)OC(C)(C)C)C3)c1]

[Int-4.1] tert-Butyl 1-(3-methoxycarbonylphenyl)-3-(trifluoromethyl)-6,7-dihydro-4H-pyrazolo[4,3-c]pyridine-5-carboxylate A flame-dried round-bottom flask was loaded with [Int-1.1] (2.5 g, 6.1 mmol) and methanol (15 mL) under nitrogen atmosphere. The resulting solution was cooled to 0° C. and EDC hydrochloride (1.5 g, 7.9 mmol) was added. The ice-bath was removed and the reaction mixture was allowed to stir 16 h. The solvent was concentrated and water (15 mL) and AcOEt (25 mL) were added. The organic phase was washed with brine (2×20 mL), dried over $Na_2SO_4$ and concentrated to afford a white solid (2.6 g). The product was used in the next step without any purification. UPLC-MS: tR=2.69 min (Generic method); MS (ESI) m/z calcd for $C_{20}H_{23}F_3N_3O_4$ (M+H)$^+$: 426.4, found: 426.4.

General Procedure 4b

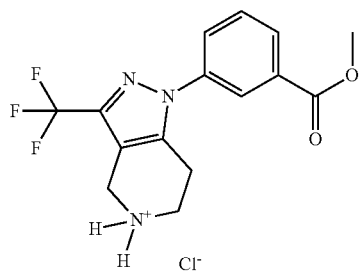 [SMILES: COC(=O)c1cccc(-n2nc(C(F)(F)F)c3c2CC[NH+](O)C3)c1 ; [Cl-]]

[Int-4.2] Methyl 3-[3-(trifluoromethyl)-4,5,6,7-tetrahydropyrazolo[4,3-c]pyridin-5-ium-1-yl]benzoate hydrochloride

[Int-4.1] (2.6 g, 6.1 mmol) was dissolved in dioxane (10 mL) and HCl (15 mL, 4M in dioxane) and the solution was allowed to stir 16 h at room temperature. Removal of the solvent gave a white solid which was purified by trituration with $Et_2O$ (100%). UPLC-MS: tR=1.59 min (Generic method); MS (ESI) m/z calcd for $C_{15}H_{16}F_3N_3O_2$ (M+H)$^+$: 326.3, found: 326.4.

General Procedure 4c

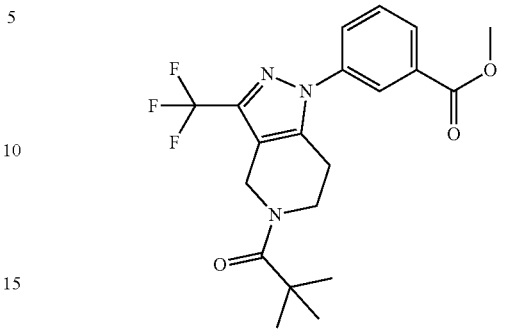

[Int-4.3] Methyl 3-[5-(2,2-Dimethylpropanoyl)-3-(trifluoromethyl)-6,7-dihydro-4H-pyrazolo[4,3-c]pyridin-1-yl]benzoate A flame-dried round-bottom flask was loaded with [Int-4.2] (6.1 mmol), DIPEA (1.7 g, 13.4 mmol) and DCM (30 mL) under nitrogen atmosphere. The resulting solution was cooled to 0° C. and pivaloyl chloride (0.88 g, 7.3 mmol) was added dropwise. After stirring for 16 h at room temperature, a sat. aq. $NH_4Cl$ (30 mL) was added. The aqueous phase was extracted with DCM (2×30 mL) and the combined organic layers were dried over $Na_2SO_4$ and concentrated. Subsequent flash chromatography (cyclohexane/AcOEt 70:30) afforded the title compound as a white solid (72%): $^1$H NMR (400 MHz, DMSO-d$_6$) δ 8.14 (app t, J=1.9 Hz, 1H), 8.06-8.02 (m, 1H), 7.95 (ddd, J=8.1, 2.3, 1.1 Hz, 1H), 7.72 (app t, J=7.9 Hz, 1H), 4.66 (s, 2H), 3.90 (s, 3H), 3.85 (app t, J=5.6 Hz, 2H), 2.95 (app t, J=5.6 Hz, 2H), 1.25 (s, 9H). UPLC-MS: t$_R$=1.37 min (Apolar method); MS (ESI) m/z calcd for $C_{20}H_{23}F_3N_3O_3$ (M+H)$^+$: 410.4. found: 410.5.

General Procedure 4d

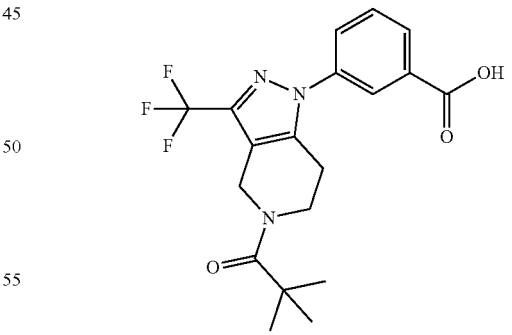

[Int-4.4] 3-[5-(2,2-Dimethylpropanoyl)-3-(trifluoromethyl)-6,7-dihydro-4H-pyrazolo[4,3-c]pyridin-1-yl]benzoic acid To a solution of [Int-4.3] (1.5 g, 3.6 mmol) in THF (12 mL) was added an aqueous solution of LiOH (1M, 6 mL) and the mixture was allowed to stir at room temperature for 12 h. The reaction was quenched adding HCl (2N) until pH=4. The aqueous layer was extracted with AcOEt (3×15 mL) and the combined organic phases were dried over Na$_2$SO$_4$ and concentrated. The product was used in the next step without any purification: $^1$H NMR (400 MHz, DMSO-d$_6$) δ 13.25 (bs, 1H), 8.13 (app t, 1H), 8.05-8.02 (m, 1H), 7.93 (ddd, J=8.1, 2.3, 1.1 Hz, 1H), 7.70 (app t, 1H), 4.67 (s, 2H), 3.86 (app t, J=5.6 Hz, 2H), 2.96 (app t, J=5.6 Hz, 2H), 1.26 (s, 9H). UPLC-MS: t$_R$=0.37 min (Apolar method); MS (ESI) m/z calcd for C$_{19}$H$_{21}$F$_3$N$_3$O$_3$ (M+H)$^+$: 396.4. found: 396.4.

3-[5-(2,2-Dimethylpropanoyl)-3-(trifluoromethyl)-6,7-dihydro-4Hpyrazolo[4,3-c]pyridin-1-yl]-N-(2-methyl-[1,2,4]triazolo[1,5-a]pyridin-6-yl)benzamide Following general procedure 1b, the title compound was obtained from compound [Int-4.4] and 2-methyl-[1,2,4]triazolo[1,5-a]pyridin-6-amine (42 mg, 0.29 mmol), after flash chromatography, eluting with DCM/MeOH (0 to 5%) as white solid in 31% yield: $^1$H NMR (400 MHz, DMSO-d$_6$) δ 10.70 (s, 1H), 9.46 (dd, J=2.1, 0.9 Hz, 1H), 8.20 (t, J=1.9 Hz, 1H), 8.10 (dt, J=7.9, 1.4 Hz, 1H), 7.92 (ddd, J=8.1, 2.2, 1.0 Hz, 1H), 7.83 (dd, J=9.5, 2.0 Hz, 1H), 7.78-7.71 (m, 2H), 4.68 (s, 2H), 3.86 (app t, J=5.6 Hz, 2H), 2.97 (app t, J=5.6 Hz, 2H), 2.46 (s, 3H), 1.26 (s, 9H). UPLC-MS: t$_R$=2.19 min (General method); MS (ESI) m/z calcd for C$_{26}$H$_{27}$F$_3$N$_7$O$_2$ (M+H)$^+$: 526.5. found: 526.5.

3-[5-(2,2-Dimethylpropanoyl)-3-(trifluoromethyl)-6,7-dihydro-4Hpyrazolo[4,3-c]pyridin-1-yl]-N-(3-methyl-1H-pyrazolo[3,4-b]pyridin-5-yl)benzamide Following general procedure 1b, the title compound was obtained from compound [Int-4.4] and 3-methyl-1H-pyrazolo[3,4-b]pyridin-5-amine, after flash chromatography, eluting with DCM/MeOH (0 to 5%) as white solid in 74% yield: $^1$H NMR (400 MHz, DMSO-d$_6$) δ 10.49 (s, 1H), 9.25 (s, 1H), 8.19 (t, J=1.9 Hz, 1H), 8.10 (dt, J=7.8, 1.3 Hz, 1H), 7.91 (ddd, J=8.1, 2.3, 1.1 Hz, 1H), 7.81 (s, 1H), 7.76 (t, J=7.9 Hz, 1H), 7.50 (d, J=9.6 Hz, 1H), 7.42 (dd, J=9.1 Hz, 1H), 4.69 (s, 2H), 3.87 (app t, J=5.4 Hz, 2H), 2.98 (app t, J=5.6 Hz, 2H), 2.34 (s, 3H), 1.27 (s, 9H). UPLC-MS: t$_R$=2.10 min (General method); MS (ESI) m/z calcd for C$_{26}$H$_{27}$F$_3$N$_7$O$_2$ (M+H)$^+$: 526.5. found: 526.5.

3-[5-(2,2-Dimethylpropanoyl)-3-(trifluoromethyl)-6,7-dihydro-4Hpyrazolo[4,3-c]pyridin-1-yl]-N-(6-methoxy-3-pyridyl)benzamide Following general procedure 1b, the title compound was obtained from compound [Int-4.4] and 6-methoxypyridin-3-amine, after flash chromatography, eluting with DCM/MeOH (0 to 5%) as white solid in 69% yield: $^1$H NMR (400 MHz, DMSO-d$_6$) δ 10.44 (s, 1H), 8.52 (dd, J=2.7, 0.7 Hz, 1H), 8.18 (t, J=1.9 Hz, 1H), 8.09 (dt, J=7.9, 1.3 Hz, 1H), 8.05 (dd, J=8.9, 2.7 Hz, 1H), 7.90 (ddd, J=8.0, 2.3, 1.0 Hz, 1H), 7.74 (app t, J=7.9 Hz, 1H), 6.87 (dd, J=8.9, 0.7 Hz, 1H), 4.69 (s, 2H), 3.86 (s, 5H), 2.97 (app t, J=5.6 Hz, 2H), 1.27 (s, 9H). UPLC-MS: t$_R$=2.41 min (General method); MS (ESI) m/z calcd for C$_{25}$H$_{27}$F$_3$N$_5$O$_3$ (M+H)$^+$: 502.5. found: 502.5.

3-[5-(2,2-Dimethylpropanoyl)-3-(trifluoromethyl)-6,7-dihydro-4H-pyrazolo[4,3-c]pyridin-1-yl]-N-(2-methoxy pyrimidin-5-yl)benzamide Following general procedure 1b, the title compound was obtained from compound [Int-4.4] and 2-methoxypyrimidin-5-amine, after flash chromatography, eluting with DCM/MeOH (0 to 5%), as white solid in 55% yield: $^1$H NMR (400 MHz, DMSO-d$_6$) δ 10.62 (s, 1H), 8.92 (s, 2H), 8.19 (t, J=1.9 Hz, 1H), 8.13-8.05 (m, 1H), 7.91 (ddd, J=8.0, 2.2, 1.0 Hz, 1H), 7.76 (app t, J=7.9 Hz, 1H), 4.68 (s, 2H), 3.92 (s, 3H), 3.86 (app t, J=5.6 Hz, 2H), 2.96 (app t, J=5.7 Hz, 2H), 1.26 (s, 9H). UPLC-MS: t$_R$=2.21 min (General method); MS (ESI) m/z calcd for C$_{24}$H$_{26}$F$_3$N$_6$O$_3$ (M+H)$^+$: 503.5. found: 503.6.

General Procedure 4e

3-[5-(2,2-Dimethylpropanoyl)-3-(trifluoromethyl)-6,7-dihydro-4Hpyrazolo[4,3-c]pyridin-1-yl]-N-(2-methoxy-4-pyridyl)benzamide To a solution of [Int-4.4] (75 mg, 0.19 mmol) in DCM (2.0 mL) and DMF (50 µL) was added oxalyl chloride (72 mg, 0.57 mmol) dropwise and the resulting solution was stirred 1 h at room temperature. Removal of the solvent gave a residue, which was taken up with DCM and added to a solution of 2-methoxypyridin-4-amine (28 mg, 0.22 mmol) and DIPEA (30 mg, 0.23 mmol) in DCM (1.0 mL) at 0° C. After stirring for 2 h of, the solution was partitioned between DCM (5 mL) and sat. aq. NH$_4$Cl (5 mL). The aqueous phase was extracted with DCM (2×5 mL) and the combined organic layers were washed with brine (10 mL), dried over Na$_2$SO$_4$, filtered and the solvent evaporated. The resulting residue was purified by silica gel flash chromatography, eluting with DCM/MeOH (0 to 5%) to afford the title compound as white solid (84%): $^1$H NMR (400 MHz, DMSO-d$_6$) δ 10.66 (s, 1H), 8.15 (t, J=1.9 Hz, 1H), 8.09 (dd, J=5.7, 0.6 Hz, 1H), 8.06 (ddd, J=7.8, 1.7, 1.0 Hz, 1H), 7.91 (ddd, J=8.1, 2.2, 1.0 Hz, 1H), 7.75 (app t, J=7.9 Hz, 1H), 7.35 (dd, J=5.7, 1.8 Hz, 1H), 7.32 (dd, J=1.8, 0.6 Hz, 1H), 4.68 (s, 2H), 3.89-3.79 (m, 5H), 2.96 (app t, J=5.5 Hz, 2H), 1.26 (s, 9H). UPLC-MS: t$_R$=2.44 min (General method); MS (ESI) m/z calcd for C$_{25}$H$_{27}$F$_3$N$_5$O$_3$ (M+H)$^+$: 502.5. found: 502.5.

3-[5-(2,2-Dimethylpropanoyl)-3-(trifluoromethyl)-6,7-dihydro-4H-pyrazolo[4,3-c]pyridin-1-yl]-N-(2-methylimidazo [1,2-a]pyridin-6-yl)benzamide Following general procedure 4e, the title compound was obtained from compound [Int-4.4] and 2-methylimidazo[1,2-a]pyridin-6-amine, after flash chromatography, eluting with DCM/MeOH (0 to 5%) as white solid in 26% yield: $^1$H NMR (400 MHz, DMSO-d$_6$) δ 10.50 (s, 1H), 9.25 (dd, J=2.0, 1.0 Hz, 1H), 8.19 (t, J=1.9 Hz, 1H), 8.09 (dt, J=7.9, 1.2 Hz, 1H), 7.90 (ddd, J=8.0, 2.2, 1.0 Hz, 1H), 7.80 (s, 1H), 7.75 (app t, J=7.9 Hz, 1H), 7.49 (dt, J=9.6, 0.8 Hz, 1H), 7.42 (dd, J=9.6, 2.0 Hz, 1H), 4.69 (s, 2H), 3.86 (app t, J=5.5 Hz, 2H), 2.97 (app t, J=5.5 Hz, 2H), 2.33 (s, 3H), 1.26 (s, 9H). UPLC-MS: t$_R$=2.19 min (General method); MS (ESI) m/z calcd for C$_{27}$H$_{28}$F$_3$N$_6$O$_2$ (M+H)$^+$: 525.5. found: 525.5.

General Procedure 4f

3-[5-(2,2-Dimethylpropanoyl)-3-(trifluoromethyl)-6,7-dihydro-4Hpyrazolo[4,3-c]pyridin-1-yl]-N-(6-methoxy-3-pyridyl)-N-methylbenzamide To a solution of [080] (47 mg, 0.09 mmol) and Cs$_2$CO$_3$ (59 mg, 0.18 mmol) in DMF (0.5 mL) was added iodomethane (18 mg, 0.13 mmol) at room temperature. The reaction mixture was stirred for 3 h, then partitioned between AcOEt (5 mL) and sat. aq. NH₄Cl (5 mL). The aqueous phase was extracted with AcOEt (2×5 mL) and the combined organic layers were washed with brine (10 mL), dried over Na₂SO₄, filtered and the solvent evaporated. The resulting residue was purified by silica gel flash chromatography, eluting with DCM/MTBE (0 to 50%) to afford the title compound as white solid (89%): ¹H NMR (400 MHz, DMSO-d₆) δ 8.03 (bs, 1H), 7.69 (dd, J=8.0, 2.1 Hz, 1H), 7.61-7.53 (m, 2H), 7.52-7.36 (m, 2H), 4.63 (s, 2H), 3.83-3.74 (m, 5H), 3.37 (s, 3H), 2.69-2.59 (m, 2H), 1.27 (s, 9H). UPLC-MS: $t_R$=2.42 min (General method); MS (ESI) m/z calcd for $C_{26}H_{29}F_3N_5O_3$ (M+H)⁺: 516.5, found: 516.5.

3-[5-(2,2-Dimethylpropanoyl)-3-(trifluoromethyl)-6,7-dihydro-4H-pyrazolo[4,3-c]pyridin-1-yl]-N-(2-methoxy-4-pyridyl)-N-methyl-benzamide Following general procedure 4f, the title compound was obtained from compound [083], after flash chromatography, eluting with DCM/MTBE (0 to 50%) to afford the title compound as white solid (79%): ¹H NMR (400 MHz, DMSO-d₆) δ 7.99 (dd, J=5.6, 0.6 Hz, 1H), 7.65 (ddd, J=7.9, 2.3, 1.3 Hz, 1H), 7.59 (t, J=1.8 Hz, 1H), 7.53 (app t, J=7.8 Hz, 1H), 7.47 (dt, J=7.7, 1.4 Hz, 1H), 6.76 (dd, J=5.6, 1.9 Hz, 1H), 6.72 (dd, J=1.9, 0.6 Hz, 1H), 4.62 (s, 2H), 3.80-3.75 (m, 5H), 3.41 (s, 3H), 2.57 (app t, J=5.6 Hz, 2H), 1.26 (s, 9H). UPLC-MS: $t_R$=2.43 min (General method); MS (ESI) m/z calcd for $C_{26}H_{29}F_3N_5O_3$ (M+H)⁺: 515.5, found: 515.5.

3-[5-(2,2-Dimethylpropanoyl)-3-(trifluoromethyl)-6,7-dihydro-4H-pyrazolo[4,3-c]pyridin-1-yl]-N-methyl-N-(2-methylimidazo[1,2-a]pyridin-6-yl)benzamide Following general procedure 4f, the title compound was obtained from compound [084], after flash chromatography, eluting with DCM/MTBE (0 to 50%) to afford the title compound as white solid (56%): ¹H NMR (400 MHz, DMSO-d₆) δ 8.50 (s, 1H), 7.60-7.50 (m, 3H), 7.45 (s, 2H), 7.36 (d, J=9.5 Hz, 1H), 7.17 (dd, J=9.5, 2.0 Hz, 1H), 4.59 (s, 2H), 3.68 (bs, 2H), 3.39 (s, 3H), 2.43 (bs, 2H), 2.28 (s, 3H), 1.25 (s, 9H). UPLC-MS: tR=0.84 min (Apolar method); MS (ESI) m/z calcd for $C_{28}H_{30}F_3N_6O_2$ (M+H)⁺: 539.5. found: 539.5.

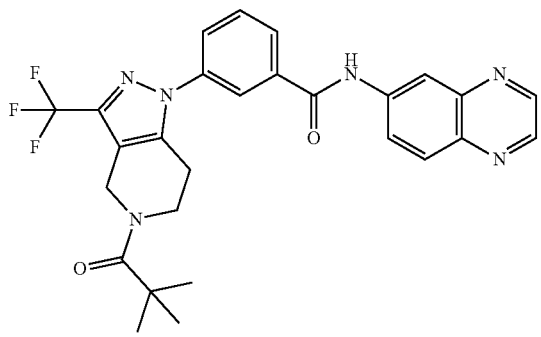

[Int-4.5] 3-[5-(2,2-Dimethylpropanoyl)-3-(trifluoromethyl)-6,7-dihydro-4H-pyrazolo[4,3-c]pyridin-1-yl]-N-quinoxalin-6-yl-benzamide Following general procedure 1b, the title compound was obtained from compound [Int-4.4] and quinoxalin-6-amine, after flash chromatography, eluting with DCM/MeOH (0 to 5%) as white solid in 34% yield: UPLC-MS: $t_R$=2.25 min (General method); MS (ESI) m/z calcd for $C_{27}H_{26}F_3N_6O_2$ (M+H)⁺: 523.2. found: 523.6.

3-[5-(2,2-Dimethylpropanoyl)-3-(trifluoromethyl)-6,7-dihydro-4H-pyrazolo[4,3-c]pyridin-1-yl]-N-methyl-N-quinoxalin-6-yl-benzamide Following general procedure 4f, the title compound was obtained from compound [Int-4.5], after flash chromatography on neutral alumina gel (pH=7), eluting with DCM, as white solid in 41% yield: ¹H NMR (400 MHz, DMSO-d₆) δ 8.93-8.90 (m, 2H), 7.99 (d, J=6.9 Hz, 1H), 7.97 (s, 1H), 7.76-7.71 (m, 1H), 7.60 (t, J=1.9 Hz, 1H), 7.56-7.48 (m, 2H), 7.45 (app-t, J=7.7 Hz, 1H), 4.56 (s, 2H), 3.58-3.53 (m, 5H), 2.34 (app-t, J=5.8 Hz, 2H), 1.23 (s, 9H). UPLC-MS: tR=2.28 min (General method); MS (ESI) m/z calcd for $C_{28}H_{28}F_3N_6O_2$ (M+H)⁺: 537.2. found: 537.6.

3-[5-(2,2-Dimethylpropanoyl)-3-(trifluoromethyl)-6,7-dihydro-4H-pyrazolo[4,3-c]pyridin-1-yl]-N-(2-methoxypyrimidin-5-yl)-N-methyl-benzamide Step 1. 2-Methoxy-N-methyl-pyrimidin-5-amine: A solution of 2-methoxypyrimidin-5-amine (100 mg, 0.8 mmol) and activated molecular sieves 3 Å (60 mg) in DCE (2.0 mL) was treated with paraformaldehyde (144 mg, 4.8 mmol) and sodium triacetoxyborohydride (509 mg, 2.4 mmol). The resulting mixture was allowed to stir at room temperature for 18 h, then filtered over a glass filter and the resulting crude mixture was washed few times with DCM. Removal of the solvent gave a crude product which was subjected to flash chromatography on neutral alumina gel Al₂O₃, pH=7) eluting with DCM as solvent To give the compound as white solid in 31% yield: ¹H NMR (400 MHz, DMSO-d₆) δ 7.94 (s, 2H), 5.57-5.44 (m, 1H), 3.78 (s, 3H), 2.67 (d, J=5.3 Hz, 3H).

Step 2. Following general procedure 4e, the title compound was obtained from compound [Int-4.4], after silica gel flash chromatography eluting with DCM/AcOEt (0 to 60%), as white solid in 22% yield: ¹H NMR (400 MHz, Chloroform-d) δ 8.29 (bs, 2H), 7.56-7.47 (m, 2H), 7.39 (app-t, J=7.8 Hz, 1H), 7.27 (bs, 1H), 4.73 (s, 2H), 3.97 (s, 3H), 3.82 (app-t, J=5.6 Hz, 2H), 3.47 (s, 3H), 2.74 (s, 2H), 1.31 (s, 9H). UPLC-MS: $t_R$=2.25 min (General method); MS (ESI) m/z calcd for $C_{25}H_{28}F_3N_6O_3$ (M+H)⁺: 517.2. found: 517.5.

General Protocol 5
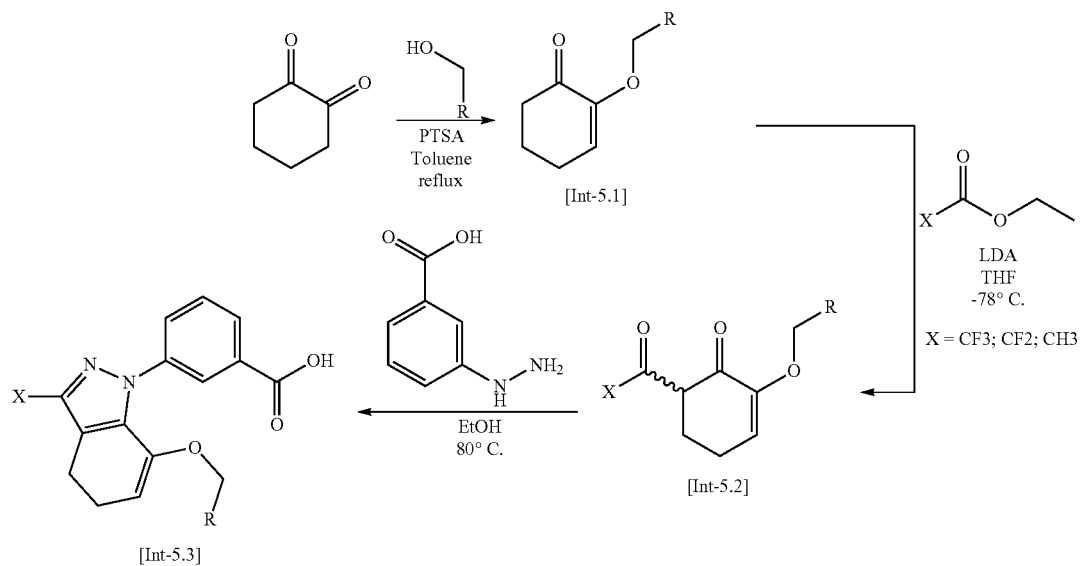
Pathway A
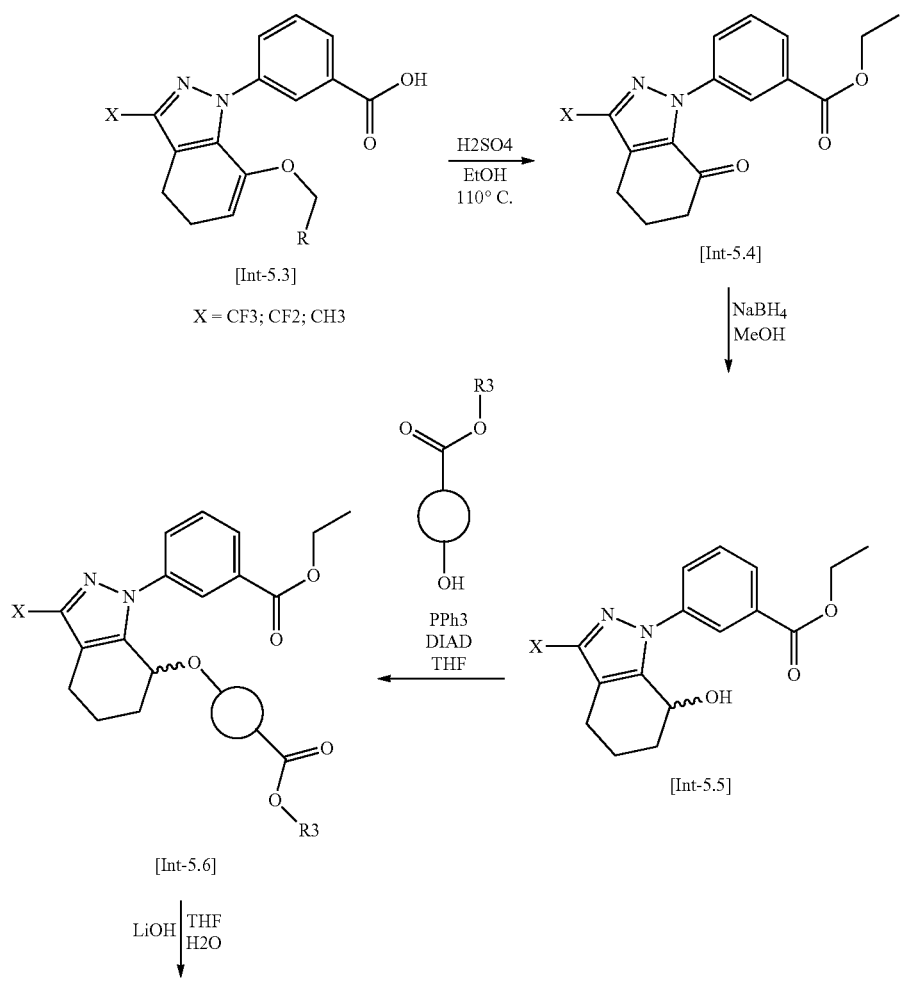

-continued
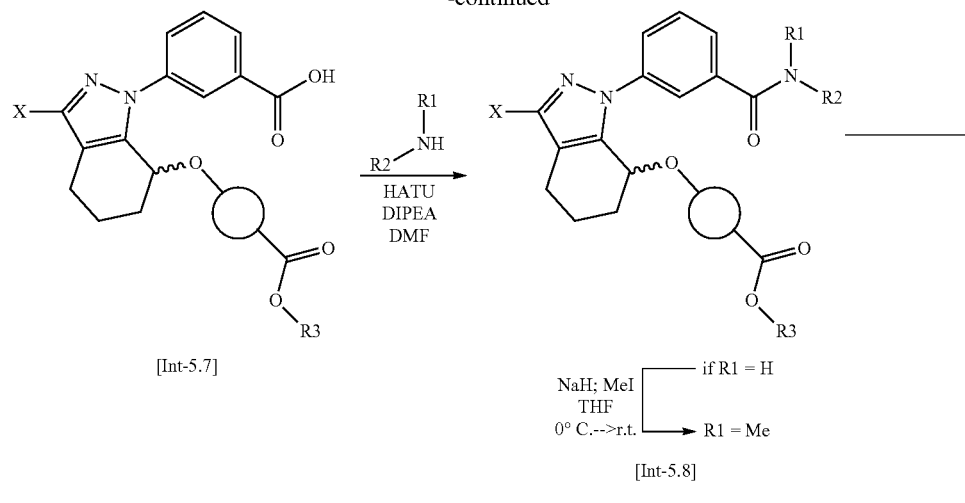
[Int-5.7]
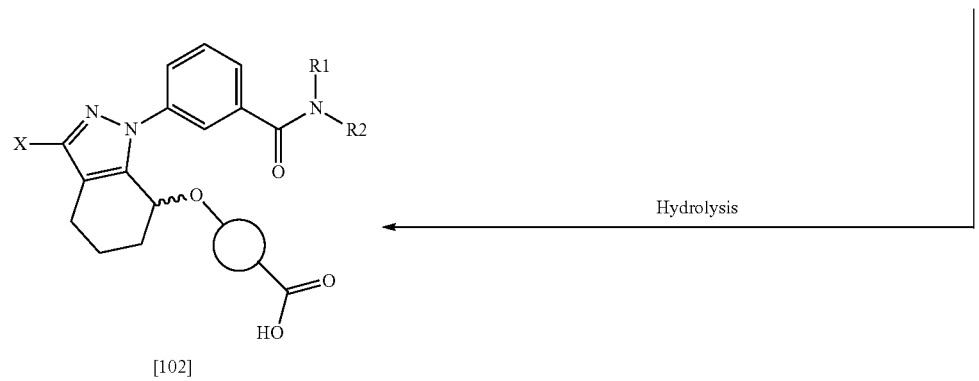
[102]
Pathway B
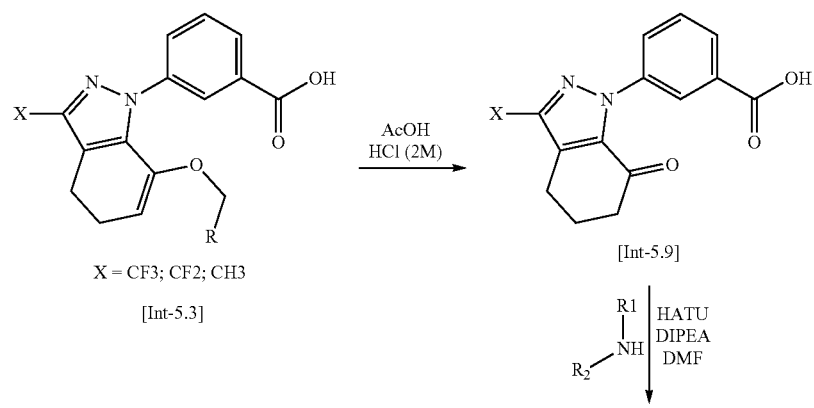
[Int-5.3]

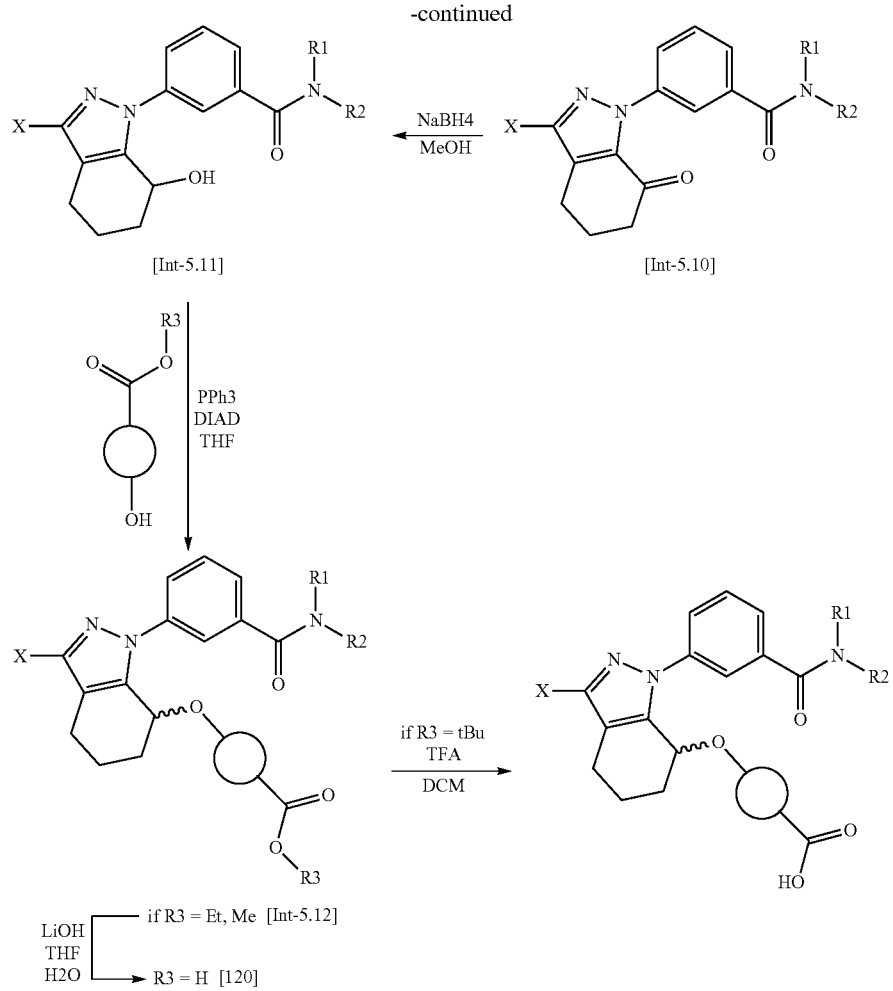

Example of General Protocol 5

General Procedure 5a

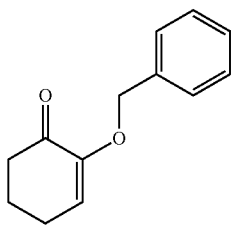 [SMILES: O=C1CCCC=C1OCc1ccccc1]

[Int-5.1] 2-Benzyloxycyclohex-2-en-1-one

In a round-bottom flask, at room temperature, cyclohexane-1,2-dione (4.35 g, 38.84 mmol) was dissolved in dry toluene (100 mL), followed by benzyl alcohol (2.89 mL, 27.74 mmol) and p-toluensulphonic acid (0.478 g, 2.77 mmol). The mixture was stirred at refluxing temperature using a Dean-Stark device for 16 h, and cooled to room temperature. The mixture was poured carefully in a sat. aq. Na$_2$CO$_3$ (50 mL) solution, and aqueous layer extracted with Et$_2$O (300 mL). The organics were washed with sat. aq. Na$_2$CO$_3$ (2×50 mL) solution, brine (50 mL), dried over Na$_2$SO$_4$, filtered, and the solvent evaporated under reduced pressure. After silica gel flash chromatography, eluting with cyclohexane/EtOAC (90:10), the title compound was obtained (2.0 g, 36%), as a pale yellow oil. $^1$H NMR (400 MHz, DMSO-d$_6$) δ 7.38-7.36 (m, 2H), 7.33-7.27 (m, 3H), 6.13 (t, J=4.6 Hz, 1H), 4.50 (d, J=5.7 Hz, 1H), 2.45-2.30 (m, 4H), 1.87 (p, J=6.1 Hz, 2H). UPLC-MS: t$_R$=1.96 min (Generic method); MS (ESI) m/z calcd for C$_{13}$H$_{15}$O$_2$ (M+H)$^+$: 203.1, found: 203.4.

General Procedure 5b

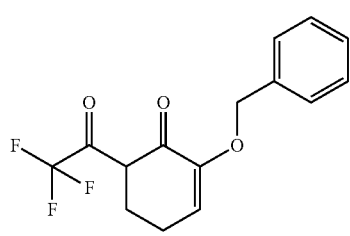 [SMILES: O=C1C(OCc2ccccc2)=CCCC1C(=O)C(F)(F)F]

[Int-5.2] 2-Benzyloxy-6-(2,2,2-trifluoroacetyl)cyclohex-2-en-1-one

Under nitrogen atmosphere, a flame-dried flask was charged with [Int-5.1] (1.89 g, 9.34 mmol) and dry THF (40 mL). The temperature was lowered down to −78° C., and LDA (9.4 mL, 18.7 mmol, 2.0 M in THF) was added dropwise over 10 min. The resulting solution was allowed to stir 10 min at the same temperature, then ethyl 2,2,2-trifluoroacetate (2.23 mL g, 18.69 mmol) was added. The mixture was stirred at the same temperature for 4 h, and the reaction quenched adding sat. aq. NH$_4$Cl solution. The aqueous layer was extracted with EtOAc (3×40 mL), and the collected organic layers were washed with brine (40 mL), dried over Na$_2$SO$_4$, filtered and concentrated under reduced pressure. After silica gel flash chromatography, eluting with cyclohexane/EtOAC (90:10), the title compound was obtained (1.99 g, 72%), as a viscous oil. $^1$H NMR (400 MHz, DMSO-d$_6$) δ 8.18-6.91 (m, 5H), 6.75-5.93 (m, 1H), 4.88 (s, 1H), 2.58 (app-t, J=7.0 Hz, 2H), 2.44-2.33 (m, 2H), 2.22-2.10 (m, 1H), 1.33 (d, J=6.7 Hz, 1H), 1.21 (d, J=6.6 Hz, 1H). UPLC-MS: t$_R$=2.04 min (Generic method); MS (ESI) m/z calcd for C$_{15}$H$_{12}$F$_3$O$_3$ (M−H)$^-$: 297.1, found: 297.4.

General Procedure 5c

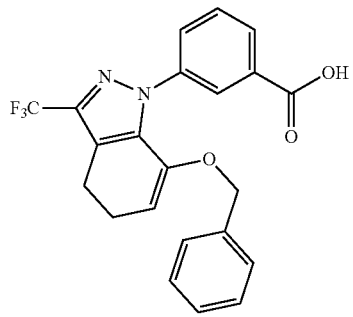 [SMILES: O=C(O)c1cccc(-n2nc(C(F)(F)F)c3c2C(OCc2ccccc2)=CCC3)c1]

[Int-5.3] 3-[7-Benzyloxy-3-(trifluoromethyl)-4,5-dihydroindazol-1-yl]benzoic acid To a suspension of 3-hydrazinobenzoic acid (1.01 g, 6.63 mmol) in EtOH (45 mL), [Int-5.2] (1.98 g, 6.63 mmol) was added, and mixture stirred at 80° C. for 3 h. The solution was concentrated and the crude compound was used in the next step without any further purification (ca. 1.7 g). UPLC-MS: t$_R$=2.18 min (Generic method); MS (ESI) m/z calcd for C$_{22}$H$_{18}$F$_3$N$_2$O$_3$ (M+H)$^+$: 415.1, found: 415.4.

General Procedure 5d

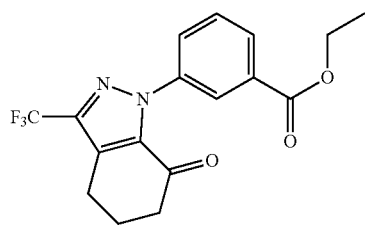 [SMILES: CCOC(=O)c1cccc(-n2nc(C(F)(F)F)c3c2C(=O)CCC3)c1]

[Int-5.4] Ethyl 3-[7-oxo-3-(trifluoromethyl)-5,6-dihydro-4H-indazol-1-yl]benzoate To a suspension of crude [Int-5.3](1.0 g, 2.41 mmol) in EtOH (55 mL), H$_2$SO$_4$ 95% (1.5 mL) was added, and mixture stirred at 110° C. for 2 h 30 min. Mixture was cooled to room temperature and sat. aq. NaHCO$_3$ was carefully added until pH=7. The aqueous layer was extracted with EtOAc (3×20 mL), and the collected organic layers were dried with Na$_2$SO$_4$, filtered and concentrated under vacuum. After silica gel flash chromatography, eluting with cyclohexane/DCM/EtOAc (80:10:10), the title compound was obtained (0.71 g, 52% over two steps), as a viscous oil. 1H NMR (400 MHz, CDCl$_3$) δ 8.12-8.16 (m, 2H), 7.68 (ddd, J=8.0, 2.1, 1.2 Hz, 1H), 7.54 (app t, J=7.7 Hz, 1H), 4.40 (q, J=7.1 Hz, 2H), 2.97 (t, J=6.1 Hz, 2H), 2.63 (m, 2H), 2.23 (p, J=6.4 Hz, 2H), 1.41 (t, J=7.1 Hz, 3H); UPLC-MS: t$_R$=2.51 min (Generic method); MS (ESI) m/z calcd for C$_{17}$H$_{15}$F$_3$N$_2$O$_3$ (M+H)$^+$: 353.3, found: 353.4.

General Procedure 5e

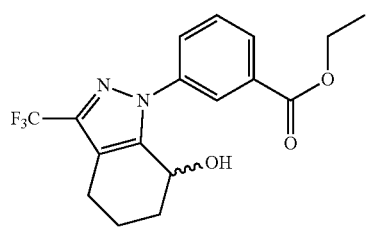 [SMILES: CCOC(=O)c1cccc(-n2nc(C(F)(F)F)c3c2C(O)CCC3)c1]

[Int-5.5] Ethyl 3-[(7-hydroxy-3-(trifluoromethyl)-4,5,6,7-tetrahydroindazol-1-yl]benzoate Int-5.4 (0.476 g, 1.35 mmol) was dissolved in MeOH (8.0 mL), and the solution cooled to 0° C. NaBH$_4$ (0.059 g, 1.55 mmol) was then added portion-wise. The corresponding mixture was stirred at room temperature for 40 minutes and the reaction quenched with sat. aq. NH$_4$Cl (10 mL) solution. The aqueous layer was extracted with EtOAc (2×20 mL), and the collected organic layers were washed with brine, dried over Na$_2$SO$_4$ and concentrated under vacuum. After silica gel flash chromatography, eluting with DCM/TBME (90:10), the title compound (0.43 g, 90%) was obtained, as viscous oil.

General Procedure 5f

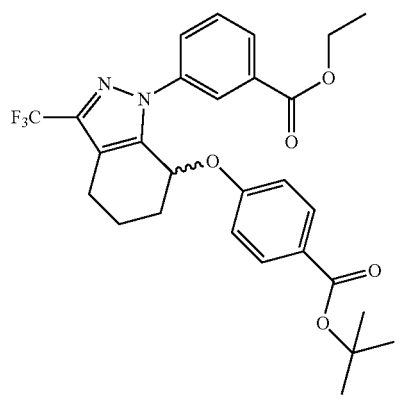 [SMILES: CCOC(=O)c1cccc(-n2nc(C(F)(F)F)c3c2C(Oc2ccc(C(=O)OC(C)(C)C)cc2)CCC3)c1]

[Int-5.6] Ethyl 3-[7-(4-tert-butoxycarbonylphenoxy)-3-(trifluoromethyl)-4,5,6,7-tetrahydroindazol-1-yl]benzoate A solution of tert-butyl 4-hydroxybenzoate (0.423 g, 2.18 mmol) in THF (14 mL) was treated with triphenylphosphine (0.572 g, 2.18 mmol) and DIAD (0.440 g, 2.18 mmol). The resulting solution was stirred for 30 minutes at r.t. and a solution of [Int-5.5] (0.515 g, 1.45 mmol) in THF (5 mL) was added dropwise over 5 minutes. The mixture was stirred for 4 h and solvent was evaporated. The crude product was purified by flash chromatography using cyclohexane:EtOAc=95:5 as eluting mixture To give the title compound as an off-white solid (0.5 g, 65): $^1$H NMR (400 MHz, DMSO-$d_6$) δ 8.05 (app t, J=1.9 Hz, 1H), 7.93 (dt, J=7.8, 1.3 Hz, 1H), 7.85 (ddd, J=8.1, 2.3, 1.1 Hz, 1H), 7.80-7.75 (m, 2H), 7.57 (app t, J=7.9 Hz, 1H), 6.99-6.93 (m, 2H), 5.85-5.82 (m, 1H), 4.23-4.08 (m, 2H), 2.80 (app d, J=16.5 Hz, 1H), 2.61 (dt, J=15.7, 7.5 Hz, 1H), 2.13-2.04 (m, 1H), 1.97-1.80 (m, 3H), 1.52 (s, 9H), 1.16 (t, J=7.1 Hz, 3H). UPLC-MS: $t_R$=2.71 min (apolar method); MS (ESI) m/z calcd for $C_{28}H_{30}F_3N_2O_5$ (M+H)$^+$: 531.5, found: 531.3.

General Procedure 5g

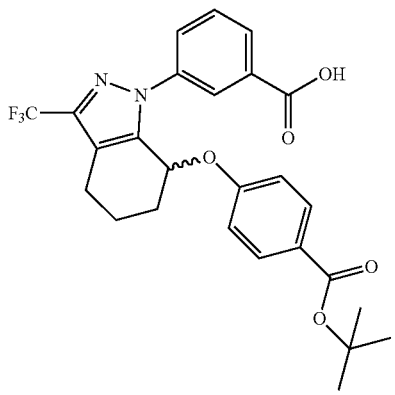 [SMILES: CC(C)(C)OC(=O)c1ccc(OC2CCCc3c(C(F)(F)F)nn(-c4cccc(C(=O)O)c4)c32)cc1]

[Int-5.7] 3-[7-(4-tert-Butoxycarbonylphenoxy)-3-(trifluoromethyl)-4,5,6,7-tetrahydroindazol-1-yl]benzoic acid To a solution of [Int-5.6] (0.212 g, 0.40 mmol) in THF (2.5 mL), water (0.5 mL) and lithium hydroxide (0.019 g, 0.80 mmol) were added. The resulting mixture was stirred 18 h at room temperature and quenched by adding a solution HCl 1 M until pH=4/5. The aqueous phase was extracted with EtOAc (3×15 mL) and the combined organic layers were dried over $Na_2SO_4$, filtered and concentrated. The crude product was used in the next step without further purification (0.187, 93%): $^1$H NMR (400 MHz, DMSO-$d_6$) δ 13.16 (s, 1H), 8.09 (app t, J=1.9 Hz, 1H), 7.92 (dt, J=7.8, 1.3 Hz, 1H), 7.81 (ddd, J=8.3, 2.4, 1.2 Hz, 1H), 7.79-7.75 (m, 2H), 7.52 (app t, J=7.9 Hz, 1H), 5.85-5.81 (m, 1H), 2.81 (app d, J=16.6 Hz, 1H), 2.62 (q, J=8.1 Hz, 1H), 2.13-2.06 (m, 1H), 1.96-1.79 (m, 3H), 1.52 (s, 9H). UPLC-MS: $t_R$=1.28 min (apolar method); MS (ESI) m/z calcd for $C_{26}H_{26}F_3N_2O_5$ (M+H)$^+$: 503.5, found: 503.4.

General Procedure 5h tert-Butyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate At room temperature, [Int-5.7] (0.48 g, 0.96 mmol) was dissolved in DMF (6.4 mL) followed by HATU (0.438 g, 1.15 mmol) and TEA (0.126 g, 1.25 mmol). The solution was stirred for 30 min and 2,2-difluoro-N-methyl-1,3-benzodioxol-5-amine hydrochloride (1.15 mmol) was added in one aliquot. After 16 h the mixture was partitioned between $Et_2O$ and sat. $NH_4Cl$. The organic phase was washed with brine, dried over $Na_2SO_4$ and concentrated to give after flash chromatography (cyclohexane/AcOEt 80:20) the title compound, as a white solid (0.251 g, 39%): $^1$H NMR (400 MHz, DMSO-$d_6$) δ 7.83-7.75 (m, 2H), 7.56 (s, 1H), 7.49 (d, J=7.6 Hz, 1H), 7.32 (d, J=2.1 Hz, 1H), 7.28-7.19 (m, 1H), 7.15 (d, J=8.5 Hz, 1H), 6.99-6.92 (m, 1H), 6.78 (d, J=8.6 Hz, 1H), 5.75 (s, 1H), 3.24 (s, 3H), 2.82-2.74 (m, 1H), 2.64-2.54 (m, 1H), 2.12-2.04 (m, 1H), 1.96-1.77 (m, 3H), 1.49 (s, 9H). UPLC-MS: $t_R$=2.60 min (Apolar method); MS (ESI) m/z calcd for $C_{34}H_{31}F_5N_3O_6$ (M+H)$^+$: 672.6, found: 672.5.

General Procedure 5i

4-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]benzoic acid Compound [143](0.054 g, 0.08 mmol) was dissolved in a solution of 10% TFA in dichloromethane at room temperature. The solution was stirred 5 h and the solvent was removed under vacuum. The resulting oil was subjected to silica gel flash chromatography (DCM/EtOAc 70:30) to give the pure title compound, as a white solid (0.037 g, 75%). $^1$H NMR (400 MHz, DMSO-$d_6$) δ 12.66 (bs, 1H), 7.85 (d, J=8.8 Hz, 2H), 7.55 (s, 1H), 7.50 (d, J=6.8 Hz, 1H), 7.38 (d, J=2.1 Hz, 1H), 7.24 (s, 2H), 7.16 (d, J=8.5 Hz, 1H), 7.01-6.92 (m, 2H), 6.82-6.72 (m, 1H), 5.77 (s, 1H), 3.24 (s, 3H), 2.86-2.76 (m, 1H), 2.65-2.56 (m, 1H), 2.15-2.05 (m, 1H), 1.98-1.80 (m, 3H). UPLC-MS: $t_R$=2.44 min (Generic method); MS (ESI) m/z calcd for $C_{31}H_{22}F_5N_3O_6$ (M+H)$^+$: 616.5, found: 616.5.

General Procedure 5l

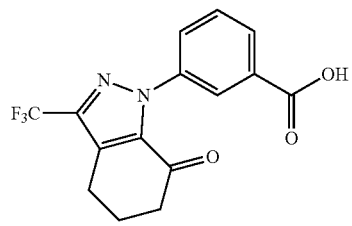 [SMILES: O=C(O)c1cccc(-n2nc(C(F)(F)F)c3c2C(=O)CCC3)c1]

[Int-5.9] 3-[7-Oxo-3-(trifluoromethyl)-5,6-dihydro-4H-indazol-1-yl]benzoic acid The crude [Int-5.3] (1.7 g) was dissolved in AcOH (7.0 mL) and aq. HCl 2M solution (3.5 mL) was added. The resulting dark red mixture was stirred for 1 h at room temperature. The reaction was poured with water (20 mL)

and diluted with EtOAc (50 mL). The layers were divided and organics were washed with H$_2$O (2×20 ml), dried over Na$_2$SO$_4$, filtered and concentrated under vacuum. The crude oil was dissolved in dichloromethane (ca. 5.0 mL), followed by addition of cyclohexane (30 mL). The corresponding solution was evaporated under vacuum to remove acetic acid (the procedure was repeated three times). After silica gel flash chromatography, eluting with dichloromethane/EtOAc (60:40), the title compound (1.2 g, 56% over two steps) was obtained, as a white solid. $^1$H NMR (400 MHz, DMSO-d$_6$) δ 13.32 (s, 1H), 8.18-7.97 (m, 2H), 7.82 (app-dt, J=8.0, 1.5 Hz, 1H), 7.66 (app-t, J=8.0 Hz, 1H), 2.90 (app-t, J=6.1 Hz, 2H), 2.61 (dd, J=7.2, 5.5 Hz, 2H), 2.16 (p, J=6.3 Hz, 2H). UPLC-MS: t$_R$=1.61 min (Generic method); MS (ESI) m/z calcd for C$_{15}$H$_{10}$F$_3$N$_2$O$_3$ (M–H)$^-$: 323.3, found: 323.4.

General Procedure 5m

N-(2,2-Difluoro-1,3-benzodioxol-5-yl)-N-methyl-3-[7-oxo-3-(trifluoromethyl)-5,6-dihydro-4H-indazol-1-yl]benzamide At room temperature, [Int-5.9] (0.7 g, 2.16 mmol) was dissolved in DMF (5.0 mL) followed by HATU (0.444 g, 2.37 mmol) and DIPEA (1.1 mL g, 6.48 mmol). The solution was stirred for 10 min and 2,2-difluoro-N-methyl-1,3-benzodioxol-5-amine (0.407 g, 2.37 mmol) was added. After 16 h the mixture was partitioned between Et$_2$O and sat. aq. NH$_4$Cl solution. The organic layer was washed with brine, dried over Na$_2$SO$_4$ and solvent concentrated under vacuum. After silica gel flash chromatography, eluting with cyclohexane/EtOAc (60:40), the title compound was obtained (0.75 g, 70%), as a white foam: $^1$H NMR (400 MHz, DMSO-d$_6$) δ 7.52-7.39 (m, 5H), 7.28 (d, J=8.5 Hz, 1H), 7.03 (d, J=8.6 Hz, 1H), 3.36 (s, 3H), 2.87 (app-t, J=6.0 Hz, 2H), 2.55 (app-t, J=6.5 Hz, 1H), 2.20-2.07 (m, 2H). UPLC-MS: t$_R$=1.59 min (Apolar method); MS (ESI) m/z calcd for C$_{23}$H$_{17}$F$_5$N$_3$O$_4$ (M+H)$^+$: 494.1, found: 494.4.

N-(2,2-Difluoro-1,3-benzodioxol-5-yl)-N-methyl-3-[7-oxo-3-(trifluoromethyl)-5,6-dihydro-4H-indazol-1-yl]benzamide Following general procedure 5e, the title compound was obtained from [144], after flash chromatography eluting with cyclohexane/EtOAc (0 to 50%), as white solid in 70% yield: $^1$H NMR (400 MHz, DMSO-d$_6$) δ 7.82-7.73 (m, 2H), 7.52 (d, J=2.1 Hz, 1H), 7.48-7.41 (m, 1H), 7.37 (app-d, J=7.7 Hz, 1H), 7.27 (d, J=8.5 Hz, 1H), 7.02 (dd, J=8.6, 2.1 Hz, 1H), 5.48 (d, J=6.4 Hz, 1H), 4.55-4.41 (m, 1H), 2.67 (app-d, J=15.3 Hz, 1H), 2.48-2.42 (m, 1H), 2.05-1.82 (m, 2H), 1.81-1.59 (m, 2H). UPLC-MS: t$_R$=1.51 min (Apolar method); MS (ESI) m/z calcd for C$_{23}$H$_{19}$F$_5$N$_3$O$_4$ (M+H)$^+$: 496.1, found: 496.5.

Methyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-fluoro-benzoate Following general procedure 5f, the title compound was obtained from [145] and methyl 2-fluoro-4-hydroxy-benzoate, after flash chromatography eluting with cyclohexane/EtOAc (0 to 30%), as white solid in 81% yield: $^1$H NMR (400 MHz, DMSO-d$_6$) δ 7.79 (t, J=8.7 Hz, 1H), 7.52 (s, 1H), 7.48 (d, J=7.7 Hz, 1H), 7.38 (d, J=2.1 Hz, 1H), 7.31-7.11 (m, 3H), 6.96 (dd, J=13.0, 2.4 Hz, 1H), 6.87 (d, J=8.5 Hz, 1H), 6.80 (dd, J=8.8, 2.4 Hz, 1H), 5.83 (t, J=2.9 Hz, 2H), 3.80 (s, 3H), 3.24 (s, 3H), 2.95-2.72 (m, 1H), 2.64-2.54 (m, 1H), 2.16-2.02 (m, 1H), 2.00-1.87 (m, 1H), 1.86-1.70 (m, 2H). UPLC-MS: t$_R$=2.13 min (Apolar method); MS (ESI) m/z calcd for C$_{31}$H$_{24}$F$_6$N$_3$O$_6$ (M+H)$^+$: 648.2. found: 648.4.5.

General Procedure 50

2-Fluoro-4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid To a solution of [146] (0.05 g, 0.08 mmol) in THF (1.0 mL), LiOH$_{aq}$ (0.5M, 0.8 mL) was added. Mixture was stirred at room temperature for 4 h and the reaction quenched with aq. HCl (1M) until pH=4/5. The aqueous layer was extracted with EtOAc (2×20 mL), and the collected organic layers were washed with brine, dried over Na$_2$SO$_4$ and concentrated under vacuum. After silica gel flash chromatography, eluting with DCM/EtOAc (50:50), the title compound was obtained, as a white solid (0.02 g, 35%): $^1$H NMR (400 MHz, DMSO-d$_6$) δ 12.90 (s, 1H), 7.77 (t, J=8.8 Hz, 1H), 7.53 (app-t, J=1.8 Hz, 1H), 7.49 (d, J=7.8 Hz, 1H), 7.39 (d, J=2.1 Hz, 1H), 7.35-7.20 (m, 2H), 7.17 (d, J=8.6 Hz, 1H), 6.90 (dd, J=12.9, 2.4 Hz, 1H), 6.83 (d, J=8.6 Hz, 1H), 6.77 (dd, J=8.8, 2.4 Hz, 1H), 5.80 (t, J=3.3 Hz, 1H), 3.25 (s, 3H), 2.87-2.72 (m, 1H), 2.64-2.54 (m, 1H), 2.15-2.01 (m, 1H), 2.00-1.70 (m, 3H). UPLC-MS: t$_R$=1.03 min (Apolar method); MS (ESI) m/z calcd for C$_{30}$H$_{22}$F$_6$N$_3$O$_6$ (M+H)$^+$: 634.1, found: 634.5.

(R) or (S)-tert-Butyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate The title compound was obtained from [143] after chiral purification, using an isocratic mode on a Daicel ChiralPak AD column (250×10 mmID, particle size 10 μm) with heptane/2-propanol (90:10) as mobile phase (flow rate: 5.0 mL/min). $^1$H NMR (400 MHz, DMSO-d$_6$) δ 7.83-7.75 (m, 2H), 7.56 (s, 1H), 7.49 (d, J=7.6 Hz, 1H), 7.32 (d, J=2.1 Hz, 1H), 7.28-7.19 (m, 1H), 7.15 (d, J=8.5 Hz, 1H), 6.99-6.92 (m, 1H), 6.78 (d, J=8.6 Hz, 1H), 5.75 (s, 1H), 3.24 (s, 3H), 2.82-2.74 (m, 1H), 2.64-2.54 (m, 1H), 2.12-2.04 (m, 1H), 1.96-1.77 (m, 3H), 1.49 (s, 9H). UPLC-MS: t$_R$=2.60 min (Apolar method); MS (ESI) m/z calcd for C$_{34}$H$_{31}$F$_5$N$_3$O$_6$ (M+H)$^+$: 672.6, found: 672.5. Chiral analysis: t$_R$=15.426 min; >99.5% ee.

(S) or (R)-tert-Butyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate The title compound was obtained from [143] after chiral purification, using an isocratic mode on a Daicel ChiralPak AD column (250×10 mmID, with heptane/2-propanol (90:10) as mobile phase (flow rate: 5.0 mL/min). $^1$H NMR (400 MHz, DMSO-d$_6$) δ 7.83-7.75 (m, 2H), 7.56 (s, 1H), 7.49 (d, J=7.6 Hz, 1H), 7.32 (d, J=2.1 Hz, 1H), 7.28-7.19 (m, 1H), 7.15 (d, J=8.5 Hz, 1H), 6.99-6.92 (m, 1H), 6.78 (d, J=8.6 Hz, 1H), 5.75 (s, 1H), 3.24 (s, 3H), 2.82-2.74 (m, 1H), 2.64-2.54 (m, 1H), 2.12-2.04 (m, 1H), 1.96-1.77 (m, 3H), 1.49 (s, 9H). UPLC-MS: t$_R$=2.60 min (Apolar method); MS (ESI) m/z calcd for C$_{34}$H$_{31}$F$_5$N$_3$O$_6$ (M+H)$^+$: 672.6, found: 672.5. Chiral analysis: t$_R$=23.877 min>99.5% ee.

(R) or (S)-4-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]benzoic acid Following general procedure 5i, the title compound was obtained from [148], after silica gel flash chromatography, eluting with DCM/MeOH (0 to 5%), as white solid in 75% yield: $^1$H NMR (400 MHz, DMSO-d$_6$) δ 12.66 (bs, 1H), 7.85 (d, J=8.8 Hz, 2H), 7.55 (s, 1H), 7.50 (d, J=6.8 Hz, 1H), 7.38 (d, J=2.1 Hz, 1H), 7.24 (s, 2H), 7.16 (d, J=8.5 Hz, 1H), 7.01-6.92 (m, 2H), 6.82-6.72 (m, 1H), 5.77 (s, 1H), 3.24 (s, 3H), 2.86-2.76 (m, 1H), 2.65-2.56 (m, 1H), 2.15-2.05 (m, 1H), 1.98-1.80 (m, 3H). UPLC-MS: $t_R$=2.44 min (Generic method); MS (ESI) m/z calcd for $C_{31}H_{22}F_5N_3O_6$ (M+H)$^+$: 616.5, found: 616.5. The chiral analysis was performed in isocratic mode on a Daicel ChiralCel OD-H column (250× 4.6 mmID, particle size 5 μm) with heptane/2-propanol (90:10)$^+$0.1% TFA as mobile phase (flowrate: 1.0 mL/min); $t_R$=33.86 min; >99.5% ee.

(S) or (R)-4-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]benzoic acid Following general procedure 5i, the title compound was obtained from [149], after silica gel flash chromatography, eluting with DCM/MeOH (0 to 5%), as white solid in 75% yield: $^1$H NMR (400 MHz, DMSO-d$_6$) δ 12.66 (bs, 1H), 7.85 (d, J=8.8 Hz, 2H), 7.55 (s, 1H), 7.50 (d, J=6.8 Hz, 1H), 7.38 (d, J=2.1 Hz, 1H), 7.24 (s, 2H), 7.16 (d, J=8.5 Hz, 1H), 7.01-6.92 (m, 2H), 6.82-6.72 (m, 1H), 5.77 (s, 1H), 3.24 (s, 3H), 2.86-2.76 (m, 1H), 2.65-2.56 (m, 1H), 2.15-2.05 (m, 1H), 1.98-1.80 (m, 3H). UPLC-MS: $t_R$=2.44 min (Generic method); MS (ESI) m/z calcd for $C_{31}H_{22}F_5N_3O_6$ (M+H)$^+$: 616.5, found: 616.5. The chiral analysis was performed in isocratic mode on a Daicel ChiralCel OD-H column (250× 4.6 mmID, particle size 5 μm) with heptane/2-propanol (90:10)$^+$0.1% TFA as mobile phase (flowrate: 1.0 mL/min); $t_R$=42.50 min; >99.5% ee.

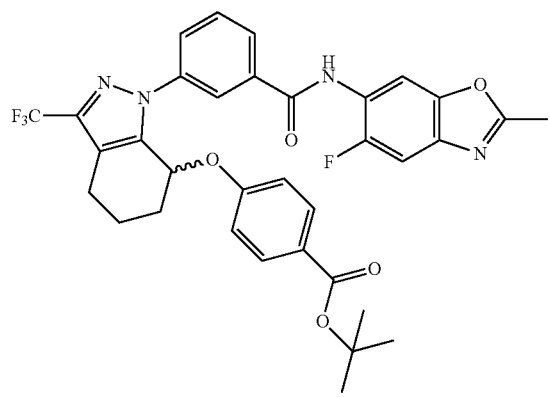 [SMILES: Cc1nc2cc(F)c(NC(=O)c3cccc(-n4nc(C(F)(F)F)c5c4C(Oc4ccc(C(=O)OC(C)(C)C)cc4)CCC5)c3)cc2o1]

[Int-5.13] tert-Butyl 4-[[1-[3-[(5-fluoro-2-methyl-1,3-benzoxazol-6-yl)carbamoyl]phenyl]-3-(trifluoromethyl)-4,5,6,7-tetrahydroindazol-7-yl]oxy]benzoate Following general procedure 5h, the title compound was obtained from compound [Int-5.7], after flash chromatography, eluting with 20% AcOEt in cyclohexane to afford the title compound as white solid (36%); UPLC-MS: $t_R$=2.40 min (Generic method); MS (ESI) m/z calcd for $C_{34}H_{31}F_4N_4O_5$ (M+H)$^+$: 651.2. found: 651.5.

tert-Butyl 4-[[1-[3-[(5-fluoro-2-methyl-1,3-benzoxazol-6-yl)-methyl-carbamoyl]phenyl]-3-(trifluoromethyl)-4,5,6,7-tetrahydroindazol-7-yl]oxy]benzoate Following general procedure 4f and starting from compound [Int-5.13], the title compound was obtained as a white solid and was used in the next step without purification; UPLC-MS: tR=2.42 min (Apolar method); MS (ESI) m/z calcd for $C_{35}H_{33}F_4N_4O_5$ (M+H)$^+$: 665.2, found: 665.6.

4-[[1-[3-[(5-Fluoro-2-methyl-1,3-benzoxazol-6-yl)-methyl-carbamoyl]phenyl]-3-(trifluoromethyl)-4,5,6,7-tetrahydroindazol-7-yl]oxy]benzoic acid Following general procedure 5i, the title compound was obtained from compound [152], after flash chromatography, eluting with 40% AcOEt in DCM to afford the title compound as white solid (38%). 1H NMR (400 MHz, DMSO-d$_6$) δ 12.65 (bs, 1H), 7.92-7.65 (m, 3H), 7.62-7.31 (m, 3H), 7.31-7.00 (m, 2H), 6.98-6.63 (m, 2H), 5.73 (app-bs, 1H), 3.27 (s, 3H), 2.85-2.73 (m, 1H), 2.66-2.54 (m, 4H), 2.16-1.71 (m, 4H). UPLC-MS: $t_R$=2.22 min (Generic method); MS (ESI) m/z calcd for $C_{31}H_{25}F_4N_4O_5$ (M+H)$^+$: 609.2, found: 609.5.

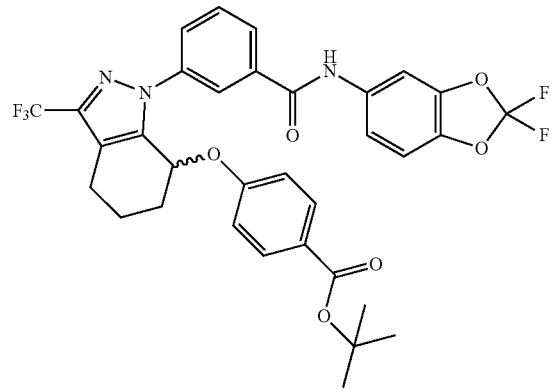 [SMILES: CC(C)(C)OC(=O)c1ccc(OC2CCCc3c(C(F)(F)F)nn(-c4cccc(C(=O)Nc5ccc6c(c5)OC(F)(F)O6)c4)c32)cc1]

[Int-5.15] tert-Butyl 4-[[1-[3-[(2,2-difluoro-1,3-benzodioxol-5-yl)carbamoyl]phenyl]-3-(trifluoromethyl)-4,5,6,7-tetrahydroindazol-7-yl]oxy]benzoate Following general procedure 5h, the title compound was obtained from [Int-5.7] and 2,2-difluoro-1,3-benzodioxol-5-amine, after flash chromatography eluting with cyclohexane/EtOAc (80/20), as white solid in 88% yield: $^1$H NMR (400 MHz, DMSO-d$_6$) δ 10.36 (s, 1H), 8.14 (app-t, J=1.9 Hz, 1H), 8.10 (d, J=1.9 Hz, 1H), 7.96 (app-dt, J=7.8, 1.3 Hz, 1H), 7.86-7.74 (m, 1H), 7.69-7.62 (m, 2H), 7.62-7.55 (m, 2H), 7.51 (dd, J=8.6, 1.9 Hz, 1H), 7.03-6.91 (m, 2H), 5.81 (t, J=3.6 Hz, 1H), 2.91-2.78 (m, 1H), 2.70-2.64 (m, 1H), 2.20-2.07 (m, 1H), 1.97-1.84 (m, 3H), 1.45 (s, 9H). UPLC-MS: $t_R$=2.63 min (Apolar method); MS (ESI) m/z calcd for $C_{33}H_{27}F_5N_3O_6$ (M−H)$^-$: 656.2; found: 656.6.

4-[[1-[3-[(2,2-Difluoro-1,3-benzodioxol-5-yl) carbamoyl]phenyl]-3-(trifluoromethyl)-4,5,6,7-tetrahydroindazol-7-yl]oxy]benzoic acid Following general procedure 5i, the title compound was obtained from [Int-5.15], after flash chromatography eluting with cyclohexane/EtOAc (0% t0 100%), as white solid in 86% yield: $^1$H NMR (400 MHz, DMSO-d$_6$) δ 12.56 (s, 1H), 10.38 (s, 1H), 8.10 (t, J=1.9 Hz, 1H), 7.93 (app-dt, J=7.8, 1.3 Hz, 1H), 7.80 (ddd, J=8.0, 2.2, 1.0 Hz, 1H), 7.76-7.67 (m, 3H), 7.58 (t, J=7.9 Hz, 1H), 7.40 (dd, J=8.8, 2.0 Hz, 1H), 7.35 (d, J=8.7 Hz, 1H), 7.14-6.70 (m, 2H), 6.12-5.48 (m, 1H), 2.91-2.77 (m, 1H), 2.72-2.58 (m, 1H), 2.11 (t, J=7.4 Hz, 1H), 1.97-1.84 (m, 3H). UPLC-MS: t$_R$=2.63 min (Apolar method); MS (ESI) m/z calcd for C$_{29}$H$_{19}$F$_5$N$_3$O$_6$ (M−H)$^-$: 600.1; found: 600.4.

tert-Butyl 4-[[1-[3-[(2,2-difluoro-1,3-benzodioxol-5-yl)-(trideuteriomethyl)carbamoyl]phenyl]-3-(trifluoromethyl)-4,5,6,7-tetrahydroindazol-7-yl]oxy]benzoate Following general procedure 1j, the title compound was obtained from [Int-5.15] and trideuterio(iodo)methane, after flash chromatography eluting with cyclohexane/EtOAc (0% t0 30%), as white solid in 82% yield: UPLC-MS: t$_R$=2.58 min (Apolar method); MS (ESI) m/z calcd for C$_{34}$H$_{28}$D$_3$F$_5$N$_3$O$_6$ (M+H)$^+$: 675.2; found: 675.6.

4-[[1-[3-[(2,2-Difluoro-1,3-benzodioxol-5-yl)-(trideuteriomethyl)carbamoyl]phenyl]-3-(trifluoromethyl)-4,5,6,7-tetrahydroindazol-7-yl]oxy]benzoic acid Following general procedure 5i, the title compound was obtained from compound [154], after flash chromatography eluting with cyclohexane/EtOAc (0% t0 100%), as white solid in 77% yield: $^1$H NMR (400 MHz, DMSO-d$_6$) δ 12.65 (s, 1H), 7.92-7.77 (m, 2H), 7.56 (s, 1H), 7.50 (d, J=6.7 Hz, 1H), 7.37 (d, J=2.1 Hz, 1H), 7.29-7.21 (m, 2H), 7.16 (d, J=8.5 Hz, 1H), 7.01-6.88 (m, 2H), 6.78 (d, J=8.6 Hz, 1H), 5.80-5.76 (m, 1H), 2.83-2.75 (m, 1H), 2.66-2.55 (m, 1H), 2.17-2.05 (m, 1H), 1.97-1.78 (m, 3H). UPLC-MS: t$_R$=1.26 min (Apolar method); MS (ESI) m/z calcd for C$_{30}$H$_{18}$D$_3$F$_5$N$_3$O$_6$ (M−H)$^-$: 617.1; found: 617.5.

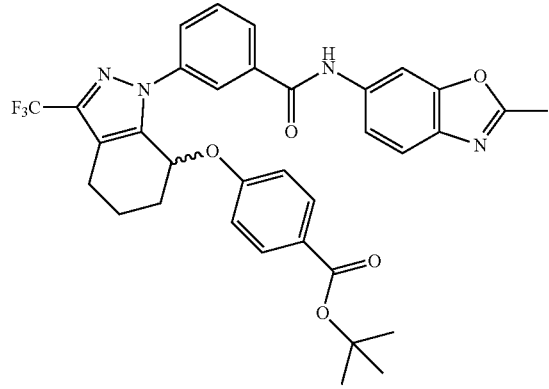 [SMILES: Cc1nc2ccc(NC(=O)c3cccc(-n4nc(C(F)(F)F)c5c4C(Oc4ccc(C(=O)OC(C)(C)C)cc4)CCC5)c3)cc2o1]

[Int-5.17] tert-Butyl 4-[[1-[3-[(2-methyl-1,3-benzoxazol-6-yl)carbamoyl]phenyl]-3-(trifluoromethyl)-4,5,6,7-tetrahydroindazol-7-yl]oxy]benzoate Following general procedure 5h, the title compound was obtained from [Int-5.7] and 2-methyl-1,3-benzoxazol-6-amine, after flash chromatography eluting with cyclohexane/EtOAc (0% to 60%), as white solid in 90% yield: UPLC-MS: tR=2.20 min (Apolar method); MS (ESI) m/z calcd for C$_{34}$H$_{32}$F$_3$N$_4$O$_5$ (M+H)$^+$: 633.2; found: 633.6.

tert-Butyl 4-[[1-[3-[methyl-(2-methyl-1,3-benzoxazol-6-yl)carbamoyl]phenyl]-3-(trifluoromethyl)-4,5,6,7-tetrahydroindazol-7-yl]oxy]benzoate Following general procedure 1j, the title compound was obtained from [Int-5.17] and iodomethane, after flash chromatography eluting with cyclohexane/EtOAc (0% to 50%), as white solid in 65% yield: UPLC-MS: tR=2.16 min (Apolar method); MS (ESI) m/z calcd for C$_{35}$H$_{34}$F$_3$N$_4$O$_5$ (M+H)$^+$: 647.2; found: 647.5.

4-[[1-[3-[Methyl-(2-methyl-1,3-benzoxazol-6-yl)carbamoyl]phenyl]-3-(trifluoromethyl)-4,5,6,7-tetrahydroindazol-7-yl]oxy]benzoic acid Following general procedure 5i, the title compound was obtained from [156], after flash chromatography eluting with DCM/EtOAc (0% to 100%), as white solid in 57% yield: $^1$H NMR (400 MHz, DMSO-d$_6$) δ 12.65 (s, 1H), 8.00-7.78 (m, 2H), 7.59 (bs, J=2.1 Hz, 1H), 7.51 (d, J=1.9 Hz, 1H), 7.46-7.36 (m, 2H), 7.26-7.10 (m, 2H), 6.97-6.85 (m, 3H), 5.72 (t, J=3.6 Hz, 1H), 3.28 (s, 3H), 2.91-2.73 (m, 1H), 2.65-2.58 (m, 1H), 2.56 (s, 3H), 2.18-2.04 (m, 1H), 1.95-1.78 (m, 3H). UPLC-MS: t$_R$=0.76 min (Apolar method); MS (ESI) m/z calcd for C$_{31}$H$_{24}$F$_3$N$_4$O$_5$ (M−H)$^-$: 589.2; found: 589.5.

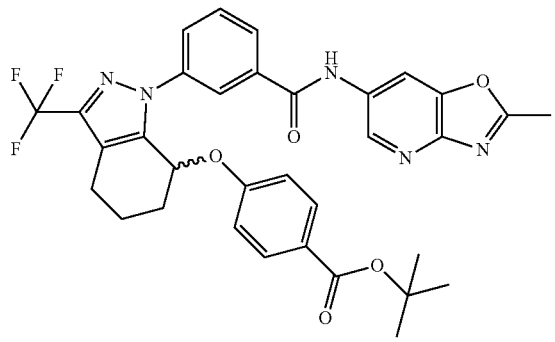 [SMILES: Cc1nc2ncc(NC(=O)c3cccc(-n4nc(C(F)(F)F)c5c4C(Oc4ccc(C(=O)OC(C)(C)C)cc4)CCC5)c3)cc2o1]

[Int-5.19] tert-Butyl 4-[[1-[3-[(2-methyloxazolo[4,5-b]pyridin-6-yl)carbamoyl]phenyl]-3-(trifluoromethyl)-4,5,6,7-tetrahydroindazol-7-yl]oxy]benzoate Step 1. tert-Butyl N-(2-methyloxazolo[4,5-b]pyridin-6-yl)carbamate: A flame-dried Schlenk tube was loaded with Pd$_2$(dba)$_3$ (0.077 g, 0.084 mmol) and (5-diphenylphosphanyl-9,9-dimethyl-xanthen-4-yl)-diphenyl-phosphane (0.122 g, 0.21 mmol). The vial was purged with nitrogen and toluene (26 mL) was added. The solution was allowed to stir for 15 min at room temperature. Following the order, tert-butyl carbamate (0.295 g, 2.52 mmol), Cs$_2$CO$_3$ (1.36 g, 4.00 mmol) and 6-bromo-2-methyl-oxazolo[4,5-b]pyridine (0.45 g, 2.10 mmol) were added and the mixture was degassed (vacuum/nitrogen 5-6 times) and put in the preheated bath. The resulting solution was stirred 16 h at 120° C., filtered over a short pad of Celite using AcOEt, and concentrated. The compound was obtained after purification by flash-column chromatography on neutral alumina gel (pH=7), eluting with a gradient of 100% DCM to 10% of a solution of EtOH 20% in DCM, as a yellow solid in 23% yield. ¹H NMR (400 MHz, DMSO-d₆) δ 9.79 (s, 1H), 8.40 (d, J=2.3 Hz, 1H), 8.24 (s, 1H), 2.63 (s, 3H), 1.49 (s, 9H).

Step 2. 2-Methyloxazolo[4,5-b]pyridin-6-amine: tert-Butyl N-(2-methyloxazolo[4,5-b]pyridin-6-yl)carbamate (0.25 g; 1.0 mmol) was dissolved in a solution of 10% TFA in DCM (1.0 mL) and stirred for 4 h. The solution was poured into a saturated aqueous solution of NaHCO₃ and extracted with AcOEt (3×). The organics were dried over Na₂SO₄, filtered and concentrated. The compound was obtained after purification by flash-column chromatography on neutral alumina gel (pH=7), eluting with a gradient of 100% DCM to 20% of a solution of MeOH in DCM, as a yellow solid in 52% yield. ¹H NMR (400 MHz, DMSO-d₆) δ 7.83 (d, J=2.4 Hz, 1H), 7.11 (d, J=2.4 Hz, 1H), 5.45 (bs, 2H), 2.53 (s, 3H).

Step 3. tert-Butyl 4-[[1-[3-[(2-methyloxazolo[4,5-b]pyridin-6-yl)carbamoyl]phenyl]-3-(trifluoromethyl)-4,5,6,7-tetrahydroindazol-7-yl]oxy]benzoate: Following general procedure 5h, the title compound was obtained from compound [Int-5.7] and 2-methyloxazolo[4,5-b]pyridin-6-amine, as a yellowish solid. The title compound was used in the next step without purification. UPLC-MS: $t_R$=2.02 min (Apolar method); MS (ESI) m/z calcd for $C_{33}H_{31}F_3N_5O_5$ (M+H)⁺: 634.2, found: 634.4.

tert-Butyl 4-[[1-[3-[methyl-(2-methyloxazolo[4,5-b]pyridin-6-yl)carbamoyl]phenyl]-3-(trifluoromethyl)-4,5,6,7-tetrahydroindazol-7-yl]oxy]benzoate Following general procedure 4f, the title compound was obtained from compound [Int-5.19], after purification by flash-column chromatography on neutral alumina gel (pH=7) with DCM as the eluent, as a yellowish solid in 31% yield (over two steps): ¹H NMR (400 MHz, DMSO-d₆) δ 8.13 (s, 1H), 8.08 (d, J=2.2 Hz, 1H), 7.81-7.74 (m, 2H), 7.59 (s, 1H), 7.45 (d, J=7.2 Hz, 1H), 7.21 (bs, 2H), 6.91 (d, J=8.6 Hz, 2H), 5.72 (s, 1H), 3.31 (s, 3H), 2.83-2.73 (m, 1H), 2.64 (s, 3H), 2.62-2.54 (m, 1H), 2.10-2.03 (m, 1H), 1.96-1.78 (m, 3H), 1.49 (s, 9H). UPLC-MS: $t_R$=1.96 min (Apolar method); MS (ESI) m/z calcd for $C_{34}H_{33}F_3N_5O_5$ (M+H)⁺: 648.2, found: 648.4.

4-[[1-[3-[Methyl-(2-methyloxazolo[4,5-b]pyridin-6-yl)carbamoyl]phenyl]-3-(trifluoromethyl)-4,5,6,7-tetrahydroindazol-7-yl]oxy]benzoic acid Following general procedure 5i, the title compound was obtained from compound [158], after purification by silica gel flash-column chromatography with DCM/MeOH (95:05) as the eluent, as a white solid in 89% yield: ¹H NMR (400 MHz, DMSO-d₆) δ 8.14 (s, 1H), 8.11 (d, J=2.2 Hz, 1H), 7.80 (d, J=8.7 Hz, 2H), 7.60 (s, 1H), 7.46 (d, J=7.7 Hz, 1H), 7.28-7.14 (m, 2H), 6.89 (d, J=8.4 Hz, 2H), 5.74 (s, 1H), 3.32 (s, 3H), 2.78 (app d, J=16.7 Hz, 1H), 2.65 (s, 3H), 2.62-2.55 (m, 1H), 2.12-2.01 (m, 1H), 1.98-1.79 (m, 3H). UPLC-MS: $t_R$=1.95 min (Apolar method); MS (ESI) m/z calcd for $C_{30}H_{25}F_3N_5O_5$ (M+H)⁺: 592.2, found: 592.4.

Methyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-methoxy-benzoate Following general procedure 5f, the title compound was obtained from [145] and methyl 4-hydroxy-2-methoxy-benzoate, after flash chromatography eluting with cyclohexane/EtOAc (0% to 40%), as white solid in 74% yield: ¹H NMR (400 MHz, DMSO-d₆) δ 7.65 (d, J=8.7 Hz, 1H), 7.58 (app-s, 1H), 7.53 (app-d, J=7.8 Hz, 1H), 7.37-7.20 (m, 3H), 7.16 (d, J=8.5 Hz, 1H), 6.75 (d, J=8.5 Hz, 1H), 6.63 (d, J=2.2 Hz, 1H), 6.58 (dd, J=8.7, 2.2 Hz, 1H), 5.76 (bs, 1H), 3.78 (s, 3H), 3.72 (s, 3H), 3.23 (s, 3H), 2.90-2.73 (m, 1H), 2.64-2.56 (m, 1H), 2.24-2.10 (m, 1H), 1.95-1.76 (m, 3H). UPLC-MS: $t_R$=1.99 min (Apolar method); MS (ESI) m/z calcd for $C_{32}H_{27}F_5N_3O_7$ (M+H)⁺: 660.2; found: 660.5.

4-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]-2-methoxy-benzoic acid Following general procedure 5o, the title compound was obtained from [160], after flash chromatography eluting with DCM/EtOAc (0% to 60%), as white solid in 33% yield: ¹H NMR (400 MHz, DMSO-d₆) δ 12.17 (s, 1H), 7.66 (d, J=8.6 Hz, 1H), 7.59 (app-t, J=2.0 Hz, 1H), 7.53 (app-d, J=7.9 Hz, 1H), 7.36-7.27 (m, 2H), 7.26-7.19 (m, 1H), 7.14 (d, J=8.6 Hz, 1H), 6.70 (d, J=8.5 Hz, 1H), 6.61 (s, 1H), 6.57 (dd, J=8.7, 2.2 Hz, 1H), 5.74 (app-s, 1H), 3.78 (s, 3H), 3.24 (s, 3H), 2.94-2.69 (m, 1H), 2.66-2.55 (m, 1H), 2.28-2.10 (m, 1H), 1.96-1.72 (m, 3H). UPLC-MS: $t_R$=1.49 min (Apolar method); MS (ESI) m/z calcd for $C_{31}H_{23}F_5N_3O_7$ (M+H)⁺: 644.2; found: 644.5.

3-[7-(4-Carbamoylphenoxy)-3-(trifluoromethyl)-4,5,6,7-tetrahydroindazol-1-yl]-N-(2,2-difluoro-1,3-benzodioxol-5-yl)-N-methyl-benzamide Following general procedure 1b, the title compound was obtained from compound [150] and NH₄Cl, after flash chromatography eluting with DCM/EtOAc (0% to 40%), as white solid in 46% yield: ¹H NMR (400 MHz, DMSO-d₆) δ 7.93-7.75 (m, 3H), 7.56 (app-s, 1H), 7.51 (app-d, J=7.3 Hz, 1H), 7.39 (d, J=2.1 Hz, 1H), 7.32-7.23 (m, 2H), 7.19 (bs, 1H), 7.14 (d, J=8.6 Hz, 1H), 7.00-6.92 (m, 2H), 6.72 (d, J=8.6 Hz, 1H), 5.73 (bs, 1H), 3.23 (s, 3H), 2.91-2.74 (m, 1H), 2.65-2.55 (m, 1H), 2.25-2.06 (m, 1H), 1.94-1.77 (m, 3H). UPLC-MS: $t_R$=1.38 min (Apolar method); MS (ESI) m/z calcd for $C_{30}H_{24}F_5N_4O_5$ (M+H)⁺: 615.2; found: 615.5.

Methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylate Following general procedure 5f, the title compound was obtained from [145] and methyl 5-hydroxypyridine-2-carboxylate, after flash chromatography eluting with cyclohexane/EtOAc (0% to 40%), as white solid in 65% yield: ¹H NMR (400 MHz, DMSO-d₆) δ 8.25 (d, J=2.8 Hz, 1H), 7.97 (d, J=8.7 Hz, 1H), 7.53 (bs, J=2.2 Hz, 1H), 7.52-7.45 (m, 2H), 7.42 (d, J=2.1 Hz, 1H), 7.32-7.15 (m, 3H), 6.93-6.82 (m, 1H), 5.89 (t, J=3.6 Hz, 1H), 3.83 (s, 3H), 3.24 (s, 3H), 2.90-2.74 (m, 1H), 2.65-2.56 (m, 1H), 2.17-2.03 (m, 1H), 1.98-1.90 (m, 1H), 1.88-1.76 (m, 2H). UPLC-MS: $t_R$=1.63 min (Apolar method); MS (ESI) m/z calcd for $C_{30}H_{24}F_5N_4O_6$ (M+H)⁺: 631.1; found: 631.5.

5-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylic acid Following general procedure 5o, the title compound was obtained from [163], after flash chromatography eluting with DCM/MeOH (95/5), as white solid in 51% yield: $^1$H NMR (400 MHz, DMSO-$d_6$) δ 13.02 (s, 1H), 8.26 (d, J=2.8 Hz, 1H), 7.96 (d, J=8.7 Hz, 1H), 7.56-7.46 (m, 3H), 7.44 (d, J=2.1 Hz, 1H), 7.36-7.22 (m, 2H), 7.19 (d, J=8.6 Hz, 1H), 6.83 (d, J=8.0 Hz, 1H), 5.96-5.84 (m, 1H), 3.25 (s, 3H), 2.92-2.73 (m, 1H), 2.66-2.56 (m, 1H), 2.17-2.06 (m, 1H), 2.02-1.89 (m, 1H), 1.91-1.75 (m, 2H). UPLC-MS: $t_R$=1.38 min (Apolar method); MS (ESI) m/z calcd for $C_{29}H_{22}F_5N_4O_6$ (M+H)$^+$: 615.1; found: 615.5.

solid in 89% yield: $^1$H NMR (400 MHz, DMSO-$d_6$) δ 12.65 (bs, 1H), 8.08 (d, J=2.6 Hz, 1H), 7.88-7.81 (m, 2H), 7.76 (s, 1H), 7.58 (s, 1H), 7.49 (t, J=4.6 Hz, 1H), 7.33 (t, J=2.4 Hz, 1H), 7.23 (d, J=4.7 Hz, 2H), 6.98-6.92 (m, 2H), 5.72 (s, 1H), 3.75 (s, 3H), 3.26 (s, 3H), 2.84-2.74 (m, 1H), 2.64-2.54 (m, 1H), 2.16-2.04 (m, 1H), 1.95-1.77 (m, 3H). UPLC-MS: $t_R$=0.97 min (Apolar method); MS (ESI) m/z calcd for $C_{29}H_{26}F_3N_4O_5$ (M+H)$^+$: 567.2. found: 567.5.

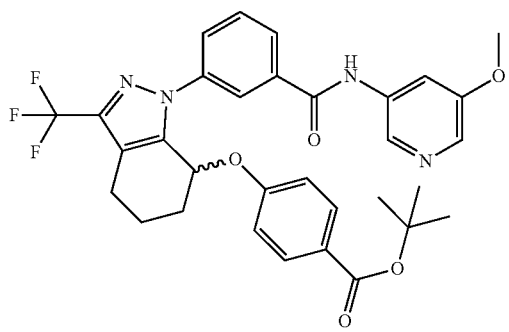 [SMILES: COc1cncc(NC(=O)c2cccc(-n3nc(C(F)(F)F)c4c3C(Oc3ccc(C(=O)OC(C)(C)C)cc3)CCC4)c2)c1]

[Int-5.23] tert-Butyl 4-[[1-[3-[(5-methoxy-3-pyridyl)carbamoyl]phenyl]-3-(trifluoromethyl)-4,5,6,7-tetrahydroindazol-7-yl]oxy]benzoate Following general procedure 5h, the title compound was obtained from compound Int-5.7 and 5-methoxypyridin-3-amine, after silica gel flash chromatography, eluting with DCM/AcOEt (0 to 40%) as white solid in 56% yield: $^1$H NMR (400 MHz, DMSO-$d_6$) δ 10.36 (s, 1H), 8.47 (d, J=2.0 Hz, 1H), 8.13 (s, 1H), 8.05 (d, J=2.6 Hz, 1H), 7.95 (dt, J=8.0, 1.2 Hz, 1H), 7.83-7.79 (m, 1H), 7.76 (t, J=2.3 Hz, 1H), 7.68-7.63 (m, 2H), 7.59 (app-t, J=7.9 Hz, 1H), 6.98-6.92 (m, 2H), 5.81 (s, 1H), 3.82 (s, 3H), 2.82 (d, J=16.6 Hz, 1H), 2.69-2.57 (m, 1H), 2.17-2.03 (m, 1H), 1.99-1.83 (m, 3H), 1.48 (s, 9H). UPLC-MS: $t_R$=2.08 min (Apolar method); MS (ESI) m/z calcd for $C_{32}H_{32}F_3N_4O_5$ (M+H)$^+$: 609.2. found: 609.5.

tert-Butyl 4-[[1-[3-[(5-methoxy-3-pyridyl)-methyl-carbamoyl]phenyl]-3-(trifluoromethyl)-4,5,6,7-tetrahydroindazol-7-yl]oxy]benzoate Following general procedure 4f, the title compound was obtained from compound [Int-5.23], after silica gel flash chromatography, eluting with DCM/AcOEt (0 to 80%), as white solid in 31% yield: 1H NMR (400 MHz, DMSO-$d_6$) δ 8.09 (d, J=2.6 Hz, 1H), 7.82-7.78 (m, 2H), 7.76 (bs, 1H), 7.58 (d, J=1.9 Hz, 1H), 7.51-7.47 (m, 1H), 7.33 (t, J=2.4 Hz, 1H), 7.26-7.20 (m, 2H), 6.98-6.92 (m, 2H), 5.72 (s, 1H), 3.75 (s, 3H), 3.26 (s, 3H), 2.79 (d, J=16.5 Hz, 1H), 2.64-2.55 (m, 1H), 2.13-2.04 (m, 1H), 1.96-1.80 (m, 3H), 1.51 (s, 9H). UPLC-MS: $t_R$=2.03 min (Apolar method); MS (ESI) m/z calcd for $C_{33}H_{34}F_3N_4O_5$ (M+H)$^+$: 623.2. found: 623.6.

4-[[1-[3-[(5-Methoxy-3-pyridyl)-methyl-carbamoyl]phenyl]-3-(trifluoromethyl)-4,5,6,7-tetrahydroindazol-7-yl]oxy]benzoic acid Following general procedure 5i, the title compound was obtained from compound [165], after silica gel flash chromatography, eluting with DCM/MeOH (0 to 5%), as white

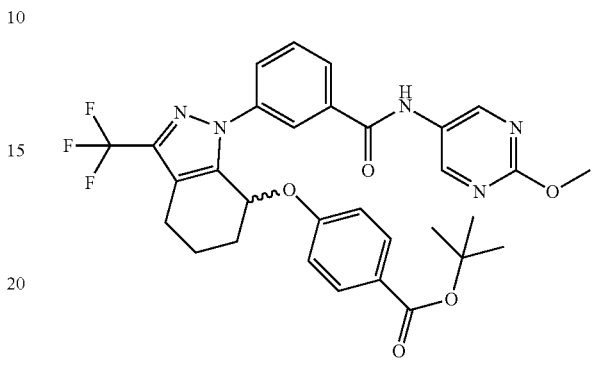

[Int-5.26] tert-Butyl 4-[[1-[3-[(2-methoxypyrimidin-5-yl)carbamoyl]phenyl]-3-(trifluoromethyl)-4,5,6,7-tetrahydroindazol-7-yl]oxy]benzoate Following general procedure 5h, the title compound was obtained from compound Int-5.7 and 2-methoxypyrimidin-5-amine, after silica gel flash chromatography, eluting with DCM/AcOEt (0 to 30%) as white solid in 82% yield: $^1$H NMR (400 MHz, DMSO-$d_6$) δ 10.37 (s, 1H), 8.79 (s, 2H), 8.10 (t, J=1.9 Hz, 1H), 7.94 (dt, J=7.9, 1.2 Hz, 1H), 7.81 (ddd, J=8.0, 2.2, 1.0 Hz, 1H), 7.70-7.65 (m, 2H), 7.60 (app-t, J=7.9 Hz, 1H), 6.99-6.91 (m, 2H), 5.85-5.79 (m, 1H), 3.92 (s, 3H), 2.82 (app d, J=16.6 Hz, 1H), 2.69-2.58 (m, 1H), 2.14-2.05 (m, 1H), 1.99-1.82 (m, 3H), 1.48 (s, 9H). UPLC-MS: $t_R$=2.05 min (Apolar method); MS (ESI) m/z calcd for $C_{31}H_{31}F_3N_5O_5$ (M+H)$^+$: 610.2. found: 610.5.

tert-Butyl 4-[[1-[3-[(2-methoxypyrimidin-5-yl)-methyl-carbamoyl]phenyl]-3-(trifluoromethyl)-4,5,6,7-tetrahydroindazol-7-yl]oxy]benzoate Following general procedure 4f, the title compound was obtained from compound [Int-5.26], after silica gel flash chromatography, eluting with DCM/AcOEt (0 to 80%), as white solid in 95% yield: 1H NMR (400 MHz, DMSO-$d_6$) δ 8.39 (bs, 2H), 7.83-7.76 (m, 2H), 7.67-7.45 (m, 2H), 7.26 (bs, 2H), 6.99-6.89 (m, 2H), 5.78 (bs, 1H), 3.86 (s, 3H), 3.24 (bs, 3H), 2.84-2.75 (m, 1H), 2.65-2.56 (m, 1H), 2.14-2.02 (m, 1H), 1.98-1.76 (m, 3H), 1.50 (s, 9H). UPLC-MS: $t_R$=2.05 min (Apolar method); MS (ESI) m/z calcd for $C_{32}H_{33}F_3N_5O_5$ (M+H)$^+$: 624.2. found: 624.6.

4-[[1-[3-[(2-Methoxypyrimidin-5-yl)-methyl-carbamoyl]phenyl]-3-(trifluoromethyl)-4,5,6,7-tetrahydroindazol-7-yl]oxy]benzoic acid Following general procedure 5i, the title compound was obtained from compound [167], after silica gel flash chromatography, eluting with DCM/MeOH (0 to 5%), as white solid in 83% yield: $^1$H NMR (400 MHz, DMSO-$d_6$) δ 12.61 (bs, 1H), 8.41 (s, 2H), 7.83 (d, J=8.8 Hz, 2H), 7.60 (s, 1H), 7.51 (s, 1H), 7.25 (bs, 2H), 6.99-6.86 (m, 2H), 5.79 (s, 1H), 3.85 (s, 3H), 3.23 (s, 3H), 2.79 (d, J=16.4 Hz, 1H), 2.65-2.55 (m, 1H), 2.14-2.05 (m, 1H), 2.00-1.78 (m, 3H). UPLC-MS: $t_R$=2.01 min (Generic method); MS (ESI) m/z calcd for $C_{28}H_{25}F_3N_5O_5$ (M+H)$^+$: 568.2. found: 568.5.

Ethyl 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate Following general procedure 5f, the title compound was obtained from [145] and ethyl 3-hydroxybenzoate, after flash chromatography eluting with cyclohexane/EtOAc (0% to 30%), as white solid in 76% yield: $^1$H NMR (400 MHz, DMSO-d$_6$) δ 7.65-7.51 (m, 3H), 7.45-7.36 (m, 2H), 7.34-7.22 (m, 3H), 7.19-7.04 (m, 2H), 6.90-6.73 (m, 1H), 5.71 (bs, 1H), 4.29 (q, J=7.1 Hz, 2H), 3.23 (s, 3H), 2.86-2.72 (m, 1H), 2.63-2.53 (m, 1H), 2.15-2.04 (m, 1H), 1.94-1.74 (m, 3H), 1.30 (t, J=7.1 Hz, 3H). UPLC-MS: $t_R$=2.33 min (Apolar method); MS (ESI) m/z calcd for $C_{32}H_{27}F_5N_3O_6$ (M+H)$^+$: 644.2; found: 644.4.

3-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]benzoic acid Following general procedure 5o, the title compound was obtained from [169], after flash chromatography eluting with DCM/EtOAc (from 0% to 60%), as white solid in 35% yield: $^1$H NMR (400 MHz, DMSO-d$_6$) δ 13.03 (s, 1H), 7.62-7.55 (m, 2H), 7.54 (s, 1H), 7.44 (app-t, J=1.9 Hz, 1H), 7.38 (t, J=8.0 Hz, 1H), 7.34 (d, J=2.1 Hz, 1H), 7.32-7.22 (m, 2H), 7.18-7.05 (m, 2H), 6.77 (app-d, J=8.6 Hz, 1H), 5.71 (t, J=3.5 Hz, 1H), 3.23 (s, 3H), 2.88-2.75 (m, 1H), 2.64-2.54 (m, 1H), 2.22-2.04 (m, 1H), 1.95-1.71 (m, 3H). UPLC-MS: $t_R$=1.16 min (Apolar method); MS (ESI) m/z calcd for $C_{30}H_{21}F_5N_3O_6$ (M+H)$^+$: 614.1; found: 614.3.

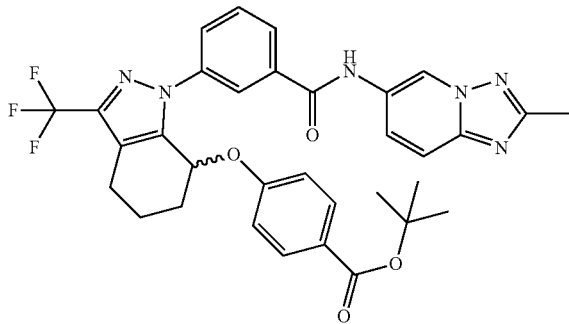 [SMILES: Cc1nc2ccc(NC(=O)c3cccc(-n4nc(C(F)(F)F)c5c4C(Oc4ccc(C(=O)OC(C)(C)C)cc4)CCC5)c3)cn2n1]

[Int-5.29] tert-Butyl 4-[[1-[3-[(2-methyl-[1,2,4]triazolo [1,5-a]pyridin-6-yl) carbamoyl]phenyl]-3-(trifluoromethyl)-4,5,6,7-tetrahydroindazol-7-yl]oxy]benzoate Following general procedure 5h, the title compound was obtained from compound [Int-5.7] and 5-methoxypyridin-3-amine, after silica gel flash chromatography, eluting with DCM/AcOEt (0 to 70%) as white solid in 49% yield: $^1$H NMR (400 MHz, DMSO-d$_6$) δ 10.45 (s, 1H), 9.33 (s, 1H), 8.14 (t, J=1.9 Hz, 1H), 7.96 (dt, J=7.9, 1.3 Hz, 1H), 7.82 (ddd, J=8.1, 2.2, 1.1 Hz, 1H), 7.76-7.65 (m, 2H), 7.67-7.58 (m, 3H), 7.01-6.93 (m, 2H), 5.82 (s, 1H), 2.83 (d, J=16.4 Hz, 1H), 2.69-2.59 (m, 1H), 2.45 (s, 3H), 2.15-2.06 (m, 1H), 1.96-1.81 (m, 3H), 1.39 (s, 9H). UPLC-MS: $t_R$=1.90 min (Generic method); MS (ESI) m/z calcd for $C_{33}H_{32}F_3N_6O_4$ (M+H)$^+$: 633.2. found: 633.6.

tert-Butyl 4-[[1-[3-[methyl-(2-methyl-[1,2,4]triazolo [1,5-a]pyridin-6-yl)carbamoyl]phenyl]-3-(trifluoromethyl)-4,5,6,7-tetrahydroindazol-7-yl]oxy]benzoate Following general procedure 4f, the title compound was obtained from compound [Int-5.29], after silica gel flash chromatography, eluting with DCM/AcOEt (0 to 80%), as white solid in 95% yield: $^1$H NMR (400 MHz, DMSO-d$_6$) δ 8.87 (d, J=1.6 Hz, 1H), 7.77-7.71 (m, 2H), 7.63 (s, 1H), 7.55 (d, J=9.4 Hz, 1H), 7.44 (s, 1H), 7.41 (dd, J=9.4, 2.1 Hz, 1H), 7.28 (s, 1H), 7.20 (s, 1H), 6.84 (d, J=8.4 Hz, 2H), 5.71 (s, 1H), 3.28 (s, 3H), 2.83-2.74 (m, 1H), 2.65-2.54 (m, 1H), 2.42 (s, 3H), 2.09-2.01 (m, 1H), 1.97-1.79 (m, 3H), 1.49 (s, 9H). UPLC-MS: $t_R$=1.88 min (Generic method); MS (ESI) m/z calcd for $C_{34}H_{34}F_3N_6O_4$ (M+H)$^+$: 647.2. found: 647.6.

4-[[1-[3-[Methyl-(2-methyl-[1,2,4]triazolo[1,5-a]pyridin-6-yl) carbamoyl]phenyl]-3-(trifluoromethyl)-4,5,6,7-tetrahydroindazol-7-yl]oxy]benzoic acid Following general procedure 5i, the title compound was obtained from compound [171], after silica gel flash chromatography, eluting with DCM/MeOH (0 to 5%), as white solid in 81% yield: $^1$H NMR (400 MHz, DMSO-d$_6$) δ 12.65 (s, 1H), 8.92 (d, J=1.2 Hz, 1H), 7.81-7.76 (m, 2H), 7.64 (bs, 1H), 7.54 (d, J=9.4 Hz, 1H), 7.49-7.44 (m, 1H), 7.41 (dd, J=9.4, 2.0 Hz, 1H), 7.29 (bs, 1H), 7.20 (bs, 1H), 6.87-6.79 (m, 2H), 5.73 (s, 1H), 3.29 (s, 3H), 2.79 (d, J=16.4 Hz, 1H), 2.65-2.56 (m, 1H), 2.43 (s, 3H), 2.12-2.03 (m, 1H), 1.98-1.89 (m, 1H), 1.88-1.79 (m, 2H). UPLC-MS: $t_R$=0.53 min (Generic method); MS (ESI) m/z calcd for $C_{30}H_{26}F_3N_6O_4$ (M+H)$^+$: 591.2. found: 591.6.

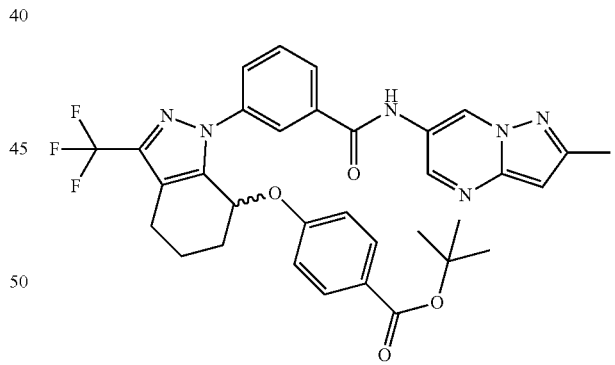

[Int-5.31] tert-Butyl 4-[[1-[3-[(2-methylpyrazolo[1,5-a]pyrimidin-6-yl) carbamoyl]phenyl]-3-(trifluoromethyl)-4,5,6,7-tetrahydroindazol-7-yl]oxy]benzoate Following general procedure 5h, the title compound was obtained from compound [Int-5.7] and 2-methylpyrazolo[1,5-a]pyrimidin-6-amine, after silica gel flash chromatography, eluting with DCM/AcOEt (0 to 50%) as white solid in 83% yield: $^1$H NMR (400 MHz, DMSO-d$_6$) δ 10.51 (s, 1H), 9.34 (dd, J=2.4, 0.9 Hz, 1H), 8.59 (d, J=2.3 Hz, 1H), 8.14 (t, J=1.9 Hz, 1H), 7.99-7.94 (m, 1H), 7.82 (ddd, J=8.0, 2.2, 1.0

Hz, 1H), 7.70-7.65 (m, 2H), 7.61 (app-t, J=7.9 Hz, 1H), 6.99-6.94 (m, 2H), 6.50 (s, 1H), 5.85-5.81 (m, 1H), 2.83 (app d, J=16.6 Hz, 1H), 2.69-2.58 (m, 1H), 2.41 (s, 3H), 2.14-2.05 (m, 1H), 2.00-1.82 (m, 3H), 1.41 (s, 9H). UPLC-MS: $t_R$=2.05 min (Apolar method); MS (ESI) m/z calcd for $C_{33}H_{32}F_3N_6O_4$ (M+H)$^+$: 633.2. found: 633.6.

tert-Butyl 4-[[1-[3-[methyl-(2-methylpyrazolo[1,5-a]pyrimidin-6-yl) carbamoyl]phenyl]-3-(trifluoromethyl)-4,5,6,7-tetrahydroindazol-7-yl]oxy]benzoate Following general procedure 4f, the title compound was obtained from compound [Int-5.31], after silica gel flash chromatography, eluting with DCM/AcOEt (0 to 70%), as white solid in 82% yield: $^1$H NMR (400 MHz, DMSO-d$_6$) δ 9.10 (dd, J=2.4, 0.9 Hz, 1H), 8.31 (s, 1H), 7.72 (d, J=8.4 Hz, 2H), 7.67 (s, 1H), 7.55-7.11 (m, 3H), 6.78 (bs, 2H), 6.50 (s, 1H), 5.71 (bs, 1H), 3.31 (s, 3H), 2.78 (d, J=16.3 Hz, 1H), 2.60 (dt, J=15.6, 7.4 Hz, 1H), 2.38 (s, 3H), 2.08-1.99 (m, 1H), 1.97-1.79 (m, 3H), 1.50 (s, 9H). UPLC-MS: $t_R$=2.14 min (Apolar method); MS (ESI) m/z calcd for $C_{34}H_{34}F_3N_6O_4$ (M+H)$^+$: 647.3. found: 647.6.

4-[[1-[3-[Methyl-(2-methylpyrazolo[1,5-a]pyrimidin-6-yl)carbamoyl]phenyl]-3-(trifluoromethyl)-4,5,6,7-tetrahydroindazol-7-yl]oxy]benzoic acid Following general procedure 5i, the title compound was obtained from compound [173], after silica gel flash chromatography, eluting with DCM/MeOH (0 to 5%), as white solid in 58% yield: $^1$H NMR (400 MHz, DMSO-d$_6$) δ 12.63 (bs, 1H), 9.13 (dd, J=2.4, 0.9 Hz, 1H), 8.31 (s, 1H), 7.76 (d, J=8.4 Hz, 2H), 7.67 (bs, 1H), 7.52-7.13 (m, 3H), 6.77 (s, 2H), 6.50 (s, 1H), 5.71 (s, 1H), 3.32 (s, 3H), 2.77 (d, J=16.4 Hz, 1H), 2.60 (q, J=8.4, 8.0 Hz, 1H), 2.38 (s, 3H), 2.08-1.99 (m, 1H), 1.99-1.78 (m, 3H). UPLC-MS: $t_R$=0.73 min (Apolar method); MS (ESI) m/z calcd for $C_{30}H_{26}F_3N_6O_4$ (M+H)$^+$: 591.2. found: 591.5.

Methyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-methyl-benzoate Following general procedure 5f, the title compound was obtained from [145] and methyl 4-hydroxy-2-methyl-benzoate, after flash chromatography eluting with cyclohexane/EtOAc (0% to 30%), as white solid in 88% yield: $^1$H NMR (400 MHz, DMSO-d$_6$) δ 7.78 (d, J=8.7 Hz, 1H), 7.56 (app-s, 1H), 7.51 (d, J=7.4 Hz, 1H), 7.31 (d, J=2.1 Hz, 1H), 7.30-7.21 (m, 2H), 7.16 (d, J=8.5 Hz, 1H), 6.87 (d, J=2.5 Hz, 1H), 6.84-6.74 (m, 2H), 5.84-5.65 (m, 1H), 3.77 (s, 3H), 3.23 (s, 3H), 2.85-2.74 (m, 1H), 2.66-2.54 (m, 1H), 2.48 (s, 3H), 2.21-2.05 (m, 1H), 1.97-1.79 (m, 3H). UPLC-MS: $t_R$=2.30 min (Apolar method); MS (ESI) m/z calcd for $C_{32}H_{27}F_5N_3O_6$ (M+H)$^+$: 644.2. found: 644.5.

4-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]-2-methyl-benzoic acid Following general procedure 5o, the title compound was obtained from [175], after flash chromatography eluting with DCM/EtOAc (0% to 60%), as white solid in 22% yield: $^1$H NMR (400 MHz, DMSO-d$_6$) δ 12.48 (bs, 1H), 7.79 (d, J=8.6 Hz, 1H), 7.56 (app-s, 1H), 7.50 (d, J=7.9 Hz, 1H), 7.31 (d, J=2.1 Hz, 1H), 7.29-7.19 (m, 2H), 7.13 (d, J=8.5 Hz, 1H), 6.92-6.70 (m, 3H), 5.71 (app-s, J=3.8 Hz, 1H), 3.23 (s, 3H), 2.86-2.74 (m, 1H), 2.64-2.54 (m, 1H), 2.47 (s, 3H), 2.18-2.04 (m, 1H), 1.94-1.76 (m, 3H). UPLC-MS: $t_R$=1.61 min (Apolar method); MS (ESI) m/z calcd for $C_{31}H_{23}F_5N_3O_6$ (M−H)$^-$: 628.2; found: 628.4.

Methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate Following general procedure 5f, the title compound was obtained from [145] and methyl 5-hydroxypyridine-3-carboxylate, after flash chromatography eluting with DCM/EtOAc (0% to 40%), as white solid in 75% yield: $^1$H NMR (400 MHz, DMSO-d$_6$) δ 8.69 (d, J=1.6 Hz, 1H), 8.35 (d, J=2.9 Hz, 1H), 7.75 (dd, J=2.9, 1.7 Hz, 1H), 7.59-7.48 (m, 2H), 7.39 (d, J=2.1 Hz, 1H), 7.32-7.23 (m, 2H), 7.17 (d, J=8.6 Hz, 1H), 6.94-6.84 (m, 1H), 5.89 (t, J=3.9 Hz, 1H), 3.88 (s, 3H), 3.26 (s, 3H), 2.89-2.74 (m, 1H), 2.66-2.56 (m, 1H), 2.14-2.04 (m, 1H), 1.97-1.79 (m, 3H). UPLC-MS: $t_R$=1.78 min (Apolar method); MS (ESI) m/z calcd for $C_{30}H_{24}F_5N_4O_6$ (M+H)$^+$: 631.2; found: 631.3.

5-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid Following general procedure 5o, the title compound was obtained from [177], after flash chromatography eluting with DCM/MeOH (0% to 10%), as white solid in 61% yield: $^1$H NMR (400 MHz, DMSO-d$_6$) δ 13.49 (s, 1H), 8.67 (d, J=1.6 Hz, 1H), 8.30 (d, J=2.9 Hz, 1H), 7.76 (dd, J=2.9, 1.7 Hz, 1H), 7.57-7.49 (m, 2H), 7.40 (d, J=2.1 Hz, 1H), 7.34-7.21 (m, 2H), 7.15 (d, J=8.6 Hz, 1H), 6.86 (dd, J=8.4, 2.1 Hz, 1H), 5.88 (t, J=3.6 Hz, 1H), 3.24 (s, 3H), 2.90-2.70 (m, 1H), 2.66-2.54 (m, 1H), 2.18-2.03 (m, 1H), 1.97-1.74 (m, 3H). UPLC-MS: $t_R$=1.94 min (Generic method); MS (ESI) m/z calcd for $C_{29}H_{20}F_5N_4O_6$ (M−H)$^-$: 615.1; found: 615.3.

Methyl 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate Following general procedure 5f, the title compound was obtained from [145] and methyl 6-hydroxypyridine-3-carboxylate, after flash chromatography eluting with DCM/EtOAc (0% to 20%), as white solid in 56% yield: $^1$H NMR (400 MHz, DMSO-d$_6$) δ 8.65 (dd, J=2.4, 0.7 Hz, 1H), 8.10 (dd, J=8.7, 2.4 Hz, 1H), 7.48-7.42 (m, 2H), 7.41 (d, J=2.1 Hz, 1H), 7.25 (d, J=8.6 Hz, 1H), 7.23-7.10 (m, 2H), 7.01-6.77 (m, 1H), 6.79-6.59 (m, 1H), 6.40 (t, J=3.9 Hz, 1H), 3.84 (s, 3H), 3.24 (s, 3H), 2.90-2.74 (m, 1H), 2.67-2.56 (m, 1H), 2.14-2.00 (m, 2H), 1.94-1.79 (m, 2H). UPLC-MS: $t_R$=2.22 min (Apolar method); MS (ESI) m/z calcd for $C_{30}H_{24}F_5N_4O_6$ (M+H)$^+$: 631.2; found: 631.3.

6-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid Following general procedure 5o, the title compound was obtained from [179], after flash chromatography eluting with DCM/MeOH (96:4), as white solid in 48% yield: $^1$H NMR (400 MHz, DMSO-d$_6$) δ 13.08 (s, 1H), 8.63 (d, J=2.3 Hz, 1H), 8.09 (dd, J=8.7, 2.3 Hz, 1H), 7.48-7.43 (m, 2H), 7.42 (d, J=2.1 Hz, 1H), 7.28-7.16 (m, 3H), 6.86 (d, J=8.5 Hz, 1H), 6.67 (d, J=8.6 Hz, 1H), 6.39 (t, J=3.5 Hz, 1H), 3.24 (s, 3H), 2.87-2.74 (m, 1H), 2.65-2.55 (m, 1H), 2.25-1.95 (m, 2H), 1.86 (dq, J=9.7, 4.9 Hz, 2H). UPLC-MS: t$_R$=1.04 min (Apolar method); MS (ESI) m/z calcd for C$_{30}$H$_{21}$F$_5$N$_3$O$_6$ (M+H)$^+$: 615.1; found: 615.4.

Methyl 2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylate Following general procedure 5f, the title compound was obtained from [145] and methyl 2-hydroxypyridine-4-carboxylate, after flash chromatography eluting with cyclohexane/EtOAc (0% to 30%), as white solid in 76% yield: $^1$H NMR (400 MHz, DMSO-d$_6$) δ 8.27 (dd, J=5.2, 0.8 Hz, 1H), 7.54-7.42 (m, 2H), 7.40 (dd, J=5.2, 1.4 Hz, 1H), 7.35 (d, J=2.1 Hz, 1H), 7.26-7.15 (m, 3H), 7.06 (app-t, J=1.0 Hz, 1H), 6.84 (d, J=8.5 Hz, 1H), 6.29 (t, J=3.6 Hz, 1H), 3.87 (s, 3H), 3.22 (s, 3H), 2.88-2.72 (m, 1H), 2.63-2.55 (m, 1H), 2.18-2.05 (m, 1H), 1.97-1.80 (m, 3H). UPLC-MS: t$_R$=2.26 min (Apolar method); MS (ESI) m/z calcd for C$_{30}$H$_{24}$F$_5$N$_4$O$_6$ (M+H)$^+$: 631.2; found: 631.3.

2-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylic acid Following general procedure 5o, the title compound was obtained from [181], after flash chromatography eluting with DCM/MeOH (from 0% to 5%), as white solid in 36% yield: 1H NMR (400 MHz, DMSO-d$_6$) δ 13.64 (s, 1H), 8.24 (d, J=5.2 Hz, 1H), 7.52-7.44 (m, 2H), 7.39 (dd, J=5.3, 1.4 Hz, 1H), 7.37 (d, J=2.1 Hz, 1H), 7.28-7.15 (m, 3H), 7.06 (s, 1H), 6.81 (d, J=8.6 Hz, 1H), 6.28 (t, J=3.2 Hz, 1H), 3.23 (s, 3H), 2.92-2.72 (m, 1H), 2.65-2.56 (m, 1H), 2.17-2.06 (m, 1H), 2.03-1.90 (m, 1H), 1.91-1.76 (m, 2H). UPLC-MS: t$_R$=0.77 min (Apolar method); MS (ESI) m/z calcd for C$_{29}$H$_{20}$F$_5$N$_4$O$_6$ (M+H)$^+$: 615.1; found: 615.4.

(S) or (R)-Methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylate The title compound as pure enantiomer was obtained from racemic compound [163], after purification by chiral column chromatography, using an isocratic mode on a Daicel ChiralPak AD column (250×10 mmID, with heptane/2-propanol (50:50) as mobile phase (flow rate: 1.0 mL/min). The pure enantiomer was obtained as a white solid UPLC-MS: t$_R$=1.63 min (Apolar method); MS (ESI) m/z calcd for C$_{30}$H$_{24}$F$_5$N$_4$O$_6$ (M+H)$^+$: 631.1; found: 631.5. Chiral analysis: t$_R$=8.866 min, >99.5% ee.

(S) or (R)-5-[[-1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylic acid Following general procedure 5o, the title compound was obtained from [183], after flash chromatography eluting with DCM/MeOH (95/5), as white solid in 58% yield: $^1$H NMR (400 MHz, DMSO-d$_6$) δ 13.02 (s, 1H), 8.26 (d, J=2.8 Hz, 1H), 7.96 (d, J=8.7 Hz, 1H), 7.56-7.46 (m, 3H), 7.44 (d, J=2.1 Hz, 1H), 7.36-7.22 (m, 2H), 7.19 (d, J=8.6 Hz, 1H), 6.83 (d, J=8.0 Hz, 1H), 5.96-5.84 (m, 1H), 3.25 (s, 3H), 2.92-2.73 (m, 1H), 2.66-2.56 (m, 1H), 2.17-2.06 (m, 1H), 2.02-1.89 (m, 1H), 1.91-1.75 (m, 2H). UPLC-MS: t$_R$=1.38 min (Apolar method); MS (ESI) m/z calcd for C$_{29}$H$_{22}$F$_5$N$_4$O$_6$ (M+H)$^+$: 615.1; found: 615.5.

(R) or (S)-Methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylate The title compound as pure enantiomer was obtained from racemic compound [163], after purification by chiral column chromatography, using an isocratic mode on a Daicel ChiralPak AD column (250×10 mmID, with heptane/2-propanol (50:50) as mobile phase (flow rate: 1.0 mL/min). The pure enantiomer was obtained as a white solid UPLC-MS: t$_R$=1.63 min (Apolar method); MS (ESI) m/z calcd for C$_{30}$H$_{24}$F$_5$N$_4$O$_6$ (M+H)$^+$: 631.1; found: 631.5. Chiral analysis: t$_R$=25.015 min, >99.5% ee.

(R) or (S)-5-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylic acid Following general procedure 5o, the title compound was obtained from [184], after flash chromatography eluting with DCM/MeOH (95/5), as white solid in 58% yield: $^1$H NMR (400 MHz, DMSO-d$_6$) δ 13.02 (s, 1H), 8.26 (d, J=2.8 Hz, 1H), 7.96 (d, J=8.7 Hz, 1H), 7.56-7.46 (m, 3H), 7.44 (d, J=2.1 Hz, 1H), 7.36-7.22 (m, 2H), 7.19 (d, J=8.6 Hz, 1H), 6.83 (d, J=8.0 Hz, 1H), 5.96-5.84 (m, 1H), 3.25 (s, 3H), 2.92-2.73 (m, 1H), 2.66-2.56 (m, 1H), 2.17-2.06 (m, 1H), 2.02-1.89 (m, 1H), 1.91-1.75 (m, 2H). UPLC-MS: t$_R$=1.38 min (Apolar method); MS (ESI) m/z calcd for C$_{29}$H$_{22}$F$_5$N$_4$O$_6$ (M+H)$^+$: 615.1; found: 615.5.

(S) or (R)-Ethyl 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate The title compound as pure enantiomer was obtained from racemic compound [169], after purification by chiral column chromatography, using an isocratic mode on a Daicel ChiralPak AD column (250×10 mmID, particle size 10 μm) with heptane/2-propanol (90:10) as mobile phase (flow rate: 5.0 mL/min). The pure enantiomer was obtained as a white solid. UPLC-MS: t$_R$=2.33 min (Apolar method); MS (ESI) m/z calcd for C$_{32}$H$_{27}$F$_5$N$_3$O$_6$ (M+H)$^+$: 644.2; found: 644.4. Chiral analysis: t$_R$=11.674 min, >99.5% ee.

(S) or (R)-3-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]benzoic acid Following general procedure 5o, the title compound was obtained from [187], after flash chromatography eluting with DCM/MeOH (95/5), as white solid in 74% yield: $^1$H NMR (400 MHz, DMSO-d$_6$) δ 13.03 (s, 1H), 7.62-7.55 (m, 2H), 7.54 (d, J=1.9 Hz, 1H), 7.44 (app-t, J=1.9 Hz, 1H), 7.38 (t, J=8.0 Hz, 1H), 7.34 (d, J=2.1 Hz, 1H), 7.32-7.22 (m, 2H), 7.18-7.05 (m, 2H), 6.77 (app-d, J=8.6 Hz, 1H), 5.71 (t, J=3.5 Hz, 1H), 3.23 (s, 3H), 2.88-2.75 (m, 1H), 2.64-2.54 (m, 1H), 2.22-2.04 (m, 1H), 1.95-1.71 (m, 3H). UPLC-MS: $t_R$=1.16 min (Apolar method); MS (ESI) m/z calcd for $C_{30}H_{21}F_5N_3O_6$ (M+H)$^+$: 614.1; found: 614.3. Chiral analysis: $t_R$=13.948 min, >99.5% ee at 254 nm.

(R) or (S)-Ethyl 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate The title compound as pure enantiomer was obtained from compound [169], after purification by chiral column chromatography, using an isocratic mode on a Daicel ChiralPak AD column (250×10 mmID, particle size 10 μm) with heptane/2-propanol (90:10) as mobile phase (flow rate: 5.0 mL/min). The pure enantiomer was obtained as a white solid. UPLC-MS: $t_R$=2.33 min (Apolar method); MS (ESI) m/z calcd for $C_{32}H_{27}F_5N_3O_6$ (M+H)$^+$: 644.2; found: 644.4. Chiral analysis: $t_R$=19.119 min, >99.5% ee.

(R) or (S)-3-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]benzoic acid Following general procedure 50, the title compound was obtained from [189], after flash chromatography eluting with DCM/MeOH (95/5), as white solid in 62% yield: $^1$H NMR (400 MHz, DMSO-$d_6$) δ 13.03 (s, 1H), 7.62-7.55 (m, 2H), 7.54 (s, 1H), 7.44 (app-t, J=1.9 Hz, 1H), 7.38 (t, J=8.0 Hz, 1H), 7.34 (d, J=2.1 Hz, 1H), 7.32-7.22 (m, 2H), 7.18-7.05 (m, 2H), 6.77 (app-d, J=8.6 Hz, 1H), 5.71 (t, J=3.5 Hz, 1H), 3.23 (s, 3H), 2.88-2.75 (m, 1H), 2.64-2.54 (m, 1H), 2.22-2.04 (m, 1H), 1.95-1.71 (m, 3H). UPLC-MS: $t_R$=1.16 min (Apolar method); MS (ESI) m/z calcd for $C_{30}H_{21}F_5N_3O_6$ (M+H)$^+$: 614.1; found: 614.3. Chiral analysis: $t_R$=21.599 min, >99.5% ee at 254 nm.

(S) or (R)-Methyl 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate The title compound as pure enantiomer was obtained from racemic compound [179], after purification by chiral column chromatography, using an isocratic mode on a Daicel ChiralPak AD column (250×10 mmID, particle size 10 μm) with heptane/2-propanol (90:10) as mobile phase (flow rate: 5.0 mL/min). The pure enantiomer was obtained as a white solid. UPLC-MS: $t_R$=2.22 min (Apolar method); MS (ESI) m/z calcd for $C_{30}H_{24}F_5N_4O_6$ (M+H)$^+$: 631.2; found: 631.3. Chiral analysis: $t_R$=9.327 min, >99.5% ee.

(S) or (R)-6-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid Following general procedure 50, the title compound was obtained from [191], after flash chromatography eluting with DCM/MeOH (96:4), as white solid in 66% yield: $^1$H NMR (400 MHz, DMSO-$d_6$) δ 13.08 (s, 1H), 8.63 (d, J=2.3 Hz, 1H), 8.09 (dd, J=8.7, 2.3 Hz, 1H), 7.48-7.43 (m, 2H), 7.42 (d, J=2.1 Hz, 1H), 7.28-7.16 (m, 3H), 6.86 (d, J=8.5 Hz, 1H), 6.67 (d, J=8.6 Hz, 1H), 6.39 (t, J=3.5 Hz, 1H), 3.24 (s, 3H), 2.87-2.74 (m, 1H), 2.65-2.55 (m, 1H), 2.25-1.95 (m, 2H), 1.86 (dq, J=9.7, 4.9 Hz, 2H). UPLC-MS: $t_R$=1.04 min (Apolar method); MS (ESI) m/z calcd for $C_{30}H_{21}F_5N_3O_6$ (M+H)$^+$: 615.1; found: 615.4. Chiral analysis: $t_R$=6.831 min, >99.5% ee at 240 nm.

(R) or (S)-Methyl 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate The title compound as pure enantiomer was obtained from racemic compound [179], after purification by chiral column chromatography, using an isocratic mode on a Daicel ChiralPak AD column (250×10 mmID, particle size 10 μm) with heptane/2-propanol (90:10) as mobile phase (flow rate: 5.0 mL/min). The pure enantiomer was obtained as a white solid. UPLC-MS: $t_R$=2.22 min (Apolar method); MS (ESI) m/z calcd for $C_{30}H_{24}F_5N_4O_6$ (M+H)$^+$: 631.2; found: 631.3. Chiral analysis: $t_R$=15.731 min, >99.5% ee.

(R) or (S)-6-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid Following general procedure 50, the title compound was obtained from [193], after flash chromatography eluting with DCM/MeOH (96:4), as white solid in 51% yield: $^1$H NMR (400 MHz, DMSO-$d_6$) δ 13.08 (s, 1H), 8.63 (d, J=2.3 Hz, 1H), 8.09 (dd, J=8.7, 2.3 Hz, 1H), 7.48-7.43 (m, 2H), 7.42 (d, J=2.1 Hz, 1H), 7.28-7.16 (m, 3H), 6.86 (d, J=8.5 Hz, 1H), 6.67 (d, J=8.6 Hz, 1H), 6.39 (t, J=3.5 Hz, 1H), 3.24 (s, 3H), 2.87-2.74 (m, 1H), 2.65-2.55 (m, 1H), 2.25-1.95 (m, 2H), 1.86 (dq, J=9.7, 4.9 Hz, 2H). UPLC-MS: $t_R$=1.04 min (Apolar method); MS (ESI) m/z calcd for $C_{30}H_{21}F_5N_3O_6$ (M+H)$^+$: 615.1; found: 615.4. Chiral analysis: $t_R$=11.047 min, >99.5% ee at 240 nm.

(S) or (R)-Methyl 2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylate The title compound as pure enantiomer was obtained from racemic compound [181], after purification by chiral column chromatography, using an isocratic mode on a Daicel ChiralPak AD column (250×10 mmID, particle size 10 μm) with heptane/2-propanol (90:10) as mobile phase (flow rate: 5.0 mL/min). The pure enantiomer was obtained as a white solid. UPLC-MS: $t_R$=2.26 min (Apolar method); MS (ESI) m/z calcd for $C_{30}H_{24}F_5N_4O_6$ (M+H)$^+$: 631.2; found: 631.3. Chiral analysis: $t_R$=11.439 min, >99.5% ee at 250 nm.

(S) or (R)-2-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylic acid Following general procedure 50, the title compound was obtained from [195], after flash chromatography eluting with DCM/MeOH (95/5), as white solid in 67% yield: $^1$H NMR (400 MHz, DMSO-$d_6$) δ 13.64 (s, 1H), 8.24 (d, J=5.2 Hz, 1H), 7.52-7.44 (m, 2H), 7.39 (dd, J=5.3, 1.4 Hz, 1H), 7.37 (d, J=2.1 Hz, 1H), 7.28-7.15 (m, 3H), 7.06 (s, 1H), 6.81 (d, J=8.6 Hz, 1H), 6.28 (t, J=3.2 Hz, 1H), 3.23 (s, 3H), 2.92-2.72 (m, 1H), 2.65-2.56 (m, 1H), 2.17-2.06 (m, 1H), 2.03-1.90 (m, 1H), 1.91-1.76 (m, 2H). UPLC-MS: $t_R$=0.77 min (Apolar method); MS (ESI). Chiral analysis: $t_R$=14.635 min, >99.5% ee at 250 nm.

(R) or (S)-Methyl 2-[[1-[3-[(2,2-difluoro-1,3-benzo-dioxol-5-yl)-methyl-carbamoyl]phenyl]-3-(trifluoromethyl)-4,5,6,7-tetrahydroindazol-7-yl]oxy]pyridine-4-carboxylate The title compound as pure enantiomer was obtained from racemic compound [181], after purification by chiral column chromatography, using an isocratic mode on a Daicel ChiralPak AD column (250×10 mmID, particle size 10 μm) with heptane/2-propanol (90:10) as mobile phase (flow rate: 5.0 mL/min). The pure enantiomer was obtained as a white solid. UPLC-MS: $t_R$=2.26 min (Apolar method); MS (ESI) m/z calcd for $C_{30}H_{24}F_5N_4O_6$ (M+H)$^+$: 631.2; found: 631.3. Chiral analysis: $t_R$=16.046 min, >99.5% ee at 250 nm.

(R) or (S)-2-[[1-[3-[(2,2-Difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylic acid Following general procedure 5o, the title compound was obtained from [197], after flash chromatography eluting with DCM/MeOH (95/5), as white solid in 61% yield: $^1$H NMR (400 MHz, DMSO-d$_6$) δ 13.64 (s, 1H), 8.24 (d, J=5.2 Hz, 1H), 7.52-7.44 (m, 2H), 7.39 (dd, J=5.3, 1.4 Hz, 1H), 7.37 (d, J=2.1 Hz, 1H), 7.28-7.15 (m, 3H), 7.06 (s, 1H), 6.81 (d, J=8.6 Hz, 1H), 6.28 (t, J=3.2 Hz, 1H), 3.23 (s, 3H), 2.92-2.72 (m, 1H), 2.65-2.56 (m, 1H), 2.17-2.06 (m, 1H), 2.03-1.90 (m, 1H), 1.91-1.76 (m, 2H). UPLC-MS: $t_R$=0.77 min (Apolar method); MS (ESI) m/z calcd for $C_{29}H_{20}F_5N_4O_6$ (M+H)$^+$: 615.1; found: 615.4. Chiral analysis: $t_R$=19.603 min, >99.5% ee at 250 nm.

General Procedure 5n

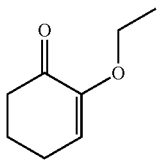

[Int-5.32] 2-ethoxycyclohex-2-en-1-one

In a round-bottom flask, at room temperature, 1,2-Cyclohexandione (14) (1 g, 8.9 mmol) was dissolved in a mixture of toluene (20 ml) and ethanol (10 ml). p-Toluenesulfonic acid (204 mg, 1.07 mmol) was added and the solution heated under reflux for 2 days. The solvent was then evaporated and the residue dissolved with dichloromethane (20 ml) and washed with a saturated solution of NaHCO$_3$ (20 ml). The organic layer was dried over Na$_2$SO$_4$ and concentrated. The crude was purified by chromatography on a silica gel column with 10% AcOEt in Cyclohexane as solvent to give 15a as a brown oil (858 mg, 69%): $^1$H NMR (400 MHz, DMSO-d$_6$) δ 5.99 (t, J=4.6 Hz, 1H), 3.68 (q, J=7.0 Hz, 2H), 2.46-2.25 (m, 4H), 1.99-1.75 (m, 2H), 1.23 (t, J=7.0 Hz, 3H). UPLC-MS: $t_R$=1.34 min (Generic method); MS (ESI) m/z calcd for $C_8H_{13}O_2$ (M+H)$^+$: 141.1, found: 141.4.

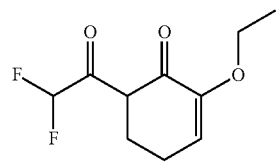

[Int-5.33] 6-(2,2-difluoroacetyl)-2-ethoxy-cyclohex-2-en-1-one

Following general procedure 5b, the title compound was obtained from compound [Int-5.32] and ethyl 2,2-difluoroacetate, after silica gel flash chromatography, eluting with Cyclohexane/EtOAc (90:10) as a viscous oil in 34% yield: UPLC-MS: $t_R$=1.81 min (Generic method); MS (ESI) m/z calcd for $C_{10}H_{11}F_2O_3$ (M–H)$^-$: 217.2, found: 217.3.

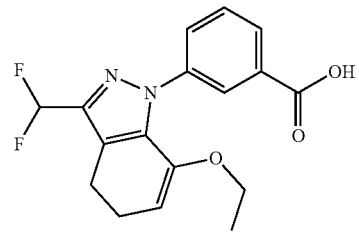 [SMILES: CCOC1=CCCc2c(C(F)F)nn(-c3cccc(C(=O)O)c3)c21]

[Int-5.34] 3-[3-(difluoromethyl)-7-ethoxy-4,5-dihydroindazol-1-yl]benzoic acid

Following general procedure 5c, the title compound was obtained from compound [Int-5.33] and 3-hydrazinobenzoic acid, as crude compound as a brown solid: UPLC-MS: $t_R$=1.82 min (Generic method); MS (ESI) m/z calcd for $C_{17}H_{17}F_2N_2O_3$ (M+H)$^+$: 335.3, found: 335.4.

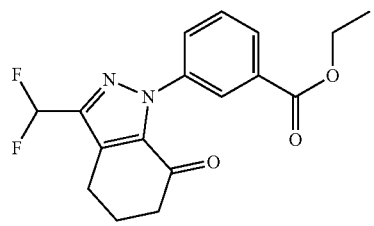 [SMILES: CCOC(=O)c1cccc(-n2nc(C(F)F)c3c2C(=O)CCC3)c1]

[Int-5.35] Ethyl 3-[3-(difluoromethyl)-7-oxo-5,6-dihydro-4H-indazol-1-yl]benzoate Following general procedure 5d, the title compound was obtained from crude [Int-5.34], after silica gel flash chromatography, eluting with Cyclohexane/EtOAc (85:15) as a viscous yellow oil in 65% yield over two steps: $^1$H NMR (400 MHz, DMSO-d$_6$) δ 8.09-8.04 (m, 2H), 7.87-7.80 (m, 1H), 7.66 (t, J=8.2 Hz, 1H), 7.21 (t, J=53.6 Hz, 1H), 4.35 (q, J=7.1 Hz, 2H), 2.90 (t, J=6.1 Hz, 2H), 2.63-2.56 (m, 2H), 2.19-2.10 (m, 2H), 1.33 (t, J=7.1 Hz, 3H). UPLC-MS: $t_R$=2.35 min (Generic method); MS (ESI) m/z calcd for $C_{17}H_{17}F_2N_2O_3$ (M+H)$^+$: 335.3, found: 335.4.

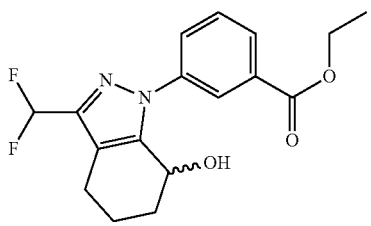 [SMILES: CCOC(=O)c1cccc(-n2nc(C(F)F)c3c2C(O)CCC3)c1]

[Int-5.36] Ethyl 3-[3-(difluoromethyl)-7-hydroxy-4,5,6,7-tetrahydroindazol-1-yl]benzoate Following general procedure 5e, the title compound was obtained from [Int-5.35], after silica gel flash chromatography, eluting with DCM/EtOAc (80:20) as a viscous oil in 88% yield: $^1$H NMR (400 MHz, DMSO-d$_6$) δ 8.39 (t, J=1.9 Hz, 1H), 8.14 (ddd, J=8.1, 2.3, 1.1 Hz, 1H), 7.98 (app-dt, J=7.8, 1.3 Hz, 1H), 7.68 (t, J=7.9 Hz, 1H), 7.09 (t, J=53.9 Hz, 1H), 5.51 (d, J=6.2 Hz, 1H), 4.80-4.66 (m, 1H), 4.36 (q, J=7.1 Hz, 2H), 2.91-2.68 (m, 1H), 2.49-2.42 (m, 1H), 1.97-1.88 (m, 2H), 1.84-1.67 (m, 2H), 1.34 (t, J=7.1 Hz, 3H).

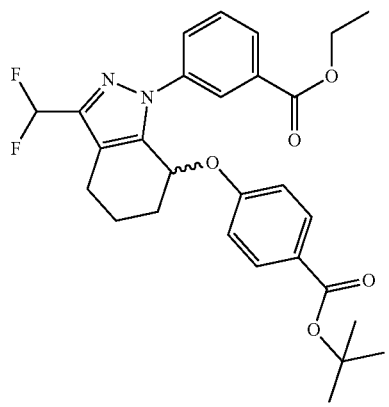 [SMILES: CCOC(=O)c1cccc(-n2nc(C(F)F)c3c2C(Oc2ccc(C(=O)OC(C)(C)C)cc2)CCC3)c1]

[Int-5.37] Ethyl 3-[7-(4-tert-butoxycarbonylphenoxy)-3-(difluoromethyl)-4,5,6,7-tetrahydroindazol-1-yl]benzoate Following general procedure 5f, the title compound was obtained from [Int-5.36], after silica gel flash chromatography, eluting with Cyclohexane/EtOAc (70:30) as a viscous oil in 62% yield: $^1$H NMR (400 MHz, DMSO-d$_6$) δ 8.04 (t, J=1.9 Hz, 1H), 7.90 (app-dt, J=7.7, 1.3 Hz, 1H), 7.82 (ddd, J=8.2, 2.3, 1.1 Hz, 1H), 7.80-7.76 (m, 2H), 7.55 (t, J=7.9 Hz, 1H), 7.14 (t, J=54.0 Hz, 1H), 7.00-6.95 (m, 2H), 5.89-5.81 (m, 1H), 4.25-3.99 (m, 2H), 2.82 (d, J=16.7 Hz, 1H), 2.65-2.54 (m, 1H), 2.17-2.03 (m, 1H), 1.97-1.78 (m, 3H), 1.16 (t, J=7.1 Hz, 3H).

[Int-5.38] 3-[7-(4-Tert-butoxycarbonylphenoxy)-3-(difluoromethyl)-4,5,6,7-tetrahydroindazol-1-yl]benzoic acid Following general procedure 5g, the title compound was obtained from [Int-5.37], as crude product as a white solid in 96% yield: $^1$H NMR (400 MHz, DMSO-d$_6$) δ 13.11 (s, 1H), 8.09 (t, J=1.9 Hz, 1H), 7.88 (app-dt, J=7.8, 1.3 Hz, 1H), 7.83-7.72 (m, 3H), 7.50 (t, J=7.9 Hz, 1H), 7.14 (t, J=54.0 Hz, 1H), 7.04-6.95 (m, 2H), 6.01-5.79 (m, 1H), 2.89-2.79 (m, 1H), 2.65-2.55 (m, 1H), 2.15-2.05 (m, 1H), 1.96-1.76 (m, 3H).

UPLC-MS: t$_R$=1.13 min (Apolar method); MS (ESI) m/z calcd for $C_{26}H_{25}F_2N_2O_5$ (M–H)$^-$: 483.5, found: 483.4.

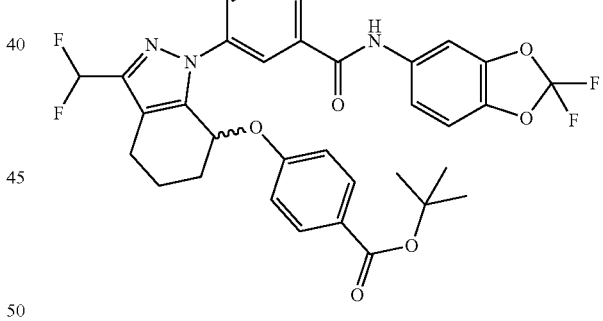

[Int-5.39] tert-Butyl 4-[[1-[3-[(2,2-difluoro-1,3-benzodioxol-5-yl)carbamoyl]phenyl]-3-(difluoromethyl)-4,5,6,7-tetrahydroindazol-7-yl]oxy]benzoate Following general procedure 5h, the title compound was obtained from compound [Int-5.38], as crude product as white solid: $^1$H NMR (400 MHz, DMSO-d$_6$) δ 10.32 (s, 1H), 8.08 (app-t, J=1.9 Hz, 1H), 7.88 (app-dt, J=7.9, 1.3 Hz, 1H), 7.81-7.72 (m, 2H), 7.69-7.62 (m, 2H), 7.57 (t, J=7.9 Hz, 1H), 7.43-7.33 (m, 2H), 7.15 (t, J=53.9 Hz, 1H), 6.99-6.92 (m, 2H), 5.80 (d, J=3.9 Hz, 1H), 2.88-2.80 (m, 1H), 2.65-2.55 (m, 1H), 2.17-2.05 (m, 1H), 1.97-1.80 (m, 3H), 1.47 (s, 9H).

113 tert-Butyl 4-[[1-[3-[(2,2-difluoro-1,3-benzodioxol-5-yl)-methyl-carbamoyl]phenyl]-3-(difluoromethyl)-4,5,6,7-tetrahydroindazol-7-yl]oxy]benzoate Following general procedure 4f, the title compound was obtained from crude [Int-5.39], a after silica gel flash chromatography, eluting with Cyclohexane/EtOAc (70:30) as a viscous oil in 82% yield over two steps: $^1$H NMR (400 MHz, DMSO-$d_6$) δ 7.91-7.74 (m, 2H), 7.56 (app-t, J=1.9 Hz, 1H), 7.46 (d, J=7.9 Hz, 1H), 7.29 (d, J=2.1 Hz, 1H), 7.25-7.12 (m, 3H), 7.08 (t, J=53.9 Hz, 1H), 7.01-6.95 (m, 2H), 6.77 (d, J=8.6 Hz, 1H), 5.80-5.71 (m, 1H), 3.22 (s, 3H), 2.89-2.77 (m, 1H), 2.63-2.54 (m, 1H), 2.20-2.04 (m, 1H), 1.96-1.75 (m, 3H), 1.49 (s, 9H). UPLC-MS: $t_R$=2.40 min (Apolar method); MS (ESI) m/z calcd for $C_{34}H_{32}F_4N_3O_6$ (M+H)$^+$: 654.6, found: 654.4.

114

4-[[1-[3-[(2,2-Difluoro-1,3-benzodioxol-5-yl)-methyl-carbamoyl]phenyl]-3-(difluoromethyl)-4,5,6,7-tetrahydroindazol-7-yl]oxy]benzoic acid Following general procedure 5l, the title compound was obtained from compound[207], a after silica gel flash chromatography, eluting with DCM/EtOAc (70:30) as a white solid in 71% yield: $^1$H NMR (400 MHz, DMSO-$d_6$) δ 12.62 (s, 1H), 7.90-7.82 (m, 2H), 7.55 (app-t, J=1.8 Hz, 1H), 7.46 (app-d, J=7.9 Hz, 1H), 7.34 (d, J=2.2 Hz, 1H), 7.28-7.12 (m, 3H), 7.07 (t, J=53.8 Hz, 1H), 7.00-6.95 (m, 2H), 6.76 (d, J=8.9 Hz, 1H), 5.93-5.55 (m, 1H), 3.21 (s, 3H), 2.91-2.75 (m, 1H), 2.63-2.53 (m, 1H), 2.17-2.05 (m, 1H), 1.95-1.74 (m, 3H). UPLC-MS: $t_R$=1.06 min (Apolar method); MS (ESI) m/z calcd for $C_{30}H_{24}F_4N_3O_6$ (M+H)$^+$: 598.5, found: 598.3.

General Protocol 6

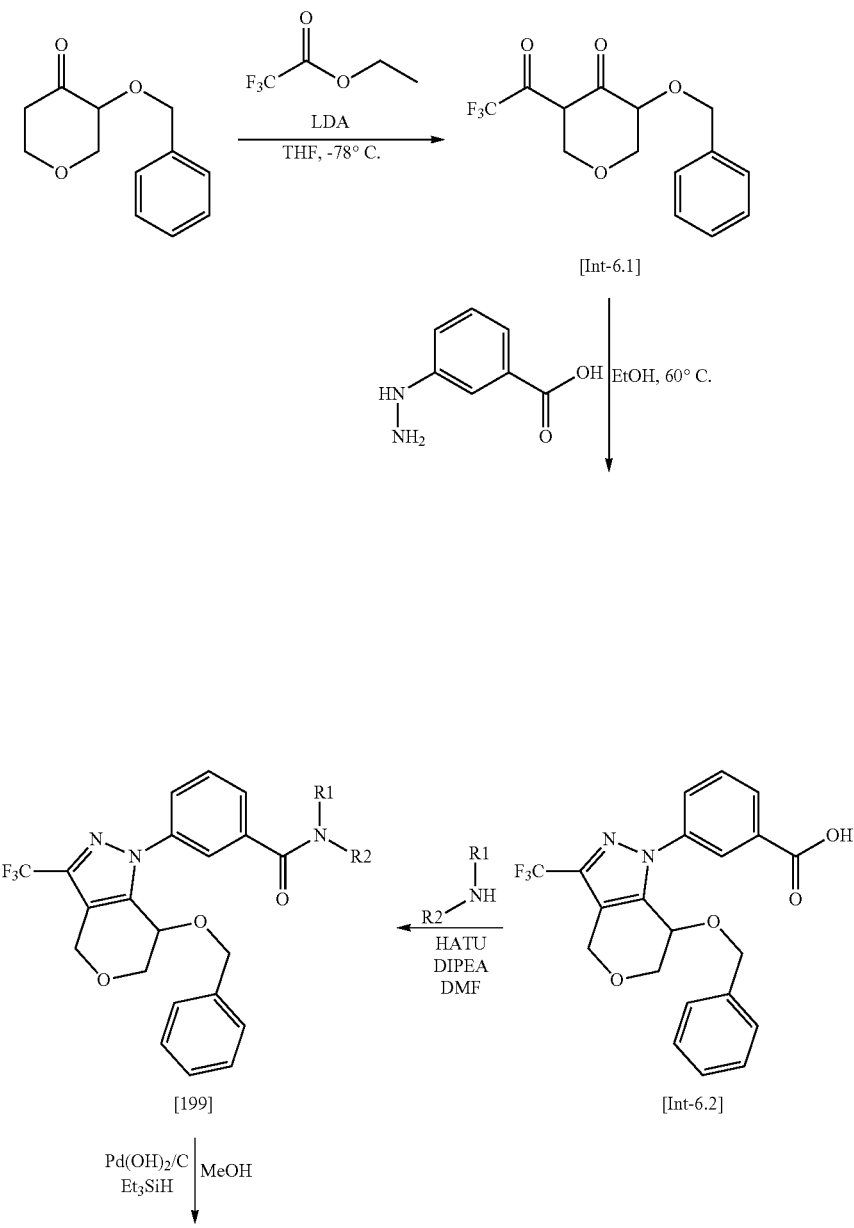

-continued

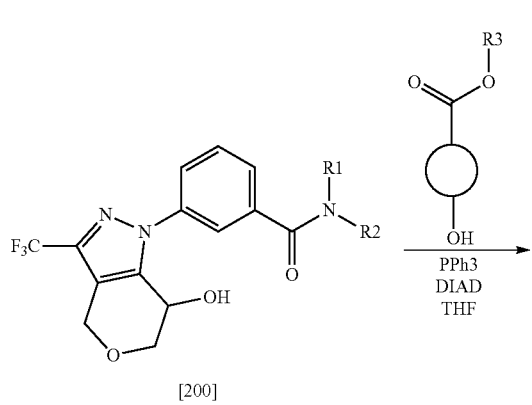

[200]

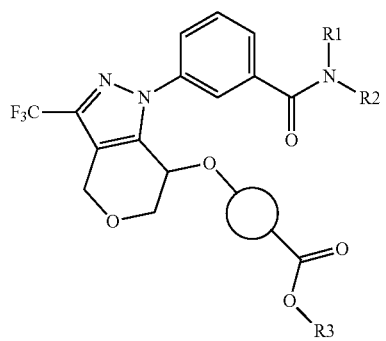

[201]

if R3 = tBu
TFA
DCM

LiOH
THF
H2O if R3 = Et, Me
→ R3 = H

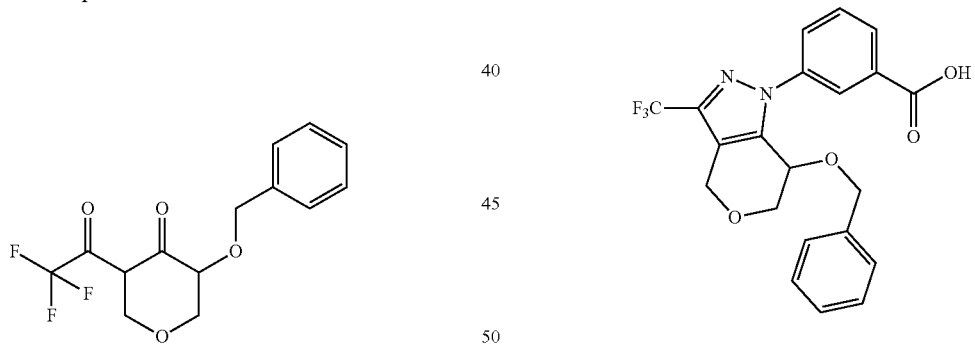

[202]

Example of General Protocol 6

[Int-6.1] 3-Benzyloxy-5-(2,2,2-trifluoroacetyl) tetrahydropyran-4-one

Following general procedure 5b, the title compound was obtained from 3-benzyloxytetrahydropyran-4-one. The crude compound was used in the next step without further purification (dense oil); UPLC-MS: tR=1.88 min (Generic method); MS (ESI) m/z calcd for $C_{14}H_{12}F_3O_4$ (M–H)⁻: 301.1, found: 301.4.

[Int-6.2] 3-[7-Benzyloxy-3-(trifluoromethyl)-6,7-dihydro-4H-pyrano[4,3-c]pyrazol-1-yl]benzoic acid Following general procedure 5c, the title compound was obtained from compound [Int-6.1], after flash chromatography, eluting with 40% AcOEt in cyclohexane to afford the title compound as pale brown solid (35% over two steps). H NMR (400 MHz, DMSO-$d_6$) δ 13.36 (bs, 1H), 8.27 (t, J=1.9 Hz, 1H), 8.08 (dt, J=7.8, 1.3 Hz, 1H), 7.99 (ddd, J=8.1, 2.3, 1.1 Hz, 1H), 7.70 (t, J=7.9 Hz, 1H), 7.35-7.19 (m, 3H), 7.19-7.07 (m, 2H), 4.90 (d, J=14.1 Hz, 1H), 4.79 (app-bs, 1H), 4.66 (d, J=14.5 Hz, 1H), 4.61 (d, J=11.1 Hz, 1H), 4.51 (d, J=11.1 Hz, 1H), 4.39 (dd, J=12.8, 1.8 Hz, 1H), 3.69 (dd, J=12.8, 2.3 Hz, 1H). UPLC-MS: tR=1.83 min (Generic method); MS (ESI) m/z calcd for $C_{21}H_{16}F_3N_2O_4$ (M–H)⁻: 417.1, found: 417.5.

3-[7-Benzyloxy-3-(trifluoromethyl)-6,7-dihydro-4H-pyrano[4,3-c]pyrazol-1-yl]-N-(2,2-difluoro-1,3-benzodioxol-5-yl)-N-methyl-benzamide Following general procedure 5h, the title compound was obtained from compound [Int-6.2], after flash chromatography, eluting with 10% MTBE in DCM to afford the title compound as a white foam (16%): $^1$H NMR (400 MHz, DMSO-$d_6$) δ 7.72 (app-s, 1H), 7.67-7.58 (m, 1H), 7.52 (d, J=2.1 Hz, 1H), 7.48-7.38 (m, 2H), 7.30-7.22 (m, 3H), 7.22-7.15 (m, 1H), 7.09-6.95 (m, 3H), 4.86 (d, J=14.4 Hz, 1H), 4.70 (app-s, 1H), 4.63 (d, J=14.5 Hz, 1H), 4.51 (d, J=11.2 Hz, 1H), 4.43-4.28 (m, 2H), 3.68 (dd, J=12.8, 2.4 Hz, 1H), 3.35 (s, 3H). UPLC-MS: tR=1.88 min (Apolar method); MS (ESI) m/z calcd for $C_{29}H_{23}F_5N_3O_5$ (M+H)$^+$: 588.1, found: 588.5.

General Procedure 6a

N-(2,2-Difluoro-1,3-benzodioxol-5-yl)-3-[7-hydroxy-3-(trifluoromethyl)-6,7-dihydro-4H-pyrano[4,3-c]pyrazol-1-yl]-N-methyl-benzamide At room temperature, [199] (0.17 g, 0.29 mmol) was suspended in MeOH (26 mL) followed by Pd(OH)$_2$/C 20 wt % (0.12 g, 0.09 mmol) and triethylsilane (0.41 mL, 2.569 mmol). After 4 h the mixture was diluted with MeOH, filtered over celite and solvent concentrated under vacuum. After silica gel flash chromatography, eluting with 40% AcOEt in cyclohexane, the title compound was obtained (0.059 g, 42%), as a white solid: $^1$H NMR (400 MHz, DMSO-$d_6$) δ 7.95-7.74 (m, 2H), 7.54 (d, J=2.1 Hz, 1H), 7.51-7.43 (m, 1H), 7.43-7.35 (m, 1H), 7.28 (d, J=8.6 Hz, 1H), 7.04 (d, J=8.5 Hz, 1H), 5.92 (d, J=7.4 Hz, 1H), 4.82 (d, J=14.7 Hz, 1H), 4.61 (d, J=14.5 Hz, 1H), 4.46 (app-d, J=7.4 Hz, 1H), 3.91 (dd, J=12.0, 2.3 Hz, 1H), 3.66 (dd, J=12.0, 2.5 Hz, 1H), 3.38 (s, 3H). UPLC-MS: tR=1.13 min (Apolar method); MS (ESI) m/z calcd for $C_{22}H_{17}F_5N_3O_5$ (M+H)$^+$: 498.1, found: 498.5.

tert-Butyl 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoate Following general procedure 5f, the title compound was obtained from compound [200], after flash chromatography, eluting with 10% AcOEt in cyclohexane to afford the title compound as a white solid (60%): $^1$H NMR (400 MHz, DMSO-$d_6$) δ 7.88-7.77 (m, 2H), 7.61 (app-s, 1H), 7.55 (d, J=8.0 Hz, 1H), 7.42-7.11 (m, 4H), 7.08-6.96 (m, 2H), 6.79 (d, J=8.6 Hz, 1H), 5.78 (app-s, 1H), 4.95 (d, J=14.5 Hz, 1H), 4.73 (d, J=14.3 Hz, 1H), 4.21 (d, J=12.9 Hz, 1H), 3.85 (d, J=12.3 Hz, 1H), 3.25 (s, 3H), 1.50 (s, 9H). UPLC-MS: tR=2.20 min (apolar method); MS (ESI) m/z calcd for $C_{33}H_{29}F_5N_3O_7$ (M+H)$^+$: 674.2, found: 674.6.

4-[[1-[3-[(2,2-Difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoic acid Following general procedure 5i, the title compound was obtained from compound [201], after flash chromatography, eluting with 20% AcOEt in DCM to afford the title compound as white solid (25%); $^1$H NMR (400 MHz, DMSO-$d_6$) δ 12.70 (bs, 1H), 7.92-7.78 (m, 2H), 7.60 (app-s, 1H), 7.55 (d, J=7.7 Hz, 1H), 7.37 (d, J=2.1 Hz, 1H), 7.28 (d, J=9.4 Hz, 2H), 7.16 (d, J=8.6 Hz, 1H), 7.08-6.95 (m, 2H), 6.77 (d, J=8.6 Hz, 1H), 5.78 (app-bs, 1H), 4.95 (d, J=14.6 Hz, 1H), 4.73 (d, J=14.6 Hz, 1H), 4.22 (dd, J=13.0, 1.6 Hz, 1H), 3.84 (dd, J=12.9, 2.2 Hz, 1H), 3.24 (s, 3H). UPLC-MS: tR=2.19 min (Generic method); MS (ESI) m/z calcd for $C_{29}H_{19}F_5N_3O_7$ (M–H)$^-$: 616.1, found: 616.4.

(R) or (S)-tert-Butyl 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoate The title compound as pure enantiomer was obtained from racemic compound [201], after purification by chiral column chromatography using an isocratic mode on a ChiralPak AD column (250×10 mm, 10 μm, 215 nm), with heptane-2-propanol (80:20) as a mobile phase (flow rate: 5 mL/min). The pure enantiomer was obtained as a white solid: $^1$H NMR (400 MHz, DMSO-$d_6$) δ 7.88-7.77 (m, 2H), 7.61 (app-s, 1H), 7.55 (d, J=8.0 Hz, 1H), 7.42-7.11 (m, 4H), 7.08-6.96 (m, 2H), 6.79 (d, J=8.6 Hz, 1H), 5.78 (app-s, 1H), 4.95 (d, J=14.5 Hz, 1H), 4.73 (d, J=14.3 Hz, 1H), 4.21 (d, J=12.9 Hz, 1H), 3.85 (d, J=12.3 Hz, 1H), 3.25 (s, 3H), 1.50 (s, 9H); Chiral analysis: $t_R$=14.0 min, >99.5% ee.

(S) or (R)-tert-Butyl 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoate The title compound as pure enantiomer was obtained from racemic compound [201], after purification by chiral column chromatography using an isocratic mode on a ChiralPak AD column (250×10 mm, 10 μm, 215 nm), with heptane-2-propanol (80:20) as a mobile phase (flow rate: 5 mL/min). The pure enantiomer was obtained as a white solid: $^1$H NMR (400 MHz, DMSO-$d_6$) δ 7.88-7.77 (m, 2H), 7.61 (app-s, 1H), 7.55 (d, J=8.0 Hz, 1H), 7.42-7.11 (m, 4H), 7.08-6.96 (m, 2H), 6.79 (d, J=8.6 Hz, 1H), 5.78 (app-s, 1H), 4.95 (d, J=14.5 Hz, 1H), 4.73 (d, J=14.3 Hz, 1H), 4.21 (d, J=12.9 Hz, 1H), 3.85 (d, J=12.3 Hz, 1H), 3.25 (s, 3H), 1.50 (s, 9H). Chiral analysis $t_R$=28.2 min, >99.5% ee.

(R) or (S)-4-[[1-[3-[(2,2-Difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoic acid Following general procedure 5i, the title compound was obtained as pure enantiomer from compound [203], after flash chromatography, eluting with 30% DCM/MeOH in DCM to afford the title compound as white solid (86%); $^1$H NMR (400 MHz, DMSO-$d_6$) δ 12.70 (bs, 1H), 7.92-7.78 (m, 2H), 7.60 (app-s, 1H), 7.55 (d, J=7.7 Hz, 1H), 7.37 (d, J=2.1 Hz, 1H), 7.28 (d, J=9.4 Hz, 2H), 7.16 (d, J=8.6 Hz, 1H), 7.08-6.95 (m, 2H), 6.77 (d, J=8.6 Hz, 1H), 5.78 (app-bs, 1H), 4.95 (d, J=14.6 Hz, 1H), 4.73 (d, J=14.6 Hz, 1H), 4.22 (dd, J=13.0, 1.6 Hz, 1H), 3.84 (dd, J=12.9, 2.2 Hz, 1H), 3.24 (s, 3H). UPLC-MS: $t_R$=2.19 min (Generic method); MS (ESI) m/z calcd for $C_{29}H_{19}F_5N_3O_7$ (M–H)$^-$: 616.1, found: 616.4. Analytical chiral column chromatography was performed using Heptane-2-Propanol (75:25)$^+$0.1% TFA as a mobile phase with a flow rate of 1 mL/min: $t_R$=27.25 min, >99.5% ee.

(S) or (R)-4-[[1-[3-[(2,2-Difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoic acid Following general procedure 5i, the title compound was obtained as pure enantiomer from compound [204], after flash chromatography, eluting with 30% DCM/MeOH in DCM to afford the title compound as white solid (83%); $^1$H NMR (400 MHz, DMSO-$d_6$) δ 12.70 (bs, 1H), 7.92-7.78 (m, 2H), 7.60 (app-s, 1H), 7.55 (d, J=7.7 Hz, 1H), 7.37 (d, J=2.1 Hz, 1H), 7.28 (d, J=9.4 Hz, 2H), 7.16 (d, J=8.6 Hz, 1H), 7.08-6.95 (m, 2H), 6.77 (d, J=8.6 Hz, 1H), 5.78 (app-bs, 1H), 4.95 (d, J=14.6 Hz, 1H), 4.73 (d, J=14.6 Hz, 1H), 4.22 (dd, J=13.0, 1.6 Hz, 1H), 3.84 (dd, J=12.9, 2.2 Hz, 1H), 3.24 (s, 3H). UPLC-MS: $t_R$=2.19 min (Generic method); MS (ESI) m/z calcd for $C_{29}H_{19}F_5N_3O_7$ (M−H)$^-$: 616.1, found: 616.4. Analytical chiral column chromatography was performed using Heptane-2-Propanol (75:25)$^+$0.1% TFA as a mobile phase with a flow rate of 1 mL/min: $t_R$=37.23 min, >99.5% ee.

Methyl 5-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylate Following general procedure 5f, the title compound was obtained from compound [200], after flash chromatography, eluting with 80% AcOEt in cyclohexane to afford the title compound as a white solid (47%). UPLC-MS: $t_R$=1.41 min (apolar method); MS (ESI) m/z calcd for $C_{29}H_{22}F_5N_4O_7$ (M+H)$^+$: 633.1, found: 633.3.

5-[[1-[3-[(2,2-Difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylic acid Following general procedure 5o, the title compound was obtained from compound [209], after flash chromatography, eluting with 60% DCM/MeOH (9:1) in DCM to afford the title compound as a white solid (88%). $^1$H NMR signal of carboxylic acid was not observed: $^1$H NMR (400 MHz, DMSO-$d_6$) δ 8.68 (app-d, J=1.5 Hz, 1H), 8.30 (d, J=2.8 Hz, 1H), 7.78 (dd, J=2.9, 1.6 Hz, 1H), 7.66-7.52 (m, 2H), 7.44 (d, J=2.1 Hz, 1H), 7.39-7.23 (m, 2H), 7.16 (d, J=8.6 Hz, 1H), 6.83 (d, J=8.7 Hz, 1H), 5.87 (s, 1H), 4.95 (d, J=14.6 Hz, 1H), 4.72 (d, J=14.6 Hz, 1H), 4.32-4.14 (m, 1H), 3.83 (d, J=13.0 Hz, 1H), 3.25 (s, 3H). UPLC-MS: $t_R$=1.86 min (generic method); MS (ESI) m/z calcd for $C_{28}H_{20}F_5N_4O_7$ (M+H)$^+$: 619.1, found: 619.3.

Methyl 6-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylate Following general procedure 5f, the title compound was obtained from compound [200], after flash chromatography, eluting with 25% AcOEt in cyclohexane to afford the title compound as a white solid (30%). $^1$H NMR (400 MHz, DMSO-$d_6$) δ 8.66 (d, J=2.3 Hz, 1H), 8.16 (dd, J=8.7, 2.4 Hz, 1H), 7.53 (s, 2H), 7.40 (d, J=2.1 Hz, 1H), 7.23 (d, J=8.5 Hz, 4H), 6.88 (d, J=9.0 Hz, 1H), 6.84 (d, J=8.7 Hz, 1H), 6.36 (s, 1H), 4.96 (d, J=14.6 Hz, 1H), 4.72 (d, J=14.5 Hz, 1H), 4.22 (d, J=12.7 Hz, 1H), 3.98-3.90 (m, 1H), 3.85 (s, 3H), 3.31 (s, 3H). UPLC-MS: $t_R$=1.74 min (apolar method); MS (ESI) m/z calcd for $C_{29}H_{22}F_5N_4O_7$ (M+H)$^+$: 633.1, found: 633.2.

Methyl 1-[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]-6-oxo-pyridine-3-carboxylate Following general procedure 5f, the title compound was obtained from compound [200], after flash chromatography, eluting with 25% AcOEt in cyclohexane to afford the title compound as a white solid (37%). $^1$H NMR (400 MHz, Chloroform-d) δ 7.94 (d, J=2.4 Hz, 1H), 7.84 (dd, J=9.6, 2.5 Hz, 1H), 7.42 (s, 1H), 7.23-7.10 (m, 3H), 6.98-6.90 (m, 2H), 6.81 (dd, J=8.4, 2.2 Hz, 1H), 6.52 (d, J=9.6 Hz, 1H), 6.27 (s, 1H), 5.14 (d, 1H), 4.80 (d, J=14.9 Hz, 1H), 4.22-4.08 (m, 1H), 4.06-3.88 (m, 1H), 3.83 (s, 3H), 3.44 (s, 3H). UPLC-MS: $t_R$=1.28 min (apolar method); MS (ESI) m/z calcd for $C_{29}H_{22}F_5N_4O_7$ (M+H)$^+$: 633.1, found: 633.2.

6-[[1-[3-[(2,2-Difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylic acid Following general procedure 5o, the title compound was obtained from compound [211], after flash chromatography, eluting with 30% DCM/MeOH (9:1) in DCM to afford the title compound as a white solid (78%). $^1$H NMR (400 MHz, DMSO-$d_6$) δ 13.21 (s, 1H), 8.63 (d, J=2.3 Hz, 1H), 8.13 (dd, J=8.6, 2.3 Hz, 1H), 7.53 (d, J=8.9 Hz, 2H), 7.41 (d, J=2.1 Hz, 1H), 7.32-7.13 (m, 3H), 6.83 (d, J=8.8 Hz, 1H), 6.79 (d, J=8.6 Hz, 1H), 6.35 (s, 1H), 4.96 (d, J=14.6 Hz, 1H), 4.71 (d, J=14.6 Hz, 1H), 4.22 (d, J=12.8 Hz, 1H), 3.93 (d, J=12.0 Hz, 1H), 3.24 (s, 3H). UPLC-MS: $t_R$=2.02 min (generic method); MS (ESI) m/z calcd for $C_{28}H_{20}F_5N_4O_7$ (M+H)$^+$: 619.1, found: 619.2.

1-[1-[3-[(2,2-Difluoro-1,3-benzodioxol-5-yl)-methyl-carbamoyl]phenyl]-3-(trifluoromethyl)-6,7-dihydro-4H-pyrano[4,3-c]pyrazol-7-yl]-6-oxo-pyridine-3-carboxylic acid Following general procedure 5o, the title compound was obtained from compound [212], after flash chromatography, eluting with 30% DCM/MeOH (9:1) in DCM to afford the title compound as a white solid (88%). $^1$H NMR (400 MHz, DMSO-$d_6$) δ 13.08 (s, 1H), 7.74 (s, 1H), 7.72-7.62 (m, 1H), 7.55-7.05 (m, 6H), 6.94 (s, OH), 6.45-6.16 (m, 2H), 5.06 (d, J=14.7 Hz, 1H), 4.79 (d, J=14.7 Hz, 1H), 4.04 (s, 2H), 3.32 (s, 3H). UPLC-MS: $t_R$=1.76 min (generic method); MS (ESI) m/z calcd for $C_{28}H_{20}F_5N_4O_7$ (M+H)$^+$: 619.1, found: 619.3.

(S) or (R)-tert-Butyl 4-[[1-[3-[methyl-(2-methyl-pyrazolo[1,5-a] pyrimidin-6-yl)carbamoyl]phenyl]-3-(trifluoromethyl)-4,5,6,7-tetrahydroindazol-7-yl]oxy]benzoate The title compound as pure enantiomer was obtained from racemic compound [173], after purification by chiral column chromatography. The pure enantiomer was obtained as a white solid. UPLC-MS: $t_R$=2.14 min (Apolar method); MS (ESI) m/z calcd for $C_{34}H_{34}F_3N_6O_4$ (M+H)$^+$: 647.3. found: 647.6. Chiral analysis: $t_R$=47.599 min, >99.5% ee.

(R) or (S)-tert-Butyl 4-[[1-[3-[methyl-(2-methyl-pyrazolo[1,5-a] pyrimidin-6-yl)carbamoyl]phenyl]-3-(trifluoromethyl)-4,5,6,7-tetrahydroindazol-7-yl]oxy]benzoate The title compound as pure enantiomer was obtained from racemic compound [173], after purification by chiral column chromatography. The pure enantiomer was obtained as a white solid. UPLC-MS: $t_R$=2.14 min (Apolar method); MS (ESI) m/z calcd for $C_{34}H_{34}F_3N_6O_4$ (M+H)$^+$: 647.3. found: 647.6. Chiral analysis: $t_R$=58.527 min, >99.5% ee.

(S) or (R)-4-[[1-[3-[Methyl-(2-methylpyrazolo[1,5-a]pyrimidin-6-yl)carbamoyl]phenyl]-3-(trifluoromethyl)-4,5,6,7-tetrahydroindazol-7-yl]oxy]benzoic acid Following general procedure 5i, the title compound was obtained from compound [215], after silica gel flash chromatography, eluting with DCM/MeOH (0 to 5%), as white solid in 72% yield: $^1$H NMR (400 MHz, DMSO-d$_6$) δ 12.63 (bs, 1H), 9.13 (dd, J=2.4, 0.9 Hz, 1H), 8.31 (s, 1H), 7.76 (d, J=8.4 Hz, 2H), 7.67 (bs, 1H), 7.52-7.13 (m, 3H), 6.77 (s, 2H), 6.50 (s, 1H), 5.71 (s, 1H), 3.32 (s, 3H), 2.77 (d, J=16.4 Hz, 1H), 2.60 (q, J=8.4, 8.0 Hz, 1H), 2.38 (s, 3H), 2.08-1.99 (m, 1H), 1.99-1.78 (m, 3H). UPLC-MS: $t_R$=0.73 min (Apolar method); MS (ESI) m/z calcd for $C_{30}H_{26}F_3N_6O_4$ (M+H)$^+$: 591.2. found: 591.5, >99.5% ee.

(R) or (S)-4-[[1-[3-[Methyl-(2-methylpyrazolo[1,5-a]pyrimidin-6-yl) carbamoyl]phenyl]-3-(trifluoromethyl)-4,5,6,7-tetrahydroindazol-7-yl]oxy]benzoic acid Following general procedure 5i, the title compound was obtained from compound [216], after silica gel flash chromatography, eluting with DCM/MeOH (0 to 5%), as white solid in 75% yield: $^1$H NMR (400 MHz, DMSO-d$_6$) δ 12.63 (bs, 1H), 9.13 (dd, J=2.4, 0.9 Hz, 1H), 8.31 (s, 1H), 7.76 (d, J=8.4 Hz, 2H), 7.67 (bs, 1H), 7.52-7.13 (m, 3H), 6.77 (s, 2H), 6.50 (s, 1H), 5.71 (s, 1H), 3.32 (s, 3H), 2.77 (d, J=16.4 Hz, 1H), 2.60 (q, J=8.4, 8.0 Hz, 1H), 2.38 (s, 3H), 2.08-1.99 (m, 1H), 1.99-1.78 (m, 3H). UPLC-MS: $t_R$=0.73 min (Apolar method); MS (ESI) m/z calcd for $C_{30}H_{26}F_3N_6O_4$ (M+H)$^+$: 591.2. found: 591.5, >99.5% ee.

Methods

Fluorescence Assay for CFTR Activity

Mutant CFTR activity was determined with the functional assay based on the halide-sensitive yellow fluorescent protein, HS-YFP (Galietta et al., *FEBS Lett* 499:220-224, 2001). CFBE41o- and FRT cells with stable expression of mutant CFTR and HS-YFP were plated on clear-bottom 96-well black microplates (Code 3603, Corning Life Sciences) at a density of 50,000 cells/well and kept at 37° C. in 5% $CO_2$ for 24 hours. For the corrector assay, cells were treated for further 24 hours with test compounds, vehicle (DMSO), or the positive control VX-809. After treatment, the culture medium was removed and cells in each well were stimulated for 30 min at 37° C. with 60 μL PBS (containing 137 mM NaCl, 2.7 mM KCl, 8.1 mM $Na_2HPO_4$, 1.5 mM $KH_2PO_4$, 1 mM $CaCl_2$, and 0.5 mM $MgCl_2$) plus forskolin (20 μM) and genistein (50 μM).

For determination of potentiator activity on F508del-CFTR, cells were incubated for 24 hours at 27° C. to allow trafficking of the mutant protein to plasma membrane. Cells were then stimulated with for 30 min with PBS containing forskolin (20 μM) plus the compound to be tested at the desired concentration.

For determination of potentiator activity on G551D-CFTR or G1349D-CFTR, cells were directly stimulated with forskolin plus test compound without previous incubation at low temperature. At the time of assay, microplates carrying CFBE41o- or FRT cells were transferred to microplate readers (BMG Labtech) equipped with high-quality excitation (HQ500/20x: 500±10 nm) and emission (HQ535/30M: 535±15 nm) filters for YFP (Chroma Technology). The assay consisted of a continuous 14 s fluorescence reading with 2 s before and 12 s after injection of an iodide-containing solution (165 μL of a modified PBS containing I$^-$ instead of Cl$^-$; final I$^-$ concentration in the well: 100 mM). Data were normalized to the initial background-subtracted fluorescence. Enhanced CFTR activity, induced by correctors and/or potentiators, results in accelerated I$^-$ influx that in turn causes faster HS-YFP quenching (Pedemonte et al., *Mol Pharmacol* 68:1736-1746, 2005; Pedemonte et al., *J Clin Invest* 115:2564-2571, 2015). To determine fluorescence quenching rate associated with I$^-$ influx, the final 10 s of data for each well were fitted with an exponential function to extrapolate initial slope (dF/dt).

$EC_{50}$ obtained are illustrated in table 1 wherein +: $EC_{50}$>2 μM; ++: 1.0 μM<$EC_{50}$<2 μM; +++: $EC_{50}$<1 μM.

TABLE 1

| # | | Substance Name | Substance Formula | activity |
|---|---|---|---|---|
| 001 | | tert-butyl 1-[3-[1,3-benzodioxol-5-yl(methyl)carbamoyl]phenyl]-3-(trifluoromethyl)-6,7-dihydro-4H-pyrazolo[4,3-c]pyridine-5-carboxylate | C27 H27 F3 N4 O5 | +++ |

TABLE 1-continued

| # | Substance Name | Substance Formula | activity |
|---|---|---|---|
| 002 | N-(1,3-benzodioxol-5-yl)-N-methyl-3-[3-(trifluoromethyl)-4,5,6,7-tetrahydropyrazolo[4,3-c]pyridin-1-yl]benzamide hydrochloride | C22 H19 F3 N4 O3•Cl H | +++ |
| 003 | N-(1,3-benzodioxol-5-yl)-N-methyl-3-[5-methyl-3-(trifluoromethyl)-6,7-dihydro-4H-pyrazolo[4,3-c]pyridin-1-yl]benzamide | C23 H21 F3 N4 O3 | +++ |
| 004 | 3-[5-acetyl-3-(trifluoromethyl)-6,7-dihydro-4H-pyrazolo[4,3-c]pyridin-1-yl]-N-(1,3-benzodioxol-5-yl)-N-methyl-benzamide | C24 H21 F3 N4 O4 | +++ |
| 005 | N-(1,3-benzodioxol-5-yl)-N-methyl-3-[3-(trifluoromethyl)-4,5,6,7-tetrahydroindazol-1-yl]benzamide | C23 H20 F3 N4 O3 | +++ |
| 006 | N-(1,3-benzodioxol-5-yl)-N-methyl-3-[5-methylsulfonyl-3-(trifluoromethyl)-6,7-dihydro-4H-pyrazolo[4,3-c]pyridin-1-yl]benzamide | C23 H21 F3 N4 O5 S | +++ |
| 007 | 3-[5-(benzenesulfonyl)-3-(trifluoromethyl)-6,7-dihydro-4H-pyrazolo[4,3-c]pyridin-1-yl]-N-(1,3-benzodioxol-5-yl)-N-methyl-benzamide | C28 H23 F3 N4 O5 S | +++ |

TABLE 1-continued

| # | | Substance Name | Substance Formula | activity |
|---|---|---|---|---|
| 008 | 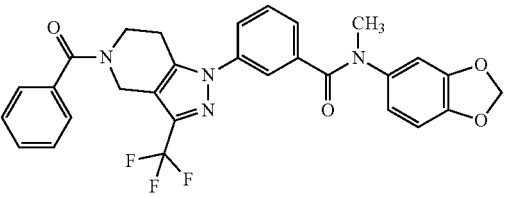 [SMILES: CN(C(=O)c1cccc(-n2nc(C(F)(F)F)c3c2CCN(C(=O)c2ccccc2)C3)c1)c1ccc2c(c1)OCO2] | N-(1,3-benzodioxol-5-yl)-3-[5-benzoyl-3-(trifluoromethyl)-6,7-dihydro-4H-pyrazolo[4,3-c]pyridin-1-yl]-N-methyl-benzamide | C29 H23 F3 N4 O4 | +++ |
| 009 | 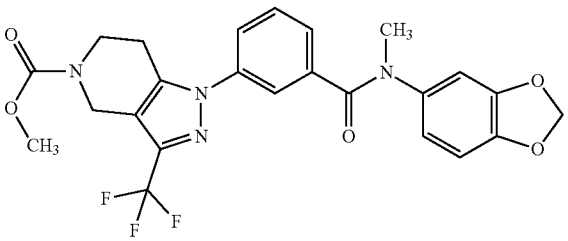 [SMILES: COC(=O)N1CCc2c(c(C(F)(F)F)nn2-c2cccc(C(=O)N(C)c3ccc4c(c3)OCO4)c2)C1] | methyl 1-[3-[1,3-benzodioxol-5-yl(methyl)carbamoyl]phenyl]-3-(trifluoromethyl)-6,7-dihydro-4H-pyrazolo[4,3-c]pyridine-5-carboxylate | C24 H21 F3 N4 O5 | +++ |
| 010 | 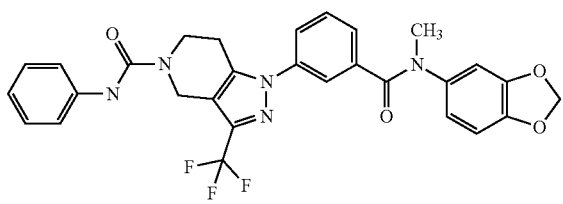 [SMILES: CN(C(=O)c1cccc(-n2nc(C(F)(F)F)c3c2CCN(C(=O)Nc2ccccc2)C3)c1)c1ccc2c(c1)OCO2] | 1-[3-[1,3-benzodioxol-5-yl(methyl)carbamoyl]phenyl]-N-phenyl-3-(trifluoromethyl)-6,7-dihydro-4H-pyrazolo[4,3-c]pyridine-5-carboxamide | C29 H24 F3 N5 O4 | +++ |
| 011 | 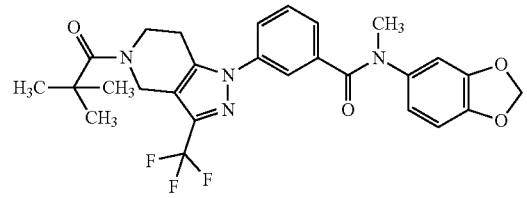 [SMILES: CN(C(=O)c1cccc(-n2nc(C(F)(F)F)c3c2CCN(C(=O)C(C)(C)C)C3)c1)c1ccc2c(c1)OCO2] | N-(1,3-benzodioxol-5-yl)-3-[5-(2,2-dimethylpropanoyl)-3-(trifluoromethyl)-6,7-dihydro-4H-pyrazolo[4,3-c]pyridin-1-yl]-N-methyl-benzamide | C27 H27 F3 N4 O4 | +++ |
| 012 | 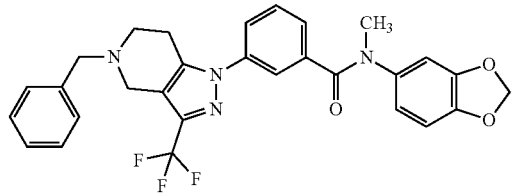 [SMILES: CN(C(=O)c1cccc(-n2nc(C(F)(F)F)c3c2CCN(Cc2ccccc2)C3)c1)c1ccc2c(c1)OCO2] | N-(1,3-benzodioxol-5-yl)-3-[5-benzyl-3-(trifluoromethyl)-6,7-dihydro-4H-pyrazolo[4,3-c]pyridin-1-yl]-N-methyl-benzamide | C29 H25 F3 N4 O3 | +++ |
| 013 | 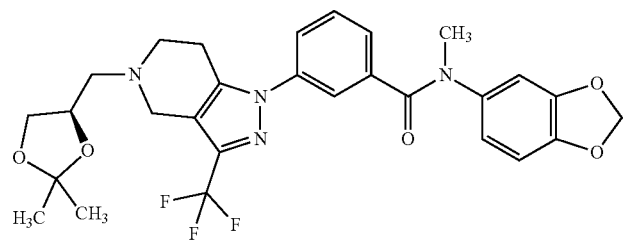 [SMILES: CN(C(=O)c1cccc(-n2nc(C(F)(F)F)c3c2CCN(C[C@@H]2COC(C)(C)O2)C3)c1)c1ccc2c(c1)OCO2] | N-(1,3-benzodioxol-5-yl)-3-[5-[[(4R)-2,2-dimethyl-1,3-dioxolan-4-yl]methyl]-3-(trifluoromethyl)-6,7-dihydro-4H-pyrazolo[4,3-c]pyridin-1-yl]-N-methyl-benzamide | C28 H29 F3 N4 O5 | +++ |

TABLE 1-continued

| # | Substance Name | Substance Formula | activity |
|---|---|---|---|
| 014 | N-(1,3-benzodioxol-5-yl)-3-[5-[[(4S)-2,2-dimethyl-1,3-dioxolan-4-yl]methyl]-3-(trifluoromethyl)-6,7-dihydro-4H-pyrazolo[4,3-c]pyridin-1-yl]-N-methyl-benzamide | C28 H29 F3 N4 O5 | +++ |
| 015 | N-(1,3-benzodioxol-5-yl)-3-[5-[(2R)-2,3-dihydroxypropyl]-3-(trifluoromethyl)-6,7-dihydro-4H-pyrazolo[4,3-c]pyridin-1-yl]-N-methyl-benzamide | C25 H25 F3 N4 O5 | +++ |
| 016 | N-(1,3-benzodioxol-5-yl)-3-[5-[(2S)-2,3-dihydroxypropyl]-3-(trifluoromethyl)-6,7-dihydro-4H-pyrazolo[4,3-c]pyridin-1-yl]-N-methyl-benzamide | C25 H25 F3 N4 O5 | +++ |
| 017 | N-(1,3-benzodioxol-5-yl)-N-methyl-3-[5-methyl-3-(trifluoromethyl)-6,7-dihydro-4H-pyrazolo[4,3-f][1,4]oxazepin-1-yl]benzamide | C23 H21 F3 N4 O4 | +++ |
| 018 | tert-butyl 1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate | C29 H29 F3 N4 O5 | +++ |
| 019 | N-(1,3-benzodioxol-5-yl)-3-[5-(cyclopropylmethyl)-3-(trifluoromethyl)-6,7-dihydro-4H-pyrazolo[4,3-c]pyridin-1-yl]-N-methyl-benzamide | C26 H25 F3 N4 O3 | +++ |

TABLE 1-continued

| # | Substance Name | Substance Formula | activity |
|---|---|---|---|
| 020 | methyl 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]methyl]benzoate | C31 H27 F3 N4 O5 | +++ |
| 021 | N-(1,3-benzodioxol-5-yl)-3-[5-isopropyl-3-(trifluoromethyl)-6,7-dihydro-4H-pyrazolo[4,3-c]pyridin-1-yl]-N-methyl-benzamide | C25 H25 F3 N4 O3 | +++ |
| 022 | N-(benzo[d][1,3]dioxol-5-yl)-N-methyl-3-(3-(trifluoromethyl)-5,6,7,8-tetrahydro-4,7-epiminocyclohepta[c]pyrazol-1(4H)-yl)benzamide hydrochloride | C24 H21 F3 N4 O3·Cl H | +++ |
| 023 | N-(benzo[d][1,3]dioxol-5-yl)-N-methyl-3-(9-methyl-3-(trifluoromethyl)-5,6,7,8-tetrahydro-4,7-epiminocyclohepta[c]pyrazol-1(4H)-yl)benzamide | C25 H23 F3 N4 O3 | +++ |
| 024 | N-(1,3-benzodioxol-5-yl)-N-methyl-3-[5-[rac-(1S)-1-methylpropyl]-3-(trifluoromethyl)-6,7-dihydro-4H-pyrazolo[4,3-c]pyridin-1-yl]benzamide | C26 H27 F3 N4 O3 | +++ |

TABLE 1-continued

| # | Substance Name | Substance Formula | activity |
|---|---|---|---|
| 025 | 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]methyl]benzoic acid | C30 H25 F3 N4 O5 | +++ |
| 026 | 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]methyl]benzoic acid | C30 H25 F3 N4 O5 | +++ |
| 027 | tert-butyl 1-[3-[1,3-benzodioxol-5-yl(methyl)carbamoyl]phenyl]-3-(trifluoromethyl)-5,7-dihydro-4H-pyrazolo[3,4-c]pyridine-6-carboxylate | C27 H27 F3 N4 O5 | +++ |
| 028 | tert-butyl 1-[3-[1,3-benzodioxol-5-yl(methyl)carbamoyl]phenyl]-3-(trifluoromethyl)-6,7-dihydro-5H-pyrazolo[4,3-b]pyridine-4-carboxylate | C27 H27 F3 N4 O5 | +++ |
| 029 | N-(1,3-benzodioxol-5-yl)-N-methyl-3-[6-methyl-3-(trifluoromethyl)-5,7-dihydro-4H-pyrazolo[3,4-c]pyridin-1-yl]benzamide | C23 H21 F3 N4 O3 | +++ |
| 030 | N-methyl-N-(2-methyl-1,3-benzoxazol-6-yl)-3-[3-(trifluoromethyl)-4,5,6,7-tetrahydropyrazolo[4,3-c]pyridin-1-yl]benzamide hydrochloride | C23 H20 F3 N4 O2•Cl H | ++ |

TABLE 1-continued

| # | | Substance Name | Substance Formula | activity |
|---|---|---|---|---|
| 031 | 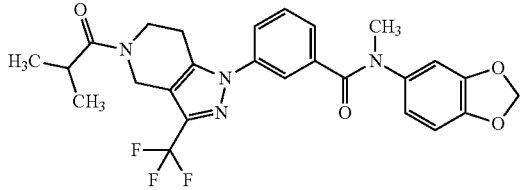 [SMILES: CC(C)C(=O)N1CCc2c(c(C(F)(F)F)nn2-c2cccc(C(=O)N(C)c3ccc4c(c3)OCO4)c2)C1] | N-(1,3-benzodioxol-5-yl)-N-methyl-3-[5-(2-methylpropanoyl)-3-(trifluoromethyl)-6,7-dihydro-4H-pyrazolo[4,3-c]pyridin-1-yl]benzamide | C26 H25 F3 N4 O4 | +++ |
| 032 | 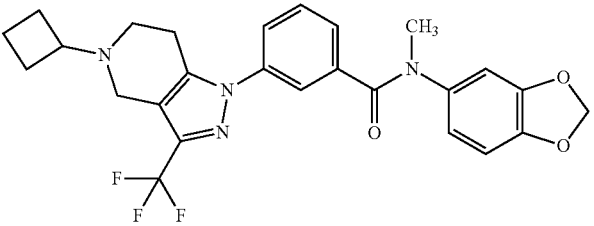 [SMILES: CN(C(=O)c1cccc(-n2nc(C(F)(F)F)c3c2CCN(C2CCC2)C3)c1)c1ccc2c(c1)OCO2] | N-(1,3-benzodioxol-5-yl)-3-[5-cyclobutyl-3-(trifluoromethyl)-6,7-dihydro-4H-pyrazolo[4,3-c]pyridin-1-yl]-N-methyl-benzamide | C26 H25 F3 N4 O3 | +++ |
| 033 | 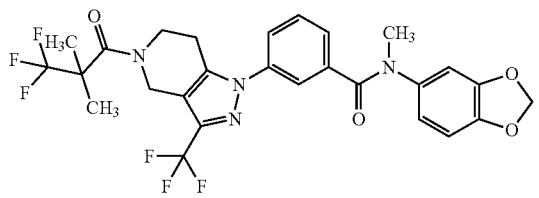 [SMILES: CN(C(=O)c1cccc(-n2nc(C(F)(F)F)c3c2CCN(C(=O)C(C)(C)C(F)(F)F)C3)c1)c1ccc2c(c1)OCO2] | N-(1,3-benzodioxol-5-yl)-N-methyl-3-[5-(3,3,3-trifluoro-2,2-dimethyl-propanoyl)-3-(trifluoromethyl)-6,7-dihydro-4H-pyrazolo[4,3-c]pyridin-1-yl]benzamide | C27 H24 F6 N4 O4 | +++ |
| 034 | 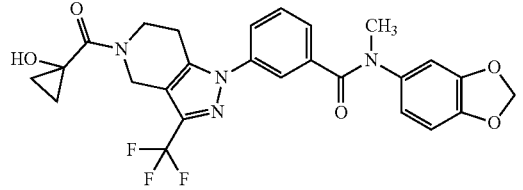 [SMILES: CN(C(=O)c1cccc(-n2nc(C(F)(F)F)c3c2CCN(C(=O)C2(O)CC2)C3)c1)c1ccc2c(c1)OCO2] | N-(1,3-benzodioxol-5-yl)-3-[5-(1-hydroxycyclopropanecarbonyl)-3-(trifluoromethyl)-6,7-dihydro-4H-pyrazolo[4,3-c]pyridin-1-yl]-N-methyl-benzamide | C26 H23 F3 N4 O5 | +++ |
| 035 | 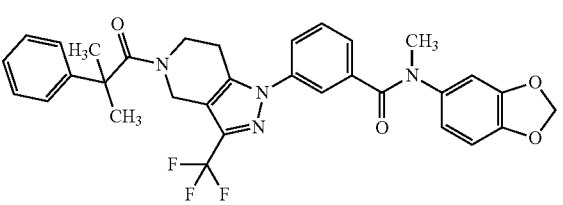 [SMILES: CN(C(=O)c1cccc(-n2nc(C(F)(F)F)c3c2CCN(C(=O)C(C)(C)c2ccccc2)C3)c1)c1ccc2c(c1)OCO2] | N-(1,3-benzodioxol-5-yl)-N-methyl-3-[5-(2-methyl-2-phenyl-propanoyl)-3-(trifluoromethyl)-6,7-dihydro-4H-pyrazolo[4,3-c]pyridin-1-yl]benzamide | C32 H29 F3 N4 O4 | +++ |
| 036 | 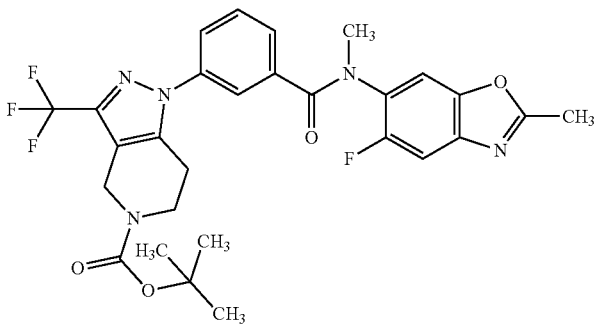 [SMILES: Cc1nc2cc(F)c(N(C)C(=O)c3cccc(-n4nc(C(F)(F)F)c5c4CCN(C(=O)OC(C)(C)C)C5)c3)cc2o1] | tert-butyl 1-[3-[(5-fluoro-2-methyl-1,3-benzoxazol-6-yl)-methyl-carbamoyl]phenyl]-3-(trifluoromethyl)-6,7-dihydro-4H-pyrazolo[4,3-c]pyridine-5-carboxylate | C28 H27 F4 N5 O4 | +++ |

TABLE 1-continued

| # | | Substance Name | Substance Formula | activity |
|---|---|---|---|---|
| 037 | 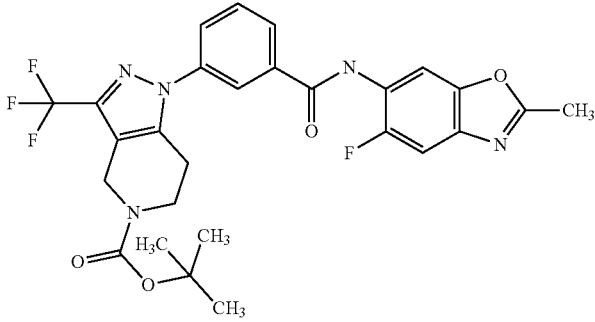 [SMILES: Cc1nc2cc(F)c(NC(=O)c3cccc(-n4nc(C(F)(F)F)c5c4CCN(C(=O)OC(C)(C)C)C5)c3)cc2o1] | tert-butyl 1-[3-[(5-fluoro-2-methyl-1,3-benzoxazol-6-yl)carbamoyl]phenyl]-3-(trifluoromethyl)-6,7-dihydro-4H-pyrazolo[4,3-c]pyridine-5-carboxylate | C27 H25 F4 N5 O4 | + |
| 038 | 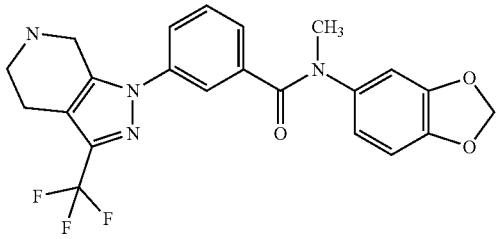 [SMILES: CN(C(=O)c1cccc(-n2nc(C(F)(F)F)c3c2CNCC3)c1)c1ccc2c(c1)OCO2] | N-(1,3-benzodioxol-5-yl)-N-methyl-3-[3-(trifluoromethyl)-4,5,6,7-tetrahydropyrazolo[3,4-c]pyridin-1-yl]benzamide hydrochloride | C22 H19 F3 N4 O3•Cl H | +++ |
| 039 | 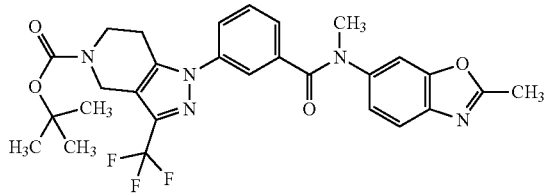 [SMILES: Cc1nc2ccc(N(C)C(=O)c3cccc(-n4nc(C(F)(F)F)c5c4CCN(C(=O)OC(C)(C)C)C5)c3)cc2o1] | tert-butyl 1-[3-[methyl-(2-methyl-1,3-benzoxazol-6-yl)carbamoyl]phenyl]-3-(trifluoromethyl)-6,7-dihydro-4H-pyrazolo[4,3-c]pyridine-5-carboxylate | C28 H28 F3 N5 O4 | +++ |
| 040 | 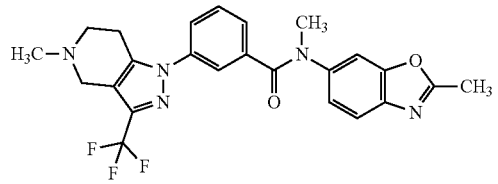 | N-methyl-N-(2-methyl-1,3-benzoxazol-6-yl)-3-[5-methyl-3-(trifluoromethyl)-6,7-dihydro-4H-pyrazolo[4,3-c]pyridin-1-yl]benzamide | C24 H22 F3 N5 O2 | +++ |
| 041 | 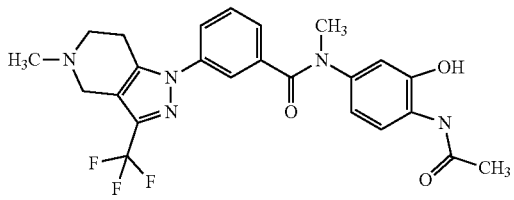 [SMILES: CC(=O)Nc1ccc(N(C)C(=O)c2cccc(-n3nc(C(F)(F)F)c4c3CCN(C)C4)c2)cc1O] | N-(4-acetamido-3-hydroxy-phenyl)-N-methyl-3-[5-methyl-3-(trifluoromethyl)-6,7-dihydro-4H-pyrazolo[4,3-c]pyridin-1-yl]benzamide | C24 H24 F3 N5 O3 | + |
| 042 | 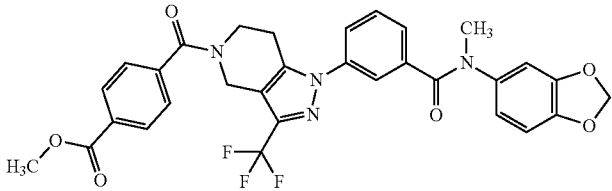 [SMILES: COC(=O)c1ccc(C(=O)N2CCc3c(c(C(F)(F)F)nn3-c3cccc(C(=O)N(C)c4ccc5c(c4)OCO5)c3)C2)cc1] | methyl 4-[1-[3-[1,3-benzodioxol-5-yl(methyl)carbamoyl]phenyl]-3-(trifluoromethyl)-6,7-dihydro-4H-pyrazolo[4,3-c]pyridine-5-carbonyl]benzoate | C31 H25 F3 N4 O6 | +++ |

TABLE 1-continued

| # | Substance Name | Substance Formula | activity |
|---|---|---|---|
| 043 | methyl 3-[1-[3-[1,3-benzodioxol-5-yl(methyl)carbamoyl]phenyl]-3-(trifluoromethyl)-6,7-dihydro-4H-pyrazolo[4,3-c]pyridin-5-yl]-3-oxo-propanoate | C26 H23 F3 N4 O6 | ++ |
| 044 | 4-[1-[3-[1,3-benzodioxol-5-yl(methyl)carbamoyl]phenyl]-3-(trifluoromethyl)-6,7-dihydro-4H-pyrazolo[4,3-c]pyridine-5-carbonyl]benzoic acid | C30 H23 F3 N4 O6 | + |
| 045 | 3-[1-[3-[1,3-benzodioxol-5-yl(methyl)carbamoyl]phenyl]-3-(trifluoromethyl)-6,7-dihydro-4H-pyrazolo[4,3-c]pyridin-5-yl]-3-oxo-propanoic acid | C25 H21 F3 N4 O6 | + |
| 046 | N-(5-fluoro-2-methyl-1,3-benzoxazol-6-yl)-N-methyl-3-[5-methyl-3-(trifluoromethyl)-6,7-dihydro-4H-pyrazolo[4,3-c]pyridin-1-yl]benzamide | C24 H21 F4 N5 O2 | +++ |
| 047 | N-(5-fluoro-2-methyl-1,3-benzoxazol-6-yl)-3-[5-methyl-3-(trifluoromethyl)-6,7-dihydro-4H-pyrazolo[4,3-c]pyridin-1-yl]benzamide | C23 H19 F4 N5 O2 | + |
| 048 | (4R,7S)- or (4S,7R)-N-(benzo[d][1,3]dioxol-5-yl)-N-methyl-3-(3-(trifluoromethyl)-5,6,7,8-tetrahydro-4,7-epiminocyclohepta[c]pyrazol-1(4H)-yl)benzamide | C24 H21 F3 N4 O3 | +++ |

TABLE 1-continued

| # | Substance Name | Substance Formula | activity |
|---|---|---|---|
| 049 | OR Enantiomer (4S,7R)- or (4R,7S)-N-(benzo[d][1,3]dioxol-5-yl)-N-methyl-3-(3-(trifluoromethyl)-5,6,7,8-tetrahydro-4,7-epiminocyclohepta[c]pyrazol-1(4H)-yl)benzamide | C24 H21 F3 N4 O3 | ++ |
| 050 | OR Enantiomer (4R,7S)- or (4S,7R)-N-(benzo[d][1,3]dioxol-5-yl)-N-methyl-3-(9-methyl-3-(trifluoromethyl)-5,6,7,8-tetrahydro-4,7-epiminocyclohepta[c]pyrazol-1(4H)-yl)benzamide | C25 H23 F3 N4 O3 | +++ |
| 051 | OR Enantiomer (4S,7R)- or (4R,7S)-N-(benzo[d][1,3]dioxol-5-yl)-N-methyl-3-(9-methyl-3-(trifluoromethyl)-5,6,7,8-tetrahydro-4,7-epiminocyclohepta[c]pyrazol-1(4H)-yl)benzamide | C25 H23 F3 N4 O3 | ++ |
| 052 | OR Enantiomer (4R,7S)- or (4S,7R)-tert-butyl-1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate | C29 H29 F3 N4 O5 | +++ |
| 053 | OR Enantiomer (4S,7R)- or (4R,7S)-tert-butyl-1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate | C29 H29 F3 N4 O5 | +++ |

TABLE 1-continued

| # | Substance Name | Substance Formula | activity |
|---|---|---|---|
| 054 | N-(1,3-benzodioxol-5-yl)-N-methyl-3-[3-(trifluoromethyl)-6,7-dihydro-4H-pyrano[4,3-c]pyrazol-1-yl]benzamide | C22 H18 F3 N3 O4 | +++ |
| 055 | methyl 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoate | C30 H25 F3 N4 O7 S | +++ |
| 056 | 1-[3-[1,3-benzodioxol-5-yl(methyl)carbamoyl]phenyl]-N-methyl-3-(trifluoromethyl)-6,7-dihydro-4H-pyrazolo[4,3-c]pyridine-5-carboxamide | C24 H22 F3 N5 O4 | +++ |
| 057 | 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoic acid | C29 H23 F3 N4 O7 S | ++ |
| 058 | N-(1,3-benzodioxol-5-yl)-3-[5-(2-hydroxy-2-methyl-propanoyl)-3-(trifluoromethyl)-6,7-dihydro-4H-pyrazolo[4,3-c]pyridin-1-yl]-N-methyl-benzamide | C26 H25 F3 N4 O5 | +++ |
| 059 | methyl 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoate | C30 H25 F3 N4 O7 S | +++ |
| 060 | methyl 2-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoate | C30 H25 F3 N4 O7 S | +++ |

TABLE 1-continued

| # | | Substance Name | Substance Formula | activity |
|---|---|---|---|---|
| 061 | 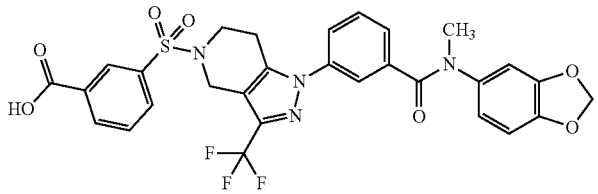 [SMILES: CN(C(=O)c1cccc(-n2nc(C(F)(F)F)c3c2CCN(S(=O)(=O)c2cccc(C(=O)O)c2)C3)c1)c1ccc2c(c1)OCO2] | 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoic acid | C29 H23 F3 N4 O7 S | + |
| 062 | 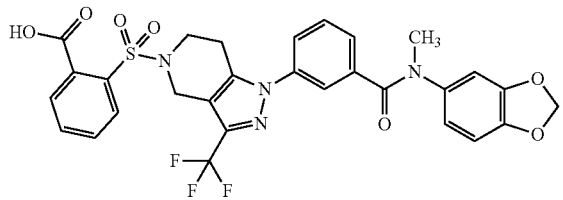 [SMILES: CN(C(=O)c1cccc(-n2nc(C(F)(F)F)c3c2CCN(S(=O)(=O)c2ccccc2C(=O)O)C3)c1)c1ccc2c(c1)OCO2] | 2-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoic acid | C29 H23 F3 N4 O7 S | + |
| 063 | 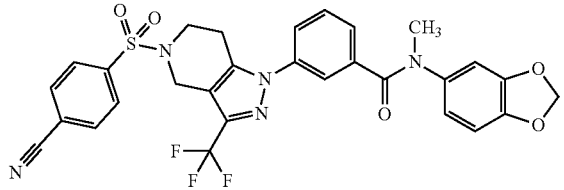 [SMILES: CN(C(=O)c1cccc(-n2nc(C(F)(F)F)c3c2CCN(S(=O)(=O)c2ccc(C#N)cc2)C3)c1)c1ccc2c(c1)OCO2] | N-(1,3-benzodioxol-5-yl)-3-[5-(4-cyanophenyl)sulfonyl-3-(trifluoromethyl)-6,7-dihydro-4H-pyrazolo[4,3-c]pyridin-1-yl]-N-methyl-benzamide | C29 H22 F3 N5 O5 S | +++ |
| 064 | 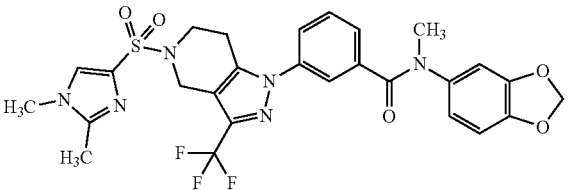 [SMILES: Cc1nc(S(=O)(=O)N2CCc3c(c(C(F)(F)F)nn3-c3cccc(C(=O)N(C)c4ccc5c(c4)OCO5)c3)C2)cn1C] | N-(1,3-benzodioxol-5-yl)-3-[5-(1,2-dimethylimidazol-4-yl)sulfonyl-3-(trifluoromethyl)-6,7-dihydro-4H-pyrazolo[4,3-c]pyridin-1-yl]-N-methyl-benzamide | C27 H25 F3 N6 O5 S | +++ |
| 065 | 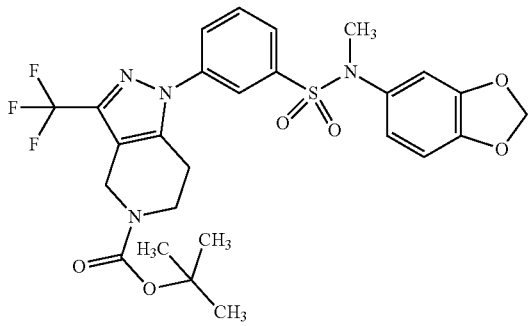 [SMILES: CN(c1ccc2c(c1)OCO2)S(=O)(=O)c1cccc(-n2nc(C(F)(F)F)c3c2CCN(C(=O)OC(C)(C)C)C3)c1] | tert-butyl 1-[3-[1,3-benzodioxol-5-yl(methyl)sulfamoyl]phenyl]-3-(trifluoromethyl)-6,7-dihydro-4H-pyrazolo[4,3-c]pyridine-5-carboxylate | C26 H27 F3 N4 O6 S | + |
| 066 | 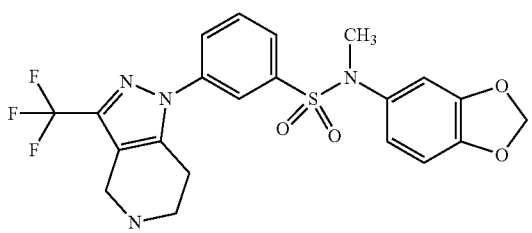 [SMILES: CN(c1ccc2c(c1)OCO2)S(=O)(=O)c1cccc(-n2nc(C(F)(F)F)c3c2CCNC3)c1] | N-(1,3-benzodioxol-5-yl)-N-methyl-3-[3-(trifluoromethyl)-4,5,6,7-tetrahydropyrazolo[4,3-c]pyridin-1-yl]benzenesulfonamide; hydrochloride | Cl H•C21 H19 F3 N4 O4 S | +++ |

TABLE 1-continued

| # | Substance Name | Substance Formula | activity |
|---|---|---|---|
| 067 | N-(1,3-benzodioxol-5-yl)-3-[5-(3,5-dimethylisoxazol-4-yl)sulfonyl-3-(trifluoromethyl)-6,7-dihydro-4H-pyrazolo[4,3-c]pyridin-1-yl]-N-methyl-benzamide | C27 H24 F3 N5 O6 S | +++ |
| 068 | N-(1,3-benzodioxol-5-yl)-3-[5-(2-methoxyethylsulfonyl)-3-(trifluoromethyl)-6,7-dihydro-4H-pyrazolo[4,3-c]pyridin-1-yl]-N-methyl-benzamide | C25 H25 F3 N4 O6 S | +++ |
| 069 | N-(1,3-benzodioxol-5-yl)-3-[5-[(3,5-dimethyl-1H-pyrazol-4-yl)sulfonyl]-3-(trifluoromethyl)-6,7-dihydro-4H-pyrazolo[4,3-c]pyridin-1-yl]-N-methyl-benzamide | C27 H25 F3 N6 O5 S | +++ |
| 070 | methyl 4-((1-(3-(benzo[d][1,3]dioxol-5-yl)(methyl)carbamoyl)phenyl)-3-(trifluoromethyl)-1,4,5,6,7,8-hexahydro-4,7-epiminocyclohepta[c]pyrazol-9-yl)sulfonyl)benzoate | C32 H27 F3 N4 O7 S | +++ |
| 071 | N-(1,3-benzodioxol-5-yl)-N-methyl-3-[5-methyl-3-(trifluoromethyl)-6,7-dihydro-4H-pyrazolo[4,3-c]pyridin-1-yl]benzenesulfonamide | C22 H21 F3 N4 O4 S | + |

TABLE 1-continued

| # | Substance Name | Substance Formula | activity |
|---|---|---|---|
| 072 | N-(1,3-benzodioxol-5-yl)-3-[6-(2,2-dimethylpropanoyl)-3-(trifluoromethyl)-5,7-dihydro-4H-pyrazolo[3,4-c]pyridin-1-yl]-N-methyl-benzamide | C27 H27 F3 N4 O4 | +++ |
| 073 | N-(1,3-benzodioxol-5-yl)-3-[5-(2,4-dimethylpyrazol-3-yl)-3-(trifluoromethyl)-6,7-dihydro-4H-pyrazolo[4,3-c]pyridin-1-yl]-N-methyl-benzamide | C27 H25 F3 N6 O3 | +++ |
| 074 | N-(1,3-benzodioxol-5-yl)-N-methyl-3-[3-(trifluoromethyl)-5-(1,3,5-trimethylpyrazol-4-yl)-6,7-dihydro-4H-pyrazolo[4,3-c]pyridin-1-yl]benzamide | C27 H27 F3 N6 O3 | +++ |
| 075 | methyl 4-[[1-[3-[1,3-benzodioxol-5-yl(methyl)carbamoyl]phenyl]-3-(trifluoromethyl)-5,7-dihydro-4H-pyrazolo[3,4-c]pyridin-6-yl]sulfonyl]benzoate | C30 H25 F3 N4 O7 S | +++ |
| 076 | N-(1,3-benzodioxol-5-yl)-N-methyl-3-[5-tetrahydropyran-4-yl-3-(trifluoromethyl)-6,7-dihydro-4H-pyrazolo[4,3-c]pyridin-1-yl]benzamide | C27 H27 F3 N4 O4 | +++ |

TABLE 1-continued

| # | | Substance Name | Substance Formula | activity |
|---|---|---|---|---|
| 077 | 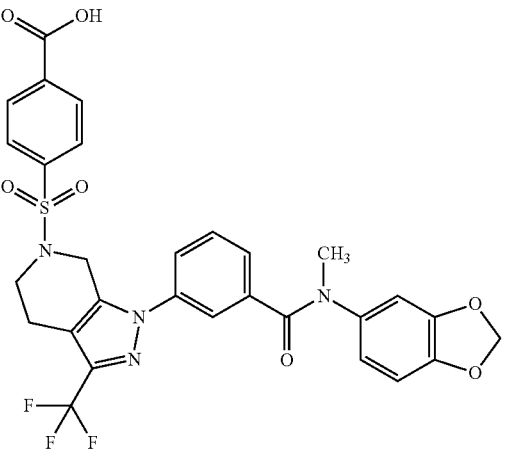 [SMILES: CN(C(=O)c1cccc(-n2nc(C(F)(F)F)c3c2CN(S(=O)(=O)c2ccc(C(=O)O)cc2)CC3)c1)c1ccc2c(c1)OCO2] | 4-[[1-[3-[1,3-benzodioxol-5-yl(methyl)carbamoyl]phenyl]-3-(trifluoromethyl)-5,7-dihydro-4H-pyrazolo[3,4-c]pyridin-6-yl]sulfonyl]benzoic acid | C29 H23 F3 N4 O7 S | ++ |
| 078 | 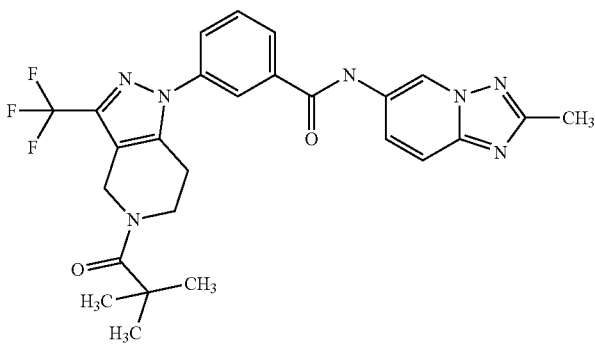 [SMILES: Cc1nc2ccc(NC(=O)c3cccc(-n4nc(C(F)(F)F)c5c4CCN(C(=O)C(C)(C)C)C5)c3)cn2n1] | 3-[5-(2,2-dimethylpropanoyl)-3-(trifluoromethyl)-6,7-dihydro-4Hpyrazolo[4,3-c]pyridin-1-yl]-N-(2-methyl-[1,2,4]triazolo[1,5-a]pyridin-6-yl)benzamide | C26H26F3N7O2 | + |
| 079 | 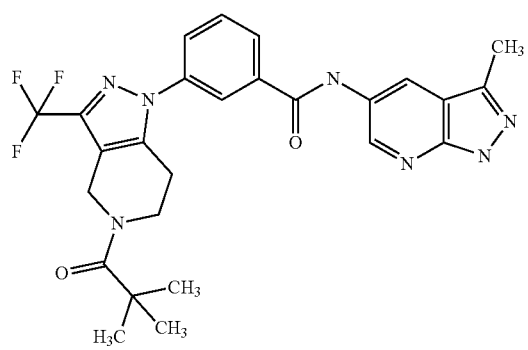 [SMILES: Cc1n[nH]c2ncc(NC(=O)c3cccc(-n4nc(C(F)(F)F)c5c4CCN(C(=O)C(C)(C)C)C5)c3)cc12] | 3-[5-(2,2-dimethylpropanoyl)-3-(trifluoromethyl)-6,7-dihydro-4H-pyrazolo[4,3-c]pyridin-1-yl]-N-(3-methyl-1H-pyrazolo[3,4-b]pyridin-5-yl)benzamide | C26 H26 F3 N7 O2 | + |
| 080 | 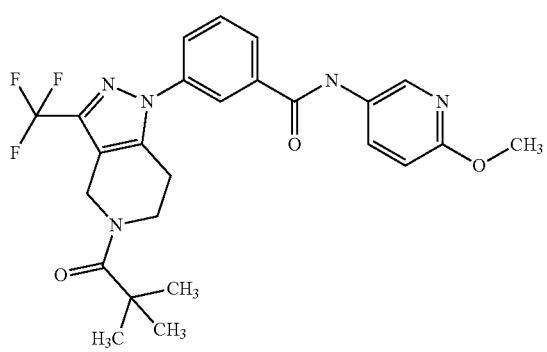 [SMILES: COc1ccc(NC(=O)c2cccc(-n3nc(C(F)(F)F)c4c3CCN(C(=O)C(C)(C)C)C4)c2)cn1] | 3-[5-(2,2-dimethylpropanoyl)-3-(trifluoromethyl)-6,7-dihydro-4H-pyrazolo[4,3-c]pyridin-1-yl]-N-(6-methoxy-3-pyridyl)benzamide | C25 H26 F3 N5 O3 | + |

TABLE 1-continued

| # | Substance Name | Substance Formula | activity |
|---|---|---|---|
| 081 | 3-[5-(2,2-dimethylpropanoyl)-3-(trifluoromethyl)-6,7-dihydro-4H-pyrazolo[4,3-c]pyridin-1-yl]-N-(2-methoxypyrimidin-5-yl)benzamide | C24 H25 F3 N6 O3 | + |
| 082 | tert-butyl 3-[4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]-3,5-dimethyl-pyrazol-1-yl]propanoate | C34 H37 F3 N6 O7 S | +++ |
| 083 | 3-[5-(2,2-dimethylpropanoyl)-3-(trifluoromethyl)-6,7-dihydro-4H-pyrazolo[4,3-c]pyridin-1-yl]-N-(2-methoxy-4-pyridyl)benzamide | C25 H26 F3 N5 O3 | + |
| 084 | 3-[5-(2,2-dimethylpropanoyl)-3-(trifluoromethyl)-6,7-dihydro-4H-pyrazolo[4,3-c]pyridin-1-yl]-N-(2-methylimidazo[1,2-a]pyridin-6-yl)benzamide | C27 H27 F3 N6 O2 | + |

TABLE 1-continued

| # | Substance Name | Substance Formula | activity |
|---|---|---|---|
| 085 | 3-[5-(2,2-dimethylpropanoyl)-3-(trifluoromethyl)-6,7-dihydro-4H-pyrazolo[4,3-c]pyridin-1-yl]-N-(6-methoxy-3-pyridyl)-N-methyl-benzamide | C26 H28 F3 N5 O3 | +++ |
| 086 | 3-[4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]-3,5-dimethyl-pyrazol-1-yl]propanoic acid | C30 H29 F3 N6 O7 S | +++ |
| 087 | (4R,7S)- or (4S,7R)-N-(benzo[d][1,3]dioxol-5-yl)-N-methyl-3-[(9-pivaloyl-3-(trifluoromethyl)-5,6,7,8-tetrahydro-4,7-epiminocyclohepta[c]pyrazol-1(4H)-yl)]benzamide | C29 H29 F3 N4 O4 | +++ |
| 088 | (4S,7R)- or (4R,7S)-N-(benzo[d][1,3]dioxol-5-yl)-N-methyl-3-[(9-pivaloyl-3-(trifluoromethyl)-5,6,7,8-tetrahydro-4,7-epiminocyclohepta[c]pyrazol-1(4H)-yl)]benzamide | C29 H29 F3 N4 O4 | +++ |
| 089 | 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]-5-methyl-1H-pyrazole-3-carboxylic acid | C27 H23 F3 N6 O7 S | +++ |
| 090 | 3-[5-(2,2-dimethylpropanoyl)-3-(trifluoromethyl)-6,7-dihydro-4H-pyrazolo[4,3-c]pyridin-1-yl]-N-(2-methoxy-4-pyridyl)-N-methyl-benzamide | C26 H28 F3 N5 O3 | +++ |

TABLE 1-continued

| # | Substance Name | Substance Formula | activity |
|---|---|---|---|
| 091 | 3-[5-(2,2-dimethylpropanoyl)-3-(trifluoromethyl)-6,7-dihydro-4H-pyrazolo[4,3-c]pyridin-1-yl]-N-methyl-N-(2-methylimidazo[1,2-a]pyridin-6-yl)benzamide | C28 H29 F3 N6 O2 | ++ |
| 096 | N-(2,2-difluoro-1,3-benzodioxol-5-yl)-3-[5-[(3,5-dimethylisoxazol-4-yl)sulfonyl]-3-(trifluoromethyl)-6,7-dihydro-4H-pyrazolo[4,3-c]pyridin-1-yl]-N-methyl-benzamide | C27 H22 F5 N5 O6 S | +++ |
| 102 | N-(2,2-difluoro-1,3-benzodioxol-5-yl)-3-(3-isopropyl-4,5,6,7-tetrahydroindazol-1-yl)-N-methyl-benzamide | C25 H25 F2 N3 O3 | ++ |
| 103 | N-(2,2-difluoro-1,3-benzodioxol-5-yl)-N-methyl-3-(3-methyl-4,5,6,7-tetrahydroindazol-1-yl)benzamide | C23 H21 F2 N3 O3 | + |
| 109 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid | C30 H22 F5 N3 O6 | +++ |

TABLE 1-continued

| # | Substance Name | Substance Formula | activity |
|---|---|---|---|
| 128 | (4S,7R)- or (4R,7S)-N-(benzo[d][1,3]dioxol-5-yl)-3-(9-((3,5-dimethylisoxazol-4-yl)sulfonyl)-3-(trifluoromethyl)-5,6,7,8-tetrahydro-4,7-epiminocyclohepta[c]pyrazol-1(4H)-yl)-N-methylbenzamide | C29 H26 F3 N5 O6 S | +++ |
| 129 | (4R,7S)- or (4S,7R)-N-(benzo[d][1,3]dioxol-5-yl)-3-(9-((3,5-dimethylisoxazol-4-yl)sulfonyl)-3-(trifluoromethyl)-5,6,7,8-tetrahydro-4,7-epiminocyclohepta[c]pyrazol-1(4H)-yl)-N-methylbenzamide | C29 H26 F3 N5 O6 S | +++ |
| 130 | (4R,7S)- or (4S,7R)-N-(benzo[d][1,3]dioxol-5-yl)-3-(9-((3,5-dimethyl-1H-pyrazol-4-yl)sulfonyl)-3-(trifluoromethyl)-5,6,7,8-tetrahydro-4,7-epiminocyclohepta[c]pyrazol-1(4H)-yl)-N-methylbenzamide | C29 H27 F3 N6 O5 S | +++ |
| 131 | (4R,7S)- or (4S,7R)-N-(benzo[d][1,3]dioxol-5-yl)-3-((4R,7S)-9-cyclobutyl-3-(trifluoromethyl)-5,6,7,8-tetrahydro-4,7-epiminocyclohepta[c]pyrazol-1(4H)-yl)-N-methylbenzamide | C28 H27 F3 N4 O3 | +++ |

TABLE 1-continued

| # | Substance Name | Substance Formula | activity |
|---|---|---|---|
| 132 | N-(1,3-benzodioxol-5-yl)-N-methyl-3-(3-methyl-4,5,6,7-tetrahydroindazol-1-yl)benzamide | C23 H23 N3 O3 | ++ |
| 133 | N-(1,3-benzodioxol-5-yl)-3-(3-isopropyl-4,5,6,7-tetrahydroindazol-1-yl)-N-methyl-benzamide | C25 H27 N3 O3 | +++ |
| 135 | 4-[1-[3-[1,3-benzodioxol-5-yl(methyl)carbamoyl]phenyl]-3-(trifluoromethyl)-6,7-dihydro-4H-pyrazolo[4,3-c]pyridin-5-yl]butanoic acid | C26 H25 F3 N4 O5 | + |
| 137 | 3-[5-(3,5-dimethylisoxazol-4-yl)sulfonyl-3-(trifluoromethyl)-6,7-dihydro-4H-pyrazolo[4,3-c]pyridin-1-yl]-N-methyl-N-(2-methyl-1,3-benzoxazol-6-yl)benzamide | C28H25F3N6O5S | +++ |

TABLE 1-continued

| # | Substance Name | Substance Formula | activity |
|---|---|---|---|
| 138 | 3-[5-(3,5-dimethylisoxazol-4-yl)sulfonyl-3-(trifluoromethyl)-6,7-dihydro-4H-pyrazolo[4,3-c]pyridin-1-yl]-N-(5-fluoro-2-methyl-1,3-benzoxazol-6-yl)-N-methyl-benzamide | C28H24F4N6O5S | +++ |
| 140 | 3-[1-[3-[[1,3-benzodioxol-5-yl(methyl)carbamoyl]phenyl]-3-(trifluoromethyl)-6,7-dihydro-4H-pyrazolo[4,3-c]pyridin-5-yl]cyclobutanecarboxylic acid | C27H25F3N4O5 | ++ |
| 141 | 3-[5-(2,2-dimethylpropanoyl)-3-(trifluoromethyl)-6,7-dihydro-4H-pyrazolo[4,3-c]pyridin-1-yl]-N-methyl-N-quinoxalin-6-yl-benzamide | C28H27F3N6O2 | +++ |
| 142 | 3-[5-(2,2-dimethylpropanoyl)-3-(trifluoromethyl)-6,7-dihydro-4H-pyrazolo[4,3-c]pyridin-1-yl]-N-(2-methoxypyrimidin-5-yl)-N-methyl-benzamide | C25H27F3N6O3 | + |

TABLE 1-continued

| # | | Substance Name | Substance Formula | activity |
|---|---|---|---|---|
| 147 | 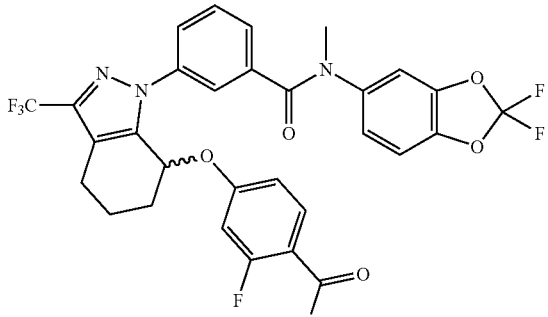 | 2-fluoro-4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid | C30 H21 F6 N3 O6 | +++ |
| 150 | 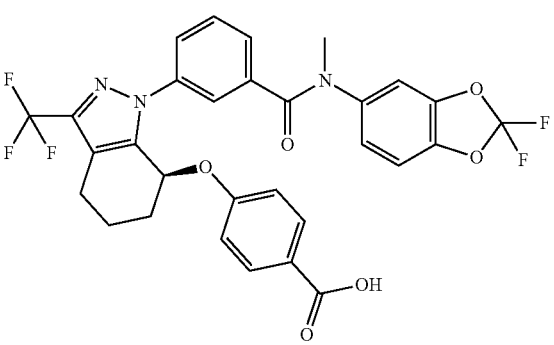 [SMILES: CN(C(=O)c1cccc(-n2nc(C(F)(F)F)c3c2[C@@H](Oc2ccc(C(=O)O)cc2)CCC3)c1)c1ccc2c(c1)OC(F)(F)O2] | (R) or (S)-4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid | C30 H22 F5 N3 O6 | +++ |
| 151 | 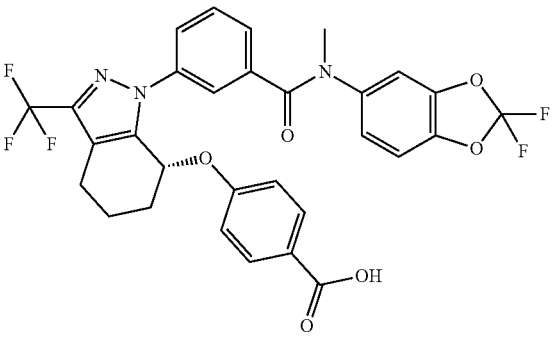 [SMILES: CN(C(=O)c1cccc(-n2nc(C(F)(F)F)c3c2[C@H](Oc2ccc(C(=O)O)cc2)CCC3)c1)c1ccc2c(c1)OC(F)(F)O2] | (S) or (R)-4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid | C30 H22 F5 N3 O6 | +++ |
| 153 | 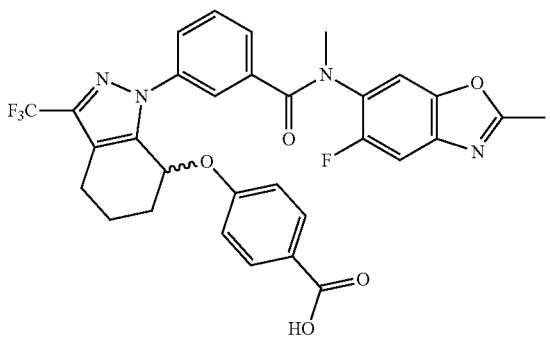 [SMILES: Cc1nc2cc(F)c(N(C)C(=O)c3cccc(-n4nc(C(F)(F)F)c5c4C(Oc4ccc(C(=O)O)cc4)CCC5)c3)cc2o1] | 4-[[1-[3-[(5-fluoro-2-methyl-1,3-benzoxazol-6-yl)-methyl-carbamoyl]phenyl]-3-(trifluoromethyl)-4,5,6,7-tetrahydroindazol-7-yl]oxy]benzoic acid | C31 H24 F4 N4 O5 | +++ |

TABLE 1-continued

| # | Substance Name | Substance Formula | activity |
|---|---|---|---|
| 155 | 4-[[1-[3-[(2,2-difluoro-1,3-benzodioxol-5-yl)-(trideuteriomethyl)carbamoyl]phenyl]-3-(trifluoromethyl)-4,5,6,7-tetrahydroindazol-7-yl]oxy]benzoic acid | C30 H19 D3 F5 N3 O6 | +++ |
| 157 | 4-[[1-[3-[methyl-(2-methyl-1,3-benzoxazol-6-yl)carbamoyl]phenyl]-3-(trifluoromethyl)-4,5,6,7-tetrahydroindazol-7-yl]oxy]benzoic acid | C31 H25 F3 N4 O5 | +++ |
| 159 | 4-[[1-[3-[methyl-(2-methyloxazolo[4,5-b]pyridin-6-yl)carbamoyl]phenyl]-3-(trifluoromethyl)-4,5,6,7-tetrahydroindazol-7-yl]oxy]benzoic acid: | C30 H24 F3 N5 O5 | ++ |
| 161 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-methoxy-benzoic acid | C31 H24 F5 N3 O7 | +++ |

TABLE 1-continued

| # | Substance Name | Substance Formula | activity |
|---|---|---|---|
| 162 | 3-[7-(4-carbamoylphenoxy)-3-(trifluoromethyl)-4,5,6,7-tetrahydroindazol-1-yl]-N-(2,2-difluoro-1,3-benzodioxol-5-yl)-N-methyl-benzamide | C30 H23 F5 N4 O5 | +++ |
| 164 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylic acid | C29 H21 F5 N4 O6 | +++ |
| 166 | 4-[[1-[3-[(5-methoxy-3-pyridyl)-methyl-carbamoyl]phenyl]-3-(trifluoromethyl)-4,5,6,7-tetrahydroindazol-7-yl]oxy]benzoic acid | C29 H25 F3 N4 O5 | +++ |
| 168 | 4-[[1-[3-[(2-methoxypyrimidin-5-yl)-methyl-carbamoyl]phenyl]-3-(trifluoromethyl)-4,5,6,7-tetrahydroindazol-7-yl]oxy]benzoic acid | C28 H24 F3 N5 O5 | +++ |

TABLE 1-continued

| # | | Substance Name | Substance Formula | activity |
|---|---|---|---|---|
| 170 | 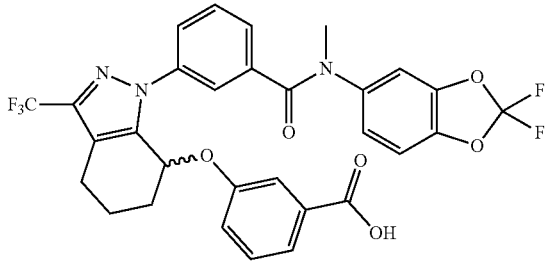 [SMILES: CN(C(=O)c1cccc(-n2nc(C(F)(F)F)c3c2C(Oc2cccc(C(=O)O)c2)CCC3)c1)c1ccc2c(c1)OC(F)(F)O2] | 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid | C30 H22 F5 N3 O6 | +++ |
| 172 | 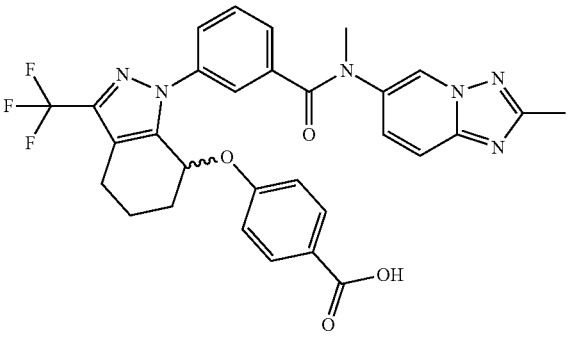 [SMILES: Cc1nc2ccc(N(C)C(=O)c3cccc(-n4nc(C(F)(F)F)c5c4C(Oc4ccc(C(=O)O)cc4)CCC5)c3)cn2n1] | 4-[[1-[3-[methyl-(2-methyl-[1,2,4]triazolo[1,5-a]pyridin-6-yl)carbamoyl]phenyl]-3-(trifluoromethyl)-4,5,6,7-tetrahydroindazol-7-yl]oxy]benzoic acid | C30 H25 F3 N6 O4 | +++ |
| 174 | 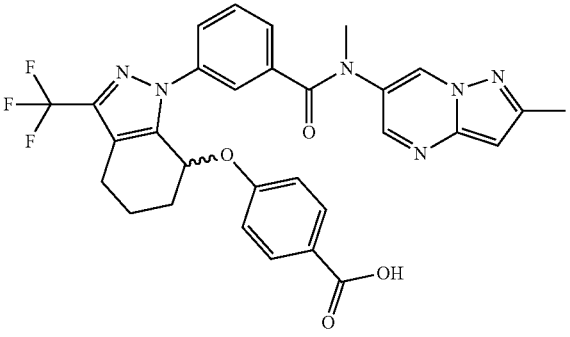 [SMILES: Cc1cc2ncc(N(C)C(=O)c3cccc(-n4nc(C(F)(F)F)c5c4C(Oc4ccc(C(=O)O)cc4)CCC5)c3)cn2n1] | 4-[[1-[3-[methyl-(2-methylpyrazolo[1,5-a]pyrimidin-6-yl)carbamoyl]phenyl]-3-(trifluoromethyl)-4,5,6,7-tetrahydroindazol-7-yl]oxy]benzoic acid | C30 H25 F3 N6 O4 | +++ |
| 176 | 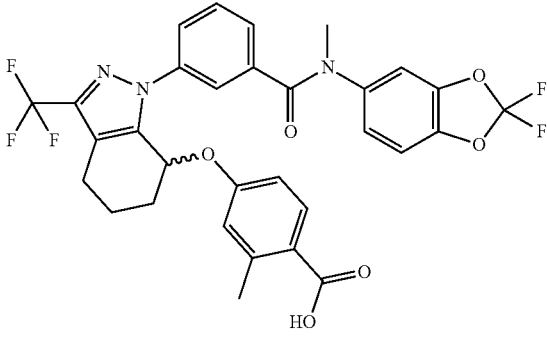 [SMILES: Cc1cc(OC2CCCc3c(C(F)(F)F)nn(-c4cccc(C(=O)N(C)c5ccc6c(c5)OC(F)(F)O6)c4)c32)ccc1C(=O)O] | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-methyl-benzoic acid | C31 H24 F5 N3 O6 | +++ |

TABLE 1-continued

| # | | Substance Name | Substance Formula | activity |
|---|---|---|---|---|
| 178 | 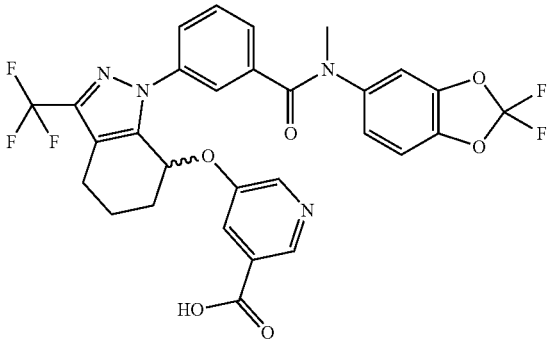 [SMILES: CN(C(=O)c1cccc(-n2nc(C(F)(F)F)c3c2C(Oc2cncc(C(=O)O)c2)CCC3)c1)c1ccc2c(c1)OC(F)(F)O2] | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid | C29 H21 F5 N4 O6 | +++ |
| 180 | 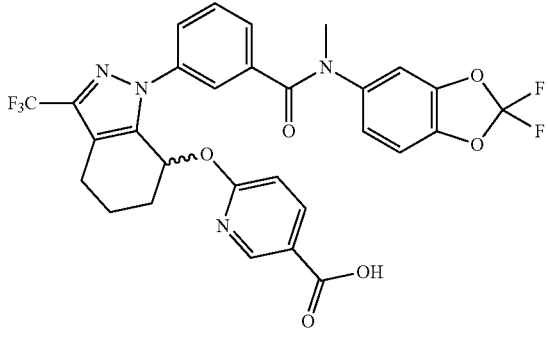 [SMILES: CN(C(=O)c1cccc(-n2nc(C(F)(F)F)c3c2C(Oc2ccc(C(=O)O)cn2)CCC3)c1)c1ccc2c(c1)OC(F)(F)O2] | 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid | C29 H21 F5 N4 O6 | +++ |
| 182 | 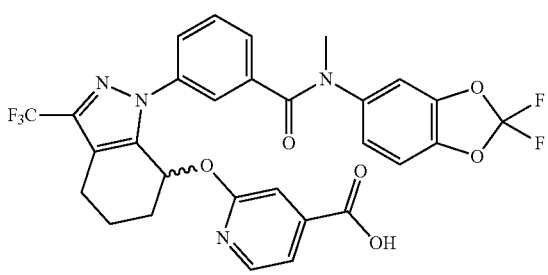 [SMILES: CN(C(=O)c1cccc(-n2nc(C(F)(F)F)c3c2C(Oc2cc(C(=O)O)ccn2)CCC3)c1)c1ccc2c(c1)OC(F)(F)O2] | 2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylic acid | C29 H21 F5 N4 O6 | +++ |
| 185 | 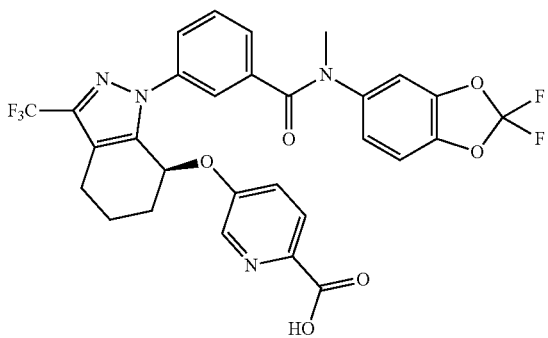 [SMILES: CN(C(=O)c1cccc(-n2nc(C(F)(F)F)c3c2[C@@H](Oc2ccc(C(=O)O)nc2)CCC3)c1)c1ccc2c(c1)OC(F)(F)O2] | (R) or (S)-5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylic acid | C29 H21 F5 N4 O6 | +++ |

TABLE 1-continued

| # | Substance Name | Substance Formula | activity |
|---|---|---|---|
| 186 | (S) or (R)-5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylic acid | C29 H21 F5 N4 O6 | +++ |
| 188 | (S) or (R)-3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid | C30 H22 F5 N3 O6 | +++ |
| 190 | (R) or (S)-3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid | C30 H22 F5 N3 O6 | +++ |
| 192 | (S) or (R)-6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid | C29 H21 F5 N4 O6 | +++ |
| 194 | (R) or (S)-6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid | C29 H21 F5 N4 O6 | +++ |

TABLE 1-continued

| # | Substance Name | Substance Formula | activity |
|---|---|---|---|
| 196 | (S) or (R)-2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylic acid | C29 H21 F5 N4 O6 | +++ |
| 198 | (R) or (S)-2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylic acid | C29 H21 F5 N4 O6 | +++ |
| 202 | 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoic acid | C29 H20 F5 N3 O7 | +++ |
| 205 | (R)- or (S)-4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoic acid | C29 H20 F5 N3 O7 | +++ |

TABLE 1-continued

| # | Substance Name | Substance Formula | activity |
|---|---|---|---|
| 206 | (S)- or (R)-4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoic acid | C29 H20 F5 N3 O7 | +++ |
| 253 | 4-[[1-[3-[(2,2-Difluoro-1,3-benzodioxol-5-yl)carbamoyl]phenyl]-3-(trifluoromethyl)-4,5,6,7-tetrahydroindazol-7-yl]oxy]benzoic acid | C29 H20 F5 N3 O7 | + |

Transepithelial Electrical Conductance (TEEC)

FRT cells expressing F508del-CFTR were plated on HTS Transwell-24 well permeable supports (Code 3379, Corning Life Sciences) at a density of 200,000 cells/well. After six days, cells were incubated for 24 hrs with test correctors, vehicle, or VX-809. Compounds were dissolved in both basolateral (800 µL) and apical (300 µL) culture medium. After treatment, the culture medium was removed and replaced on both sides with a saline solution containing (in mM): 130 NaCl, 2.7 KCl, 1.5 $KH_2PO_4$, 1 $CaCl_2$, 0.5 $MgCl_2$, 10 glucose, 10 Na-Hepes (pH 7.4). The basolateral and apical side received 800 µL and 100 µL, respectively. The 24-well tray with cells was placed on a block heater (SBH 130D, Stuart) to keep the temperature at 37° C. during the entire experiment. After 10 min, the basal transepithelial electrical resistance (TEER) across each layer of FRT cells was measured with a STX100C electrode pair connected to an EVOM2 voltohmeter (World Precision Instruments). To stimulate F508del-CFTR, each well received (apical side) 50 µL of saline solution containing 60 µM forskolin and 150 µM genistein (final concentrations: 20 µM forskolin, 50 µM genistein). Forskolin was also pipetted in the basolateral medium to obtain the 20 µM concentration. After 10 min TEER was measured again in each well. To block F508del-CFTR function, the inhibitor PPQ-102 was used at the final concentration of 30 µM. To achieve the desired concentration, 75 µL of the apical solution in each well was replaced with an equal volume of saline solution containing 20 µM forskolin, 50 µM genistein, and 60 µM PPQ-102. After further 10 min, the transepithelial electrical resistance was measured. All values of TEER were converted to transepithelial electrical conductance (TEEC) using the formula TEEC=1/TEER. The parameter to indicate activity of F508del-CFTR in each well (ΔTEEC) was calculated from the difference in TEEC measured after maximal stimulation of F508del-CFTR with forskolin and genistein and after block with PPQ-102.

Corrector activities obtained on selected compounds tested at 5.0 µM (expressed as ΔTEEC values) are illustrated in table 2, wherein +: ΔTEEC<2000 µS; ++: 2000 µS<ΔTEEC<3000 µS; +++: ΔTEEC>3000 µS.

TABLE 2

| # | Substance Name | activity |
|---|---|---|
| 003 | N-(1,3-benzodioxol-5-yl)-N-methyl-3-[5-methyl-3-(trifluoromethyl)-6,7-dihydro-4H-pyrazolo[4,3-c]pyridin-1-yl]benzamide | ++ |
| 010 | 1-[3-[1,3-benzodioxol-5-yl(methyl)carbamoyl]phenyl]-N-phenyl-3-(trifluoromethyl)-6,7-dihydro-4H-pyrazolo[4,3-c]pyridine-5-carboxamide | ++ |
| 011 | N-(1,3-benzodioxol-5-yl)-3-[5-(2,2-dimethylpropanoyl)-3-(trifluoromethyl)-6,7-dihydro-4H-pyrazolo[4,3-c]pyridin-1-yl]-N-methyl-benzamide | ++ |
| 012 | N-(1,3-benzodioxol-5-yl)-3-[5-benzyl-3-(trifluoromethyl)-6,7-dihydro-4H-pyrazolo[4,3-c]pyridin-1-yl]-N-methyl-benzamide | ++ |
| 018 | tert-butyl 1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate | +++ |
| 020 | methyl 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]methyl]benzoate | +++ |

TABLE 2-continued

| # | Substance Name | activity |
|---|---|---|
| 032 | N-(1,3-benzodioxol-5-yl)-3-[5-cyclobutyl-3-(trifluoromethyl)-6,7-dihydro-4H-pyrazolo[4,3-c]pyridin-1-yl]-N-methyl-benzamide | ++ |

Western Blot Analysis of F508del-CFTR Protein Maturation

Biochemical analysis of corrector effect was evaluated by determining the electrophoretic mobility of F508del-CFTR protein (Tomati et al., *Sci Rep* 5:12138, 2015). Under normal conditions, F508del-CFTR mostly migrates as a 150 kDa band that corresponds to the immature form of the protein (Band B). Active correctors cause appearance of the mature form of F508del-CFTR that migrates as a 180 kDa band (Band C). Cells expressing F508del-CFTR were grown to confluence on 60 mm diameter dishes and lysed in RIPA buffer containing a complete protease inhibitor (Roche). Lysate protein concentration was calculated using the BCA assay (Euroclone) following the manufacturer's instructions. Equal amounts of protein (30 μg total per lysate) were separated on 4-12% gradient NuPAGE Bis-Tris gels (Life Tecnologies) and analyzed by Western blotting. CFTR protein was detected with the mouse monoclonal anti-CFTR antibody (596, Cystic Fibrosis Foundation Therapeutics, University of North Carolina, Chapel Hill) diluted 1:5,000. GAPDH protein was detected with the mouse monoclonal anti-GAPDH antibody clone 6C5 (Santa Cruz Biotech Inc.) diluted 1:5,000. The secondary antibody was IgG goat anti-mouse (Ab 97023, Abcam) conjugated with horseradish peroxidase (HRP) and diluted 1:10,000. Proteins were visualized by chemiluminescence using the SuperSignal West Femto Substrate (Thermo Scientific). Chemiluminescence was monitored using the Molecular Imager ChemiDoc XRS System. Images were analyzed with ImageJ software (National Institutes of Health). Under control conditions, F508del-CFTR protein migrates as a 150 kDa.

FIG. 1 illustrates the analysis of electrophoretic mobility of F508del-CFTR. The image shows a representative western blot experiment with lysates from null FRT cells (no CFTR expressed) and FRT cells expressing F508del-CFTR treated with correctors or vehicle (control). In the immunoblot, the positions of band C and band B are indicated.

Short-Circuit Current Recordings on Human Bronchial Epithelial Cells

Human bronchial epithelial (HBE) cells obtained from CF patients (F508del/F508del genotype) were plated on Snapwell inserts (Code 3801, Corning Life Sciences) at a density of 500,000 cells per insert. Cells were cultured for two weeks in a differentiating medium whose compositions has been previously described (Scudieri et al., *J Physiol* 590: 6141-6155, 2012). For the first week, the medium was kept on both apical and basolateral sides of inserts (submerged condition). For the second week, the apical medium was removed (air-liquid condition, ALC). To test the activity of correctors, cells were treated for 24 hrs with compounds dissolved in the basolateral medium. After treatment, Snapwell inserts carrying differentiated bronchial epithelia were mounted in a vertical chamber resembling an Using system with internal fluid circulation. Both apical and basolateral hemichambers were filled with 5 mL of a Krebs bicarbonate solution containing (in mM): 126 NaCl, 0.38 $KH_2PO_4$, 2.13 $K_2HPO_4$, 1 $MgSO_4$, 1 $CaCl_2$, 24 $NaHCO_3$, and 10 glucose. Both sides were continuously bubbled with a gas mixture containing 5% $CO_2$-95% air and the temperature of the solution was kept at 37° C. The transepithelial voltage was short-circuited with a voltage-clamp (DVC-1000, World Precision Instruments) connected to the apical and basolateral chambers via Ag/AgCl electrodes and agar bridges (1 M KCl in 1% agar). The offset between voltage electrodes and the fluid resistance were canceled before experiments. The short-circuit current was recorded with a PowerLab 4/25 (ADInstruments) analogical to digital converter connected to a Macintosh computer. During recordings, cells were sequentially treated with: amiloride (10 μM, apical side) to block $Na^+$ absorption through ENaC channel; CPT-cAMP (100 μM, apical and basolateral side) plus VX-770 (1 μM, apical side) to stimulate F508del-CFTR activity; $CFTR_{inh}$-172 (10 μM, apical side) to fully inhibit F508del-CFTR. The difference between the current measured with CPT-cAMP plus potentiator and the current remaining after $CFTR_{inh}$-172 treatment ($\Delta I_{CFTR}$) was taken as the parameter reflecting F508del-CFTR expression in the apical membrane.

Activities of selected compounds on HBE cells tested at 1.0 μM (expressed as $\Delta I_{CFTR}$) are illustrated in table 3 wherein +: $\Delta I_{CFTR}<2.0$ μA; ++: 2.0 μA$<\Delta I_{CFTR}<3.0$ μA; +++: $\Delta I_{CFTR}>3.0$ μA.

TABLE 3

| # | Substance Name | activity |
|---|---|---|
| 003 | N-(1,3-benzodioxol-5-yl)-N-methyl-3-[5-methyl-3-(trifluoromethyl)-6,7-dihydro-4H-pyrazolo[4,3-c]pyridin-1-yl]benzamide | ++ |
| 010 | 1-[3-[1,3-benzodioxol-5-yl(methyl)carbamoyl]phenyl]-N-phenyl-3-(trifluoromethyl)-6,7-dihydro-4H-pyrazolo[4,3-c]pyridine-5-carboxamide | ++ |
| 011 | N-(1,3-benzodioxol-5-yl)-3-[5-(2,2-dimethylpropanoyl)-3-(trifluoromethyl)-6,7-dihydro-4H-pyrazolo[4,3-c]pyridin-1-yl]-N-methyl-benzamide | ++ |
| 012 | N-(1,3-benzodioxol-5-yl)-3-[5-benzyl-3-(trifluoromethyl)-6,7-dihydro-4H-pyrazolo[4,3-c]pyridin-1-yl]-N-methyl-benzamide | + |
| 018 | tert-butyl 1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate | +++ |
| 020 | methyl 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]methyl]benzoate | ++ |
| 032 | N-(1,3-benzodioxol-5-yl)-3-[5-cyclobutyl-3-(trifluoromethyl)-6,7-dihydro-4H-pyrazolo[4,3-c]pyridin-1-yl]-N-methyl-benzamide | ++ |

The invention claimed is:

1. A compound of formula I:

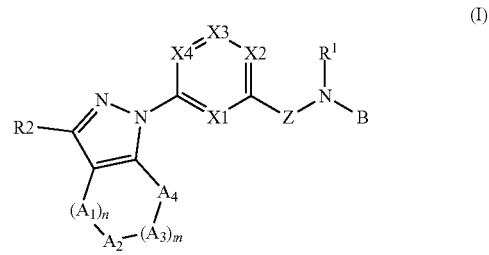

(I)

or pharmaceutically acceptable salts or solvates thereof wherein:

$R_1$ is selected from the group consisting of $C_{1-6}$alkyl, $C_{3-6}$cycloalkyl and hydroxyl-$C_{1-6}$alkyl;

Z is C=O or $SO_2$;

$X_1$, $X_2$, $X_3$ and $X_4$ are independently selected from the group consisting of $CR^{vii}$ and N, with the proviso that the number of nitrogen atoms in the ring is comprised from 0 to 2;

$R_2$ is selected from the group consisting of hydrogen, $C_{1-6}$alkyl, halo$C_{1-6}$alkyl, $C_{3-6}$cycloalkyl, aryl, heteroaryl, $COR^{viii}$, $COOR^{viii}$, heterocycloalkyl, $CONHR^{viii}$, $CONR^{viii}R^{ix}$, OH, O—$C_{1-6}$alkyl, O—$C_{1-6}$alkylaryl, O—$C_{3-6}$cycloalkyl, O-heterocycloalkyl, O-heteroaryl, O-aryl, O-halo$C_{1-6}$alkyl, $C_{1-6}$alkyl-O—$C_{1-6}$alkyl, $C_{1-6}$alkyl-O—$C_{3-6}$cycloalkyl, $C_{1-6}$alkyl-O-heterocycloalkyl, $C_{1-6}$alkyl-O-aryl, $C_{1-6}$alkyl-O-heteroaryl, CN, $NO_2$, $NR^xR^{xi}$, $N(R^{ix})COR^x$, $N(R^{ix})COOR^{xi}$, $N(R^{ix})CONR^{xi}R^x$, $N(R^{ix})SO_2R^x$, $SO_2R^x$, $SO_2NR^{ix}R^x$, halogen, and hydroxy-$C_{1-6}$alkyl;

$A_1$, $A_2$, $A_3$, and $A_4$, are independently selected from the group consisting of $CR^{xii}R^{xiii}$, O, $NR^{xiv}$, CO and $SO_2$, wherein $R^{xii}$ and $R^{xiii}$ are independently selected from the group consisting of hydrogen, $C_{1-6}$alkyl, $C_{3-6}$cycloalkyl, heterocycloalkyl, halo$C_{1-6}$alkyl, $COR^{viii}$, $COOR^{viii}$, $CONHR^{viii}$, $CONR^{viii}R^{ix}$, OH, O—$C_{1-6}$alkyl, O-aryl, O—$C_{1-6}$alkylaryl, O-heteroaryl, O—$C_{3-6}$cycloalkyl, O-heterocycloalkyl, $C_{1-6}$alkylaryl, $C_{3-6}$cycloalkylaryl, $C_{3-6}$cycloalkylheteroaryl, $C_{3-6}$cycloheteroalkylaryl, $C_{3-6}$cycloheteroalkylheteroaryl, $C_{1-6}$alkylheteroaryl, S-aryl, S-heteroaryl, SO-aryl, SO-heteroaryl, $SO_2$-aryl, $SO_2$-heteroaryl, $C_{1-6}$alkyl-O—$C_{1-6}$alkyl, CN, halogen, $NR^xR^{xi}$, $N(R^{ix})COR^x$;

$R^{xiv}$ is selected from the group consisting of hydrogen, $C_{1-6}$alkyl, $C_{1-6}$alkylaryl, $C_{1-6}$alkyl-$C_{3-6}$cycloalkyl, $C_{1-6}$alkyl-heterocycloalkyl, $C_{3-6}$cycloalkyl, heterocycloalkyl, hydroxyl-$C_{1-6}$alkyl, $COR^{viii}$, $CONHR^{viii}$, $CONR^{viii}$, $CONR^{viii}R^{ix}$, $SO_2R^{viii}$, $C_{1-6}$alkyl-O—$C_{1-6}$alkyl, $C_{1-6}$ alkyl-O-aryl, $C_{1-6}$alkyl-O-heteroaryl, $C_{1-6}$alkyl-O-heterocycloalkyl, $C_{1-6}$alkylCOOR$^{viii}$;

or when each of $A_1$ and $A_3$, or $A_2$ and $A_4$, or $A_1$ and $A_4$ represents $CR^{xii}R^{xiii}$, the two groups $R^{xii}$ can be linked together to form a ring and thus the moiety

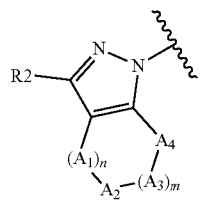

has a meaning selected from the group consisting of:

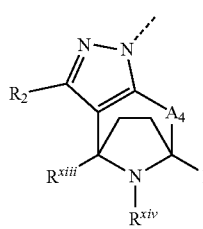 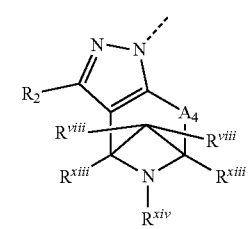

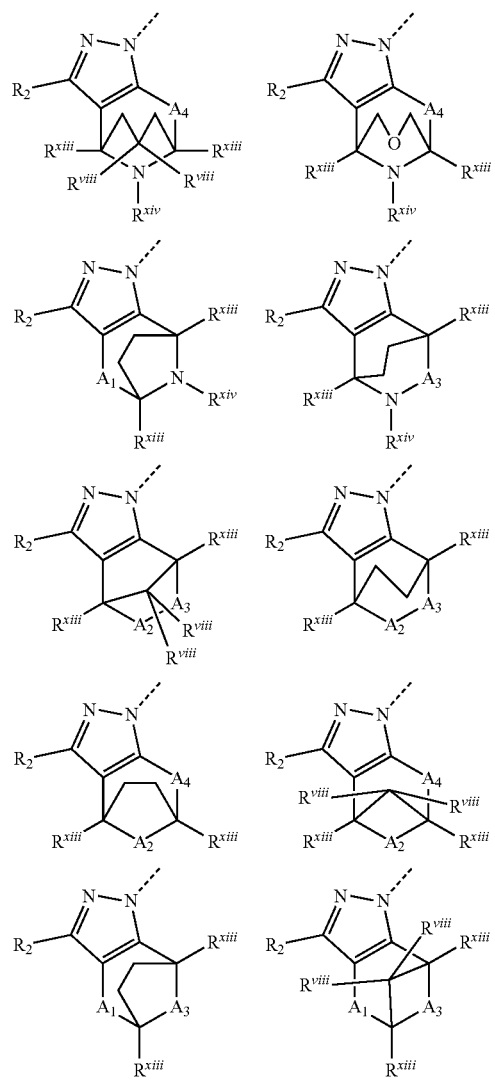

n and m are each independently selected from the group consisting of 0, 1, 2;

B represents an unsubstituted or a substituted aromatic or heteroaromatic ring selected from the group consisting of:

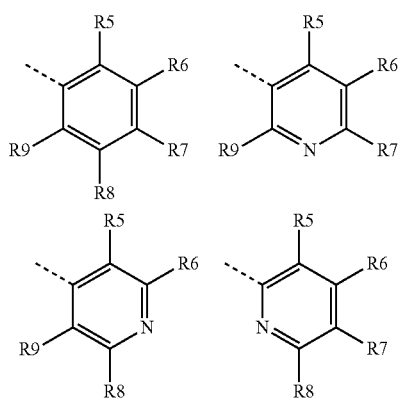

-continued

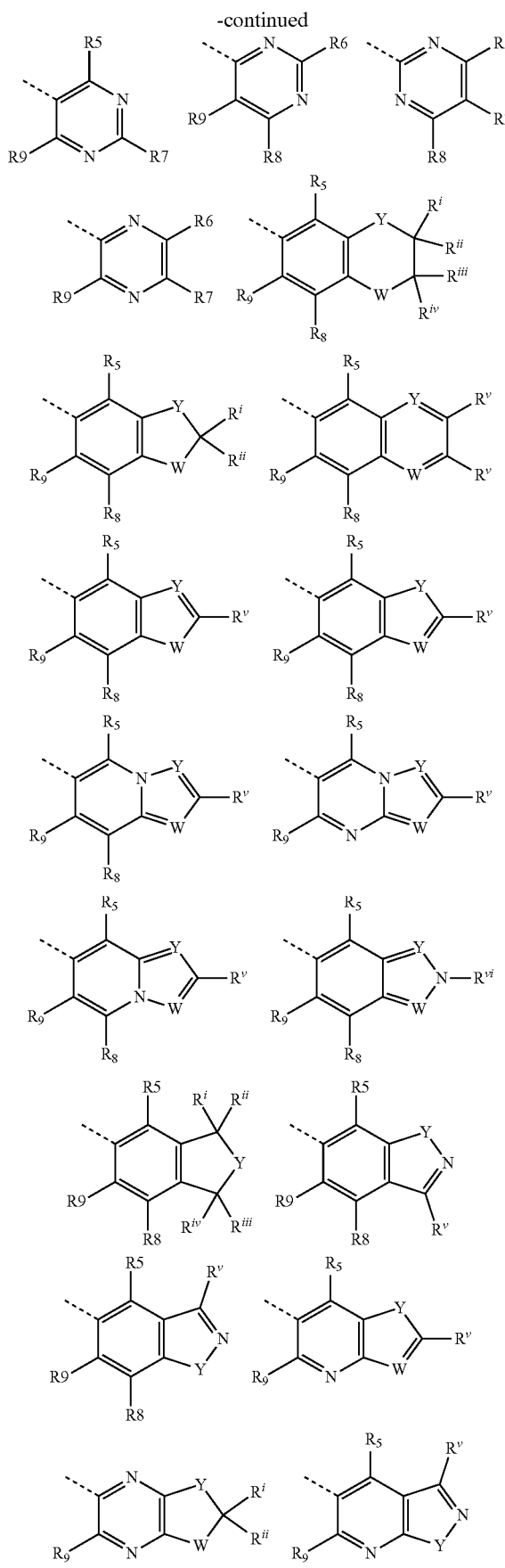
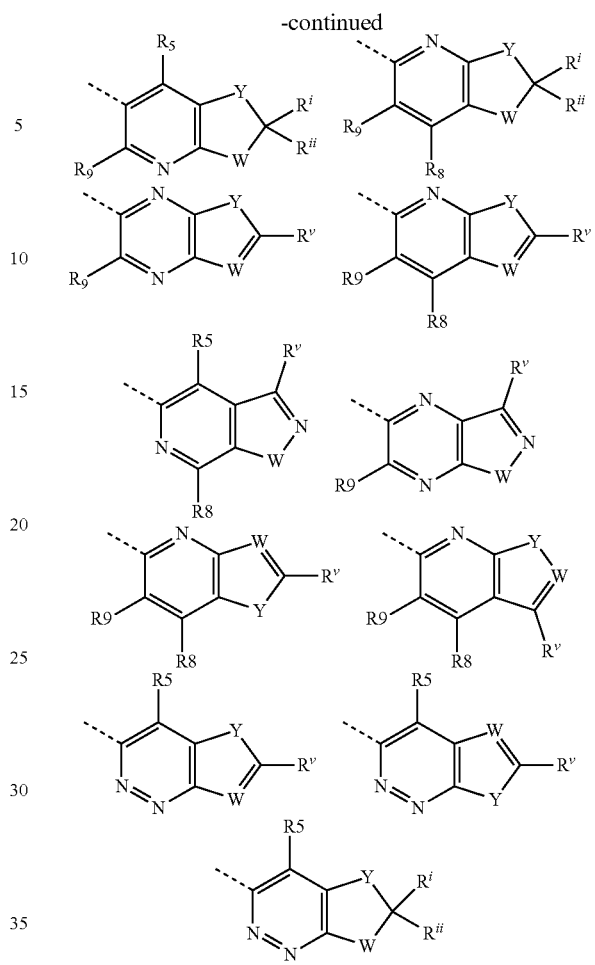

wherein
R_5, R_6, R_7, R_8, and R_9 are independently selected from the group consisting of hydrogen, halogen, $C_{1-6}$alkyl, halo$C_{1-6}$alkyl, $C_{3-6}$cycloalkyl, O—$C_{1-6}$alkyl, O—$C_{3-6}$cycloalkyl, O-heterocycloalkyl, O-halo$C_{1-6}$alkyl, $COR^{viii}$, $COOR^{viii}$, $CONHR^{viii}$, $CONR^{viii}R^{ix}$, OH, CN, $NR^xR^{xi}$, $N(R^{ix})COR^x$, $N(R^{ix})CONR^xR^{xi}$ and hydroxy-$C_{1-6}$alkyl or
when R_6 and R_7 are present on a 6-membered heteroaromatic ring, taken together with the carbon atoms to whom they are bound, they can form a saturated or unsaturated 5-membered or 6-membered carbocyclic ring or a 5-membered or 6-membered heterocycloalkyl containing from 1 to 3 heteroatoms selected from O, N, and S or a 5-membered or 6-membered heteroaryl ring containing from 1 to 3 heteroatoms selected from O, N, and S;

Y and W are independently selected from the group consisting of O, S, SO_2, $CR^{iv}R^v$, $CR^v$, N, and $NR^{vi}$;

$R^i$, $R^{ii}$, $R^{iii}$ and $R^{iv}$ are independently selected from the group consisting of hydrogen, $C_{1-6}$alkyl, halo$C_{1-6}$alkyl, halogen, OH, O—$C_{1-6}$alkyl and O-halo$C_{1-6}$alkyl or
when $R^i$ and $R^{ii}$, or $R^{iii}$ and $R^{iv}$ are taken together with the carbon atoms to whom they are bound, they can represent C=O;

$R^v$ is selected from the group consisting of hydrogen, $C_{1-6}$alkyl, halo$C_{1-6}$alkyl, O—$C_{1-6}$alkyl, halogen, $C_{3-6}$cycloalkyl, OH and O-halo$C_{1-6}$alkyl;

$R^{vi}$ is selected from the group consisting of hydrogen and $C_{1-6}$alkyl;

$R^{vii}$ is selected from the group consisting of hydrogen, $C_{1-6}$alkyl, $C_{3-6}$cycloalkyl, haloC$_{1-6}$alkyl, O-haloC$_{1-6}$alkyl, COR$^{viii}$, COOR$^{viii}$, CONHR$^{viii}$, CONR$^{viii}$R$^{ix}$, OH, O—C$_{1-6}$alkyl, halogen, CN, NO$_2$, NR$^x$R$^{xi}$, N(R$^{ix}$)COR$^x$, N(R$^{ix}$)COOR$^{xi}$, N(R$^{ix}$)CONR$^x$R$^{xi}$, and N(R$^{ix}$)SO$_2$R$^x$;

$R^{viii}$ is selected from the group consisting of hydrogen, $C_{1-6}$alkyl, $C_{3-6}$cycloalkyl, aryl, heteroaryl, heterocycloalkyl, hydroxy-$C_{1-6}$alkyl and $C_{1-6}$alkyl-O—$C_{1-6}$alkyl;

$R^{ix}$ is selected from the group consisting of hydrogen, $C_{1-6}$alkyl, hydroxy-$C_{1-6}$alkyl, and $C_{1-6}$alkyl-O—$C_{1-6}$alkyl;

$R^x$ is selected from the group consisting of hydrogen, $C_{1-6}$alkyl, $C_{3-6}$cycloalkyl, heterocycloalkyl, aryl, heteroaryl, hydroxy-$C_{1-6}$alkyl, and $C_{1-6}$alkyl-O—$C_{1-6}$alkyl;

$R^{xi}$ is selected from the group consisting of hydrogen, $C_{1-6}$alkyl, hydroxy-$C_{1-6}$alkyl, $C_{1-6}$alkyl-O—$C_{1-6}$alkyl, aryl-$C_{1-6}$alkyl, heteroaryl-$C_{1-6}$alkyl, and heterocycloalkyl-$C_{1-6}$alkyl.

2. The compound of formula I according to claim 1, wherein $R_1$ is selected from the group consisting of $C_{1-6}$alkyl and $C_{3-6}$cycloalkyl;

Z is C=O or SO$_2$;

$X_1$, $X_2$, $X_3$ and $X_4$ are independently selected from the group consisting of CR$^{vii}$ and N, with the proviso that the number of nitrogen atoms in the ring is comprised from 0 to 2;

$R_2$ is selected from the group consisting of hydrogen, $C_{1-6}$alkyl, haloC$_{1-6}$alkyl, $C_{3-6}$cycloalkyl, aryl, heteroaryl, COR$^{viii}$, COOR$^{viii}$, CONHR$^{viii}$, CONR$^{viii}$R$^{ix}$, O—C$_{1-6}$alkyl, O—C$_{1-6}$alkylaryl, O-heterocycloalkyl, O-aryl, O-haloC$_{1-6}$alkyl, $C_{1-6}$alkyl-O—$C_{1-6}$alkyl, $C_{1-6}$alkyl-O-aryl, CN, NR$^x$R$^{xi}$, halogen, and hydroxy-$C_{1-6}$alkyl;

$A_1$, $A_2$, $A_3$, and $A_4$, are independently selected from the group consisting of CR$^{xii}$R$^{xiii}$, O, NR$^{xiv}$, and CO wherein $R^{xii}$ and $R^{xiii}$ are independently selected from the group consisting of hydrogen, $C_{1-6}$alkyl, haloC$_{1-6}$alkyl, COR$^{viii}$, COOR$^{viii}$, CONHR$^{viii}$, CONR$^{viii}$R$^{ix}$, OH, O—$C_{1-6}$alkyl, O-aryl, O—$C_{1-6}$alkylaryl, O-heteroaryl, O—$C_{3-6}$cycloalkyl, O-heterocycloalkyl, $C_{1-6}$alkylaryl, $C_{1-6}$alkylheteroaryl, NR$^x$R$^{xi}$, N(R$^{ix}$)COR$^x$, $C_{1-6}$alkyl-O—$C_{1-6}$alkyl, CN and halogen;

$R^{xiv}$ is selected from the group consisting of hydrogen, $C_{1-6}$alkyl, $C_{1-6}$alkylaryl, $C_{1-6}$alkyl-$C_{3-6}$cycloalkyl, $C_{1-6}$alkyl-heterocycloalkyl, $C_{3-6}$cycloalkyl, hydroxy-$C_{1-6}$alkyl, heterocycloalkyl, COR$^{viii}$, COOR$^{viii}$, CONHR$^{viii}$ and SO$_2$R$^{viii}$, $C_{1-6}$alkylCOOR$^{viii}$;

or when each of $A_1$ and $A_3$, or $A_2$ and $A_4$, or $A_1$ and $A_4$ represents CR$^{xii}$R$^{xiii}$, the two groups R$^{xii}$ can be linked together to form a ring and thus the moiety

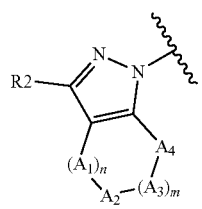

has a meaning selected from the group consisting of:

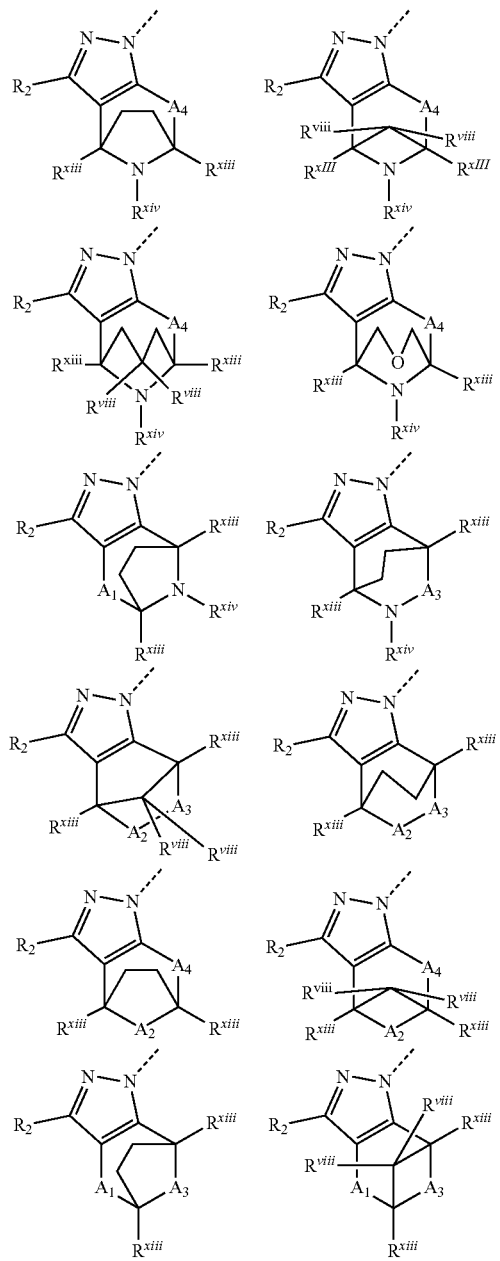

n and m are each independently selected from the group consisting of 0, 1, 2;

B represents an unsubstituted or a substituted aromatic or heteroaromatic ring selected from the group consisting of:

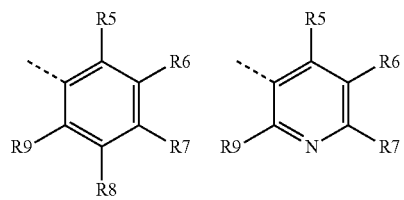

-continued

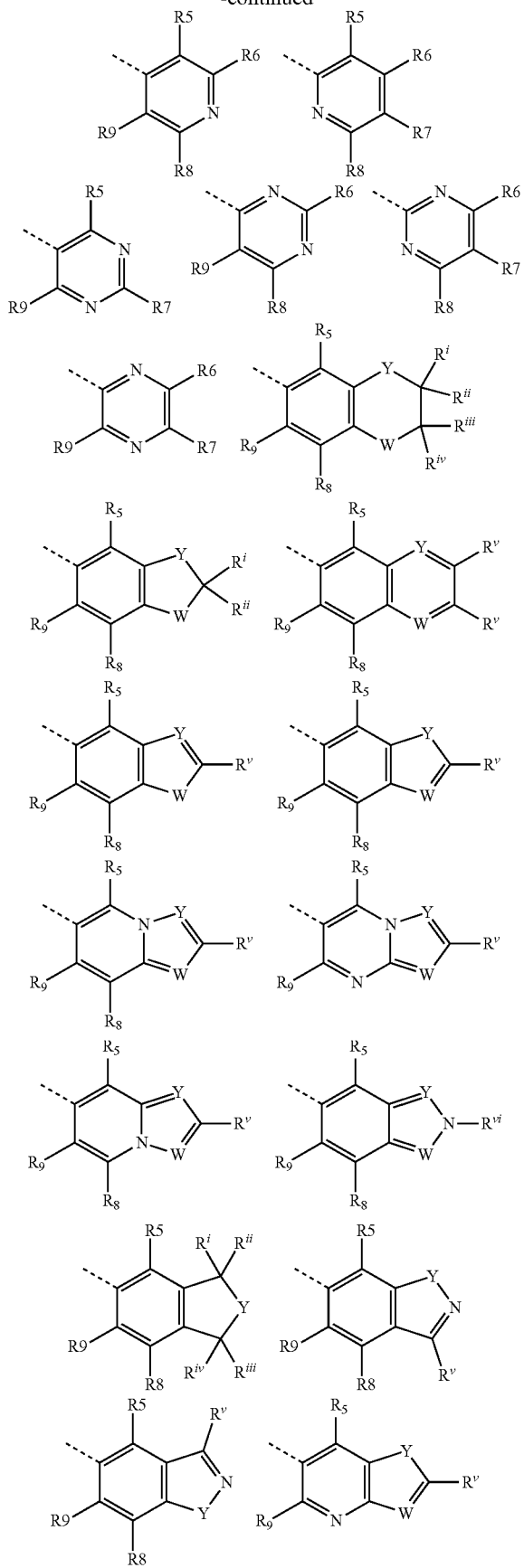
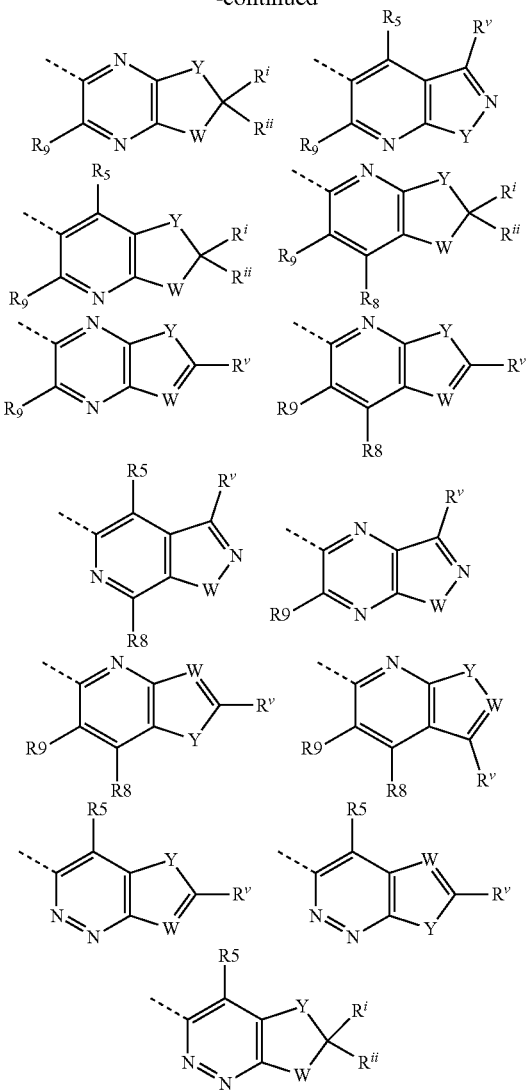

wherein
$R_5$, $R_6$, $R_7$, $R_8$, and $R_9$ are independently selected from the group consisting of hydrogen, halogen, $C_{1-6}$alkyl O—$C_{1-6}$alkyl, $COR^{viii}$, $COOR^{viii}$, OH, CN, $NR^xR^{xi}$ and hydroxy-$C_{1-6}$alkyl or when $R_6$ and $R_7$ are present on a 6-membered heteroaromatic ring, taken together with the carbon atoms to whom they are bound, they can form a saturated or unsaturated 5-membered or 6-membered carbocyclic ring or a 5-membered or 6-membered heterocycloalkyl containing from 1 to 3 heteroatoms selected from O, N, and S or a 5-membered or 6-membered heteroaryl ring containing from 1 to 3 heteroatoms selected from O, N, and S;

Y and W are independently selected from the group consisting of O, S, $CR^{iv}R^v$, $CR^v$, N, and $NR^{vi}$;

$R^i$, $R^{ii}$, $R^{iii}$ and $R^{iv}$ are independently selected from the group consisting of hydrogen, $C_{1-6}$alkyl, halogen and O—$C_{1-6}$alkyl;

$R^v$ is selected from the group consisting of hydrogen, $C_{1-6}$alkyl, halo$C_{1-6}$alkyl, O—$C_{1-6}$alkyl, halogen and $C_{3-6}$cycloalkyl;

$R^{vi}$ is selected from the group consisting of hydrogen and $C_{1-6}$alkyl;

$R^{vii}$ is selected from the group consisting of hydrogen, $C_{1-6}$alkyl, halo$C_{1-6}$alkyl, COOR$^{viii}$, OH, O—$C_{1-6}$alkyl, O-aryl, halogen and NR$^x$R$^{xi}$;

$R^{viii}$ is selected from the group consisting of hydrogen, $C_{1-6}$alkyl, $C_{3-6}$cycloalkyl, aryl, heteroaryl, heterocycloalkyl, hydroxy$C_{1-6}$alkyl and $C_{1-6}$alkyl-O—$C_{1-6}$alkyl;

$R^{ix}$ is selected from the group consisting of hydrogen, $C_{1-6}$alkyl, and $C_{1-6}$alkyl-O—$C_{1-6}$alkyl;

$R^x$ is selected from the group consisting of hydrogen, $C_{1-6}$alkyl, $C_{3-6}$cycloalkyl, heterocycloalkyl, aryl, heteroaryl and hydroxy-$C_{1-6}$alkyl;

$R^{xi}$ is selected from the group consisting of hydrogen, $C_{1-6}$alkyl, $C_{1-6}$alkyl-O—$C_{1-6}$alkyl, aryl-$C_{1-6}$alkyl, heteroaryl-$C_{1-6}$alkyl, and heterocycloalkyl-$C_{1-6}$alkyl.

3. The compound of formula I according to claim 1, wherein $R_1$ is selected from the group consisting of $C_{1-4}$alkyl;

Z is C=O;

$X_1$, $X_2$, $X_3$ and $X_4$ are CR$^{vii}$;

$R_2$ is selected from the group consisting of hydrogen, $C_{1-4}$alkyl, halo$C_{1-4}$alkyl, COOR$^{viii}$, CONHR$^{viii}$, CN, NR$^x$R$^{xi}$ and hydroxy-$C_{1-6}$alkyl;

$A_1$, $A_2$, $A_3$, and $A_4$ are independently selected from the group consisting of CR$^{xii}$R$^{xiii}$, O and NR$^{xiv}$, wherein R$^{xii}$ and R$^{xiii}$ are independently selected from the group consisting of hydrogen, $C_{1-4}$alkyl, COOR$^{viii}$, CONHR$^{viii}$, O-aryl, O—$C_{1-6}$alkylaryl, O-heteroaryl, O—$C_{3-6}$cycloalkyl, O-heterocycloalkyl, $C_{1-6}$alkylaryl, $C_{1-6}$alkylheteroaryl, NR$^x$R$^{xi}$, N(R$^{ix}$)COR$^x$ and CN;

R$^{xiv}$ is selected from the group consisting of hydrogen, $C_{1-4}$alkyl, $C_{3-6}$cycloalkyl, COR$^{viii}$, COOR$^{viii}$, CONHR$^{viii}$, SO$_2$R$^{viii}$, $C_{1-6}$alkylCOOR$^{viii}$;

or when each of $A_1$ and $A_3$, or $A_2$ and $A_4$, or $A_1$ and $A_4$ represents CR$^{xii}$R$^{xiii}$, the two groups R$_{xii}$ can be linked together to form a ring and thus the moiety

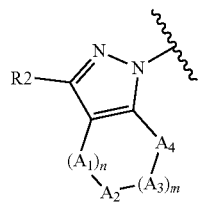

has a meaning selected from the group consisting of:

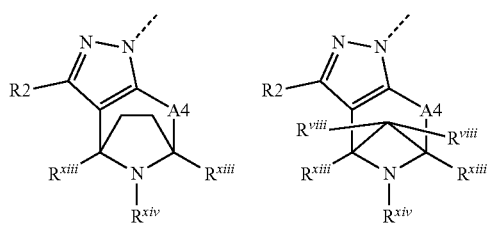

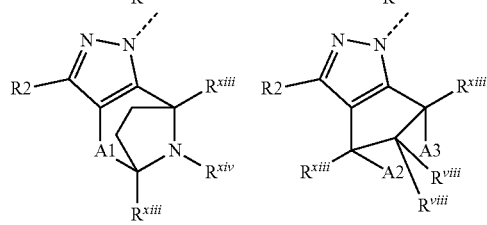

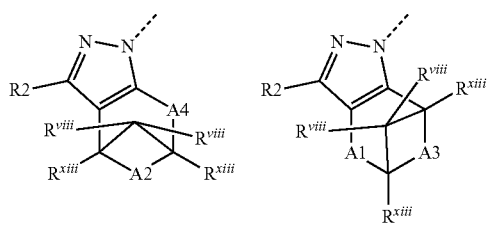

n and m are each independently selected from the group consisting of 0, 1, 2;

B represents an unsubstituted or a substituted aromatic or heteroaromatic ring selected from the group consisting of:

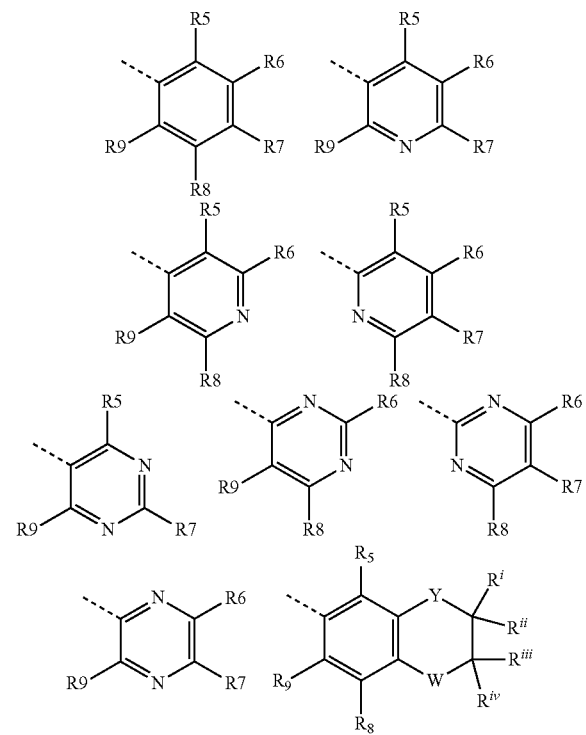

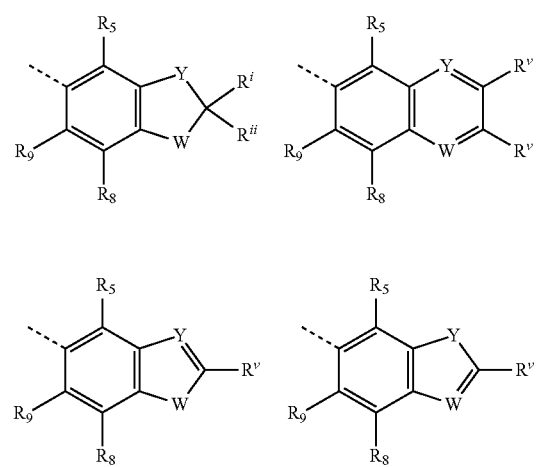

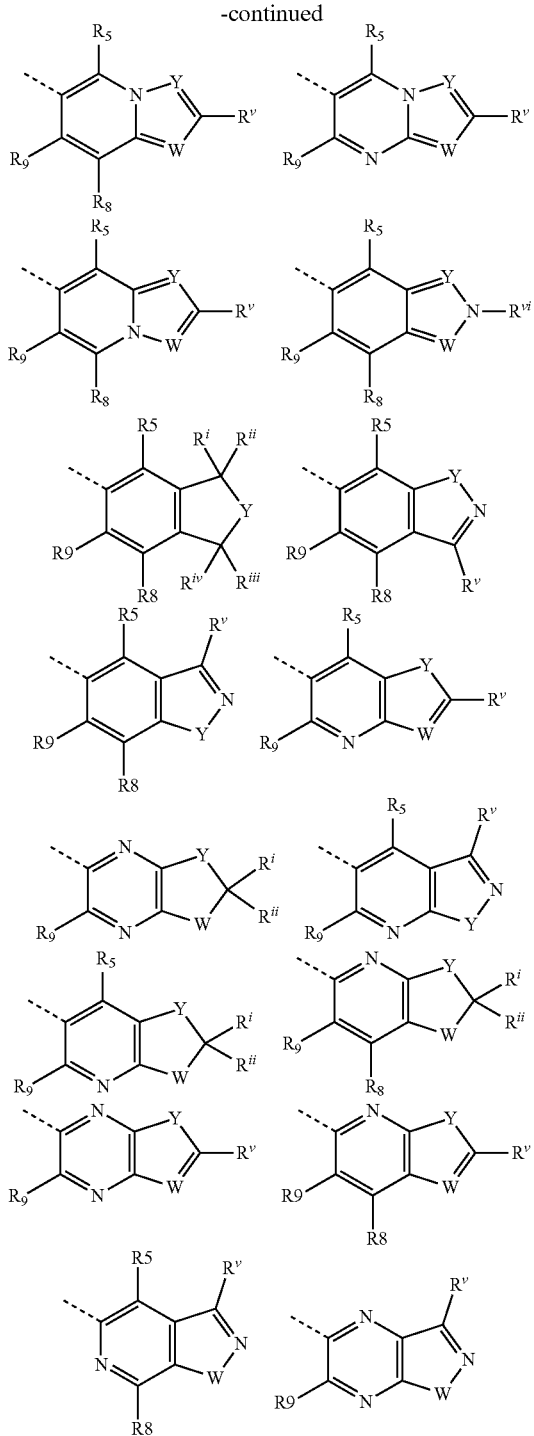
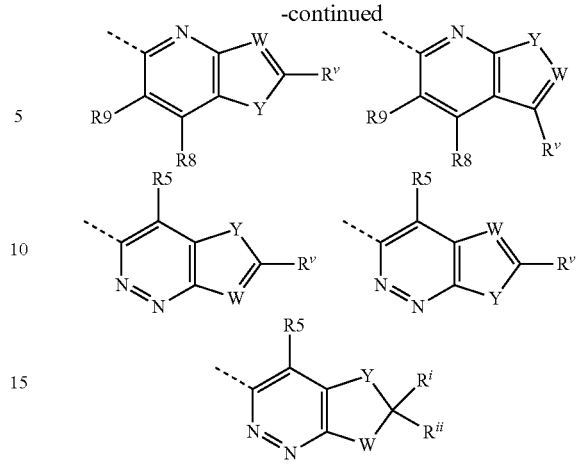

wherein $R_5$, $R_6$, $R_7$, $R_8$, and $R_9$ are independently selected from the group consisting of hydrogen, fluorine, chlorine, $C_{1-4}$alkyl, O—$C_{1-4}$alkyl, $COR^{viii}$, $COOR^{viii}$, $CONHR^{viii}$, OH and $N(R^{ix})COR^x$ or when $R_6$ and $R_7$ are present on a 6-membered heteroaromatic ring, taken together with the carbon atoms to whom they are bound, they can form a saturated or unsaturated 5-membered or 6-membered carbocyclic ring or a 5-membered or 6-membered heterocycloalkyl containing from 1 to 3 heteroatoms selected from O, N, and S or a 5-membered or 6-membered heteroaryl ring containing from 1 to 3 heteroatoms selected from O, N, and S;

Y and W are independently selected from the group consisting of O, S, $CR^v$, N, and $NR^{vi}$;

$R^i$, $R^{ii}$, $R^{iii}$ and $R^{iv}$ are independently selected from the group consisting of hydrogen, fluorine, chlorine, and O—$C_{1-6}$alkyl;

$R^v$ is selected from the group consisting of hydrogen, $C_{1-4}$alkyl, and O—$C_{1-6}$alkyl;

$R^{vi}$ is selected from the group consisting of hydrogen and $C_{1-6}$alkyl;

$R^{vii}$ is hydrogen;

$R^{viii}$ is selected from the group consisting of hydrogen, $C_{1-4}$alkyl, $C_{3-6}$cycloalkyl, aryl, heterocycloalkyl, hydroxy-$C_{1-6}$alkyl and $C_{1-4}$alkyl-O—$C_{1-4}$alkyl;

$R^{ix}$ is hydrogen;

$R^x$ is selected from the group consisting of hydrogen, and $C_{1-4}$alkyl;

$R^{xi}$ is selected from the group consisting of hydrogen, $C_{1-4}$alkyl, hydroxy-$C_{1-6}$alkyl, and $C_{1-4}$alkyl-O—$C_{1-4}$alkyl.

4. A compound according to claim 1 selected from the group consisting of:

| # | Substance Name |
|---|---|
| 1 | tert-butyl 1-[3-[1,3-benzodioxol-5-yl(methyl)carbamoyl] phenyl]-3-(trifluoromethyl)-6,7-dihydro-4H-pyrazolo[4,3-c]pyridine-5-carboxylate |
| 2 | N-(1,3-benzodioxol-5-yl)-N-methyl-3-[3-(trifluoromethyl)-4,5,6,7-tetrahydropyrazolo[4,3-c]pyridin-1-yl]benzamide hydrochloride |
| 3 | N-(1,3-benzodioxol-5-yl)-N-methyl-3-[5-methyl-3-(trifluoromethyl)-6,7-dihydro-4H-pyrazolo[4,3-c]pyridin-1-yl]benzamide |
| 4 | 3-[5-acetyl-3-(trifluoromethyl)-6,7-dihydro-4H-pyrazolo[4,3-c]pyridin-1-yl]-N-(1,3-benzodioxol-5-yl)-N-methyl-benzamide |

| # | Substance Name |
|---|---|
| 5 | N-(1,3-benzodioxol-5-yl)-N-methyl-3-[3-(trifluoromethyl)-4,5,6,7-tetrahydroindazol-1-yl]benzamide |
| 6 | N-(1,3-benzodioxol-5-yl)-N-methyl-3-[5-methylsulfonyl-3-(trifluoromethyl)-6,7-dihydro-4H-pyrazolo[4,3-c]pyridin-1-yl]benzamide |
| 7 | 3-[5-(benzenesulfonyl)-3-(trifluoromethyl)-6,7-dihydro-4H-pyrazolo[4,3-c]pyridin-1-yl]-N-(1,3-benzodioxol-5-yl)-N-methyl-benzamide |
| 8 | N-(1,3-benzodioxol-5-yl)-3-[5-benzoyl-3-(trifluoromethyl)-6,7-dihydro-4H-pyrazolo[4,3-c]pyridin-1-yl]-N-methyl-benzamide |
| 9 | methyl 1-[3-[1,3-benzodioxol-5-yl(methyl)carbamoyl]phenyl]-3-(trifluoromethyl)-6,7-dihydro-4H-pyrazolo[4,3-c]pyridine-5-carboxylate |
| 10 | 1-[3-[1,3-benzodioxol-5-yl(methyl)carbamoyl]phenyl]-N-phenyl-3-(trifluoromethyl)-6,7-dihydro-4H-pyrazolo[4,3-c]pyridine-5-carboxamide |
| 11 | N-(1,3-benzodioxol-5-yl)-3-[5-(2,2-dimethylpropanoyl)-3-(trifluoromethyl)-6,7-dihydro-4H-pyrazolo[4,3-c]pyridin-1-yl]-N-methyl-benzamide |
| 12 | N-(1,3-benzodioxol-5-yl)-3-[5-benzyl-3-(trifluoromethyl)-6,7-dihydro-4H-pyrazolo[4,3-c]pyridin-1-yl]-N-methyl-benzamide |
| 13 | N-(1,3-benzodioxol-5-yl)-3-[5-[[(4R)-2,2-dimethyl-1,3-dioxolan-4-yl]methyl]-3-(trifluoromethyl)-6,7-dihydro-4H-pyrazolo[4,3-c]pyridin-1-yl]-N-methyl-benzamide |
| 14 | N-(1,3-benzodioxol-5-yl)-3-[5-[[(4S)-2,2-dimethyl-1,3-dioxolan-4-yl]methyl]-3-(trifluoromethyl)-6,7-dihydro-4H-pyrazolo[4,3-c]pyridin-1-yl]-N-methyl-benzamide |
| 15 | N-(1,3-benzodioxol-5-yl)-3-[5-[(2R)-2,3-dihydroxypropyl]-3-(trifluoromethyl)-6,7-dihydro-4H-pyrazolo[4,3-c]pyridin-1-yl]-N-methyl-benzamide |
| 16 | N-(1,3-benzodioxol-5-yl)-3-[5-[(2S)-2,3-dihydroxypropyl]-3-(trifluoromethyl)-6,7-dihydro-4H-pyrazolo[4,3-c]pyridin-1-yl]-N-methyl-benzamide |
| 17 | N-(1,3-benzodioxol-5-yl)-N-methyl-3-[5-methyl-3-(trifluoromethyl)-6,7-dihydro-4H-pyrazolo[4,3-f][1,4]oxazepin-1-yl]benzamide |
| 18 | tert-butyl 1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate |
| 19 | N-(1,3-benzodioxol-5-yl)-3-[5-(cyclopropylmethyl)-3-(trifluoromethyl)-6,7-dihydro-4H-pyrazolo[4,3-c]pyridin-1-yl]-N-methyl-benzamide |
| 20 | methyl 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]methyl]benzoate |
| 21 | N-(1,3-benzodioxol-5-yl)-3-[5-isopropyl-3-(trifluoromethyl)-6,7-dihydro-4H-pyrazolo[4,3-c]pyridin-1-yl]-N-methyl-benzamide |
| 22 | N-(benzo[d][1,3]dioxol-5-yl)-N-methyl-3-(3-(trifluoromethyl)-5,6,7,8-tetrahydro-4,7-epiminocyclohepta[c]pyrazol-1(4H)-yl)benzamide hydrochloride |
| 23 | N-(benzo[d][1,3]dioxol-5-yl)-N-methyl-3-(9-methyl-3-(trifluoromethyl)-5,6,7,8-tetrahydro-4,7-epiminocyclohepta[c]pyrazol-1(4H)-yl)benzamide |
| 24 | N-(1,3-benzodioxol-5-yl)-N-methyl-3-[5-[rac-(1S)-1-methylpropyl]-3-(trifluoromethyl)-6,7-dihydro-4H-pyrazolo[4,3-c]pyridin-1-yl]benzamide |
| 25 | 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]methyl]benzoic acid |
| 26 | 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]methyl]benzoic acid |
| 27 | tert-butyl 1-[3-[1,3-benzodioxol-5-yl(methyl)carbamoyl]phenyl]-3-(trifluoromethyl)-5,7-dihydro-4H-pyrazolo[3,4-c]pyridine-6-carboxylate |
| 28 | tert-butyl 1-[3-[1,3-benzodioxol-5-yl(methyl)carbamoyl]phenyl]-3-(trifluoromethyl)-6,7-dihydro-5H-pyrazolo[4,3-b]pyridine-4-carboxylate |
| 29 | N-(1,3-benzodioxol-5-yl)-N-methyl-3-[6-methyl-3-(trifluoromethyl)-5,7-dihydro-4H-pyrazolo[3,4-c]pyridin-1-yl]benzamide |
| 30 | N-methyl-N-(2-methyl-1,3-benzoxazol-6-yl)-3-[3-(trifluoromethyl)-4,5,6,7-tetrahydropyrazolo[4,3-c]pyridin-1-yl]benzamide hydrochloride |
| 31 | N-(1,3-benzodioxol-5-yl)-N-methyl-3-[5-(2-methylpropanoyl)-3-(trifluoromethyl)-6,7-dihydro-4H-pyrazolo[4,3-c]pyridin-1-yl]benzamide |
| 32 | N-(1,3-benzodioxol-5-yl)-3-[5-cyclobutyl-3-(trifluoromethyl)-6,7-dihydro-4H-pyrazolo[4,3-c]pyridin-1-yl]-N-methyl-benzamide |
| 33 | N-(1,3-benzodioxol-5-yl)-N-methyl-3-[5-(3,3,3-trifluoro-2,2-dimethyl-propanoyl)-3-(trifluoromethyl)-6,7-dihydro-4H-pyrazolo[4,3-c]pyridin-1-yl]benzamide |
| 34 | N-(1,3-benzodioxol-5-yl)-3-[5-(1-hydroxycyclopropanecarbonyl)-3-(trifluoromethyl)-6,7-dihydro-4H-pyrazolo[4,3-c]pyridin-1-yl]-N-methyl-benzamide |
| 35 | N-(1,3-benzodioxol-5-yl)-N-methyl-3-[5-(2-methyl-2-phenyl-propanoyl)-3-(trifluoromethyl)-6,7-dihydro-4H-pyrazolo[4,3-c]pyridin-1-yl]benzamide |
| 36 | tert-butyl 1-[3-[(5-fluoro-2-methyl-1,3-benzoxazol-6-yl)-methyl-carbamoyl]phenyl]-3-(trifluoromethyl)-6,7-dihydro-4H-pyrazolo[4,3-c]pyridine-5-carboxylate |
| 38 | N-(1,3-benzodioxol-5-yl)-N-methyl-3-[3-(trifluoromethyl)-4,5,6,7-tetrahydropyrazolo[3,4-c]pyridin-1-yl]benzamide hydrochloride |
| 39 | tert-butyl 1-[3-[methyl-(2-methyl-1,3-benzoxazol-6-yl)carbamoyl]phenyl]-3-(trifluoromethyl)-6,7-dihydro-4H-pyrazolo[4,3-c]pyridine-5-carboxylate |
| 40 | N-methyl-N-(2-methyl-1,3-benzoxazol-6-yl)-3-[5-methyl-3-(trifluoromethyl)-6,7-dihydro-4H-pyrazolo[4,3-c]pyridin-1-yl]benzamide |
| 41 | N-(4-acetamido-3-hydroxy-phenyl)-N-methyl-3-[5-methyl-3-(trifluoromethyl)-6,7-dihydro-4H-pyrazolo[4,3-c]pyridin-1-yl]benzamide |
| 42 | methyl 4-[1-[3-[1,3-benzodioxol-5-yl(methyl)carbamoyl]phenyl]-3-(trifluoromethyl)-6,7-dihydro-4H-pyrazolo[4,3-c]pyridine-5-carbonyl]benzoate |
| 43 | methyl 3-[1-[3-[1,3-benzodioxol-5-yl(methyl)carbamoyl]phenyl]-3-(trifluoromethyl)-6,7-dihydro-4H-pyrazolo[4,3-c]pyridin-5-yl]-3-oxo-propanoate |

-continued

| # | Substance Name |
|---|---|
| 44 | 4-[1-[3-[1,3-benzodioxol-5-yl(methyl)carbamoyl]phenyl]-3-(trifluoromethyl)-6,7-dihydro-4H-pyrazolo[4,3-c]pyridine-5-carbonyl]benzoic acid |
| 45 | 3-[1-[3-[1,3-benzodioxol-5-yl(methyl)carbamoyl]phenyl]-3-(trifluoromethyl)-6,7-dihydro-4H-pyrazolo[4,3-c]pyridin-5-yl]-3-oxo-propanoic acid |
| 46 | N-(5-fluoro-2-methyl-1,3-benzoxazol-6-yl)-N-methyl-3-[5-methyl-3-(trifluoromethyl)-6,7-dihydro-4H-pyrazolo[4,3-c]pyridin-1-yl]benzamide |
| 48 | (4R,7S)- or (4S,7R)-N-(benzo[d][1,3]dioxol-5-yl)-N-methyl-3-(3-(trifluoromethyl)-5,6,7,8-tetrahydro-4,7-epiminocyclohepta[c]pyrazol-1(4H)-yl)benzamide |
| 49 | (4S,7R)- or (4R,7S)-N-(benzo[d][1,3]dioxol-5-yl)-N-methyl-3-(3-(trifluoromethyl)-5,6,7,8-tetrahydro-4,7-epiminocyclohepta[c]pyrazol-1(4H)-yl)benzamide |
| 50 | (4R,7S)- or (4S,7R)-N-(benzo[d][1,3]dioxol-5-yl)-N-methyl-3-(9-methyl-3-(trifluoromethyl)-5,6,7,8-tetrahydro-4,7-epiminocyclohepta[c]pyrazol-1(4H)-yl)benzamide |
| 51 | (4S,7R)- or (4R,7S)-N-(benzo[d][1,3]dioxol-5-yl)-N-methyl-3-(9-methyl-3-(trifluoromethyl)-5,6,7,8-tetrahydro-4,7-epiminocyclohepta[c]pyrazol-1(4H)-yl)benzamide |
| 52 | (4R,7S)- or (4S,7R)-tert-butyl-1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate |
| 53 | (4S,7R)- or (4R,7S)-tert-butyl-1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate |
| 54 | N-(1,3-benzodioxol-5-yl)-N-methyl-3-[3-(trifluoromethyl)-6,7-dihydro-4H-pyrano[4,3-c]pyrazol-1-yl]benzamide |
| 55 | methyl 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoate |
| 56 | 1-[3-[1,3-benzodioxol-5-yl(methyl)carbamoyl]phenyl]-N-methyl-3-(trifluoromethyl)-6,7-dihydro-4H-pyrazolo[4,3-c]pyridine-5-carboxamide |
| 57 | 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoic acid |
| 58 | N-(1,3-benzodioxol-5-yl)-3-[5-(2-hydroxy-2-methyl-propanoyl)-3-(trifluoromethyl)-6,7-dihydro-4H-pyrazolo[4,3-c]pyridin-1-yl]-N-methyl-benzamide |
| 59 | methyl 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoate |
| 60 | methyl 2-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoate |
| 61 | 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoic acid |
| 62 | 2-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoic acid |
| 63 | N-(1,3-benzodioxol-5-yl)-3-[5-(4-cyanophenyl)sulfonyl-3-(trifluoromethyl)-6,7-dihydro-4H-pyrazolo[4,3-c]pyridin-1-yl]-N-methyl-benzamide |
| 64 | N-(1,3-benzodioxol-5-yl)-3-[5-(1,2-dimethylimidazol-4-yl)sulfonyl-3-(trifluoromethyl)-6,7-dihydro-4H-pyrazolo[4,3-c]pyridin-1-yl]-N-methyl-benzamide |
| 65 | tert-butyl 1-[3-[1,3-benzodioxol-5-yl(methyl)sulfamoyl]phenyl]-3-(trifluoromethyl)-6,7-dihydro-4H-pyrazolo[4,3-c]pyridine-5-carboxylate |
| 66 | N-(1,3-benzodioxol-5-yl)-N-methyl-3-[3-(trifluoromethyl)-4,5,6,7-tetrahydropyrazolo[4,3-c]pyridin-1-yl]benzenesulfonamide; hydrochloride |
| 67 | N-(1,3-benzodioxol-5-yl)-3-[5-(3,5-dimethylisoxazol-4-yl)sulfonyl-3-(trifluoromethyl)-6,7-dihydro-4H-pyrazolo[4,3-c]pyridin-1-yl]-N-methyl-benzamide |
| 68 | N-(1,3-benzodioxol-5-yl)-3-[5-(2-methoxyethylsulfonyl)-3-(trifluoromethyl)-6,7-dihydro-4H-pyrazolo[4,3-c]pyridin-1-yl]-N-methyl-benzamide |
| 69 | N-(1,3-benzodioxol-5-yl)-3-[5-[(3,5-dimethyl-1H-pyrazol-4-yl)sulfonyl]-3-(trifluoromethyl)-6,7-dihydro-4H-pyrazolo[4,3-c]pyridin-1-yl]-N-methyl-benzamide |
| 70 | methyl 4-((1-(3-(benzo[d][1,3]dioxol-5-yl)(methyl)carbamoyl)phenyl)-3-(trifluoromethyl)-1,4,5,6,7,8-hexahydro-4,7-epiminocyclohepta[c]pyrazol-9-yl)sulfonyl)benzoate |
| 71 | N-(1,3-benzodioxol-5-yl)-N-methyl-3-[5-methyl-3-(trifluoromethyl)-6,7-dihydro-4H-pyrazolo[4,3-c]pyridin-1-yl]benzenesulfonamide |
| 72 | N-(1,3-benzodioxol-5-yl)-3-[6-(2,2-dimethylpropanoyl)-3-(trifluoromethyl)-5,7-dihydro-4H-pyrazolo[3,4-c]pyridin-1-yl]-N-methyl-benzamide |
| 73 | N-(1,3-benzodioxol-5-yl)-3-[5-(2,4-dimethylpyrazol-3-yl)-3-(trifluoromethyl)-6,7-dihydro-4H-pyrazolo[4,3-c]pyridin-1-yl]-N-methyl-benzamide |
| 74 | N-(1,3-benzodioxol-5-yl)-N-methyl-3-[3-(trifluoromethyl)-5-(1,3,5-trimethylpyrazol-4-yl)-6,7-dihydro-4H-pyrazolo[4,3-c]pyridin-1-yl]benzamide |
| 75 | methyl 4-[[1-[3-[1,3-benzodioxol-5-yl(methyl)carbamoyl]phenyl]-3-(trifluoromethyl)-5,7-dihydro-4H-pyrazolo[3,4-c]pyridin-6-yl]sulfonyl]benzoate |
| 76 | N-(1,3-benzodioxol-5-yl)-N-methyl-3-[5-tetrahydropyran-4-yl-3-(trifluoromethyl)-6,7-dihydro-4H-pyrazolo[4,3-c]pyridin-1-yl]benzamide |
| 77 | 4-[[1-[3-[1,3-benzodioxol-5-yl(methyl)carbamoyl]phenyl]-3-(trifluoromethyl)-5,7-dihydro-4H-pyrazolo[3,4-c]pyridin-6-yl]sulfonyl]benzoic acid |
| 82 | tert-butyl 3-[4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]-3,5-dimethyl-pyrazol-1-yl]propanoate |
| 85 | 3-[5-(2,2-dimethylpropanoyl)-3-(trifluoromethyl)-6,7-dihydro-4H-pyrazolo[4,3-c]pyridin-1-yl]-N-(6-methoxy-3-pyridyl)-N-methyl-benzamide |

-continued

| # | Substance Name |
|---|---|
| 86 | 3-[4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]-3,5-dimethyl-pyrazol-1-yl]propanoic acid |
| 87 | (4R,7S)- or (4S,7R)-N-(benzo[d][1,3]dioxol-5-yl)-N-methyl-3-[(9-pivaloyl-3-(trifluoromethyl)-5,6,7,8-tetrahydro-4,7-epiminocyclohepta[c]pyrazol-1(4H)-yl)]benzamide |
| 88 | (4S,7R)- or (4R,7S)-N-(benzo[d][1,3]dioxol-5-yl)-N-methyl-3-[(9-pivaloyl-3-(trifluoromethyl)-5,6,7,8-tetrahydro-4,7-epiminocyclohepta[c]pyrazol-1(4H)-yl)]benzamide |
| 89 | 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]-5-methyl-1H-pyrazole-3-carboxylic acid |
| 90 | 3-[5-(2,2-dimethylpropanoyl)-3-(trifluoromethyl)-6,7-dihydro-4H-pyrazolo[4,3-c]pyridin-1-yl]-N-(2-methoxy-4-pyridyl)-N-methyl-benzamide |
| 91 | 3-[5-(2,2-dimethylpropanoyl)-3-(trifluoromethyl)-6,7-dihydro-4H-pyrazolo[4,3-c]pyridin-1-yl]-N-methyl-N-(2-methylimidazo[1,2-a]pyridin-6-yl)benzamide |
| 92 | N-(2,2-difluoro-1,3-benzodioxol-5-yl)-N-methyl-3-[3-(trifluoromethyl)-4,5,6,7-tetrahydropyrazolo[4,3-c]pyridin-1-yl]benzamide |
| 93 | 3-[5-cyclobutyl-3-(trifluoromethyl)-6,7-dihydro-4H-pyrazolo[4,3-c]pyridin-1-yl]-N-(2,2-difluoro-1,3-benzodioxol-5-yl)-N-methyl-benzamide |
| 94 | N-(2,2-difluoro-1,3-benzodioxol-5-yl)-3-[5-(2,2-dimethylpropanoyl)-3-(trifluoromethyl)-6,7-dihydro-4H-pyrazolo[4,3-c]pyridin-1-yl]-N-methyl-benzamide |
| 95 | tert-butyl 1-(3-((2,2-difluorobenzo[d][1,3]dioxol-5-yl)(methyl)carbamoyl)phenyl)-3-(trifluoromethyl)-1,4,5,6,7,8-hexahydro-4,7-epiminocyclohepta[c]pyrazole-9-carboxylate |
| 96 | N-(2,2-difluoro-1,3-benzodioxol-5-yl)-3-[5-[(3,5-dimethylisoxazol-4-yl)sulfonyl-3-(trifluoromethyl)-6,7-dihydro-4H-pyrazolo[4,3-c]pyridin-1-yl]-N-methyl-benzamide |
| 97 | methyl 4-((1-(3-((2,2-difluorobenzo[d][1,3]dioxol-5-yl)(methyl)carbamoyl)phenyl)-3-(trifluoromethyl)-1,4,5,6,7,8-hexahydro-4,7-epiminocyclohepta[c]pyrazol-9-yl)sulfonyl)benzoate yl)sulfonyl]benzoate |
| 98 | N-(2,2-difluorobenzo[d][1,3]dioxol-5-yl)-N-methyl-3-(9-pivaloyl-3-(trifluoromethyl)-5,6,7,8-tetrahydro-4,7-epiminocyclohepta[c]pyrazol-1(4H)-yl)benzamide benzamide |
| 99 | N-methyl-N-(2-methylbenzo[d]oxazol-6-yl)-3-(9-pivaloyl-3-(trifluoromethyl)-5,6,7,8-tetrahydro-4,7-epiminocyclohepta[c]pyrazol-1(4H)-yl)benzamide |
| 100 | 3-(9-((3,5-dimethylisoxazol-4-yl)sulfonyl)-3-(trifluoromethyl)-5,6,7,8-tetrahydro-4,7-epiminocyclohepta[c]pyrazol-1(4H)-yl)-N-methyl-N-(2-methylbenzo[d]oxazol-6-yl)benzamide |
| 101 | 3-(9-((3,5-dimethylisoxazol-4-yl)sulfonyl)-3-(trifluoromethyl)-5,6,7,8-tetrahydro-4,7-epiminocyclohepta[c]pyrazol-1(4H)-yl)-N-methyl-N-(2-methylpyrazolo[1,5-a]pyridin-5-yl)benzamide |
| 102 | N-(2,2-difluoro-1,3-benzodioxol-5-yl)-3-(3-isopropyl-4,5,6,7-tetrahydroindazol-1-yl)-N-methyl-benzamide |
| 103 | N-(2,2-difluoro-1,3-benzodioxol-5-yl)-N-methyl-3-(3-methyl-4,5,6,7-tetrahydroindazol-1-yl)benzamide |
| 104 | ethyl 1-[3-[(2,2-difluoro-1,3-benzodioxol-5-yl)-methyl-carbamoyl]phenyl]-5-methyl-6,7-dihydro-4H-pyrazolo[4,3-c]pyridine-3-carboxylate |
| 105 | 3-(3-isopropyl-4,5,6,7-tetrahydroindazol-1-yl)-N-methyl-N-(2-methylpyrazolo[1,5-a]pyridin-5-yl)benzamide |
| 106 | N-(2,2-difluoro-1,3-benzodioxol-5-yl)-N-methyl-3-[7-(4-methylphenoxy)-3-(trifluoromethyl)-6,7-dihydro-4H-pyrano[4,3-c]pyrazol-1-yl]benzamide |
| 107 | N-methyl-N-(2-methyl-1,3-benzoxazol-6-yl)-3-[7-(4-methylphenoxy)-3-(trifluoromethyl)-6,7-dihydro-4H-pyrano[4,3-c]pyrazol-1-yl]benzamide |
| 108 | 4-[[1-[3-[(2,2-difluoro-1,3-benzodioxol-5-yl)-methyl-carbamoyl]phenyl]-5-methyl-3-(trifluoromethyl)-6,7-dihydro-4H-pyrazolo[4,3-c]pyridin-7-yl]oxy]benzoic acid |
| 109 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 110 | N-(1,3-benzodioxol-5-yl)-N-methyl-3-[4-methyl-3-(trifluoromethyl)-6,7-dihydro-5H-pyrazolo[4,3-b]pyridin-1-yl]benzamide |
| 111 | N-(2,2-difluoro-1,3-benzodioxol-5-yl)-3-[4-(2,2-dimethylpropanoyl)-3-(trifluoromethyl)-6,7-dihydro-5H-pyrazolo[4,3-b]pyridin-1-yl]-N-methyl-benzamide |
| 112 | N-(1,3-benzodioxol-5-yl)-N-methyl-3-[5-methyl-6-oxo-3-(trifluoromethyl)-4,7-dihydropyrazolo[4,3-c]pyridin-1-yl]benzamide |
| 113 | N-methyl-N-(2-methyl-1,3-benzoxazol-6-yl)-3-[5-methyl-6-oxo-3-(trifluoromethyl)-4,7-dihydropyrazolo[4,3-c]pyridin-1-yl]benzamide |
| 114 | 3-[5-(2,2-dimethylpropanoyl)-3-(trifluoromethyl)-6,7-dihydro-4H-pyrazolo[4,3-c]pyridin-1-yl]-N-methyl-N-(3-methyl-1H-pyrazolo[3,4-b]pyridin-5-yl)benzamide |
| 115 | 3-[5-(2,2-dimethylpropanoyl)-3-(trifluoromethyl)-6,7-dihydro-4H-pyrazolo[4,3-c]pyridin-1-yl]-N-(2-methoxypyrimidin-5-yl)-N-methyl-benzamide |
| 116 | N-(1,3-benzodioxol-5-yl)-N-methyl-3-[5-methyl-3-(trifluoromethyl)-4,6-dihydropyrrolo[3,4-c]pyrazol-1-yl]benzamide |
| 117 | N-(2,2-difluoro-1,3-benzodioxol-5-yl)-3-[5-(2,2-dimethylpropanoyl)-3-(trifluoromethyl)-4,6-dihydropyrrolo[3,4-c]pyrazol-1-yl]-N-methyl-benzamide |
| 118 | N-(1,3-benzodioxol-5-yl)-N-methyl-3-[6-methyl-3-(trifluoromethyl)-4,5,7,8-tetrahydropyrazolo[3,4-d]azepin-1-yl]benzamide |
| 119 | N-(2,2-difluoro-1,3-benzodioxol-5-yl)-3-[6-(2,2-dimethylpropanoyl)-3-(trifluoromethyl)-4,5,7,8-tetrahydropyrazolo[3,4-d]azepin-1-yl]-N-methyl-benzamide |

| # | Substance Name |
|---|---|
| 120 | N-(2,2-difluoro-1,3-benzodioxol-5-yl)-3-[5,7-dimethyl-3-(trifluoromethyl)-6,7-dihydro-4H-pyrazolo[4,3-c]pyridin-1-yl]-N-methyl-benzamide |
| 121 | 1-[3-[(2,2-difluoro-1,3-benzodioxol-5-yl)-methyl-carbamoyl]phenyl]-5-methyl-3-(trifluoromethyl)-6,7-dihydro-4H-pyrazolo[4,3-c]pyridine-7-carboxylic acid |
| 122 | 3-[7-cyano-5-methyl-3-(trifluoromethyl)-6,7-dihydro-4H-pyrazolo[4,3-c]pyridin-1-yl]-N-(2,2-difluoro-1,3-benzodioxol-5-yl)-N-methyl-benzamide |
| 123 | N-(2,2-difluoro-1,3-benzodioxol-5-yl)-N-methyl-3-[5,7,7-trimethyl-3-(trifluoromethyl)-4,6-dihydropyrazolo[4,3-c]pyridin-1-yl]benzamide |
| 124 | 1-[3-[(2,2-difluoro-1,3-benzodioxol-5-yl)-methyl-carbamoyl]phenyl]-5-methyl-3-(trifluoromethyl)-6,7-dihydro-4H-pyrazolo[4,3-c]pyridine-6-carboxylic acid |
| 125 | N-(2,2-difluoro-1,3-benzodioxol-5-yl)-3-[5,6-dimethyl-3-(trifluoromethyl)-6,7-dihydro-4H-pyrazolo[4,3-c]pyridin-1-yl]-N-methyl-benzamide |
| 126 | N-(2,2-difluoro-1,3-benzodioxol-5-yl)-3-[5-(2,2-dimethylpropanoyl)-3-(trifluoromethyl)-6,7-dihydro-4H-pyrazolo[4,3-c]pyridin-1-yl]-N-(trideuteromethyl)benzamide |
| 127 | 3-[5-(2,2-dimethylpropanoyl)-3-(trifluoromethyl)-6,7-dihydro-4H-pyrazolo[4,3-c]pyridin-1-yl]-N-(2-methyl-1,3-benzoxazol-6-yl)-N-(trideuteromethyl)benzamide |
| 128 | (4S,7R)- or (4R,7S)-N-(benzo[d][1,3]dioxol-5-yl)-3-(9-((3,5-dimethylisoxazol-4-yl)sulfonyl)-3-(trifluoromethyl)-5,6,7,8-tetrahydro-4,7-epiminocyclohepta[c]pyrazol-1(4H)-yl)-N-methylbenzamide |
| 129 | (4R,7S)- or (4S,7R)-N-(benzo[d][1,3]dioxol-5-yl)-3-(9-((3,5-dimethylisoxazol-4-yl)sulfonyl)-3-(trifluoromethyl)-5,6,7,8-tetrahydro-4,7-epiminocyclohepta[c]pyrazol-1(4H)-yl)-N-methylbenzamide |
| 130 | (4R,7S)- or (4S,7R)-N-(benzo[d][1,3]dioxol-5-yl)-3-(9-((3,5-dimethyl-1H-pyrazol-4-yl)sulfonyl)-3-(trifluoromethyl)-5,6,7,8-tetrahydro-4,7-epiminocyclohepta[c]pyrazol-1(4H)-yl)-N-methylbenzamide |
| 131 | (4R,7S)- or (4S,7R)-N-(benzo[d][1,3]dioxol-5-yl)-3-((4R,7S)-9-cyclobutyl-3-(trifluoromethyl)-5,6,7,8-tetrahydro-4,7-epiminocyclohepta[c]pyrazol-1(4H)-yl)-N-methylbenzamide |
| 132 | N-(1,3-benzodioxol-5-yl)-N-methyl-3-(3-methyl-4,5,6,7-tetrahydroindazol-1-yl)benzamide |
| 133 | N-(1,3-benzodioxol-5-yl)-3-(3-isopropyl-4,5,6,7-tetrahydroindazol-1-yl)-N-methyl-benzamide |
| 134 | ethyl 4-[1-[3-[1,3-benzodioxol-5-yl(methyl)carbamoyl]phenyl]-3-(trifluoromethyl)-6,7-dihydro-4H-pyrazolo[4,3-c]pyridin-5-yl]butanoate |
| 135 | 4-[1-[3-[1,3-benzodioxol-5-yl(methyl)carbamoyl]phenyl]-3-(trifluoromethyl)-6,7-dihydro-4H-pyrazolo[4,3-c]pyridin-5-yl]butanoic acid |
| 136 | tert-butyl 1-[3-[(2,2-difluoro-1,3-benzodioxol-5-yl)-methyl-carbamoyl]phenyl]-3-(trifluoromethyl)-6,7-dihydro-4H-pyrazolo[4,3-c]pyridine-5-carboxylate |
| 137 | 3-[5-(3,5-dimethylisoxazol-4-yl)sulfonyl-3-(trifluoromethyl)-6,7-dihydro-4H-pyrazolo[4,3-c]pyridin-1-yl]-N-methyl-N-(2-methyl-1,3-benzoxazol-6-yl)benzamide |
| 138 | 3-[5-(3,5-dimethylisoxazol-4-yl)sulfonyl-3-(trifluoromethyl)-6,7-dihydro-4H-pyrazolo[4,3-c]pyridin-1-yl]-N-(5-fluoro-2-methyl-1,3-benzoxazol-6-yl)-N-methyl-benzamide |
| 139 | benzyl 3-[1-[3-[1,3-benzodioxol-5-yl(methyl)carbamoyl]phenyl]-3-(trifluoromethyl)-6,7-dihydro-4H-pyrazolo[4,3-c]pyridin-5-yl]cyclobutanecarboxylate |
| 140 | 3-[1-[3-[1,3-benzodioxol-5-yl(methyl)carbamoyl]phenyl]-3-(trifluoromethyl)-6,7-dihydro-4H-pyrazolo[4,3-c]pyridin-5-yl]cyclobutanecarboxylic acid |
| 141 | 3-[5-(2,2-dimethylpropanoyl)-3-(trifluoromethyl)-6,7-dihydro-4H-pyrazolo[4,3-c]pyridin-1-yl]-N-methyl-N-quinoxalin-6-yl-benzamide |
| 142 | 3-[5-(2,2-dimethylpropanoyl)-3-(trifluoromethyl)-6,7-dihydro-4H-pyrazolo[4,3-c]pyridin-1-yl]-N-(2-methoxypyrimidin-5-yl)-N-methyl-benzamide |
| 143 | tert-butyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 144 | N-(2,2-difluoro-1,3-benzodioxol-5-yl)-N-methyl-3-[7-oxo-3-(trifluoromethyl)-5,6-dihydro-4H-indazol-1-yl]benzamide |
| 145 | N-(2,2-difluoro-1,3-benzodioxol-5-yl)-N-methyl-3-[7-oxo-3-(trifluoromethyl)-5,6-dihydro-4H-indazol-1-yl]benzamide |
| 146 | methyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-fluoro-benzoate |
| 147 | 2-fluoro-4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 148 | (R) or (S)-tert-butyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 149 | (S) or (R)-tert-butyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 150 | (R) or (S)-4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 151 | (S) or (R)-4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 152 | tert-butyl 4-[[1-[3-[(5-fluoro-2-methyl-1,3-benzoxazol-6-yl)-methyl-carbamoyl]phenyl]-3-(trifluoromethyl)-4,5,6,7-tetrahydroindazol-7-yl]oxy]benzoate |
| 153 | 4-[[1-[3-[(5-fluoro-2-methyl-1,3-benzoxazol-6-yl)-methyl-carbamoyl]phenyl]-3-(trifluoromethyl)-4,5,6,7-tetrahydroindazol-7-yl]oxy]benzoic acid |
| 154 | tert-butyl 4-[[1-[3-[(2,2-difluoro-1,3-benzodioxol-5-yl)-(trideuteriomethyl)carbamoyl]phenyl]-3-(trifluoromethyl)-4,5,6,7-tetrahydroindazol-7-yl]oxy]benzoate |

| # | Substance Name |
|---|---|
| 155 | 4-[[1-[3-[(2,2-difluoro-1,3-benzodioxol-5-yl)-(trideuteriomethyl)carbamoyl]phenyl]-3-(trifluoromethyl)-4,5,6,7-tetrahydroindazol-7-yl]oxy]benzoic acid |
| 156 | tert-butyl 4-[[1-[3-[methyl-(2-methyl-1,3-benzoxazol-6-yl)carbamoyl]phenyl]-3-(trifluoromethyl)-4,5,6,7-tetrahydroindazol-7-yl]oxy]benzoate |
| 157 | 4-[[1-[3-[methyl-(2-methyl-1,3-benzoxazol-6-yl)carbamoyl]phenyl]-3-(trifluoromethyl)-4,5,6,7-tetrahydroindazol-7-yl]oxy]benzoic acid |
| 158 | tert-butyl 4-[[1-[3-[methyl-(2-methyloxazolo[4,5-b]pyridin-6-yl)carbamoyl]phenyl]-3-(trifluoromethyl)-4,5,6,7-tetrahydroindazol-7-yl]oxy]benzoate |
| 159 | 4-[[1-[3-[methyl-(2-methyloxazolo[4,5-b]pyridin-6-yl)carbamoyl]phenyl]-3-(trifluoromethyl)-4,5,6,7-tetrahydroindazol-7-yl]oxy]benzoic acid |
| 160 | methyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-methoxy-benzoate |
| 161 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-methoxy-benzoic acid |
| 162 | 3-[7-(4-carbamoylphenoxy)-3-(trifluoromethyl)-4,5,6,7-tetrahydroindazol-1-yl]-N-(2,2-difluoro-1,3-benzodioxol-5-yl)-N-methyl-benzamide |
| 163 | methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylate |
| 164 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylic acid |
| 165 | tert-butyl 4-[[1-[3-[(5-methoxy-3-pyridyl)-methyl-carbamoyl]phenyl]-3-(trifluoromethyl)-4,5,6,7-tetrahydroindazol-7-yl]oxy]benzoate |
| 166 | 4-[[1-[3-[(5-methoxy-3-pyridyl)-methyl-carbamoyl]phenyl]-3-(trifluoromethyl)-4,5,6,7-tetrahydroindazol-7-yl]oxy]benzoic acid |
| 167 | tert-butyl 4-[[1-[3-[(2-methoxypyrimidin-5-yl)-methyl-carbamoyl]phenyl]-3-(trifluoromethyl)-4,5,6,7-tetrahydroindazol-7-yl]oxy]benzoate |
| 168 | 4-[[1-[3-[(2-methoxypyrimidin-5-yl)-methyl-carbamoyl]phenyl]-3-(trifluoromethyl)-4,5,6,7-tetrahydroindazol-7-yl]oxy]benzoic acid |
| 169 | ethyl 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 170 | 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 171 | tert-butyl 4-[[1-[3-[methyl-(2-methyl-[1,2,4]triazolo[1,5-a]pyridin-6-yl)carbamoyl]phenyl]-3-(trifluoromethyl)-4,5,6,7-tetrahydroindazol-7-yl]oxy]benzoate |
| 172 | 4-[[1-[3-[methyl-(2-methyl-[1,2,4]triazolo[1,5-a]pyridin-6-yl)carbamoyl]phenyl]-3-(trifluoromethyl)-4,5,6,7-tetrahydroindazol-7-yl]oxy]benzoic acid |
| 173 | tert-butyl 4-[[1-[3-[methyl-(2-methylpyrazolo[1,5-a]pyrimidin-6-yl)carbamoyl]phenyl]-3-(trifluoromethyl)-4,5,6,7-tetrahydroindazol-7-yl]oxy]benzoate |
| 174 | 4-[[1-[3-[methyl-(2-methylpyrazolo[1,5-a]pyrimidin-6-yl)carbamoyl]phenyl]-3-(trifluoromethyl)-4,5,6,7-tetrahydroindazol-7-yl]oxy]benzoic acid |
| 175 | methyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-methyl-benzoate |
| 176 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-methyl-benzoic acid |
| 177 | methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate |
| 178 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid |
| 179 | methyl 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate |
| 180 | 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid |
| 181 | methyl 2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylate |
| 182 | 2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylic acid |
| 183 | (S)- or (R)-methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylate |
| 184 | (R)- or (S)-methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylate |
| 185 | (R) or (S)-5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylic acid |
| 186 | (S) or (R)-5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylic acid |
| 187 | (S) or (R)-ethyl 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 188 | (S) or (R)-3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 189 | (R) or (S)-ethyl 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 190 | (R) or (S)-3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 191 | (S) or (R)-methyl 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate |

| # | Substance Name |
|---|---|
| 192 | (S) or (R)-6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid |
| 193 | (R) or (S)-methyl 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate |
| 194 | (R) or (S)-6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid |
| 195 | (S) or (R)-methyl 2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylate |
| 196 | (S) or (R)-2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylic acid |
| 197 | (R) or (S)-methyl 2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylate |
| 198 | (R) or (S)-2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylic acid |
| 199 | 3-[7-benzyloxy-3-(trifluoromethyl)-6,7-dihydro-4H-pyrano[4,3-c]pyrazol-1-yl]-N-(2,2-difluoro-1,3-benzodioxol-5-yl)-N-methyl-benzamide |
| 200 | N-(2,2-difluoro-1,3-benzodioxol-5-yl)-3-[7-hydroxy-3-(trifluoromethyl)-6,7-dihydro-4H-pyrano[4,3-c]pyrazol-1-yl]-N-methyl-benzamide |
| 201 | tert-butyl 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoate |
| 202 | 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoic acid |
| 203 | (R)- or (S)-tert-butyl 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoate |
| 204 | (S)- or (R)-tert-butyl 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoate |
| 205 | (R)- or (S)-4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoic acid |
| 206 | (S)- or (R)-4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoic acid |
| 207 | tert-butyl 4-[[1-[3-[(2,2-difluoro-1,3-benzodioxol-5-yl)-methyl-carbamoyl]phenyl]-3-(difluoromethyl)-4,5,6,7-tetrahydroindazol-7-yl]oxy]benzoate |
| 208 | 4-[[1-[3-[(2,2-difluoro-1,3-benzodioxol-5-yl)-methyl-carbamoyl]phenyl]-3-(difluoromethyl)-4,5,6,7-tetrahydroindazol-7-yl]oxy]benzoic acid |
| 209 | Methyl 5-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylate |
| 210 | 5-[[1-[3-[(2,2-Difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylic acid |
| 211 | Methyl 6-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylate |
| 212 | Methyl 1-[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]-6-oxo-pyridine-3-carboxylate |
| 213 | 6-[[1-[3-[(2,2-Difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylic acid |
| 214 | 1-[1-[3-[(2,2-Difluoro-1,3-benzodioxol-5-yl)-methyl-carbamoyl]phenyl]-3-(trifluoromethyl)-6,7-dihydro-4H-pyrano[4,3-c]pyrazol-7-yl]-6-oxo-pyridine-3-carboxylic acid |
| 215 | (S) or (R)-tert-Butyl 4-[[1-[3-[methyl-(2-methylpyrazolo[1,5-a] pyrimidin-6-yl)carbamoyl]phenyl]-3-(trifluoromethyl)-4,5,6,7-tetrahydroindazol-7-yl]oxy]benzoate |
| 216 | (R) or (S)-tert-Butyl 4-[[1-[3-[methyl-(2-methylpyrazolo[1,5-a] pyrimidin-6-yl)carbamoyl]phenyl]-3-(trifluoromethyl)-4,5,6,7-tetrahydroindazol-7-yl]oxy]benzoate |
| 217 | (S) or (R)-4-[[1-[3-[Methyl-(2-methylpyrazolo[1,5-a]pyrimidin-6-yl)carbamoyl]phenyl]-3-(trifluoromethyl)-4,5,6,7-tetrahydroindazol-7-yl]oxy]benzoic acid |
| 218 | (R) or (S)-4-[[1-[3-[Methyl-(2-methylpyrazolo[1,5-a]pyrimidin-6-yl)carbamoyl]phenyl]-3-(trifluoromethyl)-4,5,6,7-tetrahydroindazol-7-yl]oxy]benzoic acid |
| 219 | 4-[[1-[3-[[2-(difluoromethoxy)pyrimidin-5-yl]-methyl-carbamoyl]phenyl]-3-(trifluoromethyl)-4,5,6,7-tetrahydroindazol-7-yl]oxy]benzoic acid |
| 220 | 4-[[1-[3-[methyl-[2-(trifluoromethoxy)pyrimidin-5-yl]carbamoyl]phenyl]-3-(trifluoromethyl)-4,5,6,7-tetrahydroindazol-7-yl]oxy]benzoic acid |
| 221 | 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridazine-3-carboxylic acid |
| 222 | 4-[[1-[3-[(2,2-difluoro-3H-furo[3,2-b]pyridin-6-yl)-methyl-carbamoyl]phenyl]-3-(trifluoromethyl)-4,5,6,7-tetrahydroindazol-7-yl]oxy]benzoic acid |
| 223 | 4-[[1-[3-[methyl-[5-(trifluoromethoxy)-3-pyridyl]carbamoyl]phenyl]-3-(trifluoromethyl)-4,5,6,7-tetrahydroindazol-7-yl]oxy]benzoic acid |

-continued

| # | Substance Name |
|---|---|
| 224 | 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]cyclobutanecarboxylic acid |
| 225 | 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]bicyclo[1.1.1]pentane-1-carboxylic acid |
| 226 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]cyclohexanecarboxylic acid |
| 227 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]cyclohexanecarboxylic acid |
| 228 | 5-[[1-[3-[methyl-(2-methyl-1,3-benzoxazol-6-yl)carbamoyl]phenyl]-3-(trifluoromethyl)-6,7-dihydro-4H-pyrano[4,3-c]pyrazol-7-yl]oxy]pyridine-2-carboxylic acid |
| 229 | 5-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-2-carboxylic acid |
| 230 | 4-[[1-[3-[[2-(difluoromethoxy)pyrimidin-5-yl]-methyl-carbamoyl]phenyl]-3-(trifluoromethyl)-6,7-dihydro-4H-pyrano[4,3-c]pyrazol-7-yl]oxy]benzoic acid |
| 231 | 2-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-4-carboxylic acid |
| 232 | 6-[[1-[3-[methyl-(2-methyloxazolo[4,5-b]pyridin-6-yl)carbamoyl]phenyl]-3-(trifluoromethyl)-6,7-dihydro-4H-pyrano[4,3-c]pyrazol-7-yl]oxy]pyridine-3-carboxylic acid |
| 233 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]amino]benzoic acid |
| 234 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]amino]pyridine-2-carboxylic acid |
| 235 | 4-[methyl-[1-[3-[methyl-(2-methyl-1,3-benzoxazol-6-yl)carbamoyl]phenyl]-3-(trifluoromethyl)-4,5,6,7-tetrahydroindazol-7-yl]amino]benzoic acid |
| 236 | 4-[methyl-[1-[3-[methyl-(2-methyl-1,3-benzoxazol-6-yl)carbamoyl]phenyl]-3-(trifluoromethyl)-4,5,6,7-tetrahydroindazol-7-yl]amino]benzoic acid |
| 237 | 4-[[1-[6-[methyl(pyrazolo[1,5-a]pyrimidin-5-yl)carbamoyl]-2-pyridyl]-3-(trifluoromethyl)-4,5,6,7-tetrahydroindazol-7-yl]oxy]benzoic acid |
| 238 | 4-[[1-[3-[methyl-(2-methyloxazolo[4,5-b]pyridin-6-yl)carbamoyl]phenyl]-3-(trifluoromethyl)-5,6-dihydro-4H-cyclopenta[c]pyrazol-6-yl]oxy]benzoic acid |
| 239 | 4-[[1-[3-[methyl-(2-methylpyrazolo[1,5-a]pyrimidin-6-yl)carbamoyl]phenyl]-3-(trifluoromethyl)-5,6-dihydro-4H-cyclopenta[c]pyrazol-6-yl]oxy]benzoic acid |
| 240 | 4-[[1-[3-[(2,2-difluoro-1,3-benzodioxol-5-yl)-methyl-carbamoyl]phenyl]-3-(trifluoromethyl)-5,6-dihydro-4H-cyclopenta[c]pyrazol-6-yl]oxy]benzoic acid |
| 241 | 4-[[1-[3-[(2,2-difluoro-1,3-benzodioxol-5-yl)-methyl-carbamoyl]phenyl]-3-(trifluoromethoxy)-4,5,6,7-tetrahydroindazol-7-yl]oxy]benzoic acid |
| 242 | 4-[[1-[3-[(2,2-difluoro-1,3-benzodioxol-5-yl)-methyl-carbamoyl]phenyl]-3-(difluoromethoxy)-4,5,6,7-tetrahydroindazol-7-yl]oxy]benzoic acid |
| 243 | 4-[1-[1-[3-[(2,2-difluoro-1,3-benzodioxol-5-yl)-methyl-carbamoyl]phenyl]-3-(trifluoromethyl)-4,5,6,7-tetrahydroindazol-7-yl]-1-methyl-ethyl]benzoic acid |
| 244 | 4-[1-[1-[3-[(2,2-difluoro-1,3-benzodioxol-5-yl)-methyl-carbamoyl]phenyl]-3-(difluoromethyl)-4,5,6,7-tetrahydroindazol-7-yl]cyclopropyl]benzoic acid |
| 245 | 4-[[1-[3-[(2,2-difluoro-1,3-benzodioxol-5-yl)-methyl-carbamoyl]phenyl]-3-(difluoromethyl)-4,5,6,7-tetrahydroindazol-7-yl]sulfonyl]benzoic acid |
| 246 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]methyl]pyridine-2-carboxylic acid |
| 247 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]methyl]pyridine-2-carboxylic acid |
| 248 | 4-[[1-[3-[(2,2-difluoro-1,3-benzodioxol-5-yl)-methyl-carbamoyl]phenyl]-3-(trifluoromethyl)-5,7-dihydro-4H-pyrano[3,4-c]pyrazol-7-yl]methyl]benzoic acid |
| 249 | 4-[[1-[3-[(2,2-difluoro-1,3-benzodioxol-5-yl)-methyl-carbamoyl]phenyl]-3-(trifluoromethyl)-6,7-dihydro-5H-pyrano[3,2-c]pyrazol-7-yl]oxy]benzoic acid |
| 250 | 4-[[1-[3-[methyl-(2-methylimidazo[1,2-b]pyridazin-6-yl)carbamoyl]phenyl]-3-(trifluoromethyl)-4,5,6,7-tetrahydroindazol-7-yl]oxy]benzoic acid |
| 251 | 4-[[1-[3-[(6-methoxypyrazin-2-yl)-methyl-carbamoyl]phenyl]-3-(trifluoromethyl)-4,5,6,7-tetrahydroindazol-7-yl]oxy]benzoic acid |
| 252 | 4-[[1-[3-[(2-methoxypyrimidin-4-yl)-methyl-carbamoyl]phenyl]-3-(trifluoromethyl)-4,5,6,7-tetrahydroindazol-7-yl]oxy]benzoic acid. |

5. A pharmaceutical composition comprising a compound of formula I according to any of claim 1 and at least one pharmaceutically acceptable excipient.

6. A compound of formula I according to claim 1 for the use as a medicament.

7. A method of modulating CFTR protein or ABC protein activities in a mammal in need thereof comprising administering a compound of formula I

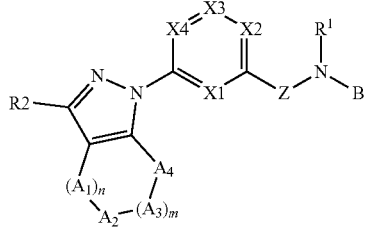
(I)

or pharmaceutically acceptable salts or solvates thereof wherein:
$R_1$ is selected from the group consisting of $C_{1-6}$alkyl, $C_{3-6}$cycloalkyl and hydroxyl-$C_{1-6}$alkyl;
Z is C=O or $SO_2$;
$X_1$, $X_2$, $X_3$ and $X_4$ are independently selected from the group consisting of $CR^{vii}$ and N, with the proviso that the number of nitrogen atoms in the ring is comprised from 0 to 2;
$R_2$ is selected from the group consisting of hydrogen, $C_{1-6}$alkyl, halo$C_{1-6}$alkyl, $C_{3-6}$cycloalkyl, aryl, heteroaryl, $COR^{viii}$, $COOR^{viii}$, heterocycloalkyl, $CONHR^{viii}$, $CONR^{viii}R^{ix}$, OH, O—$C_{1-6}$alkyl, O—$C_{1-6}$alkylaryl, O—$C_{3-6}$cycloalkyl, O-heterocycloalkyl, O-heteroaryl, O-aryl, O-halo$C_{1-6}$alkyl, $C_{1-6}$alkyl-O—$C_{1-6}$alkyl, $C_{1-6}$alkyl-O—$C_{3-6}$cycloalkyl, $C_{1-6}$alkyl-O-heterocycloalkyl, $C_{1-6}$alkyl-O-aryl, $C_{1-6}$alkyl-O-heteroaryl, CN, $NO_2$, $NR^xR^{xi}$, $N(R^{ix})COR^x$, $N(R^{ix})COOR^{xi}$, $N(R^{ix})CONR^{xi}R^x$, $N(R^{ix})SO_2R^x$, $SO_2R^x$, $SO_2NR^{ix}R^x$, halogen, and hydroxy-$C_{1-6}$alkyl;
$A_1$, $A_2$, $A_3$, and $A_4$, are independently selected from the group consisting of $CR^{xii}R^{xiii}$, O $NR^{xiv}$, CO and $SO_2$, wherein
$R^{xii}$ and $R^{xiii}$ are independently selected from the group consisting of hydrogen, $C_{1-6}$alkyl, $C_{3-6}$cycloalkyl, heterocycloalkyl, halo$C_{1-6}$alkyl, $COR^{viii}$, $COOR^{viii}$, $CONHR^{viii}$, $CONR^{viii}R^{ix}$, OH, O—$C_{1-6}$alkyl, O-aryl, O—$C_{1-6}$alkylaryl, O-heteroaryl, O—$C_{3-6}$cycloalkyl, O-heterocycloalkyl, $C_{1-6}$alkylaryl, $C_{3-6}$cycloalkylaryl, $C_{3-6}$cycloalkylheteroaryl, $C_{3-6}$cycloheteroalkylaryl, $C_{3-6}$cycloheteroalkylheteroaryl, $C_{1-6}$alkylheteroaryl, S-aryl, S-heteroaryl, SO-aryl, SO-heteroaryl, $SO_2$-aryl, $SO_2$-heteroaryl, $C_{1-6}$alkyl-O—$C_{1-6}$alkyl, CN, halogen, $NR^xR^{xi}$, $N(R^{ix})COR^x$;
$R^{xiv}$ is selected from the group consisting of hydrogen, $C_{1-6}$alkyl, $C_{1-6}$alkylaryl, $C_{1-6}$alkyl-$C_{3-6}$cycloalkyl, $C_{1-6}$alkyl-heterocycloalkyl, $C_{3-6}$cycloalkyl, heterocycloalkyl, hydroxyl-$C_{1-6}$alkyl, $COR^{viii}$, $COOR^{viii}$, $CONHR^{viii}$, $CONR^{viii}R^{ix}$, $SO_2R^{viii}$, $C_{1-6}$alkyl-O—$C_{1-6}$alkyl, $C_{1-6}$alkyl-O-aryl, $C_{1-6}$alkyl-O-heteroaryl, $C_{1-6}$alkyl-O-heterocycloalkyl, $C_{1-6}$alkylCOOR^{viii}$;
or
when each of $A_1$ and $A_3$, or $A_2$ and $A_4$, or $A_1$ and $A_4$ represents $CR^{xii}R^{xiii}$, the two groups $R^{xii}$ can be linked together to form a ring and thus the moiety

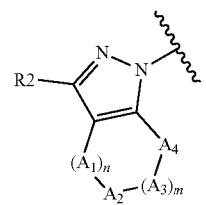

has a meaning selected from the group consisting of:

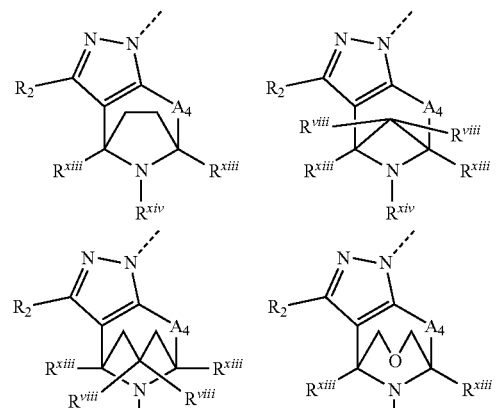

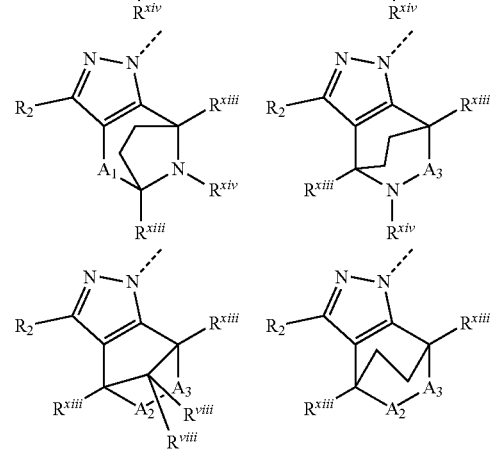

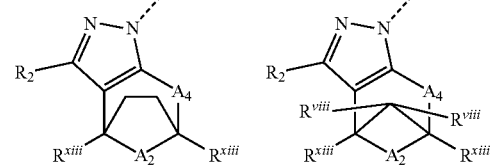

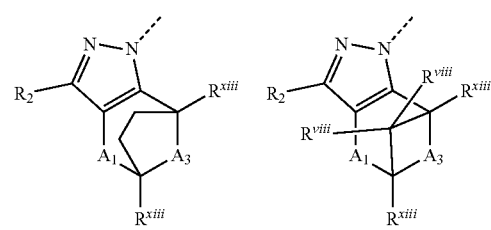

n and m are each independently selected from the group consisting of 0, 1, 2;
B represents an unsubstituted or a substituted aromatic or heteroaromatic ring selected from the group consisting of:
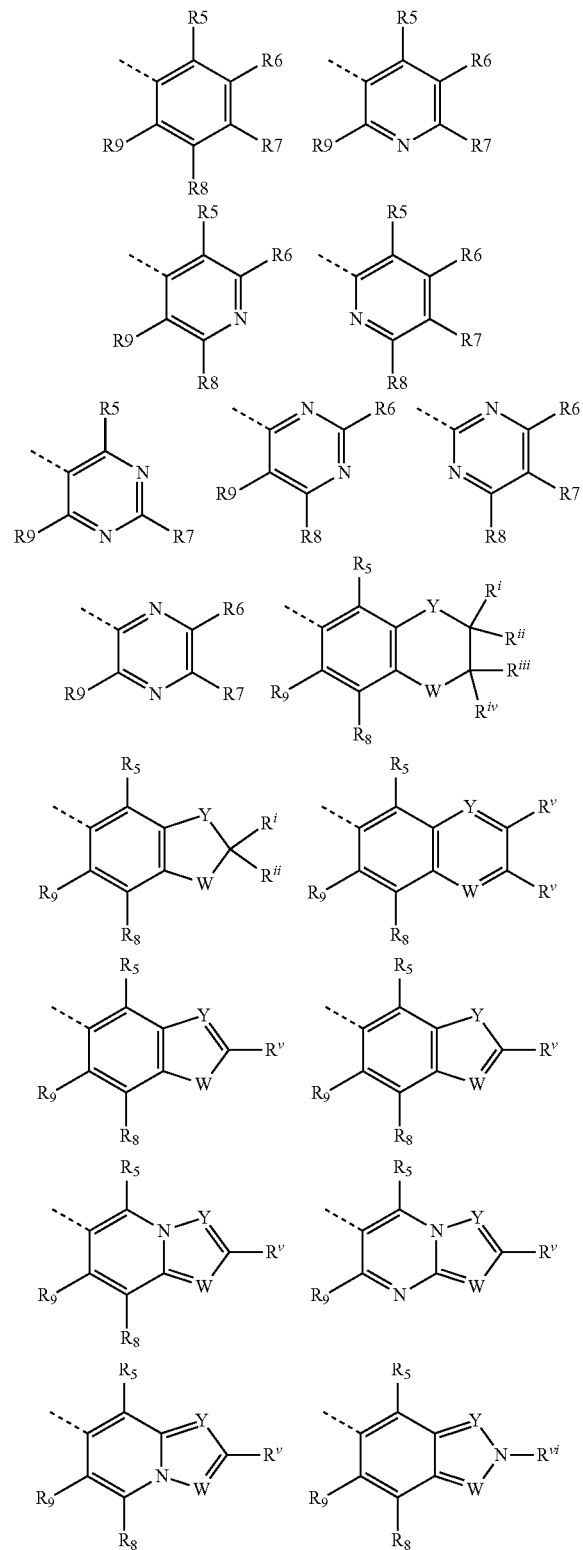
-continued
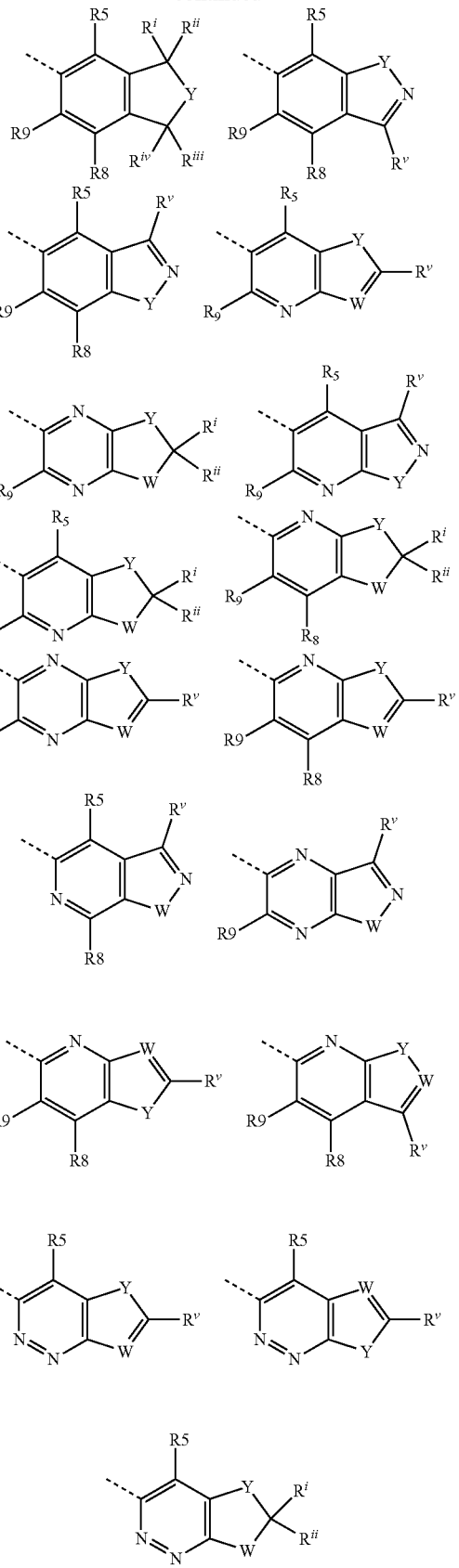

wherein

R$_5$, R$_6$, R$_7$, R$_8$, and R$_9$ are independently selected from the group consisting of hydrogen, halogen, C$_{1-6}$alkyl, haloC$_{1-6}$alkyl, C$_{3-6}$cycloalkyl, O—C$_{1-6}$ alkyl, O—C$_{3-6}$cycloalkyl, O-heterocycloalkyl, O-haloC$_{1-6}$alkyl, COR$^{viii}$, COOR$^{viii}$, CONHR$^{viii}$, CONR$^{viii}$R$^{ix}$, OH, CN, NR$^x$R$^{xi}$, N(R$^{ix}$)COR$^x$, N(R$^{ix}$)CONR$^x$R$^{xi}$ and hydroxy-C$_{1-6}$alkyl or when R$_6$ and R$_7$ are present on a 6-membered heteroaromatic ring, taken together with the carbon atoms to whom they are bound, they can form a saturated or unsaturated 5-membered or 6-membered carbocyclic ring or a 5-membered or 6-membered heterocycloalkyl containing from 1 to 3 heteroatoms selected from O, N, and S or a 5-membered or 6-membered heteroaryl ring containing from 1 to 3 heteroatoms selected from O, N, and S;

Y and W are independently selected from the group consisting of O, S, SO$_2$, CR$^{iv}$R$^v$, CR$^v$, N, and NR$^{vi}$;

R$^i$, R$^{ii}$, R$^{iii}$ and R$^{iv}$ are independently selected from the group consisting of hydrogen, C$_{1-6}$alkyl, haloC$_{1-6}$alkyl, halogen, OH, O—C$_{1-6}$alkyl and O-haloC$_{1-6}$alkyl or when R$^i$ and R$^{ii}$, or R$^{iii}$ and R$^{iv}$ are taken together with the carbon atoms to whom they are bound, they can represent C=O;

R$^v$ is selected from the group consisting of hydrogen, C$_{1-6}$alkyl, haloC$_{1-6}$alkyl, O—C$_{1-6}$alkyl, halogen, C$_{3-6}$cycloalkyl, OH and O-haloC$_{1-6}$alkyl;

R$^{vi}$ is selected from the group consisting of hydrogen and C$_{1-6}$alkyl;

R$^{vii}$ is selected from the group consisting of hydrogen, C$_{1-6}$alkyl, C$_{3-6}$cycloalkyl, haloC$_{1-6}$alkyl, O-haloC$_{1-6}$alkyl, COR$^{viii}$, COOR$^{viii}$, CONHR$^{viii}$, CONR$^{viii}$R$^{ix}$, OH, O—C$_{1-6}$alkyl, halogen, CN, NO$_2$, NR$^x$R$^{xi}$, N(R$^{ix}$)COR$^x$, N(R$^{ix}$)COOR$^{xi}$, N(R$^{ix}$)CONR$^x$R$^{xi}$, and N(R$^{ix}$)SO$_2$R$^x$;

R$^{viii}$ is selected from the group consisting of hydrogen, C$_{1-6}$alkyl, C$_{3-6}$cycloalkyl, aryl, heteroaryl, heterocycloalkyl, hydroxy-C$_{1-6}$alkyl and C$_{1-6}$alkyl-O—C$_{1-6}$alkyl;

R$^{ix}$ is selected from the group consisting of hydrogen, C$_{1-6}$alkyl, hydroxy-C$_{1-6}$alkyl, and C$_{1-6}$alkyl-O—C$_{1-6}$alkyl;

R$^x$ is selected from the group consisting of hydrogen, C$_{1-6}$alkyl, C$_{3-6}$cycloalkyl, heterocycloalkyl, aryl, heteroaryl, hydroxy-C$_{1-6}$alkyl, and C$_{1-6}$alkyl-O—C$_{1-6}$alkyl;

R$^{xi}$ is selected from the group consisting of hydrogen, C$_{1-6}$alkyl, hydroxy-C$_{1-6}$alkyl, C$_{1-6}$alkyl-O—C$_{1-6}$alkyl, aryl-C$_{1-6}$alkyl, heteroaryl-C$_{1-6}$alkyl, and heterocycloalkyl-C$_{1-6}$alkyl.

8. The method according to claim 7 wherein the modulation of CFTR or ABC protein are correlated to a disease selected from the group consisting of cystic fibrosis, Tangier disease, fatal surfactant deficiency, Stargardt disease, progressive familial intrahepatic cholestasis type 3, progressive familial intrahepatic cholestasis type 2, Dubin-Johnson syndrome, hyperinsulinemic hypoglycemia of infancy and gout.

9. The method according to claim 8 wherein the disease is cystic fibrosis.

10. The method according to claim 7, wherein the compound of formula I is selected from the group consisting of:

| # | Substance Name |
|---|---|
| 1 | tert-butyl 1-[3-[1,3-benzodioxol-5-yl(methyl)carbamoyl] phenyl]-3-(trifluoromethyl)-6,7-dihydro-4H-pyrazolo[4,3-c]pyridine-5-carboxylate |
| 2 | N-(1,3-benzodioxol-5-yl)-N-methyl-3-[3-(trifluoromethyl)-4,5,6,7-tetrahydropyrazolo[4,3-c]pyridin-1-yl]benzamide hydrochloride |
| 3 | N-(1,3-benzodioxol-5-yl)-N-methyl-3-[5-methyl-3-(trifluoromethyl)-6,7-dihydro-4H-pyrazolo[4,3-c]pyridin-1-yl]benzamide |
| 4 | 3-[5-acetyl-3-(trifluoromethyl)-6,7-dihydro-4H-pyrazolo[4,3-c]pyridin-1-yl]-N-(1,3-benzodioxol-5-yl)-N-methyl-benzamide |
| 5 | N-(1,3-benzodioxol-5-yl)-N-methyl-3-[3-(trifluoromethyl)-4,5,6,7-tetrahydroindazol-1-yl]benzamide |
| 6 | N-(1,3-benzodioxol-5-yl)-N-methyl-3-[5-methylsulfonyl-3-(trifluoromethyl)-6,7-dihydro-4H-pyrazolo[4,3-c]pyridin-1-yl]benzamide |
| 7 | 3-[5-(benzenesulfonyl)-3-(trifluoromethyl)-6,7-dihydro-4H-pyrazolo[4,3-c]pyridin-1-yl]-N-(1,3-benzodioxol-5-yl)-N-methyl-benzamide |
| 8 | N-(1,3-benzodioxol-5-yl)-3-[5-benzoyl-3-(trifluoromethyl)-6,7-dihydro-4H-pyrazolo[4,3-c]pyridin-1-yl]-N-methyl-benzamide |
| 9 | methyl 1-[3-[1,3-benzodioxol-5-yl(methyl)carbamoyl]phenyl]-3-(trifluoromethyl)-6,7-dihydro-4H-pyrazolo[4,3-c]pyridine-5-carboxylate |
| 10 | 1-[3-[1,3-benzodioxol-5-yl(methyl)carbamoyl]phenyl]-N-phenyl-3-(trifluoromethyl)-6,7-dihydro-4H-pyrazolo[4,3-c]pyridine-5-carboxamide |
| 11 | N-(1,3-benzodioxol-5-yl)-3-[5-(2,2-dimethylpropanoyl)-3-(trifluoromethyl)-6,7-dihydro-4H-pyrazolo[4,3-c]pyridin-1-yl]-N-methyl-benzamide |
| 12 | N-(1,3-benzodioxol-5-yl)-3-[5-benzyl-3-(trifluoromethyl)-6,7-dihydro-4H-pyrazolo[4,3-c]pyridin-1-yl]-N-methyl-benzamide |
| 13 | N-(1,3-benzodioxol-5-yl)-3-[5-[[(4R)-2,2-dimethyl-1,3-dioxolan-4-yl]methyl]-3-(trifluoromethyl)-6,7-dihydro-4H-pyrazolo[4,3-c]pyridin-1-yl]-N-methyl-benzamide |
| 14 | N-(1,3-benzodioxol-5-yl)-3-[5-[[(4S)-2,2-dimethyl-1,3-dioxolan-4-yl]methyl]-3-(trifluoromethyl)-6,7-dihydro-4H-pyrazolo[4,3-c]pyridin-1-yl]-N-methyl-benzamide |
| 15 | N-(1,3-benzodioxol-5-yl)-3-[5-[(2R)-2,3-dihydroxypropyl]-3-(trifluoromethyl)-6,7-dihydro-4H-pyrazolo[4,3-c]pyridin-1-yl]-N-methyl-benzamide |
| 16 | N-(1,3-benzodioxol-5-yl)-3-[5-[(2S)-2,3-dihydroxypropyl]-3-(trifluoromethyl)-6,7-dihydro-4H-pyrazolo[4,3-c]pyridin-1-yl]-N-methyl-benzamide |
| 17 | N-(1,3-benzodioxol-5-yl)-N-methyl-3-[5-methyl-3-(trifluoromethyl)-6,7-dihydro-4H-pyrazolo[4,3-f][1,4]oxazepin-1-yl]benzamide |
| 18 | tert-butyl 1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate |

-continued

| # | Substance Name |
|---|---|
| 19 | N-(1,3-benzodioxol-5-yl)-3-[5-(cyclopropylmethyl)-3-(trifluoromethyl)-6,7-dihydro-4H-pyrazolo[4,3-c]pyridin-1-yl]-N-methyl-benzamide |
| 20 | methyl 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]methyl]benzoate |
| 21 | N-(1,3-benzodioxol-5-yl)-3-[5-isopropyl-3-(trifluoromethyl)-6,7-dihydro-4H-pyrazolo[4,3-c]pyridin-1-yl]-N-methyl-benzamide |
| 22 | N-(benzo[d][1,3]dioxol-5-yl)-N-methyl-3-(3-(trifluoromethyl)-5,6,7,8-tetrahydro-4,7-epiminocyclohepta[c]pyrazol-1(4H)-yl)benzamide hydrochloride |
| 23 | N-(benzo[d][1,3]dioxol-5-yl)-N-methyl-3-(9-methyl-3-(trifluoromethyl)-5,6,7,8-tetrahydro-4,7-epiminocyclohepta[c]pyrazol-1(4H)-yl)benzamide |
| 24 | N-(1,3-benzodioxol-5-yl)-N-methyl-3-[5-[rac-(1S)-1-methylpropyl]-3-(trifluoromethyl)-6,7-dihydro-4H-pyrazolo[4,3-c]pyridin-1-yl]benzamide |
| 25 | 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]methyl]benzoic acid |
| 26 | 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]methyl]benzoic acid |
| 27 | tert-butyl 1-[3-[1,3-benzodioxol-5-yl(methyl)carbamoyl]phenyl]-3-(trifluoromethyl)-5,7-dihydro-4H-pyrazolo[3,4-c]pyridine-6-carboxylate |
| 28 | tert-butyl 1-[3-[1,3-benzodioxol-5-yl(methyl)carbamoyl]phenyl]-3-(trifluoromethyl)-6,7-dihydro-5H-pyrazolo[4,3-b]pyridine-4-carboxylate |
| 29 | N-(1,3-benzodioxol-5-yl)-N-methyl-3-[6-methyl-3-(trifluoromethyl)-5,7-dihydro-4H-pyrazolo[3,4-c]pyridin-1-yl]benzamide |
| 30 | N-methyl-N-(2-methyl-1,3-benzoxazol-6-yl)-3-[3-(trifluoromethyl)-4,5,6,7-tetrahydropyrazolo[4,3-c]pyridin-1-yl]benzamide hydrochloride |
| 31 | N-(1,3-benzodioxol-5-yl)-N-methyl-3-[5-(2-methylpropanoyl)-3-(trifluoromethyl)-6,7-dihydro-4H-pyrazolo[4,3-c]pyridin-1-yl]benzamide |
| 32 | N-(1,3-benzodioxol-5-yl)-3-[5-cyclobutyl-3-(trifluoromethyl)-6,7-dihydro-4H-pyrazolo[4,3-c]pyridin-1-yl]-N-methyl-benzamide |
| 33 | N-(1,3-benzodioxol-5-yl)-N-methyl-3-[5-(3,3,3-trifluoro-2,2-dimethyl-propanoyl)-3-(trifluoromethyl)-6,7-dihydro-4H-pyrazolo[4,3-c]pyridin-1-yl]benzamide |
| 34 | N-(1,3-benzodioxol-5-yl)-3-[5-(1-hydroxycyclopropanecarbonyl)-3-(trifluoromethyl)-6,7-dihydro-4H-pyrazolo[4,3-c]pyridin-1-yl]-N-methyl-benzamide |
| 35 | N-(1,3-benzodioxol-5-yl)-N-methyl-3-[5-(2-methyl-2-phenyl-propanoyl)-3-(trifluoromethyl)-6,7-dihydro-4H-pyrazolo[4,3-c]pyridin-1-yl]benzamide |
| 36 | tert-butyl 1-[3-[(5-fluoro-2-methyl-1,3-benzoxazol-6-yl)-methyl-carbamoyl]phenyl]-3-(trifluoromethyl)-6,7-dihydro-4H-pyrazolo[4,3-c]pyridine-5-carboxylate |
| 37 | tert-butyl 1-[3-[(5-fluoro-2-methyl-1,3-benzoxazol-6-yl)carbamoyl]phenyl]-3-(trifluoromethyl)-6,7-dihydro-4H-pyrazolo[4,3-c]pyridine-5-carboxylate |
| 38 | N-(1,3-benzodioxol-5-yl)-N-methyl-3-[3-(trifluoromethyl)-4,5,6,7-tetrahydropyrazolo[3,4-c]pyridin-1-yl]benzamide hydrochloride |
| 39 | tert-butyl 1-[3-[methyl-(2-methyl-1,3-benzoxazol-6-yl)carbamoyl]phenyl]-3-(trifluoromethyl)-6,7-dihydro-4H-pyrazolo[4,3-c]pyridine-5-carboxylate |
| 40 | N-methyl-N-(2-methyl-1,3-benzoxazol-6-yl)-3-[5-methyl-3-(trifluoromethyl)-6,7-dihydro-4H-pyrazolo[4,3-c]pyridin-1-yl]benzamide |
| 41 | N-(4-acetamido-3-hydroxy-phenyl)-N-methyl-3-[5-methyl-3-(trifluoromethyl)-6,7-dihydro-4H-pyrazolo[4,3-c]pyridin-1-yl]benzamide |
| 42 | methyl 4-[1-[3-[1,3-benzodioxol-5-yl(methyl)carbamoyl]phenyl]-3-(trifluoromethyl)-6,7-dihydro-4H-pyrazolo[4,3-c]pyridine-5-carbonyl]benzoate |
| 43 | methyl 3-[1-[3-[1,3-benzodioxol-5-yl(methyl)carbamoyl]phenyl]-3-(trifluoromethyl)-6,7-dihydro-4H-pyrazolo[4,3-c]pyridin-5-yl]-3-oxo-propanoate |
| 44 | 4-[1-[3-[1,3-benzodioxol-5-yl(methyl)carbamoyl]phenyl]-3-(trifluoromethyl)-6,7-dihydro-4H-pyrazolo[4,3-c]pyridine-5-carbonyl]benzoic acid |
| 45 | 3-[1-[3-[1,3-benzodioxol-5-yl(methyl)carbamoyl]phenyl]-3-(trifluoromethyl)-6,7-dihydro-4H-pyrazolo[4,3-c]pyridin-5-yl]-3-oxo-propanoic acid |
| 46 | N-(5-fluoro-2-methyl-1,3-benzoxazol-6-yl)-N-methyl-3-[5-methyl-3-(trifluoromethyl)-6,7-dihydro-4H-pyrazolo[4,3-c]pyridin-1-yl]benzamide |
| 47 | N-(5-fluoro-2-methyl-1,3-benzoxazol-6-yl)-3-[5-methyl-3-(trifluoromethyl)-6,7-dihydro-4H-pyrazolo[4,3-c]pyridin-1-yl]benzamide |
| 48 | (4S,7R)- or (4R,7S)-N-(benzo[d][1,3]dioxol-5-yl)-N-methyl-3-(3-(trifluoromethyl)-5,6,7,8-tetrahydro-4,7-epiminocyclohepta[c]pyrazol-1(4H)-yl)benzamide |
| 49 | (4R,7S)- or (4S,7R)-N-(benzo[d][1,3]dioxol-5-yl)-N-methyl-3-(3-(trifluoromethyl)-5,6,7,8-tetrahydro-4,7-epiminocyclohepta[c]pyrazol-1(4H)-yl)benzamide |
| 50 | (4S,7R)- or (4R,7S)-N-(benzo[d][1,3]dioxol-5-yl)-N-methyl-3-(9-methyl-3-(trifluoromethyl)-5,6,7,8-tetrahydro-4,7-epiminocyclohepta[c]pyrazol-1(4H)-yl)benzamide |
| 51 | (4R,7S)- or (4S,7R)-N-(benzo[d][1,3]dioxol-5-yl)-N-methyl-3-(9-methyl-3-(trifluoromethyl)-5,6,7,8-tetrahydro-4,7-epiminocyclohepta[c]pyrazol-1(4H)-yl)benzamide |
| 52 | (4S,7R)- or (4R,7S)-tert-butyl-1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate |
| 53 | (4R,7S)- or (4S,7R)-tert-butyl-1-(3-(benzo[d][1,3]dioxol-5-yl(methyl)carbamoyl)phenyl)-3-(trifluoromethyl)-1,4,5,6,7,8-hexahydro-4,7-epiminocyclohepta[c]pyrazole-9-carboxylate |
| 54 | N-(1,3-benzodioxol-5-yl)-N-methyl-3-[3-(trifluoromethyl)-6,7-dihydro-4H-pyrano[4,3-c]pyrazol-1-yl]benzamide |

-continued

| # | Substance Name |
|---|---|
| 55 | methyl 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoate |
| 56 | 1-[3-[1,3-benzodioxol-5-yl(methyl)carbamoyl]phenyl]-N-methyl-3-(trifluoromethyl)-6,7-dihydro-4H-pyrazolo[4,3-c]pyridine-5-carboxamide |
| 57 | 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoic acid |
| 58 | N-(1,3-benzodioxol-5-yl)-3-[5-(2-hydroxy-2-methyl-propanoyl)-3-(trifluoromethyl)-6,7-dihydro-4H-pyrazolo[4,3-c]pyridin-1-yl]-N-methyl-benzamide |
| 59 | methyl 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoate |
| 60 | methyl 2-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoate |
| 61 | 3-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoic acid |
| 62 | 2-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]benzoic acid |
| 63 | N-(1,3-benzodioxol-5-yl)-3-[5-(4-cyanophenyl)sulfonyl-3-(trifluoromethyl)-6,7-dihydro-4H-pyrazolo[4,3-c]pyridin-1-yl]-N-methyl-benzamide |
| 64 | N-(1,3-benzodioxol-5-yl)-3-[5-(1,2-dimethylimidazol-4-yl)sulfonyl-3-(trifluoromethyl)-6,7-dihydro-4H-pyrazolo[4,3-c]pyridin-1-yl]-N-methyl-benzamide |
| 65 | tert-butyl 1-[3-[1,3-benzodioxol-5-yl(methyl)sulfamoyl]phenyl]-3-(trifluoromethyl)-6,7-dihydro-4H-pyrazolo[4,3-c]pyridine-5-carboxylate |
| 66 | N-(1,3-benzodioxol-5-yl)-N-methyl-3-[3-(trifluoromethyl)-4,5,6,7-tetrahydropyrazolo[4,3-c]pyridin-1-yl]benzenesulfonamide; hydrochloride |
| 67 | N-(1,3-benzodioxol-5-yl)-3-[5-(3,5-dimethylisoxazol-4-yl)sulfonyl-3-(trifluoromethyl)-6,7-dihydro-4H-pyrazolo[4,3-c]pyridin-1-yl]-N-methyl-benzamide |
| 68 | N-(1,3-benzodioxol-5-yl)-3-[5-(2-methoxyethylsulfonyl)-3-(trifluoromethyl)-6,7-dihydro-4H-pyrazolo[4,3-c]pyridin-1-yl]-N-methyl-benzamide |
| 69 | N-(1,3-benzodioxol-5-yl)-3-[5-[(3,5-dimethyl-1H-pyrazol-4-yl)sulfonyl]-3-(trifluoromethyl)-6,7-dihydro-4H-pyrazolo[4,3-c]pyridin-1-yl]-N-methyl-benzamide |
| 70 | methyl 4-((1-(3-(benzo[d][1,3]dioxol-5-yl)(methyl)carbamoyl)phenyl)-3-(trifluoromethyl)-1,4,5,6,7,8-hexahydro-4,7-epiminocyclohepta[c]pyrazol-9-yl)sulfonyl)benzoate |
| 71 | N-(1,3-benzodioxol-5-yl)-N-methyl-3-[5-methyl-3-(trifluoromethyl)-6,7-dihydro-4H-pyrazolo[4,3-c]pyridin-1-yl]benzenesulfonamide |
| 72 | N-(1,3-benzodioxol-5-yl)-3-[6-(2,2-dimethylpropanoyl)-3-(trifluoromethyl)-5,7-dihydro-4H-pyrazolo[3,4-c]pyridin-1-yl]-N-methyl-benzamide |
| 73 | N-(1,3-benzodioxol-5-yl)-3-[5-(2,4-dimethylpyrazol-3-yl)-3-(trifluoromethyl)-6,7-dihydro-4H-pyrazolo[4,3-c]pyridin-1-yl]-N-methyl-benzamide |
| 74 | N-(1,3-benzodioxol-5-yl)-N-methyl-3-[3-(trifluoromethyl)-5-(1,3,5-trimethylpyrazol-4-yl)-6,7-dihydro-4H-pyrazolo[4,3-c]pyridin-1-yl]benzamide |
| 75 | methyl 4-[[1-[3-[1,3-benzodioxol-5-yl(methyl)carbamoyl]phenyl]-3-(trifluoromethyl)-5,7-dihydro-4H-pyrazolo[3,4-c]pyridin-6-yl]sulfonyl]benzoate |
| 76 | N-(1,3-benzodioxol-5-yl)-N-methyl-3-[5-tetrahydropyran-4-ylsulfonyl-3-(trifluoromethyl)-6,7-dihydro-4H-pyrazolo[4,3-c]pyridin-1-yl]benzamide |
| 77 | 4-[[1-[3-[1,3-benzodioxol-5-yl(methyl)carbamoyl]phenyl]-3-(trifluoromethyl)-5,7-dihydro-4H-pyrazolo[3,4-c]pyridin-6-yl]sulfonyl]benzoic acid |
| 78 | 3-[5-(2,2-dimethylpropanoyl)-3-(trifluoromethyl)-6,7-dihydro-4Hpyrazolo[4,3-c]pyridin-1-yl]-N-(2-methyl-[1,2,4]triazolo[1,5-a]pyridin-6-yl)benzamide |
| 79 | 3-[5-(2,2-dimethylpropanoyl)-3-(trifluoromethyl)-6,7-dihydro-4H-pyrazolo[4,3-c]pyridin-1-yl]-N-(3-methyl-1H-pyrazolo[3,4-b]pyridin-5-yl)benzamide |
| 80 | 3-[5-(2,2-dimethylpropanoyl)-3-(trifluoromethyl)-6,7-dihydro-4H-pyrazolo[4,3-c]pyridin-1-yl]-N-(6-methoxy-3-pyridyl)benzamide |
| 81 | 3-[5-(2,2-dimethylpropanoyl)-3-(trifluoromethyl)-6,7-dihydro-4H-pyrazolo[4,3-c]pyridin-1-yl]-N-(2-methoxypyrimidin-5-yl)benzamide |
| 82 | tert-butyl 3-[4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]-3,5-dimethyl-pyrazol-1-yl]propanoate |
| 83 | 3-[5-(2,2-dimethylpropanoyl)-3-(trifluoromethyl)-6,7-dihydro-4H-pyrazolo[4,3-c]pyridin-1-yl]-N-(2-methoxy-4-pyridyl)benzamide |
| 84 | 3-[5-(2,2-dimethylpropanoyl)-3-(trifluoromethyl)-6,7-dihydro-4H-pyrazolo[4,3-c]pyridin-1-yl]-N-(2-methylimidazo[1,2-a]pyridin-6-yl)benzamide |
| 85 | 3-[5-(2,2-dimethylpropanoyl)-3-(trifluoromethyl)-6,7-dihydro-4H-pyrazolo[4,3-c]pyridin-1-yl]-N-(6-methoxy-3-pyridyl)-N-methyl-benzamide |
| 86 | 3-[4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]-3,5-dimethyl-pyrazol-1-yl]propanoic acid |
| 87 | (4R,7S)- or (4S,7R)-N-(benzo[d][1,3]dioxol-5-yl)-N-methyl-3-[(9-pivaloyl-3-(trifluoromethyl)-5,6,7,8-tetrahydro-4,7-epiminocyclohepta[c]pyrazol-1(4H)-yl)]benzamide |
| 88 | (4S,7R)- or (4R,7S)-N-(benzo[d][1,3]dioxol-5-yl)-N-methyl-3-[(9-pivaloyl-3-(trifluoromethyl)-5,6,7,8-tetrahydro-4,7-epiminocyclohepta[c]pyrazol-1(4H)-yl)]benzamide |
| 89 | 4-[[1-[3-[1,3-benzodioxol-5-yl(methyl)carbamoyl]phenyl]-3-(trifluoromethyl)-6,7-dihydro-4H-pyrazolo[4,3-c]pyridin-5-yl]sulfonyl]-5-methyl-1H-pyrazole-3-carboxylic acid |

| # | Substance Name |
|---|---|
| 90 | 3-[5-(2,2-dimethylpropanoyl)-3-(trifluoromethyl)-6,7-dihydro-4H-pyrazolo[4,3-c]pyridin-1-yl]-N-(2-methoxy-4-pyridyl)-N-methyl-benzamide |
| 91 | 3-[5-(2,2-dimethylpropanoyl)-3-(trifluoromethyl)-6,7-dihydro-4H-pyrazolo[4,3-c]pyridin-1-yl]-N-methyl-N-(2-methylimidazo[1,2-a]pyridin-6-yl)benzamide |
| 92 | N-(2,2-difluoro-1,3-benzodioxol-5-yl)-N-methyl-3-[3-(trifluoromethyl)-4,5,6,7-tetrahydropyrazolo[4,3-c]pyridin-1-yl]benzamide |
| 93 | 3-[5-cyclobutyl-3-(trifluoromethyl)-6,7-dihydro-4H-pyrazolo[4,3-c]pyridin-1-yl]-N-(2,2-difluoro-1,3-benzodioxol-5-yl)-N-methyl-benzamide |
| 94 | N-(2,2-difluoro-1,3-benzodioxol-5-yl)-3-[5-(2,2-dimethylpropanoyl)-3-(trifluoromethyl)-6,7-dihydro-4H-pyrazolo[4,3-c]pyridin-1-yl]-N-methyl-benzamide |
| 95 | tert-butyl 1-(3-((2,2-difluorobenzo[d][1,3]dioxol-5-yl)(methyl)carbamoyl)phenyl)-3-(trifluoromethyl)-1,4,5,6,7,8-hexahydro-4,7-epiminocyclohepta[c]pyrazole-9-carboxylate |
| 96 | N-(2,2-difluoro-1,3-benzodioxol-5-yl)-3-[5-(3,5-dimethylisoxazol-4-yl)sulfonyl-3-(trifluoromethyl)-6,7-dihydro-4H-pyrazolo[4,3-c]pyridin-1-yl]-N-methyl-benzamide |
| 97 | methyl 4-((1-(3-((2,2-difluorobenzo[d][1,3]dioxol-5-yl)(methyl)carbamoyl)phenyl)-3-(trifluoromethyl)-1,4,5,6,7,8-hexahydro-4,7-epiminocyclohepta[c]pyrazol-9-yl)sulfonyl)benzoate yl]sulfonyl]benzoate |
| 98 | N-(2,2-difluorobenzo[d][1,3]dioxol-5-yl)-N-methyl-3-(9-pivaloyl-3-(trifluoromethyl)-5,6,7,8-tetrahydro-4,7-epiminocyclohepta[c]pyrazol-1(4H)-yl)benzamide benzamide |
| 99 | N-methyl-N-(2-methylbenzo[d]oxazol-6-yl)-3-(9-pivaloyl-3-(trifluoromethyl)-5,6,7,8-tetrahydro-4,7-epiminocyclohepta[c]pyrazol-1(4H)-yl)benzamide |
| 100 | 3-(9-((3,5-dimethylisoxazol-4-yl)sulfonyl)-3-(trifluoromethyl)-5,6,7,8-tetrahydro-4,7-epiminocyclohepta[c]pyrazol-1(4H)-yl)-N-methyl-N-(2-methylbenzo[d]oxazol-6-yl)benzamide |
| 101 | 3-(9-((3,5-dimethylisoxazol-4-yl)sulfonyl)-3-(trifluoromethyl)-5,6,7,8-tetrahydro-4,7-epiminocyclohepta[c]pyrazol-1(4H)-yl)-N-methyl-N-(2-methylpyrazolo[1,5-a]pyridin-5-yl)benzamide |
| 102 | N-(2,2-difluoro-1,3-benzodioxol-5-yl)-3-(3-isopropyl-4,5,6,7-tetrahydroindazol-1-yl)-N-methyl-benzamide |
| 103 | N-(2,2-difluoro-1,3-benzodioxol-5-yl)-N-methyl-3-(3-methyl-4,5,6,7-tetrahydroindazol-1-yl)benzamide |
| 104 | ethyl 1-[3-[(2,2-difluoro-1,3-benzodioxol-5-yl)-methyl-carbamoyl]phenyl]-5-methyl-6,7-dihydro-4H-pyrazolo[4,3-c]pyridine-3-carboxylate |
| 105 | 3-(3-isopropyl-4,5,6,7-tetrahydroindazol-1-yl)-N-methyl-N-(2-methylpyrazolo[1,5-a]pyridin-5-yl)benzamide |
| 106 | N-(2,2-difluoro-1,3-benzodioxol-5-yl)-N-methyl-3-[7-(4-methylphenoxy)-3-(trifluoromethyl)-6,7-dihydro-4H-pyrano[4,3-c]pyrazol-1-yl]benzamide |
| 107 | N-methyl-N-(2-methyl-1,3-benzoxazol-6-yl)-3-[7-(4-methylphenoxy)-3-(trifluoromethyl)-6,7-dihydro-4H-pyrano[4,3-c]pyrazol-1-yl]benzamide |
| 108 | 4-[[1-[3-[(2,2-difluoro-1,3-benzodioxol-5-yl)-methyl-carbamoyl]phenyl]-5-methyl-3-(trifluoromethyl)-6,7-dihydro-4H-pyrazolo[4,3-c]pyridin-7-yl]oxy]benzoic acid |
| 109 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 110 | N-(1,3-benzodioxol-5-yl)-N-methyl-3-[4-methyl-3-(trifluoromethyl)-6,7-dihydro-5H-pyrazolo[4,3-b]pyridin-1-yl]benzamide |
| 111 | N-(2,2-difluoro-1,3-benzodioxol-5-yl)-3-[4-(2,2-dimethylpropanoyl)-3-(trifluoromethyl)-6,7-dihydro-5H-pyrazolo[4,3-b]pyridin-1-yl]-N-methyl-benzamide |
| 112 | N-(1,3-benzodioxol-5-yl)-N-methyl-3-[5-methyl-6-oxo-3-(trifluoromethyl)-4,7-dihydropyrazolo[4,3-c]pyridin-1-yl]benzamide |
| 113 | N-methyl-N-(2-methyl-1,3-benzoxazol-6-yl)-3-[5-methyl-6-oxo-3-(trifluoromethyl)-4,7-dihydropyrazolo[4,3-c]pyridin-1-yl]benzamide |
| 114 | 3-[5-(2,2-dimethylpropanoyl)-3-(trifluoromethyl)-6,7-dihydro-4H-pyrazolo[4,3-c]pyridin-1-yl]-N-methyl-N-(3-methyl-1H-pyrazolo[3,4-b]pyridin-5-yl)benzamide |
| 115 | 3-[5-(2,2-dimethylpropanoyl)-3-(trifluoromethyl)-6,7-dihydro-4H-pyrazolo[4,3-c]pyridin-1-yl]-N-(2-methoxypyrimidin-5-yl)-N-methyl-benzamide |
| 116 | N-(1,3-benzodioxol-5-yl)-N-methyl-3-[5-methyl-3-(trifluoromethyl)-4,6-dihydropyrrolo[3,4-c]pyrazol-1-yl]benzamide |
| 117 | N-(2,2-difluoro-1,3-benzodioxol-5-yl)-3-[5-(2,2-dimethylpropanoyl)-3-(trifluoromethyl)-4,6-dihydropyrrolo[3,4-c]pyrazol-1-yl]-N-methyl-benzamide |
| 118 | N-(1,3-benzodioxol-5-yl)-N-methyl-3-[6-methyl-3-(trifluoromethyl)-4,5,7,8-tetrahydropyrazolo[3,4-d]azepin-1-yl]benzamide |
| 119 | N-(2,2-difluoro-1,3-benzodioxol-5-yl)-3-[6-(2,2-dimethylpropanoyl)-3-(trifluoromethyl)-4,5,7,8-tetrahydropyrazolo[3,4-d]azepin-1-yl]-N-methyl-benzamide |
| 120 | N-(2,2-difluoro-1,3-benzodioxol-5-yl)-3-[5,7-dimethyl-3-(trifluoromethyl)-6,7-dihydro-4H-pyrazolo[4,3-c]pyridin-1-yl]-N-methyl-benzamide |
| 121 | 1-[3-[(2,2-difluoro-1,3-benzodioxol-5-yl)-methyl-carbamoyl]phenyl]-5-methyl-3-(trifluoromethyl)-6,7-dihydro-4H-pyrazolo[4,3-c]pyridine-7-carboxylic acid |
| 122 | 3-[7-cyano-5-methyl-3-(trifluoromethyl)-6,7-dihydro-4H-pyrazolo[4,3-c]pyridin-1-yl]-N-(2,2-difluoro-1,3-benzodioxol-5-yl)-N-methyl-benzamide |
| 123 | N-(2,2-difluoro-1,3-benzodioxol-5-yl)-N-methyl-3-[5,7,7-trimethyl-3-(trifluoromethyl)-4,6-dihydropyrazolo[4,3-c]pyridin-1-yl]benzamide |
| 124 | 1-[3-[(2,2-difluoro-1,3-benzodioxol-5-yl)-methyl-carbamoyl]phenyl]-5-methyl-3-(trifluoromethyl)-6,7-dihydro-4H-pyrazolo[4,3-c]pyridine-6-carboxylic acid |
| 125 | N-(2,2-difluoro-1,3-benzodioxol-5-yl)-3-[5,6-dimethyl-3-(trifluoromethyl)-6,7-dihydro-4H-pyrazolo[4,3-c]pyridin-1-yl]-N-methyl-benzamide |
| 126 | N-(2,2-difluoro-1,3-benzodioxol-5-yl)-3-[5-(2,2-dimethylpropanoyl)-3- |

| # | Substance Name |
|---|---|
| | (trifluoromethyl)-6,7-dihydro-4H-pyrazolo[4,3-c]pyridin-1-yl]-N-(trideuteromethyl)benzamide |
| 127 | 3-[5-(2,2-dimethylpropanoyl)-3-(trifluoromethyl)-6,7-dihydro-4H-pyrazolo[4,3-c]pyridin-1-yl]-N-(2-methyl-1,3-benzoxazol-6-yl)-N-(trideuteromethyl)benzamide |
| 128 | (4S,7R)- or (4R,7S)-N-(benzo[d][1,3]dioxol-5-yl)-3-(9-((3,5-dimethylisoxazol-4-yl)sulfonyl)-3-(trifluoromethyl)-5,6,7,8-tetrahydro-4,7-epiminocyclohepta[c]pyrazol-1(4H)-yl)-N-methylbenzamide |
| 129 | (4R,7S)- or (4S,7R)-N-(benzo[d][1,3]dioxol-5-yl)-3-(9-((3,5-dimethylisoxazol-4-yl)sulfonyl)-3-(trifluoromethyl)-5,6,7,8-tetrahydro-4,7-epiminocyclohepta[c]pyrazol-1(4H)-yl)-N-methylbenzamide |
| 130 | (4R,7S)- or (4S,7R)-N-(benzo[d][1,3]dioxol-5-yl)-3-(9-((3,5-dimethyl-1H-pyrazol-4-yl)sulfonyl)-3-(trifluoromethyl)-5,6,7,8-tetrahydro-4,7-epiminocyclohepta[c]pyrazol-1(4H)-yl)-N-methylbenzamide |
| 131 | (4R,7S)- or (4S,7R)-N-(benzo[d][1,3]dioxol-5-yl)-3-((4R,7S)-9-cyclobutyl-3-(trifluoromethyl)-5,6,7,8-tetrahydro-4,7-epiminocyclohepta[c]pyrazol-1(4H)-yl)-N-methylbenzamide |
| 132 | N-(1,3-benzodioxol-5-yl)-N-methyl-3-(3-methyl-4,5,6,7-tetrahydroindazol-1-yl)benzamide |
| 133 | N-(1,3-benzodioxol-5-yl)-3-(3-isopropyl-4,5,6,7-tetrahydroindazol-1-yl)-N-methyl-benzamide |
| 134 | ethyl 4-[1-[3-[1,3-benzodioxol-5-yl(methyl)carbamoyl]phenyl]-3-(trifluoromethyl)-6,7-dihydro-4H-pyrazolo[4,3-c]pyridin-5-yl]butanoate |
| 135 | 4-[1-[3-[1,3-benzodioxol-5-yl(methyl)carbamoyl]phenyl]-3-(trifluoromethyl)-6,7-dihydro-4H-pyrazolo[4,3-c]pyridin-5-yl]butanoic acid |
| 136 | tert-butyl 1-[3-[(2,2-difluoro-1,3-benzodioxol-5-yl)-methyl-carbamoyl]phenyl]-3-(trifluoromethyl)-6,7-dihydro-4H-pyrazolo[4,3-c]pyridine-5-carboxylate |
| 137 | 3-[5-(3,5-dimethylisoxazol-4-yl)sulfonyl-3-(trifluoromethyl)-6,7-dihydro-4H-pyrazolo[4,3-c]pyridin-1-yl]-N-methyl-N-(2-methyl-1,3-benzoxazol-6-yl)benzamide |
| 138 | 3-[5-(3,5-dimethylisoxazol-4-yl)sulfonyl-3-(trifluoromethyl)-6,7-dihydro-4H-pyrazolo[4,3-c]pyridin-1-yl]-N-(5-fluoro-2-methyl-1,3-benzoxazol-6-yl)-N-methyl-benzamide |
| 139 | benzyl 3-[1-[3-[1,3-benzodioxol-5-yl(methyl)carbamoyl]phenyl]-3-(trifluoromethyl)-6,7-dihydro-4H-pyrazolo[4,3-c]pyridin-5-yl]cyclobutanecarboxylate |
| 140 | 3-[1-[3-[1,3-benzodioxol-5-yl(methyl)carbamoyl]phenyl]-3-(trifluoromethyl)-6,7-dihydro-4H-pyrazolo[4,3-c]pyridin-5-yl]cyclobutanecarboxylic acid |
| 141 | 3-[5-(2,2-dimethylpropanoyl)-3-(trifluoromethyl)-6,7-dihydro-4H-pyrazolo[4,3-c]pyridin-1-yl]-N-methyl-N-quinoxalin-6-yl-benzamide |
| 142 | 3-[5-(2,2-dimethylpropanoyl)-3-(trifluoromethyl)-6,7-dihydro-4H-pyrazolo[4,3-c]pyridin-1-yl]-N-(2-methoxypyrimidin-5-yl)-N-methyl-benzamide |
| 143 | tert-butyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 144 | N-(2,2-difluoro-1,3-benzodioxol-5-yl)-N-methyl-3-[7-oxo-3-(trifluoromethyl)-5,6-dihydro-4H-indazol-1-yl]benzamide |
| 145 | N-(2,2-difluoro-1,3-benzodioxol-5-yl)-N-methyl-3-[7-oxo-3-(trifluoromethyl)-5,6-dihydro-4H-indazol-1-yl]benzamide |
| 146 | methyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-fluoro-benzoate |
| 147 | 2-fluoro-4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 148 | (R) or (S)-tert-butyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 149 | (S) or (R)-tert-butyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 150 | (R) or (S)-4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 151 | (S) or (R)-4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 152 | tert-butyl 4-[[1-[3-[(5-fluoro-2-methyl-1,3-benzoxazol-6-yl)-methyl-carbamoyl]phenyl]-3-(trifluoromethyl)-4,5,6,7-tetrahydroindazol-7-yl]oxy]benzoate |
| 153 | 4-[[1-[3-[(5-fluoro-2-methyl-1,3-benzoxazol-6-yl)-methyl-carbamoyl]phenyl]-3-(trifluoromethyl)-4,5,6,7-tetrahydroindazol-7-yl]oxy]benzoic acid |
| 154 | tert-butyl 4-[[1-[3-[(2,2-difluoro-1,3-benzodioxol-5-yl)-(trideuteriomethyl)carbamoyl]phenyl]-3-(trifluoromethyl)-4,5,6,7-tetrahydroindazol-7-yl]oxy]benzoate |
| 155 | 4-[[1-[3-[(2,2-difluoro-1,3-benzodioxol-5-yl)-(trideuteriomethyl)carbamoyl]phenyl]-3-(trifluoromethyl)-4,5,6,7-tetrahydroindazol-7-yl]oxy]benzoic acid |
| 156 | tert-butyl 4-[[1-[3-[methyl-(2-methyl-1,3-benzoxazol-6-yl)carbamoyl]phenyl]-3-(trifluoromethyl)-4,5,6,7-tetrahydroindazol-7-yl]oxy]benzoate |
| 157 | 4-[[1-[3-[methyl-(2-methyl-1,3-benzoxazol-6-yl)carbamoyl]phenyl]-3-(trifluoromethyl)-4,5,6,7-tetrahydroindazol-7-yl]oxy]benzoic acid |
| 158 | tert-butyl 4-[[1-[3-[methyl-(2-methyloxazolo[4,5-b]pyridin-6-yl)carbamoyl]phenyl]-3-(trifluoromethyl)-4,5,6,7-tetrahydroindazol-7-yl]oxy]benzoate |
| 159 | 4-[[1-[3-[methyl-(2-methyloxazolo[4,5-b]pyridin-6-yl)carbamoyl]phenyl]-3-(trifluoromethyl)-4,5,6,7-tetrahydroindazol-7-yl]oxy]benzoic acid |
| 160 | methyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-methoxy-benzoate |
| 161 | 4-[[1-[3-[(2,2-difluoro-1,3-benzodioxol-5-yl)-methyl-carbamoyl]phenyl]-3- |

| # | Substance Name |
|---|---|
| | (trifluoromethyl)-4,5,6,7-tetrahydroindazol-7-yl]oxy]-2-methoxy-benzoic acid |
| 162 | 3-[7-(4-carbamoylphenoxy)-3-(trifluoromethyl)-4,5,6,7-tetrahydroindazol-1-yl]-N-(2,2-difluoro-1,3-benzodioxol-5-yl)-N-methyl-benzamide |
| 163 | methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylate |
| 164 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylic acid |
| 165 | tert-butyl 4-[[1-[3-[(5-methoxy-3-pyridyl)-methyl-carbamoyl]phenyl]-3-(trifluoromethyl)-4,5,6,7-tetrahydroindazol-7-yl]oxy]benzoate |
| 166 | 4-[[1-[3-[(5-methoxy-3-pyridyl)-methyl-carbamoyl]phenyl]-3-(trifluoromethyl)-4,5,6,7-tetrahydroindazol-7-yl]oxy]benzoic acid |
| 167 | tert-butyl 4-[[1-[3-[(2-methoxypyrimidin-5-yl)-methyl-carbamoyl]phenyl]-3-(trifluoromethyl)-4,5,6,7-tetrahydroindazol-7-yl]oxy]benzoate |
| 168 | 4-[[1-[3-[(2-methoxypyrimidin-5-yl)-methyl-carbamoyl]phenyl]-3-(trifluoromethyl)-4,5,6,7-tetrahydroindazol-7-yl]oxy]benzoic acid |
| 169 | ethyl 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 170 | 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 171 | tert-butyl 4-[[1-[3-[methyl-(2-methyl-[1,2,4]triazolo[1,5-a]pyridin-6-yl)carbamoyl]phenyl]-3-(trifluoromethyl)-4,5,6,7-tetrahydroindazol-7-yl]oxy]benzoate |
| 172 | 4-[[1-[3-[methyl-(2-methyl-[1,2,4]triazolo[1,5-a]pyridin-6-yl)carbamoyl]phenyl]-3-(trifluoromethyl)-4,5,6,7-tetrahydroindazol-7-yl]oxy]benzoic acid |
| 173 | tert-butyl 4-[[1-[3-[methyl-(2-methylpyrazolo[1,5-a]pyrimidin-6-yl)carbamoyl]phenyl]-3-(trifluoromethyl)-4,5,6,7-tetrahydroindazol-7-yl]oxy]benzoate |
| 174 | 4-[[1-[3-[methyl-(2-methylpyrazolo[1,5-a]pyrimidin-6-yl)carbamoyl]phenyl]-3-(trifluoromethyl)-4,5,6,7-tetrahydroindazol-7-yl]oxy]benzoic acid |
| 175 | methyl 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-methyl-benzoate |
| 176 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]-2-methyl-benzoic acid |
| 177 | methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate |
| 178 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid |
| 179 | methyl 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate |
| 180 | 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid |
| 181 | methyl 2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylate |
| 182 | 2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylic acid |
| 183 | (S)- or (R)-methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylate |
| 184 | (R)- or (S)-methyl 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylate |
| 185 | (R) or (S)-5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylic acid |
| 186 | (S) or (R)-5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-2-carboxylic acid |
| 187 | (S) or (R)-ethyl 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 188 | (S) or (R)-3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 189 | (R) or (S)-ethyl 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoate |
| 190 | (R) or (S)-3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]benzoic acid |
| 191 | (S) or (R)-methyl 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate |
| 192 | (S) or (R)-6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid |
| 193 | (R) or (S)-methyl 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylate |
| 194 | (R) or (S)-6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-3-carboxylic acid |
| 195 | (S) or (R)-methyl 2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylate |
| 196 | (S) or (R)-2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylic acid |
| 197 | (R) or (S)-methyl 2-[[1-[3-[(2,2-difluoro-1,3-benzodioxol-5-yl)-methyl- |

| # | Substance Name |
|---|---|
| | carbamoyl]phenyl]-3-(trifluoromethyl)-4,5,6,7-tetrahydroindazol-7-yl]oxy]pyridine-4-carboxylate |
| 198 | (R) or (S)-2-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridine-4-carboxylic acid |
| 199 | 3-[7-benzyloxy-3-(trifluoromethyl)-6,7-dihydro-4H-pyrano[4,3-c]pyrazol-1-yl]-N-(2,2-difluoro-1,3-benzodioxol-5-yl)-N-methyl-benzamide |
| 200 | N-(2,2-difluoro-1,3-benzodioxol-5-yl)-3-[7-hydroxy-3-(trifluoromethyl)-6,7-dihydro-4H-pyrano[4,3-c]pyrazol-1-yl]-N-methyl-benzamide |
| 201 | tert-butyl 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoate |
| 202 | 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoic acid |
| 203 | (R)- or (S)-tert-butyl 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoate |
| 204 | (S)- or (R)-tert-butyl 4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoate |
| 205 | (R)- or (S)-4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoic acid |
| 206 | (S)- or (R)-4-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]benzoic acid |
| 207 | tert-butyl 4-[[1-[3-[(2,2-difluoro-1,3-benzodioxol-5-yl)-methyl-carbamoyl]phenyl]-3-(difluoromethyl)-4,5,6,7-tetrahydroindazol-7-yl]oxy]benzoate |
| 208 | 4-[[1-[3-[(2,2-difluoro-1,3-benzodioxol-5-yl)-methyl-carbamoyl]phenyl]-3-(difluoromethyl)-4,5,6,7-tetrahydroindazol-7-yl]oxy]benzoic acid |
| 209 | Methyl 5-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylate |
| 210 | 5-[[1-[3-[(2,2-Difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylic acid |
| 211 | Methyl 6-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylate |
| 212 | Methyl 1-[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]-6-oxo-pyridine-3-carboxylate |
| 213 | 6-[[1-[3-[(2,2-Difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-3-carboxylic acid |
| 214 | 1-[1-[3-[(2,2-Difluoro-1,3-benzodioxol-5-yl)-methyl-carbamoyl]phenyl]-3-(trifluoromethyl)-6,7-dihydro-4H-pyrano[4,3-c]pyrazol-7-yl]-6-oxo-pyridine-3-carboxylic acid |
| 215 | (S) or (R)-tert-Butyl 4-[[1-[3-[methyl-(2-methylpyrazolo[1,5-a] pyrimidin-6-yl)carbamoyl]phenyl]-3-(trifluoromethyl)-4,5,6,7-tetrahydroindazol-7-yl]oxy]benzoate |
| 216 | (R) or (S)-tert-Butyl 4-[[1-[3-[methyl-(2-methylpyrazolo[1,5-a] pyrimidin-6-yl)carbamoyl]phenyl]-3-(trifluoromethyl)-4,5,6,7-tetrahydroindazol-7-yl]oxy]benzoate |
| 217 | (S) or (R)-4-[[1-[3-[Methyl-(2-methylpyrazolo[1,5-a]pyrimidin-6-yl)carbamoyl]phenyl]-3-(trifluoromethyl)-4,5,6,7-tetrahydroindazol-7-yl]oxy]benzoic acid |
| 218 | (R) or (S)-4-[[1-[3-[Methyl-(2-methylpyrazolo[1,5-a]pyrimidin-6-yl)carbamoyl]phenyl]-3-(trifluoromethyl)-4,5,6,7-tetrahydroindazol-7-yl]oxy]benzoic acid |
| 219 | 4-[[1-[3-[[2-(difluoromethoxy)pyrimidin-5-yl]-methyl-carbamoyl]phenyl]-3-(trifluoromethyl)-4,5,6,7-tetrahydroindazol-7-yl]oxy]benzoic acid |
| 220 | 4-[[1-[3-[methyl-[2-(trifluoromethoxy)pyrimidin-5-yl]carbamoyl]phenyl]-3-(trifluoromethyl)-4,5,6,7-tetrahydroindazol-7-yl]oxy]benzoic acid |
| 221 | 6-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]pyridazine-3-carboxylic acid |
| 222 | 4-[[1-[3-[(2,2-difluoro-3H-furo[3,2-b]pyridin-6-yl)-methyl-carbamoyl]phenyl]-3-(trifluoromethyl)-4,5,6,7-tetrahydroindazol-7-yl]oxy]benzoic acid |
| 223 | 4-[[1-[3-[methyl-[5-(trifluoromethoxy)-3-pyridyl]carbamoyl]phenyl]-3-(trifluoromethyl)-4,5,6,7-tetrahydroindazol-7-yl]oxy]benzoic acid |
| 224 | 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]cyclobutanecarboxylic acid |
| 225 | 3-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]bicyclo[1.1.1]pentane-1-carboxylic acid |
| 226 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]cyclohexanecarboxylic acid |
| 227 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]oxy]cyclohexanecarboxylic acid |
| 228 | 5-[[1-[3-[methyl-(2-methyl-1,3-benzoxazol-6-yl)carbamoyl]phenyl]-3-(trifluoromethyl)-6,7-dihydro-4H-pyrano[4,3-c]pyrazol-7-yl]oxy]pyridine-2-carboxylic acid |

| # | Substance Name |
|---|---|
| 229 | 5-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-2-carboxylic acid |
| 230 | 4-[[1-[3-[[2-(difluoromethoxy)pyrimidin-5-yl]-methyl-carbamoyl]phenyl]-3-(trifluoromethyl)-6,7-dihydro-4H-pyrano[4,3-c]pyrazol-7-yl]oxy]benzoic acid |
| 231 | 2-[[1-[3-[(2,2-difluoro-1,3-benzodioxol-5-yl)-methyl-carbamoyl]phenyl]-3-(trifluoromethyl)-6,7-dihydro-4H-pyrano[4,3-c]pyrazol-7-yl]oxy]pyridine-4-carboxylic acid |
| 232 | 6-[[1-[3-[methyl-(2-methyloxazolo[4,5-b]pyridin-6-yl)carbamoyl]phenyl]-3-(trifluoromethyl)-6,7-dihydro-4H-pyrano[4,3-c]pyrazol-7-yl]oxy]pyridine-3-carboxylic acid |
| 233 | 4-[[1-[3-[(2,2-difluoro-1,3-benzodioxol-5-yl)-methyl-carbamoyl]phenyl]-3-(trifluoromethyl)-4,5,6,7-tetrahydroindazol-7-yl]amino]benzoic acid |
| 234 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]amino]pyridine-2-carboxylic acid |
| 235 | 4-[methyl-[1-[3-[methyl-(2-methyl-1,3-benzoxazol-6-yl)carbamoyl]phenyl]-3-(trifluoromethyl)-4,5,6,7-tetrahydroindazol-7-yl]amino]benzoic acid |
| 236 | 4-[methyl-[1-[3-[methyl-(2-methyl-1,3-benzoxazol-6-yl)carbamoyl]phenyl]-3-(trifluoromethyl)-4,5,6,7-tetrahydroindazol-7-yl]amino]benzoic acid |
| 237 | 4-[[1-[6-[methyl(pyrazolo[1,5-a]pyrimidin-5-yl)carbamoyl]-2-pyridyl]-3-(trifluoromethyl)-4,5,6,7-tetrahydroindazol-7-yl]oxy]benzoic acid |
| 238 | 4-[[1-[3-[methyl-(2-methyloxazolo[4,5-b]pyridin-6-yl)carbamoyl]phenyl]-3-(trifluoromethyl)-5,6-dihydro-4H-cyclopenta[c]pyrazol-6-yl]oxy]benzoic acid |
| 239 | 4-[[1-[3-[methyl-(2-methylpyrazolo[1,5-a]pyrimidin-6-yl)carbamoyl]phenyl]-3-(trifluoromethyl)-5,6-dihydro-4H-cyclopenta[c]pyrazol-6-yl]oxy]benzoic acid |
| 240 | 4-[[1-[3-[(2,2-difluoro-1,3-benzodioxol-5-yl)-methyl-carbamoyl]phenyl]-3-(trifluoromethyl)-5,6-dihydro-4H-cyclopenta[c]pyrazol-6-yl]oxy]benzoic acid |
| 241 | 4-[[1-[3-[(2,2-difluoro-1,3-benzodioxol-5-yl)-methyl-carbamoyl]phenyl]-3-(trifluoromethoxy)-4,5,6,7-tetrahydroindazol-7-yl]oxy]benzoic acid |
| 242 | 4-[[1-[3-[(2,2-difluoro-1,3-benzodioxol-5-yl)-methyl-carbamoyl]phenyl]-3-(difluoromethoxy)-4,5,6,7-tetrahydroindazol-7-yl]oxy]benzoic acid |
| 243 | 4-[1-[1-[3-[(2,2-difluoro-1,3-benzodioxol-5-yl)-methyl-carbamoyl]phenyl]-3-(trifluoromethyl)-4,5,6,7-tetrahydroindazol-7-yl]-1-methyl-ethyl]benzoic acid |
| 244 | 4-[1-[1-[3-[(2,2-difluoro-1,3-benzodioxol-5-yl)-methyl-carbamoyl]phenyl]-3-(difluoromethyl)-4,5,6,7-tetrahydroindazol-7-yl]cyclopropyl]benzoic acid |
| 245 | 4-[[1-[3-[(2,2-difluoro-1,3-benzodioxol-5-yl)-methyl-carbamoyl]phenyl]-3-(difluoromethyl)-4,5,6,7-tetrahydroindazol-7-yl]sulfonyl]benzoic acid |
| 246 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]methyl]pyridine-2-carboxylic acid |
| 247 | 5-[[1-[3-[(2,2-difluoro-1,3-benzodioxol-5-yl)-methyl-carbamoyl]phenyl]-3-(trifluoromethyl)-4,5,6,7-tetrahydroindazol-7-yl]methyl]pyridine-2-carboxylic acid |
| 248 | 4-[[1-[3-[(2,2-difluoro-1,3-benzodioxol-5-yl)-methyl-carbamoyl]phenyl]-3-(trifluoromethyl)-5,7-dihydro-4H-pyrano[3,4-c]pyrazol-7-yl]methyl]benzoic acid |
| 249 | 4-[[1-[3-[(2,2-difluoro-1,3-benzodioxol-5-yl)-methyl-carbamoyl]phenyl]-3-(trifluoromethyl)-6,7-dihydro-5H-pyrano[3,2-c]pyrazol-7-yl]oxy]benzoic acid |
| 250 | 4-[[1-[3-[methyl-(2-methylimidazo[1,2-b]pyridazin-6-yl)carbamoyl]phenyl]-3-(trifluoromethyl)-4,5,6,7-tetrahydroindazol-7-yl]oxy]benzoic acid |
| 251 | 4-[[1-[3-[(6-methoxypyrazin-2-yl)-methyl-carbamoyl]phenyl]-3-(trifluoromethyl)-4,5,6,7-tetrahydroindazol-7-yl]oxy]benzoic acid |
| 252 | 4-[[1-[3-[(2-methoxypyrimidin-4-yl)-methyl-carbamoyl]phenyl]-3-(trifluoromethyl)-4,5,6,7-tetrahydroindazol-7-yl]oxy]benzoic acid |
| 253 | 4-[[1-[3-[(2,2-Difluoro-1,3-benzodioxol-5-yl) carbamoyl]phenyl]-3-(trifluoromethyl)-4,5,6,7-tetrahydroindazol-7-yl]oxy]benzoic acid. |

\* \* \* \* \*

UNITED STATES PATENT AND TRADEMARK OFFICE
CERTIFICATE OF CORRECTION

PATENT NO. : 10,745,407 B2
APPLICATION NO. : 16/493532
DATED : August 18, 2020
INVENTOR(S) : Tiziano Bandiera et al.

It is certified that error appears in the above-identified patent and that said Letters Patent is hereby corrected as shown below:

On the Title Page

Item (73), please add "Istituto Giannina Gaslini" and "Fondazione Per la Ricerca Sulla Fibrosi Cistica-Onlus," after "Fondazione Istituto Italiano Di Tecnologia."

Signed and Sealed this
Seventh Day of February, 2023

Katherine Kelly Vidal
*Director of the United States Patent and Trademark Office*